US009902956B2

(12) United States Patent
Maor et al.

(10) Patent No.: US 9,902,956 B2
(45) Date of Patent: Feb. 27, 2018

(54) NUCLEIC ACID AGENTS FOR OVEREXPRESSING OR DOWNREGULATING RNA INTERFERENCE TARGETS AND USES OF SAME IN IMPROVING NITROGEN USE EFFICIENCY, ABIOTIC STRESS TOLERANCE, BIOMASS, VIGOR OR YIELD OF A PLANT

(75) Inventors: Rudy Maor, Rechovot (IL); Iris Nesher, Tel-Aviv (IL); Orly Noivirt-Brik, Givataim (IL)

(73) Assignee: A.B. Seeds Ltd., Lod, IL (US)

( * ) Notice: Subject to any disclaimer, the term of this patent is extended or adjusted under 35 U.S.C. 154(b) by 387 days.

(21) Appl. No.: 14/238,745

(22) PCT Filed: Aug. 14, 2012

(86) PCT No.: PCT/IB2012/054149

§ 371 (c)(1),
(2), (4) Date: Jun. 19, 2014

(87) PCT Pub. No.: WO2013/024440

PCT Pub. Date: Feb. 21, 2013

(65) Prior Publication Data

US 2014/0298542 A1    Oct. 2, 2014

Related U.S. Application Data

(60) Provisional application No. 61/523,355, filed on Aug. 14, 2011.

(51) Int. Cl.
*C12N 15/82* (2006.01)
*C12N 15/113* (2010.01)
*C07K 14/415* (2006.01)

(52) U.S. Cl.
CPC .......... *C12N 15/113* (2013.01); *C07K 14/415* (2013.01); *C12N 15/8261* (2013.01); *C12N 15/8271* (2013.01)

(58) Field of Classification Search
None
See application file for complete search history.

(56) References Cited

U.S. PATENT DOCUMENTS

| | | | |
|---|---|---|---|
| 2004/0214272 A1 | 10/2004 | La Rosa et al. | |
| 2009/0070899 A1* | 3/2009 | Apuya ............... | C12N 15/8255 800/286 |
| 2009/0094747 A1* | 4/2009 | Bly .................. | A61G 7/012 5/611 |
| 2009/0217414 A1* | 8/2009 | La Rosa .............. | C07K 14/415 800/278 |
| 2010/0162433 A1* | 6/2010 | McLaren ........... | C12N 15/8261 800/278 |
| 2011/0179529 A1* | 7/2011 | Kwok ................ | C12N 15/8261 800/306 |
| 2014/0298541 A1 | 10/2014 | Maor et al. | |

FOREIGN PATENT DOCUMENTS

| | | |
|---|---|---|
| WO | WO 2009/141824 | 11/2009 |
| WO | WO 2013/024438 | 2/2013 |
| WO | WO 2013/024440 | 2/2013 |

OTHER PUBLICATIONS

International Search Report and the Written Opinion dated Dec. 27, 2012 From the International Searching Authority Re. Application No. PCT/IB2012/054149.
Invitation to Pay Additional Fees dated Nov. 25, 2012 From the International Searching Authority Re. Application No. PCT/IB2012/054147.
Invitation to Pay Additional Fees dated Nov. 25, 2012 From the International Searching Authority Re. Application No. PCT/IB2012/054149.
Glick et al. "Promotion of Plant Growth by ACC Deaminase-Producing Soil Bacteria", European Journal of Plant Pathology, 119: 329-339, Nov. 30, 2007.
Paterson et al. "Hypothetical Protein SORBIDRAFT_03g031980 [Sorghum Bicolor]", Database NBCI [Online], Database Accession No. XP002458357, Jul. 13, 2009.
Puzey et al. "Identification of Conserved Aquilegia Coerulea MicroRNAs and Their Targets", Gene, 448(1): 46-56, Dec. 1, 2009. Table 3, Part 3.5.3 of Results.
Shaharoona et al. "Fertilizer-Dependent Efficiency of Psuedomonads for Improving Growth, Yield, and Nutrient Use Efficiency of Wheat (*Triticum aestivum* L.)", Applied Microbiology and Biotechnology, 79(1): 147-155, May 2008. Abstract. Abstract.
Sunkar et al. "Small RNAs as Big Players in Plant Abiotic Stress Responses and Nutrient Deprivation", Trends in Plant Sciences, 12(7): 301-309, 2007. Table 1.
International Preliminary Report on Patentability dated Feb. 27, 2014 From the International Bureau of WIPO Re. Application No. PCT/IB2012/054149.

* cited by examiner

*Primary Examiner* — Brent T Page
(74) *Attorney, Agent, or Firm* — Arnold & Porter Kaye Scholer LLP

(57) ABSTRACT

A method of improving nitrogen use efficiency, abiotic stress tolerance, biomass, vigor or yield of a plant is provided by expressing within the plant an exogenous polynucleotide encoding a polypeptide having an amino acid sequence at least 80% homologous to SEQ ID NOs: 687-981, 992-1248, 1281-1310, 1389-1391, and 2806-3081. Also provided is a method of improving nitrogen use efficiency, abiotic stress tolerance, biomass, vigor or yield of a plan by expressing within the plant an exogenous polynucleotide which down-regulates an activity or expression of a polypeptide having an amino acid sequence at least 80% homologous to SEQ ID NOs: 311-514, 2007-2436, 1311-1320, 982-991, 1249-1280, 1321-1388. Transgenic plants and constructs are provided as well.

12 Claims, 1 Drawing Sheet

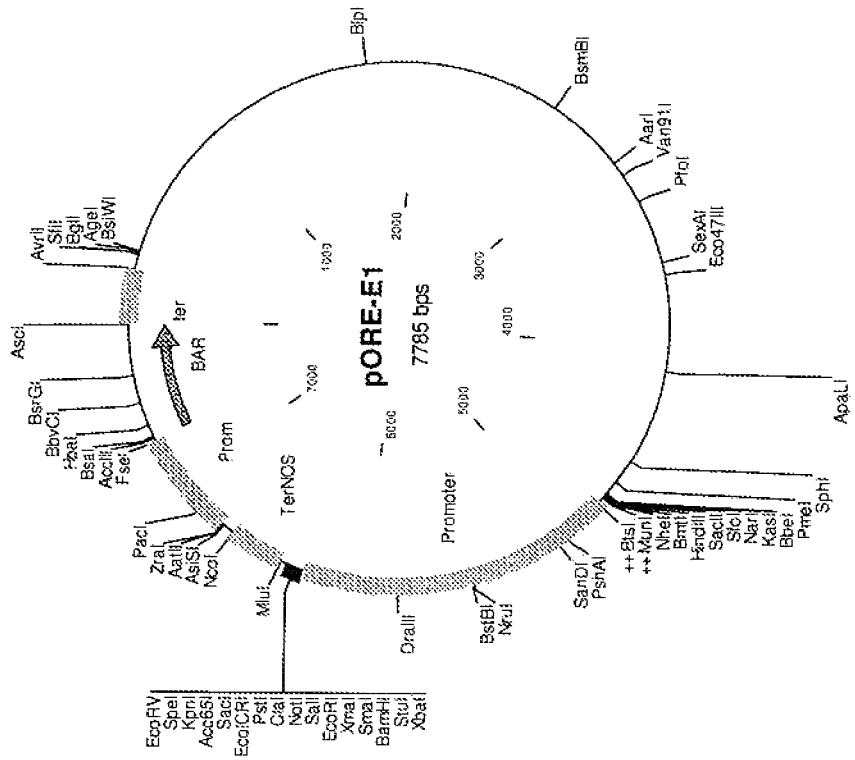

NUCLEIC ACID AGENTS FOR OVEREXPRESSING OR DOWNREGULATING RNA INTERFERENCE TARGETS AND USES OF SAME IN IMPROVING NITROGEN USE EFFICIENCY, ABIOTIC STRESS TOLERANCE, BIOMASS, VIGOR OR YIELD OF A PLANT

RELATED APPLICATIONS

This application is a National Phase of PCT Patent Application No. PCT/IB2012/054149 having International filing date of Aug. 14, 2012, which claims the benefit of priority under 35 USC § 119(e) of U.S. Provisional Patent Application No. 61/523,355 filed on Aug. 14, 2011. The contents of the above applications are all incorporated by reference as if fully set forth herein in their entirety.

SEQUENCE LISTING STATEMENT

The ASCII file, entitled 58604SequenceListing.txt, created on Feb. 13, 2014, comprising 9,493,532 bytes, submitted concurrently with the filing of this application is incorporated herein by reference.

FIELD AND BACKGROUND OF THE INVENTION

The present invention, in some embodiments thereof, relates to nucleic acid agents for overexpressing or down-regulating RNA interference targets and uses of same in improving nitrogen use efficiency, abiotic stress tolerance, biomass, vigor or yield of a plant.

Plant growth is reliant on a number of basic factors: light, air, water, nutrients, and physical support. All these factors, with the exception of light, are controlled by soil to some extent, which integrates non-living substances (minerals, organic matter, gases and liquids) and living organisms (bacteria, fungi, insects, worms, etc.). The soil's volume is almost equally divided between solids and water/gases. An adequate nutrition in the form of natural as well as synthetic fertilizers, may affect crop yield and quality, and its response to stress factors such as disease and adverse weather. The great importance of fertilizers can best be appreciated when considering the direct increase in crop yields over the last 40 years, and the fact that they account for most of the overhead expense in agriculture. Sixteen natural nutrients are essential for plant growth, three of which, carbon, hydrogen and oxygen, are retrieved from air and water. The soil provides the remaining 13 nutrients.

Nutrients are naturally recycled within a self-sufficient environment, such as a rainforest. However, when grown in a commercial situation, plants consume nutrients for their growth and these nutrients need to be replenished in the system. Several nutrients are consumed by plants in large quantities and are referred to as macronutrients. Three macronutrients are considered the basic building blocks of plant growth, and are provided as main fertilizers; Nitrogen (N), Phosphate (P) and Potassium (K). Yet, only nitrogen needs to be replenished every year since plants only absorb approximately half of the nitrogen fertilizer applied. A proper balance of nutrients is crucial; when too much of an essential nutrient is available, it may become toxic to plant growth. Utilization efficiencies of macronutrients directly correlate with yield and general plant tolerance, and increasing them will benefit the plants themselves and the environment by decreasing seepage to ground water.

Nitrogen is responsible for biosynthesis of amino and nucleic acids, prosthetic groups, plant hormones, plant chemical defenses, etc, and thus is utterly essential for the plant. For this reason, plants store nitrogen throughout their developmental stages, in the specific case of corn during the period of grain germination, mostly in the leaves and stalk. However, due to the low nitrogen use efficiency (NUE) of the main crops (e.g., in the range of only 30-70%), nitrogen supply needs to be replenished at least twice during the growing season. This requirement for fertilizer refill may become the rate-limiting element in plant growth and increase fertilizer expenses for the farmer. Limited land resources combined with rapid population growth will inevitably lead to added increase in fertilizer use. In light of this prediction, advanced, biotechnology-based solutions to allow stable high yields with an added potential to reduce fertilizer costs are highly desirable. Subsequently, developing plants with increased NUE will lower fertilizer input in crop cultivation, and allow growth on lower-quality soils.

The major agricultural crops (corn, rice, wheat, canola and soybean) account for over half of total human caloric intake, giving their yield and quality vast importance. They can be consumed either directly (eating their seeds which are also used as a source of sugars, oils and metabolites), or indirectly (eating meat products raised on processed seeds or forage). Various factors may influence a crop's yield, including but not limited to, quantity and size of the plant organs, plant architecture, vigor (e.g. seedling), growth rate, root development, utilization of water and nutrients (e.g., nitrogen), and stress tolerance. Plant yield may be amplified through multiple approaches; (1) enhancement of innate traits (e.g., dry matter accumulation rate, cellulose/lignin composition), (2) improvement of structural features (e.g., stalk strength, meristem size, plant branching pattern), and (3) amplification of seed yield and quality (e.g., fertilization efficiency, seed development, seed filling or content of oil, starch or protein). Increasing plant yield through any of the above methods would ultimately have many applications in agriculture and additional fields such as in the biotechnology industry.

Two main adverse environmental conditions, malnutrition (nutrient deficiency) and drought, elicit a response in the plant that mainly affects root architecture (Jiang and Huang (2001), *Crop Sci* 41:1168-1173; Lopez-Bucio et al. (2003), *Curr Opin Plant Biol*, 6:280-287; Morgan and Condon (1986), *Aust J Plant Physiol* 13:523-532), causing activation of plant metabolic pathways to maximize water assimilation. Improvement of root architecture, i.e. making branched and longer roots, allows the plant to reach water and nutrient/fertilizer deposits located deeper in the soil by an increase in soil coverage. Root morphogenesis has already shown to increase tolerance to low phosphorus availability in soybean (Miller et al., (2003), *Funct Plant Biol* 30:973-985) and maize (Zhu and Lynch (2004), *Funct Plant Biol* 31:949-958). Thus, genes governing enhancement of root architecture may be used to improve NUE and drought tolerance. An example for a gene associated with root developmental changes is ANR1, a putative transcription factor with a role in nitrate ($NO3^-$) signaling. When expression of ANR1 is down-regulated, the resulting transgenic lines are defective in their root response to localized supplies of nitrate (Zhang and Forde (1998), *Science* 270:407). Enhanced root system and/or increased storage capabilities, which are seen in responses to different environmental stresses, are strongly favorable at normal or optimal growing conditions as well.

Abiotic stress refers to a range of suboptimal conditions as water deficit or drought, extreme temperatures and salt levels, and high or low light levels. High or low nutrient level also falls into the category of abiotic stress. The response to any stress may involve both stress specific and common stress pathways (Pastori and Foyer (2002), *Plant Physiol,* 129: 460-468), and drains energy from the plant, eventually resulting in lowered yield. Thus, distinguishing between the genes activated in each pathway and subsequent manipulation of only specific relevant genes could lead to a partial stress response without the parallel loss in yield. Contrary to the complex polygenic nature of plant traits responsible for adaptations to adverse environmental stresses, information on miRNAs involved in these responses is very limited. The most common approach for crop and horticultural improvements is through cross breeding, which is relatively slow, inefficient, and limited in the degree of variability achieved because it can only manipulate the naturally existing genetic diversity. Taken together with the limited genetic resources (i.e., compatible plant species) for crop improvement, conventional breeding is evidently unfavorable. By creating a pool of genetically modified plants, one broadens the possibilities for producing crops with improved economic or horticultural traits.

SUMMARY OF THE INVENTION

According to an aspect of some embodiments of the present invention there is provided a method of improving nitrogen use efficiency, abiotic stress tolerance, biomass, vigor or yield of a plant, the method comprising expressing within the plant an exogenous polynucleotide encoding a polypeptide having an amino acid sequence at least 80% homologous to the polypeptide selected from the group consisting of SEQ ID NOs: 687-981, 992-1248, 1281-1310, 1389-1391, and 2806-3081, wherein the polypeptide is capable of regulating nitrogen use efficiency of the plant, thereby improving nitrogen use efficiency, abiotic stress tolerance, biomass, vigor or yield of the plant.

According to an aspect of some embodiments of the present invention there is provided a transgenic plant exogenously expressing a polynucleotide encoding a polypeptide having an amino acid sequence at least 80% homologous to the polypeptide selected from the group consisting of SEQ ID NOs: 687-981, 992-1248, 1281-1310, 1389-1391, and 2806-3081, wherein the polypeptide is capable of regulating nitrogen use efficiency of the plant.

According to an aspect of some embodiments of the present invention there is provided a nucleic acid construct comprising a polynucleotide encoding a polypeptide having an amino acid sequence at least 80% homologous to SEQ ID NOs:687-981, 992-1248, 1281-1310, 1389-1391, and 2806-3081, wherein the polypeptide is capable of regulating nitrogen use efficiency of the plant, and wherein the polynucleotide is under a transcriptional control of a cis-acting regulatory element.

According to an aspect of some embodiments of the present invention there is provided a method of improving nitrogen use efficiency, abiotic stress tolerance, biomass, vigor or yield of a plant, the method comprising expressing within the plant an exogenous polynucleotide which downregulates an activity or expression of a polypeptide having an amino acid sequence at least 80% homologous to SEQ ID NOs: 311-514, 2007-2436, 1311-1320, 982-991, 1249-1280, 1321-1388, wherein the polypeptide is capable of regulating nitrogen use efficiency of the plant, thereby improving nitrogen use efficiency, abiotic stress tolerance, biomass, vigor or yield of the plant.

According to an aspect of some embodiments of the present invention there is provided a transgenic plant exogenously expressing a polynucleotide which downregulates an activity or expression of a polypeptide having an amino acid sequence at least 80% homologous to SEQ ID NOs: 311-514, 2007-2436, 1311-1320, 982-991, 1249-1280, 1321-1388, wherein the polypeptide is capable of regulating nitrogen use efficiency of the plant.

According to an aspect of some embodiments of the present invention there is provided a nucleic acid construct comprising a polynucleotide which downregulates an activity or expression of a polypeptide having an amino acid sequence at least 80% homologous to SEQ ID NOs: 311-514, 2007-2436, 1311-1320, 982-991, 1249-1280, 1321-1388, wherein the polypeptide is capable of regulating nitrogen use efficiency of a plant, the nucleic acid sequence being under the regulation of a cis-acting regulatory element.

According to some embodiments of the invention, the polynucleotide is selected from the group consisting of SEQ ID NO: 1392-1646, 1655-1888, 1911-1938, 3082-3316.

According to some embodiments of the invention, the polypeptide is selected from the group consisting of SEQ ID NO: 687-981, 992-1248, 1281-1310, 1389-1391, and 2806-3081.

According to some embodiments of the invention, the cis-acting regulatory element comprises a promoter.

According to some embodiments of the invention, the promoter comprises a tissue-specific promoter.

According to some embodiments of the invention, the tissue-specific promoter comprises a root specific promoter.

According to some embodiments of the invention, the method further comprising growing the plant under limiting nitrogen conditions.

According to some embodiments of the invention, the method further comprising growing the plant under abiotic stress.

According to some embodiments of the invention, the abiotic stress is selected from the group consisting of salinity, drought, water deprivation, flood, etiolation, low temperature, high temperature, heavy metal toxicity, anaerobiosis, nutrient deficiency, nutrient excess, atmospheric pollution and UV irradiation.

According to some embodiments of the invention, the plant of some embodiments of the invention being a monocotyledon.

According to some embodiments of the invention, the plant of some embodiments of the invention being a dicotyledon.

According to some embodiments of the invention, the polynucleotide acts by a mechanism selected from the group consisting of sense suppression, antisense suppression, ribozyme inhibition, and gene disruption.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 is a scheme of a binary vector that can be used according to some embodiments of the invention.

DESCRIPTION OF SPECIFIC EMBODIMENTS OF THE INVENTION

The present invention, in some embodiments thereof, relates to nucleic acid agents for overexpressing or down-regulating RNA interference targets and uses of same in improving nitrogen use efficiency, abiotic stress tolerance, biomass, vigor or yield of a plant.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

The doubling of agricultural food production worldwide over the past four decades has been associated with a 7-fold increase in the use of nitrogen (N) fertilizers. As a consequence, both the recent and future intensification of the use of nitrogen fertilizers in agriculture already has and will continue to have major detrimental impacts on the diversity and functioning of the non-agricultural neighbouring bacterial, animal, and plant ecosystems. The most typical examples of such an impact are the eutrophication of freshwater and marine ecosystems as a result of leaching when high rates of nitrogen fertilizers are applied to agricultural fields. In addition, there can be gaseous emission of nitrogen oxides reacting with the stratospheric ozone and the emission of toxic ammonia into the atmosphere. Furthermore, farmers are facing increasing economic pressures with the rising fossil fuels costs required for production of nitrogen fertilizers.

It is therefore of major importance to identify the critical steps controlling plant nitrogen use efficiency (NUE). Such studies can be harnessed towards generating new energy crop species that have a larger capacity to produce biomass with the minimal amount of nitrogen fertilizer.

While reducing the present invention to practice, the present inventors have uncovered dsRNA sequences that are differentially expressed in maize plants grown under nitrogen limiting conditions versus corn plants grown under conditions wherein nitrogen is a non-limiting factor. Following further screening the present inventors were able to identify the target genes of these dsRNA sequences and suggest using same or sequences modulating expression of same in the generation of transgenic plants having improved nitrogen use efficiency.

According to some embodiments, the target genes or nucleic acid sequences controlling expression of same relay their effect by affecting at least one of:

root architecture so as to increase nutrient uptake;

activation of plant metabolic pathways so as to maximize nitrogen absorption or localization; or alternatively or additionally modulating plant surface permeability.

Each of the above mechanisms may affect water uptake as well as salt absorption and therefore embodiments of the invention further relate to enhancement of abiotic stress tolerance, biomass, vigor or yield of the plant.

Thus, according to an aspect of the invention there is provided a method of improving nitrogen use efficiency, abiotic stress tolerance, biomass, vigor or yield of a plant, the method comprising expressing within the plant an exogenous polynucleotide encoding a polypeptide having an amino acid sequence at least 80% homologous to SEQ ID NOs: 687-981, 992-1248, 1281-1310, 1389-1391, and 2806-3081—wherein the polypeptide is capable of regulating nitrogen use efficiency of the plant, thereby improving nitrogen use efficiency, abiotic stress tolerance, biomass, vigor or yield of the plant.

As used herein the phrase "nitrogen use efficiency (NUE)" refers to a measure of crop production per unit of nitrogen fertilizer input. Fertilizer use efficiency (FUE) is a measure of NUE. Crop production can be measured by biomass, vigor or yield. The plant's nitrogen use efficiency is typically a result of an alteration in at least one of the uptake, spread, absorbance, accumulation, relocation (within the plant) and use of nitrogen absorbed by the plant. Improved NUE is with respect to that of a non-transgenic plant (i.e., lacking the transgene of the transgenic plant) of the same species and of the same developmental stage and grown under the same conditions.

As used herein the phrase "nitrogen-limiting conditions" refers to growth conditions which include a level (e.g., concentration) of nitrogen (e.g., ammonium or nitrate) applied, which is below the level needed for optimal plant metabolism, growth, reproduction and/or viability.

The phrase "abiotic stress" as used herein refers to any adverse effect on metabolism, growth, viability and/or reproduction of a plant. Abiotic stress can be induced by any of suboptimal environmental growth conditions such as, for example, water deficit or drought, flooding, freezing, low or high temperature, strong winds, heavy metal toxicity, anaerobiosis, high or low nutrient levels (e.g. nutrient deficiency), high or low salt levels (e.g. salinity), atmospheric pollution, high or low light intensities (e.g. insufficient light) or UV irradiation. Abiotic stress may be a short term effect (e.g. acute effect, e.g. lasting for about a week) or alternatively may be persistent (e.g. chronic effect, e.g. lasting for example 10 days or more). The present invention contemplates situations in which there is a single abiotic stress condition or alternatively situations in which two or more abiotic stresses occur.

According to an exemplary embodiment the abiotic stress refers to salinity.

According to another exemplary embodiment the abiotic stress refers to drought.

As used herein the phrase "abiotic stress tolerance" refers to the ability of a plant to endure an abiotic stress without exhibiting substantial physiological or physical damage (e.g. alteration in metabolism, growth, viability and/or reproductivity of the plant).

As used herein the term/phrase "biomass", "biomass of a plant" or "plant biomass" refers to the amount (e.g., measured in grams of air-dry tissue) of a tissue produced from the plant in a growing season. An increase in plant biomass can be in the whole plant or in parts thereof such as aboveground (e.g. harvestable) parts, vegetative biomass, roots and/or seeds.

As used herein the term/phrase "vigor", "vigor of a plant" or "plant vigor" refers to the amount (e.g., measured by weight) of tissue produced by the plant in a given time.

Increased vigor could determine or affect the plant yield or the yield per growing time or growing area. In addition, early vigor (e.g. seed and/or seedling) results in improved field stand.

As used herein the term/phrase "yield", "yield of a plant" or "plant yield" refers to the amount (e.g., as determined by weight or size) or quantity (e.g., numbers) of tissues or organs produced per plant or per growing season. Increased yield of a plant can affect the economic benefit one can obtain from the plant in a certain growing area and/or growing time.

According to an exemplary embodiment the yield is measured by cellulose content.

According to another exemplary embodiment the yield is measured by oil content.

According to another exemplary embodiment the yield is measured by protein content.

According to another exemplary embodiment, the yield is measured by seed number per plant or part thereof (e.g., kernel).

A plant yield can be affected by various parameters including, but not limited to, plant biomass; plant vigor; plant growth rate; seed yield; seed or grain quantity; seed or grain quality; oil yield; content of oil, starch and/or protein in harvested organs (e.g., seeds or vegetative parts of the plant); number of flowers (e.g. florets) per panicle (e.g. expressed as a ratio of number of filled seeds over number of primary panicles); harvest index; number of plants grown per area; number and size of harvested organs per plant and per area; number of plants per growing area (e.g. density); number of harvested organs in field; total leaf area; carbon assimilation and carbon partitioning (e.g. the distribution/allocation of carbon within the plant); resistance to shade; number of harvestable organs (e.g. seeds), seeds per pod, weight per seed; and modified architecture [such as increase stalk diameter, thickness or improvement of physical properties (e.g. elasticity)].

As used herein the term "improving" or "increasing" refers to at least about 2%, at least about 3%, at least about 4%, at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90% or greater increase in NUE, in tolerance to abiotic stress, in yield, in biomass or in vigor of a plant, as compared to a native or wild-type plants [i.e., plants not genetically modified to express the biomolecules (polynucleotides or polypeptides) of the invention, e.g., a non-transformed plant of the same species and of the same developmental stage which is grown under the same growth conditions as the transformed plant].

Improved plant NUE is translated in the field into either harvesting similar quantities of yield, while implementing less fertilizers, or increased yields gained by implementing the same levels of fertilizers. Thus, improved NUE or FUE has a direct effect on plant yield in the field.

The term "plant" as used herein encompasses whole plants, ancestors and progeny of the plants and plant parts, including seeds, shoots, stems, roots (including tubers), and isolated plant cells, tissues and organs. The plant may be in any form including suspension cultures, embryos, meristematic regions, callus tissue, leaves, gametophytes, sporophytes, pollen, and microspores.

As used herein the phrase "plant cell" refers to plant cells which are derived and isolated from disintegrated plant cell tissue or plant cell cultures.

As used herein the phrase "plant cell culture" refers to any type of native (naturally occurring) plant cells, plant cell lines and genetically modified plant cells, which are not assembled to form a complete plant, such that at least one biological structure of a plant is not present. Optionally, the plant cell culture of this aspect of the present invention may comprise a particular type of a plant cell or a plurality of different types of plant cells. It should be noted that optionally plant cultures featuring a particular type of plant cell may be originally derived from a plurality of different types of such plant cells.

Any commercially or scientifically valuable plant is envisaged in accordance with these embodiments of the invention. Plants that are particularly useful in the methods of the invention include all plants which belong to the super family Viridiplantae, in particular monocotyledonous and dicotyledonous plants including a fodder or forage legume, ornamental plant, food crop, tree, or shrub selected from the list comprising *Acacia* spp., *Acer* spp., *Actinidia* spp., *Aesculus* spp., *Agathis australis*, *Albizia amara*, *Alsophila tricolor*, *Andropogon* spp., *Arachis* spp, *Areca catechu*, *Astelia fragrans*, *Astragalus cicer*, *Baikiaea plurijuga*, *Betula* spp., *Brassica* spp., *Bruguiera gymnorrhiza*, *Burkea africana*, *Butea frondosa*, *Cadaba farinosa*, *Calliandra* spp, *Camellia sinensis*, *Canna indica*, *Capsicum* spp., *Cassia* spp., *Centroema pubescens*, *Chacoomeles* spp., *Cinnamomum cassia*, *Coffea arabica*, *Colophospermum mopane*, *Coronillia varia*, *Cotoneaster serotina*, *Crataegus* spp., *Cucumis* spp., *Cupressus* spp., *Cyathea dealbata*, *Cydonia oblonga*, *Cryptomeria japonica*, *Cymbopogon* spp., *Cynthea dealbata*, *Cydonia oblonga*, *Dalbergia monetaria*, *Davallia divaricata*, *Desmodium* spp., *Dicksonia squarosa*, *Dibeteropogon amplectens*, *Dioclea* spp, *Dolichos* spp., *Dorycnium* rectum, *Echinochloa pyramidalis*, *Ehraffia* spp., *Eleusine coracana*, *Eragrestis* spp., *Erythrina* spp., *Eucalyptus* spp., *Euclea schimperi*, *Eulalia vi/losa*, *Pagopyrum* spp., *Feijoa sellowlana*, *Fragaria* spp., *Flemingia* spp, *Freycinetia banksli*, *Geranium thunbergii*, *GinAgo biloba*, *Glycine javanica*, *Gliricidia* spp, *Gossypium hirsutum*, *Grevillea* spp., *Guibourtia coleosperma*, *Hedysarum* spp., *Hemaffhia altissima*, *Heteropogon contoffus*, *Hordeum vulgare*, *Hyparrhenia rufa*, *Hypericum erectum*, *Hypeffhelia dissolute*, *Indigo incamata*, *Iris* spp., *Leptarrhena pyrolifolia*, *Lespediza* spp., *Lettuca* spp., *Leucaena leucocephala*, *Loudetia simplex*, *Lotonus bainesli*, *Lotus* spp., *Macrotyloma axillare*, *Malus* spp., *Manihot esculenta*, *Medicago saliva*, *Metasequoia glyptostroboides*, *Musa sapientum*, *Nicotianum* spp., *Onobrychis* spp., *Ornithopus* spp., *Oryza* spp., *Peltophorum africanum*, *Pennisetum* spp., *Persea gratissima*, *Petunia* spp., *Phaseolus* spp., *Phoenix canariensis*, *Phormium cookianum*, *Photinia* spp., *Picea glauca*, *Pinus* spp., *Pisum sativam*, *Podocarpus totara*, *Pogonarthria fleckii*, *Pogonaffhria squarrosa*, *Populus* spp., *Prosopis cineraria*, *Pseudotsuga menziesii*, *Pterolobium stellatum*, *Pyrus communis*, *Quercus* spp., *Rhaphiolepsis umbellata*, *Rhopalostylis sapida*, *Rhus natalensis*, *Ribes grossularia*, *Ribes* spp., *Robinia pseudoacacia*, *Rosa* spp., *Rubus* spp., *Salix* spp., *Schyzachyrium sanguineum*, *Sciadopitys vefficillata*, *Sequoia sempervirens*, *Sequoiadendron giganteum*, *Sorghum bicolor*, *Spinacia* spp., *Sporobolus fimbriatus*, *Stiburus alopecuroides*, *Stylosanthos humilis*, *Tadehagi* spp, *Taxodium distichum*, *Themeda triandra*, *Trifolium* spp., *Triticum* spp., *Tsuga heterophylla*, *Vaccinium* spp., *Vicia* spp., *Vitis vinifera*, *Watsonia pyramidata*, *Zantedeschia aethiopica*, *Zea mays*, amaranth, artichoke, asparagus, broccoli, Brussels sprouts, cabbage, canola, carrot, cauliflower, celery, collard greens, flax, kale, lentil, oilseed rape, okra, onion, potato, rice, soybean, straw, sugar beet, sugar cane, sunflower, tomato, squash tea, maize, wheat, barely, rye, oat, peanut, pea, lentil and alfalfa, cotton, rapeseed, canola, pepper, sunflower, tobacco, eggplant, *eucalyptus*, a tree, an ornamental plant, a perennial grass and a forage crop. Alternatively algae and other non-Viridiplantae can be used for the methods of the present invention.

According to some embodiments of the invention, the plant used by the method of the invention is a crop plant including, but not limited to, cotton, *Brassica* vegetables, oilseed rape, sesame, olive tree, palm oil, banana, wheat, corn or maize, barley, alfalfa, peanuts, sunflowers, rice, oats, sugarcane, soybean, turf grasses, barley, rye, *sorghum*, sugar cane, chicory, lettuce, tomato, zucchini, bell pepper, eggplant, cucumber, melon, watermelon, beans, hibiscus, okra, apple, rose, strawberry, chile, garlic, pea, lentil, canola, mums, *arabidopsis*, broccoli, cabbage, beet, *quinoa*, spinach, squash, onion, leek, tobacco, potato, sugarbeet, *papaya*, pineapple, mango, *Arabidopsis thaliana*, and also plants used in horticulture, floriculture or forestry, such as, but not limited to, poplar, fir, *eucalyptus*, pine, an ornamental plant, a perennial grass and a forage crop, coniferous plants, moss, algae, as well as other plants listed in World Wide Web (dot) nationmaster (dot) com/encyclopedia/Plantae.

According to a specific embodiment of the present invention, the plant comprises corn.

According to a specific embodiment of the present invention, the plant comprises *sorghum*.

As used herein, the phrase "exogenous polynucleotide" refers to a heterologous nucleic acid sequence or amino acid sequence which may not be naturally expressed within the plant or which overexpression in the plant is desired. The exogenous polynucleotide may be introduced into the plant in a stable or transient manner, so as to produce a ribonucleic acid (RNA) molecule or a polypeptide. It should be noted that the exogenous polynucleotide may comprise a nucleic acid sequence which is identical or partially homologous to an endogenous nucleic acid sequence of the plant.

A "transgenic plant" refers to a plant that has incorporated a nucleic acid sequence (i.e., polynucleotides encoding target genes or a silencing polynucleotide), including but not limited to genes that are not normally present in a host plant genome, nucleic acid sequences not normally transcribed into RNA, or any other genes or nucleic acid sequences that one desires to exogenously introduce into the wild-type plant, such as genes that normally may be present in the wild-type plant (control) but that one desires either to genetically engineer or to have altered expression.

Also contemplated are hybrids of the above described transgenic plants. A "hybrid plant" refers to a plant or a part thereof resulting from a cross between two parent plants, wherein one parent is a genetically engineered plant of the invention (transgenic plant expressing the polypeptides of the present invention). Such a cross can occur naturally by, for example, sexual reproduction, or artificially by, for example, in vitro nuclear fusion. Methods of plant breeding are well-known and within the level of one of ordinary skill in the art of plant biology.

The terms siRNA and miRNA are collectively referred to herein as RNA interfering molecules (RNAi).

As used herein, the phrase "siRNA" (also referred to herein interchangeably as "small interfering RNA" or "silencing RNA", is a class of double-stranded RNA molecules, 20-25 nucleotides in length. The most notable role of siRNA is its involvement in the RNA interference (RNAi) pathway, where it interferes with the expression of a specific gene.

The siRNA precursor relates to a long dsRNA structure (at least 90% complementarity) of at least 30 bp.

As used herein, the phrase "microRNA (also referred to herein interchangeably as "miRNA" or "miR") or a precursor thereof" refers to a microRNA (miRNA) molecule acting as a post-transcriptional regulator. Typically, the miRNA molecules are RNA molecules of about 20 to 22 nucleotides in length which can be loaded into a RISC complex and which direct the cleavage of another RNA molecule, wherein the other RNA molecule comprises a nucleotide sequence essentially complementary to the nucleotide sequence of the miRNA molecule.

Typically, a miRNA molecule is processed from a "pre-miRNA" or as used herein a precursor of a pre-miRNA molecule by proteins, such as DCL proteins, present in any plant cell and loaded onto a RISC complex where it can guide the cleavage of the target RNA molecules.

Pre-microRNA molecules are typically processed from pri-microRNA molecules (primary transcripts). The single stranded RNA segments flanking the pre-microRNA are important for processing of the pri-miRNA into the pre-miRNA. The cleavage site appears to be determined by the distance from the stem-ssRNA junction (Han et al. 2006, Cell 125, 887-901, 887-901).

As used herein, a "pre-miRNA" molecule is an RNA molecule of about 100 to about 200 nucleotides, preferably about 100 to about 130 nucleotides which can adopt a secondary structure comprising a double stranded RNA stem and a single stranded RNA loop (also referred to as "hairpin") and further comprising the nucleotide sequence of the miRNA (and its complement sequence) in the double stranded RNA stem. According to a specific embodiment, the miRNA and its complement are located about 10 to about 20 nucleotides from the free ends of the miRNA double stranded RNA stem. The length and sequence of the single stranded loop region are not critical and may vary considerably, e.g. between 30 and 50 nt in length. The complementarity between the miRNA and its complement need not be perfect and about 1 to 3 bulges of unpaired nucleotides can be tolerated. The secondary structure adopted by an RNA molecule can be predicted by computer algorithms conventional in the art such as mFOLD. The particular strand of the double stranded RNA stem from the pre-miRNA which is released by DCL activity and loaded onto the RISC complex is determined by the degree of complementarity at the 5' end, whereby the strand which at its 5' end is the least involved in hydrogen bounding between the nucleotides of the different strands of the cleaved dsRNA stem is loaded onto the RISC complex and will determine the sequence specificity of the target RNA molecule degradation. However, if empirically the miRNA molecule from a particular synthetic pre-miRNA molecule is not functional (because the "wrong" strand is loaded on the RISC complex), it will be immediately evident that this problem can be solved by exchanging the position of the miRNA molecule and its complement on the respective strands of the dsRNA stem of the pre-miRNA molecule. As is known in the art, binding between A and U involving two hydrogen bounds, or G and U involving two hydrogen bounds is less strong that between G and C involving three hydrogen bounds. Exemplary siRNA sequences or precursors thereof as well as hairpin sequences and miRNA sequences are provided in Tables 1-4, below.

The tables provided in the Examples section are to be considered an integral part of the specification.

As used herein a "target gene" refers to a gene that is processed by microRNA activity. Typically the gene encodes a polypeptide which expression is downregulated due to microRNA processing.

Target genes are typically identified using the WMD3 website (http://wmd3dotweigelworlddotorg/).

As mentioned, the method of the present invention is effected by expressing within a plant an exogenous polynucleotide encoding a target gene of the RNA interfering molecules uncovered by the present inventors, as explained below.

As used herein, the phrase "expressing within the plant an exogenous polynucleotide" refers to upregulating the expression level of an exogenous polynucleotide within the plant e.g., by introducing the exogenous polynucleotide into a plant or plant cell and expressing by recombinant means, as described in detail hereinbelow.

As used herein "expressing" refers to expression at the mRNA level (e.g., in case the target gene expresses an mRNA product but no protein) or at the polypeptide level of the desired exogenous polynucleotide.

As used herein, the phrase "exogenous polynucleotide" refers to a heterologous nucleic acid sequence which may not be naturally expressed within the plant or which overexpression in the plant is desired (i.e., overexpression of an endogenous gene). The exogenous polynucleotide may be introduced into the plant in a stable or transient manner, so as to produce a ribonucleic acid (RNA) molecule and/or a polypeptide molecule. The exogenous polynucleotide may comprise a nucleic acid sequence which is identical or partially homologous to an endogenous nucleic acid sequence expressed within the plant.

The term "endogenous" as used herein refers to any polynucleotide or polypeptide which is present and/or naturally expressed within a plant or a cell thereof.

As used herein the term "polynucleotide" refers to a single or double stranded nucleic acid sequence which is isolated and provided in the form of an RNA sequence, a complementary polynucleotide sequence (cDNA), a genomic polynucleotide sequence (e.g. sequence isolated from a chromosome) and/or a composite polynucleotide sequences (e.g., a combination of the above). This term includes polynucleotides and/or oligonucleotides derived from naturally occurring nucleic acid molecules (e.g., RNA or DNA), synthetic polynucleotide and/or oligonucleotide molecules composed of naturally occurring bases, sugars, and covalent internucleoside linkages (e.g., backbone), as well as synthetic polynucleotides and/or oligonucleotides having non-naturally occurring portions, which function similarly to the respective naturally occurring portions.

The term "isolated" refers to at least partially separated from the natural environment e.g., from a plant cell.

Nucleic acid sequences of the polypeptides of some embodiments of the invention may be optimized for expression in a specific plant host. Examples of such sequence modifications include, but are not limited to, an altered G/C content to more closely approach that typically found in the plant species of interest, and the removal of codons atypically found in the plant species commonly referred to as codon optimization.

The phrase "codon optimization" refers to the selection of appropriate DNA nucleotides for use within a structural gene or fragment thereof that approaches codon usage within the plant of interest. Therefore, an optimized gene or nucleic acid sequence refers to a gene in which the nucleotide sequence of a native or naturally occurring gene has been modified in order to utilize statistically-preferred or statistically-favored codons within the plant. The nucleotide sequence typically is examined at the DNA level and the coding region optimized for expression in the plant species determined using any suitable procedure, for example as described in Sardana et al. (1996, Plant Cell Reports 15:677-681). In this method, the standard deviation of codon usage, a measure of codon usage bias, may be calculated by first finding the squared proportional deviation of usage of each codon of the native gene relative to that of highly expressed plant genes, followed by a calculation of the average squared deviation. The formula used is: 1 SDCU=n=1 N [(Xn-Yn)/Yn]2/N, where Xn refers to the frequency of usage of codon n in highly expressed plant genes, where Yn to the frequency of usage of codon n in the gene of interest and N refers to the total number of codons in the gene of interest. A table of codon usage from highly expressed genes of dicotyledonous plants is compiled using the data of Murray et al. (1989, Nuc Acids Res. 17:477-498).

One method of optimizing the nucleic acid sequence in accordance with the preferred codon usage for a particular plant cell type is based on the direct use, without performing any extra statistical calculations, of codon optimization tables such as those provided on-line at the Codon Usage Database through the NIAS (National Institute of Agrobiological Sciences) DNA bank in Japan (wwwdotkazusadotor-dotjp/codon/). The Codon Usage Database contains codon usage tables for a number of different species, with each codon usage table having been statistically determined based on the data present in Genbank.

By using the above tables to determine the most preferred or most favored codons for each amino acid in a particular species (for example, rice), a naturally-occurring nucleotide sequence encoding a protein of interest can be codon optimized for that particular plant species. This is effected by replacing codons that may have a low statistical incidence in the particular species genome with corresponding codons, in regard to an amino acid, that are statistically more favored. However, one or more less-favored codons may be selected to delete existing restriction sites, to create new ones at potentially useful junctions (5' and 3' ends to add signal peptide or termination cassettes, internal sites that might be used to cut and splice segments together to produce a correct full-length sequence), or to eliminate nucleotide sequences that may negatively effect mRNA stability or expression.

The naturally-occurring encoding nucleotide sequence may already, in advance of any modification, contain a number of codons that correspond to a statistically-favored codon in a particular plant species. Therefore, codon optimization of the native nucleotide sequence may comprise determining which codons, within the native nucleotide sequence, are not statistically-favored with regards to a particular plant, and modifying these codons in accordance with a codon usage table of the particular plant to produce a codon optimized derivative. A modified nucleotide sequence may be fully or partially optimized for plant codon usage provided that the protein encoded by the modified nucleotide sequence is produced at a level higher than the protein encoded by the corresponding naturally occurring or native gene. Construction of synthetic genes by altering the codon usage is described in for example PCT Patent Application 93/07278.

Target genes which are contemplated according to the present teachings are provided in the polynucleotide sequences which comprise nucleic acid sequences as set forth in SEQ ID NO: 1392-1646, 1655-1888, 1911-1938, 3082-3316. However the present teachings also relate to orthologs or homologs at least about 60%, at least about 65%, at least about 70%, at least about 75%, at least about 80%, at least about 85%, at least about 90%, or at least about 95% or more identical or similar to SEQ ID NO: 1392-1646, 1655-1888, 1911-1938, 3082-3316. Parameters for determining the level of identity are provided hereinbelow.

Alternatively or additionally, target genes which are contemplated according to the present teachings are provided in the polypeptide sequences which comprise amino acid sequences as set forth in SEQ ID NO: 687-981, 992-1248, 1281-1310, 1389-1391, and 2806-3081 (Tables 6 and 8). However the present teachings also relate to of orthologs or homologs at least about 60%, at least about 65%, at least about 70%, at least about 75%, at least about 80%, at least about 85%, at least about 90%, or at least about 95% or more identical or similar to SEQ ID NO: 687-981, 992-1248, 1281-1310, 1389-1391, and 2806-3081 (Tables 6 and 8).

Homology (e.g., percent homology, identity+similarity) can be determined using any homology comparison software, including for example, the TBLASTN software of the National Center of Biotechnology Information (NCBI) such as by using default parameters, when starting from a polypeptide sequence; or the tBLASTX algorithm (available via the NCBI) such as by using default parameters, which compares the six-frame conceptual translation products of a nucleotide query sequence (both strands) against a protein sequence database.

According to some embodiments of the invention, the term "homology" or "homologous" refers to identity of two or more nucleic acid sequences; or identity of two or more amino acid sequences.

Homologous sequences include both orthologous and paralogous sequences. The term "paralogous" relates to gene-duplications within the genome of a species leading to paralogous genes. The term "orthologous" relates to homologous genes in different organisms due to ancestral relationship.

One option to identify orthologues in monocot plant species is by performing a reciprocal blast search. This may be done by a first blast involving blasting the sequence-of-interest against any sequence database, such as the publicly available NCBI database which may be found at: Hypertext Transfer Protocol://World Wide Web (dot) ncbi (dot) nlm (dot) nih (dot) gov. The blast results may be filtered. The full-length sequences of either the filtered results or the non-filtered results are then blasted back (second blast) against the sequences of the organism from which the sequence-of-interest is derived. The results of the first and second blasts are then compared. An orthologue is identified when the sequence resulting in the highest score (best hit) in the first blast identifies in the second blast the query sequence (the original sequence-of-interest) as the best hit. Using the same rational a paralogue (homolog to a gene in the same organism) is found. In case of large sequence families, the ClustalW program may be used [Hypertext Transfer Protocol://World Wide Web (dot) ebi (dot) ac (dot) uk/Tools/clustalw2/index (dot) html], followed by a neighbor-joining tree (Hypertext Transfer Protocol://en (dot) wikipedia (dot) org/wiki/Neighbor-joining) which helps visualizing the clustering.

As mentioned the present inventors have also identified genes which down-regulation thereof may be done in order to improve their NUE, biomass, vigor, yield and abiotic stress tolerance.

Thus, according to an aspect of the invention there is provided a method of improving nitrogen use efficiency, abiotic stress tolerance, biomass, vigor or yield of a plant, the method comprising expressing within the plant an exogenous polynucleotide which downregulates an activity or expression of a polypeptide having an amino acid sequence at least 80%, 85%, 90%, 95%, or 100% homologous or identical to SEQ ID NOs: 311-514, 2007-2436, 1311-1320, 982-991, 1249-1280, 1321-1388 (Tables 5, 7 and 9), wherein the polypeptide is capable of regulating nitrogen use efficiency of the plant, thereby improving nitrogen use efficiency, abiotic stress tolerance, biomass, vigor or yield of the plant.

Down regulation of activity or expression is by at least 10%, 20%, 30%, 40%, 50%, 60%, 70%, 80%, 90% or even complete (100%) loss of activity or expression. Assays for measuring gene expression can be effected at the protein level (e.g., Western blot, ELISA) or at the mRNA level such as by RT-PCR.

According to a specific embodiment the amino acid sequence of the target gene is as set forth in SEQ ID NOs: 311-514, 2007-2436, 1311-1320, 982-991, 1249-1280, 1321-1388 of Tables 5, 7 and 9.

Alternatively or additionally, the amino acid sequence of the target gene is encoded by a polynucleotide sequence as set forth in SEQ ID NOs: 515-686, 2437-2805, 1939-1948, 1647-1654, 1889-1910, 1949-2004 of Tables 5, 7 and 9.

Examples of polynucleotide downregulating agents that inhibit (also referred to herein as inhibitors or nucleic acid agents) the expression of a target gene are given below.

1. Polynucleotide-Based Inhibition of Gene Expression.

It will be appreciated, that any of these methods when specifically referring to downregulating expression/activity of the target genes can be used, at least in part, to downregulate expression or activity of endogenous RNA molecules.

i. Sense Suppression/Cosuppression

In some embodiments of the invention, inhibition of the expression of target gene may be obtained by sense suppression or cosuppression. For cosuppression, an expression cassette is designed to express an RNA molecule corresponding to all or part of a messenger RNA encoding a target gene in the "sense" orientation. Over-expression of the RNA molecule can result in reduced expression of the native gene. Accordingly, multiple plant lines transformed with the cosuppression expression cassette are screened to identify those that show the greatest inhibition of target gene expression.

The polynucleotide used for cosuppression may correspond to all or part of the sequence encoding the target gene, all or part of the 5' and/or 3' untranslated region of a target transcript, or all or part of both the coding sequence and the untranslated regions of a transcript encoding the target gene. In some embodiments where the polynucleotide comprises all or part of the coding region for the target gene, the expression cassette is designed to eliminate the start codon of the polynucleotide so that no protein product will be transcribed.

Cosuppression may be used to inhibit the expression of plant genes to produce plants having undetectable protein levels for the proteins encoded by these genes. See, for example, Broin, et al., (2002) Plant Cell 15:1517-1532. Cosuppression may also be used to inhibit the expression of multiple proteins in the same plant. Methods for using cosuppression to inhibit the expression of endogenous genes in plants are described in Flavell, et al., (1995) Proc. Natl. Acad. Sci. USA 91:3590-3596; Jorgensen, et al., (1996) Plant Mol. Biol. 31:957-973; Johansen and Carrington, (2001) Plant Physiol. 126:930-938; Broin, et al., (2002) Plant Cell 15:1517-1532; Stoutjesdijk, et al., (2002) Plant Physiol. 129:1723-1731; Yu, et al., (2003) Phytochemistry 63:753-763; and U.S. Pat. Nos. 5,035,323, 5,283,185 and 5,952,657; each of which is herein incorporated by reference. The efficiency of cosuppression may be increased by including a poly-dt region in the expression cassette at a position 3' to the sense sequence and 5' of the polyadenylation signal. See, US Patent Publication Number 20020058815, herein incorporated by reference. Typically, such a nucleotide sequence has substantial sequence identity to the sequence of the transcript of the endogenous gene, optimally greater than about 65% sequence identity, more optimally greater than about 85% sequence identity, most optimally greater than about 95% sequence identity. See, U.S. Pat. Nos. 5,283,185 and 5,035,323; herein incorporated by reference.

Transcriptional gene silencing (TGS) may be accomplished through use of hpRNA constructs wherein the inverted repeat of the hairpin shares sequence identity with the promoter region of a gene to be silenced. Processing of the hpRNA into short RNAs which can interact with the homologous promoter region may trigger degradation or methylation to result in silencing. (Aufsatz, et al., (2002) PNAS 99(4):16499-16506; Mette, et al., (2000) EMBO J. 19(19):5194-5201), ii. Antisense Suppression In some embodiments of the invention, inhibition of the expression of the target gene may be obtained by antisense suppression. For antisense suppression, the expression cassette is designed to express an RNA molecule complementary to all or part of a messenger RNA encoding the target gene. Over-expression of the antisense RNA molecule can result in reduced expression of the native gene. Accordingly, multiple plant lines transformed with the antisense suppression expression cassette are screened to identify those that show the greatest inhibition of target gene expression.

The polynucleotide for use in antisense suppression may correspond to all or part of the complement of the sequence encoding the target gene, all or part of the complement of the 5' and/or 3' untranslated region of the target gene transcript, or all or part of the complement of both the coding sequence and the untranslated regions of a transcript encoding the target gene. In addition, the antisense polynucleotide may be fully complementary (i.e., 100% identical to the complement of the target sequence) or partially complementary (i.e., less than 100% identical to the complement of the target sequence) to the target sequence. Antisense suppression may be used to inhibit the expression of multiple proteins in the same plant. Furthermore, portions of the antisense nucleotides may be used to disrupt the expression of the target gene. Generally, sequences of at least 50 nucleotides, 100 nucleotides, 200 nucleotides, 300, 500, 550, 500, 550 or greater may be used. Methods for using antisense suppression to inhibit the expression of endogenous genes in plants are described, for example, in Liu, et al., (2002) Plant Physiol. 129:1732-1753 and U.S. Pat. No. 5,759,829, which is herein incorporated by reference. Efficiency of antisense suppression may be increased by including a poly-dt region in the expression cassette at a position 3' to the antisense sequence and 5' of the polyadenylation signal. See, US Patent Publication Number 20020058815.

iii. Double-Stranded RNA Interference

In some embodiments of the invention, inhibition of the expression of a target gene may be obtained by double-stranded RNA (dsRNA) interference. For dsRNA interference, a sense RNA molecule like that described above for cosuppression and an antisense RNA molecule that is fully or partially complementary to the sense RNA molecule are expressed in the same cell, resulting in inhibition of the expression of the corresponding endogenous messenger RNA.

Expression of the sense and antisense molecules can be accomplished by designing the expression cassette to comprise both a sense sequence and an antisense sequence. Alternatively, separate expression cassettes may be used for the sense and antisense sequences. Multiple plant lines transformed with the dsRNA interference expression cassette or expression cassettes are then screened to identify plant lines that show the greatest inhibition of target gene expression. Methods for using dsRNA interference to inhibit the expression of endogenous plant genes are described in Waterhouse, et al., (1998) Proc. Natl. Acad. Sci. USA 95:13959-13965, Liu, et al., (2002) Plant Physiol. 129:1732-1753, and WO 99/59029, WO 99/53050, WO 99/61631, and WO 00/59035, iv. Hairpin RNA Interference and Intron-Containing Hairpin RNA Interference In some embodiments of the invention, inhibition of the expression of one or more target gene may be obtained by hairpin RNA (hpRNA) interference or intron-containing hairpin RNA (ihpRNA) interference. These methods are highly efficient at downregulating the expression of endogenous genes. See, Waterhouse and Helliwell, (2003) Nat. Rev. Genet. 5:29-38 and the references cited therein.

For hpRNA interference, the expression cassette is designed to express an RNA molecule that hybridizes with itself to form a hairpin structure that comprises a single-stranded loop region and a base-paired stem. The base-paired stem region comprises a sense sequence corresponding to all or part of the endogenous messenger RNA encoding the gene whose expression is to be inhibited, and an antisense sequence that is fully or partially complementary to the sense sequence. Thus, the base-paired stem region of the molecule generally determines the specificity of the RNA interference. hpRNA molecules are highly efficient at inhibiting the expression of endogenous genes, and the RNA interference they induce is inherited by subsequent generations of plants. See, for example, Chuang and Meyerowitz, (2000) Proc. Natl. Acad. Sci. USA 97:5985-5990; Stoutjesdijk, et al., (2002) Plant Physiol. 129:1723-1731; and Waterhouse and Helliwell, (2003) Nat. Rev. Genet. 5:29-38. Methods for using hpRNA interference to inhibit or silence the expression of genes are described, for example, in Chuang and Meyerowitz, (2000) Proc. Natl. Acad. Sci. USA 97:5985-5990; Stoutjesdijk, et al., (2002) Plant Physiol. 129:1723-1731; Waterhouse and Helliwell, (2003) Nat. Rev. Genet. 5:29-38; Pandolfini, et al., BMC Biotechnology 3:7, and US Patent Publication Number 20030175965; each of which is herein incorporated by reference. A transient assay for the efficiency of hpRNA constructs to silence gene expression in vivo has been described by Panstruga, et al., (2003) Mol. Biol. Rep. 30:135-150, herein incorporated by reference.

ForihpRNA, the interfering molecules have the same general structure as for hpRNA, but the RNA molecule additionally comprises an intron that is capable of being spliced in the cell in which the ihpRNA is expressed. The use of an intron minimizes the size of the loop in the hairpin RNA molecule following splicing, and this increases the efficiency of interference. See, for example, Smith, et al., (2000) Nature 507:319-320. In fact, Smith, et al., show 100% suppression of endogenous gene expression using ihpRNA-mediated interference. Methods for using ihpRNA interference to inhibit the expression of endogenous plant genes are described, for example, in Smith, et al., (2000)

Nature 507:319-320; Wesley, et al., (2001) Plant J. 27:581-590; Wang and Waterhouse, (2001) Curr. Opin. Plant Biol. 5:156-150; Waterhouse and Helliwell, (2003) Nat. Rev. Genet. 5:29-38; Helliwell and Waterhouse, (2003) Methods 30:289-295, and US Patent Publication Number 20030180955, each of which is herein incorporated by reference.

The expression cassette for hpRNA interference may also be designed such that the sense sequence and the antisense sequence do not correspond to an endogenous RNA. In this embodiment, the sense and antisense sequence flank a loop sequence that comprises a nucleotide sequence corresponding to all or part of the endogenous messenger RNA of the target gene. Thus, it is the loop region that determines the specificity of the RNA interference. See, for example, WO 02/00905, herein incorporated by reference.

v. Amplicon-Mediated Interference

Amplicon expression cassettes comprise a plant virus-derived sequence that contains all or part of the target gene but generally not all of the genes of the native virus. The viral sequences present in the transcription product of the expression cassette allow the transcription product to direct its own replication. The transcripts produced by the amplicon may be either sense or antisense relative to the target sequence (i.e., the messenger RNA for target gene). Methods of using amplicons to inhibit the expression of endogenous plant genes are described, for example, in Angell and Baulcombe, (1997) EMBO J. 16:3675-3685, Angell and Baulcombe, (1999) Plant J. 20:357-362, and U.S. Pat. No. 6,656,805, each of which is herein incorporated by reference.

vi. Ribozymes

In some embodiments, the polynucleotide expressed by the expression cassette of the invention is catalytic RNA or has ribozyme activity specific for the messenger RNA of target gene. Thus, the polynucleotide causes the degradation of the endogenous messenger RNA, resulting in reduced expression of the target gene. This method is described, for example, in U.S. Pat. No. 5,987,071, herein incorporated by reference.

2. Gene Disruption

In some embodiments of the present invention, the activity of a miRNA or a target gene is reduced or eliminated by disrupting the gene encoding the target polypeptide. The gene encoding the target polypeptide may be disrupted by any method known in the art. For example, in one embodiment, the gene is disrupted by transposon tagging. In another embodiment, the gene is disrupted by mutagenizing plants using random or targeted mutagenesis, and selecting for plants that have reduced response regulator activity.

Any of the nucleic acid agents described herein (for overexpression or downregulation) can be provided to the plant as naked RNA or expressed from a nucleic acid expression construct, where it is operaly linked to a regulatory sequence.

According to a specific embodiment of the invention, there is provided a nucleic acid construct comprising a nucleic acid sequence (a polynucleotide) encoding the RNAi target polypeptide or the nucleic acid agent for downregulating the expression of the target gene, the nucleic acid sequence being under a transcriptional control a cis-acting regulatory element.

Exemplary nucleic acid constructs which can be used for plant transformation include, but are not limited to, pORE156, pORE164, pORE167 and pORE169, which are all constructed by ligating the appropriate DNA fragments into the pORE E2 binary vector (Accession number: AY562535, FIG. 1) under the transcriptional control of a promoter.

A coding nucleic acid sequence is "operably linked" or "transcriptionally linked to a regulatory sequence (e.g., promoter)" if the regulatory sequence is capable of exerting a regulatory effect on the coding sequence linked thereto. Thus the regulatory sequence controls the transcription of the target polynucleotide.

The term "regulatory sequence", as used herein, means any DNA, that is involved in driving transcription and controlling (i.e., regulating) the timing and level of transcription of a given DNA sequence, such as a DNA coding for the target polypeptide, as described above. For example, a 5' regulatory region (or "promoter region") is a DNA sequence located upstream (i.e., 5') of a coding sequence and which comprises the promoter and the 5'-untranslated leader sequence. A 3' regulatory region is a DNA sequence located downstream (i.e., 3') of the coding sequence and which comprises suitable transcription termination (and/or regulation) signals, including one or more polyadenylation signals.

For the purpose of the invention, the promoter is a plant-expressible promoter. As used herein, the term "plant-expressible promoter" means a DNA sequence which is capable of controlling (initiating) transcription in a plant cell. This includes any promoter of plant origin, but also any promoter of non-plant origin which is capable of directing transcription in a plant cell, i.e., certain promoters of viral or bacterial origin Thus, any suitable promoter sequence can be used by the nucleic acid construct of the present invention. According to some embodiments of the invention, the promoter is a constitutive promoter, a tissue-specific promoter or an inducible promoter (e.g. an abiotic stress-inducible promoter).

Suitable constitutive promoters include, for example, hydroperoxide lyase (HPL) promoter, CaMV 35S promoter (Odell et al, Nature 313:810-812, 1985); Arabidopsis At6669 promoter (see PCT Publication No. WO04081173A2); Arabidopsis new At6669 promoter; maize Ubi 1 (Christensen et al., Plant Sol. Biol. 18:675-689, 1992); rice actin (McElroy et al., Plant Cell 2:163-171, 1990); pEMU (Last et al, Theor. Appl. Genet. 81:581-588, 1991); CaMV 19S (Nilsson et al, Physiol. Plant 100:456-462, 1997); GOS2 (de Pater et al, Plant J November; 2(6):837-44, 1992); ubiquitin (Christensen et al, Plant MoI. Biol. 18: 675-689, 1992); Rice cyclophilin (Bucholz et al, Plant MoI Biol. 25(5):837-43, 1994); Maize H3 histone (Lepetit et al, MoI. Gen. Genet. 231: 276-285, 1992); Actin 2 (An et al, Plant J. 10(1);107-121, 1996) and Synthetic Super MAS (Ni et al., The Plant Journal 7: 661-76, 1995). Other constitutive promoters include those in U.S. Pat. Nos. 5,659,026, 5,608,149; 5,608,144; 5,604,121; 5,569,597; 5,466,785; 5,399,680; 5,268,463; and 5,608,142.

Suitable tissue-specific promoters include, but not limited to, leaf-specific promoters [such as described, for example, by Yamamoto et al., Plant J. 12:255-265, 1997; Kwon et al., Plant Physiol. 105:357-67, 1994; Yamamoto et al., Plant Cell Physiol. 35:773-778, 1994; Gotor et al., Plant J. 3:509-18, 1993; Orozco et al., Plant MoI. Biol. 23:1129-1138, 1993; and Matsuoka et al., Proc. Natl. Acad. Sci. USA 90:9586-9590, 1993], seed-preferred promoters [e.g., from seed specific genes (Simon, et al., Plant MoI. Biol. 5. 191, 1985; Scofield, et al., J. Biol. Chem. 262: 12202, 1987; Baszczynski, et al., Plant MoI. Biol. 14: 633, 1990), Brazil Nut albumin (Pearson' et al., Plant MoI. Biol. 18: 235-245, 1992), legumin (Ellis, et al. Plant MoI. Biol. 10: 203-214, 1988), Glutelin (rice) (Takaiwa, et al., MoI. Gen. Genet.

208: 15-22, 1986; Takaiwa, et al., FEBS Letts. 221: 43-47, 1987), Zein (Matzke et al., Plant MoI Biol, 143)323-32 1990), napA (Stalberg, et al., Planta 199: 515-519, 1996), Wheat SPA (Albani et al, Plant Cell, 9: 171-184, 1997), sunflower oleosin (Cummins, et al, Plant MoI. Biol. 19: 873-876, 1992)], endosperm specific promoters [e.g., wheat LMW and HMW, glutenin-1 (MoI Gen Genet 216:81-90, 1989; NAR 17:461-2), wheat a, b and g gliadins (EMBO3: 1409-15, 1984), Barley ltrl promoter, barley Bl, C, D hordein (Theor Appl Gen 98:1253-62, 1999; Plant J 4:343-55, 1993; MoI Gen Genet 250:750-60, 1996), Barley DOF (Mena et al., The Plant Journal, 116(1): 53-62, 1998), Biz2 (EP99106056.7), Synthetic promoter (Vicente-Carbajosa et al., Plant J. 13: 629-640, 1998), rice prolamin NRP33, rice-globulin GIb-I (Wu et al., Plant Cell Physiology 39(8) 885-889, 1998), rice alpha-globulin REB/OHP-1 (Nakase et al. Plant MoI. Biol. 33: 513-S22, 1997), rice ADP-glucose PP (Trans Res 6:157-68, 1997), maize ESR gene family (Plant J 12:235-46, 1997), *sorghum* gamma-kafirin (PMB 32:1029-35, 1996); e.g., the Napin promoter], embryo specific promoters [e.g., rice OSH1 (Sato et al, Proc. Natl. Acad. Sci. USA, 93: 8117-8122), KNOX (Postma-Haarsma et al, Plant MoI. Biol. 39:257-71, 1999), rice oleosin (Wu et at, J. Biochem., 123:386, 1998)], and flower-specific promoters [e.g., AtPRP4, chalene synthase (chsA) (Van der Meer, et al., Plant MoI. Biol. 15, 95-109, 1990), LAT52 (Twell et al., MoI. Gen Genet. 217:240-245; 1989), apetala-3]. Also contemplated are root-specific promoters such as the ROOTP promoter described in Vissenberg K, et al. Plant Cell Physiol. 2005 January; 46(1):192-200.

The nucleic acid construct of some embodiments of the invention can further include an appropriate selectable marker and/or an origin of replication.

The nucleic acid construct of some embodiments of the invention can be utilized to stably or transiently transform plant cells. In stable transformation, the exogenous polynucleotide is integrated into the plant genome and as such it represents a stable and inherited trait. In transient transformation, the exogenous polynucleotide is expressed by the cell transformed but it is not integrated into the genome and as such it represents a transient trait.

There are various methods of introducing foreign genes into both monocotyledonous and dicotyledonous plants (Potrykus, L, Annu. Rev. Plant. Physiol, Plant. MoI. Biol. (1991) 42:205-225; Shimamoto et al., Nature (1989) 338: 274-276).

The principle methods of causing stable integration of exogenous DNA into plant genomic DNA include two main approaches:

(i) *Agrobacterium*-mediated gene transfer (e.g., T-DNA using *Agrobacterium tumefaciens* or *Agrobacterium rhizogenes*); see for example, Klee et al. (1987) Annu. Rev. Plant Physiol. 38:467-486; Klee and Rogers in Cell Culture and Somatic Cell Genetics of Plants, Vol. 6, Molecular Biology of Plant Nuclear Genes, eds. Schell, J., and Vasil, L. K., Academic Publishers, San Diego, Calif. (1989) p. 2-25; Gatenby, in Plant Biotechnology, eds. Kung, S, and Arntzen, C. J., Butterworth Publishers, Boston, Mass. (1989) p. 93-112.

(ii) Direct DNA uptake: Paszkowski et al., in Cell Culture and Somatic Cell Genetics of Plants, Vol. 6, Molecular Biology of Plant Nuclear Genes eds. Schell, J., and Vasil, L. K., Academic Publishers, San Diego, Calif. (1989) p. 52-68; including methods for direct uptake of DNA into protoplasts, Toriyama, K. et al. (1988) Bio/Technology 6:1072-1074. DNA uptake induced by brief electric shock of plant cells: Zhang et al. Plant Cell Rep. (1988) 7:379-384. Fromm et al. Nature (1986) 319:791-793. DNA injection into plant cells or tissues by particle bombardment, Klein et al. Bio/Technology (1988) 6:559-563; McCabe et al. Bio/Technology (1988) 6:923-926; Sanford, Physiol. Plant. (1990) 79:206-209; by the use of micropipette systems: Neuhaus et al., Theor. Appl. Genet. (1987) 75:30-36; Neuhaus and Spangenberg, Physiol. Plant. (1990) 79:213-217; glass fibers or silicon carbide whisker transformation of cell cultures, embryos or callus tissue, U.S. Pat. No. 5,464,765 or by the direct incubation of DNA with germinating pollen, DeWet et al. in Experimental Manipulation of Ovule Tissue, eds. Chapman, G. P. and Mantell, S. H. and Daniels, W. Longman, London, (1985) p. 197-209; and Ohta, Proc. Natl. Acad. Sci. USA (1986) 83:715-719.

The *Agrobacterium* system includes the use of plasmid vectors that contain defined DNA segments that integrate into the plant genomic DNA. Methods of inoculation of the plant tissue vary depending upon the plant species and the *Agrobacterium* delivery system. A widely used approach is the leaf disc procedure which can be performed with any tissue explant that provides a good source for initiation of whole plant differentiation. See, e.g., Horsch et al. in Plant Molecular Biology Manual A5, Kluwer Academic Publishers, Dordrecht (1988) p. 1-9. A supplementary approach employs the *Agrobacterium* delivery system in combination with vacuum infiltration. The *Agrobacterium* system is especially viable in the creation of transgenic dicotyledonous plants.

According to a specific embodiment of the present invention, the exogenous polynucleotide is introduced into the plant by infecting the plant with a bacteria, such as using a floral dip transformation method (as described in further detail in Example 5, of the Examples section which follows).

There are various methods of direct DNA transfer into plant cells. In electroporation, the protoplasts are briefly exposed to a strong electric field. In microinjection, the DNA is mechanically injected directly into the cells using very small micropipettes. In microparticle bombardment, the DNA is adsorbed on microprojectiles such as magnesium sulfate crystals or tungsten particles, and the microprojectiles are physically accelerated into cells or plant tissues.

Following stable transformation plant propagation is exercised. The most common method of plant propagation is by seed. Regeneration by seed propagation, however, has the deficiency that due to heterozygosity there is a lack of uniformity in the crop, since seeds are produced by plants according to the genetic variances governed by Mendelian rules. Basically, each seed is genetically different and each will grow with its own specific traits. Therefore, it is preferred that the transformed plant be produced such that the regenerated plant has the identical traits and characteristics of the parent transgenic plant. For this reason it is preferred that the transformed plant be regenerated by micropropagation which provides a rapid, consistent reproduction of the transformed plants.

Micropropagation is a process of growing new generation plants from a single piece of tissue that has been excised from a selected parent plant or cultivar. This process permits the mass reproduction of plants having the preferred tissue expressing the fusion protein. The new generation plants which are produced are genetically identical to, and have all of the characteristics of, the original plant. Micropropagation allows mass production of quality plant material in a short period of time and offers a rapid multiplication of selected cultivars in the preservation of the characteristics of the original transgenic or transformed plant. The advantages of cloning plants are the speed of plant multiplication and the quality and uniformity of plants produced.

Micropropagation is a multi-stage procedure that requires alteration of culture medium or growth conditions between stages. Thus, the micropropagation process involves four basic stages: Stage one, initial tissue culturing; stage two, tissue culture multiplication; stage three, differentiation and plant formation; and stage four, greenhouse culturing and hardening. During stage one, initial tissue culturing, the tissue culture is established and certified contaminant-free. During stage two, the initial tissue culture is multiplied until a sufficient number of tissue samples are produced to meet production goals. During stage three, the tissue samples grown in stage two are divided and grown into individual plantlets. At stage four, the transformed plantlets are transferred to a greenhouse for hardening where the plants' tolerance to light is gradually increased so that it can be grown in the natural environment.

Although stable transformation is presently preferred, transient transformation of leaf cells, meristematic cells or the whole plant is also envisaged by the present invention.

Transient transformation can be effected by any of the direct DNA transfer methods described above or by viral infection using modified plant viruses.

Viruses that have been shown to be useful for the transformation of plant hosts include CaMV, Tobacco mosaic virus (TMV), brome mosaic virus (BMV) and Bean Common Mosaic Virus (BV or BCMV). Transformation of plants using plant viruses is described in U.S. Pat. No. 4,855,237 (bean golden mosaic virus; BGV), EP-A 67,553 (TMV), Japanese Published Application No. 63-14693 (TMV), EPA 194,809 (BV), EPA 278,667 (BV); and Gluzman, Y. et al., Communications in Molecular Biology: Viral Vectors, Cold Spring Harbor Laboratory, New York, pp. 172-189 (1988). Pseudovirus particles for use in expressing foreign DNA in many hosts, including plants are described in WO 87/06261. According to some embodiments of the invention, the virus used for transient transformations is avirulent and thus is incapable of causing severe symptoms such as reduced growth rate, mosaic, ring spots, leaf roll, yellowing, streaking, pox formation, tumor formation and pitting. A suitable avirulent virus may be a naturally occurring avirulent virus or an artificially attenuated virus. Virus attenuation may be effected by using methods well known in the art including, but not limited to, sub-lethal heating, chemical treatment or by directed mutagenesis techniques such as described, for example, by Kurihara and Watanabe (Molecular Plant Pathology 4:259-269, 2003), Galon et al. (1992), Atreya et al. (1992) and Huet et al. (1994).

Suitable virus strains can be obtained from available sources such as, for example, the American Type culture Collection (ATCC) or by isolation from infected plants. Isolation of viruses from infected plant tissues can be effected by techniques well known in the art such as described, for example by Foster and Tatlor, Eds. "Plant Virology Protocols: From Virus Isolation to Transgenic Resistance (Methods in Molecular Biology (Humana Pr), Vol 81)", Humana Press, 1998. Briefly, tissues of an infected plant believed to contain a high concentration of a suitable virus, preferably young leaves and flower petals, are ground in a buffer solution (e.g., phosphate buffer solution) to produce a virus infected sap which can be used in subsequent inoculations.

Construction of plant RNA viruses for the introduction and expression of non-viral exogenous polynucleotide sequences in plants is demonstrated by the above references as well as by Dawson, W. O. et al, Virology (1989) 172: 285-292; Takamatsu et al. EMBO J. (1987) 6:307-311; French et al. Science (1986) 231:1294-1297; Takamatsu et al. FEBS Letters (1990) 269:73-76; and U.S. Pat. No. 5,316,931.

When the virus is a DNA virus, suitable modifications can be made to the virus itself. Alternatively, the virus can first be cloned into a bacterial plasmid for ease of constructing the desired viral vector with the foreign DNA. The virus can then be excised from the plasmid. If the virus is a DNA virus, a bacterial origin of replication can be attached to the viral DNA, which is then replicated by the bacteria. Transcription and translation of this DNA will produce the coat proteins which will encapsidate the viral DNA. If the virus is an RNA virus, the virus is generally cloned as a cDNA and inserted into a plasmid. The plasmid is then used to make all of the constructions. The RNA virus is then produced by transcribing the viral sequence of the plasmid and translation of the viral genes to produce the coat protein(s) which encapsidate the viral RNA.

In one embodiment, a plant viral nucleic acid is provided in which the native coat protein coding sequence has been deleted from a viral nucleic acid, a non-native plant viral coat protein coding sequence and a non-native promoter, preferably the subgenomic promoter of the non-native coat protein coding sequence, capable of expression in the plant host, packaging of the recombinant plant viral nucleic acid, and ensuring a systemic infection of the host by the recombinant plant viral nucleic acid, has been inserted. Alternatively, the coat protein gene may be inactivated by insertion of the non-native nucleic acid sequence within it, such that a protein is produced. The recombinant plant viral nucleic acid may contain one or more additional non-native subgenomic promoters. Each non-native subgenomic promoter is capable of transcribing or expressing adjacent genes or nucleic acid sequences in the plant host and incapable of recombination with each other and with native subgenomic promoters. Non-native (foreign) nucleic acid sequences may be inserted adjacent the native plant viral subgenomic promoter or the native and a non-native plant viral subgenomic promoters if more than one nucleic acid sequence is included. The non-native nucleic acid sequences are transcribed or expressed in the host plant under control of the subgenomic promoter to produce the desired products.

In a second embodiment, a recombinant plant viral nucleic acid is provided as in the first embodiment except that the native coat protein coding sequence is placed adjacent one of the non-native coat protein subgenomic promoters instead of a non-native coat protein coding sequence.

In a third embodiment, a recombinant plant viral nucleic acid is provided in which the native coat protein gene is adjacent its subgenomic promoter and one or more non-native subgenomic promoters have been inserted into the viral nucleic acid. The inserted non-native subgenomic promoters are capable of transcribing or expressing adjacent genes in a plant host and are incapable of recombination with each other and with native subgenomic promoters. Non-native nucleic acid sequences may be inserted adjacent the non-native subgenomic plant viral promoters such that the sequences are transcribed or expressed in the host plant under control of the subgenomic promoters to produce the desired product.

In a fourth embodiment, a recombinant plant viral nucleic acid is provided as in the third embodiment except that the native coat protein coding sequence is replaced by a non-native coat protein coding sequence.

The viral vectors are encapsidated by the coat proteins encoded by the recombinant plant viral nucleic acid to produce a recombinant plant virus. The recombinant plant viral nucleic acid or recombinant plant virus is used to infect appropriate host plants. The recombinant plant viral nucleic acid is capable of replication in the host, systemic spread in the host, and transcription or expression of foreign gene(s) (isolated nucleic acid) in the host to produce the desired protein.

In addition to the above, the nucleic acid molecule of the present invention can also be introduced into a chloroplast genome thereby enabling chloroplast expression.

A technique for introducing exogenous nucleic acid sequences to the genome of the chloroplasts is known. This technique involves the following procedures. First, plant cells are chemically treated so as to reduce the number of chloroplasts per cell to about one. Then, the exogenous nucleic acid is introduced via particle bombardment into the cells with the aim of introducing at least one exogenous nucleic acid molecule into the chloroplasts. The exogenous nucleic acid is selected such that it is integratable into the chloroplast's genome via homologous recombination which is readily effected by enzymes inherent to the chloroplast. To this end, the exogenous nucleic acid includes, in addition to a gene of interest, at least one nucleic acid stretch which is derived from the chloroplast's genome. In addition, the exogenous nucleic acid includes a selectable marker, which serves by sequential selection procedures to ascertain that all or substantially all of the copies of the chloroplast genomes following such selection will include the exogenous nucleic acid. Further details relating to this technique are found in U.S. Pat. Nos. 4,945,050; and 5,693,507 which are incorporated herein by reference. A polypeptide can thus be produced by the protein expression system of the chloroplast and become integrated into the chloroplast's inner membrane.

Since NUE, abiotic stress tolerance as well as yield, vigor or biomass of the plant can involve multiple genes acting additively or in synergy (see, for example, in Quesda et al., Plant Physiol. 130:951-063, 2002), the invention also envisages expressing a plurality of exogenous polynucleotides in a single host plant to thereby achieve superior effect on NUE, abiotic stress tolerance, yield, vigor and biomass of the plant.

Expressing a plurality of exogenous polynucleotides in a single host plant can be effected by co-introducing multiple nucleic acid constructs, each including a different exogenous polynucleotide, into a single plant cell. The transformed cell can then be regenerated into a mature plant using the methods described hereinabove. Alternatively, expressing a plurality of exogenous polynucleotides in a single host plant can be effected by co-introducing into a single plant-cell a single nucleic-acid construct including a plurality of different exogenous polynucleotides. Such a construct can be designed with a single promoter sequence which can transcribe a polycistronic messenger RNA including all the different exogenous polynucleotide sequences. To enable co-translation of the different polypeptides encoded by the polycistronic messenger RNA, the polynucleotide sequences can be inter-linked via an internal ribosome entry site (IRES) sequence which facilitates translation of polynucleotide sequences positioned downstream of the IRES sequence. In this case, a transcribed polycistronic RNA molecule encoding the different polypeptides described above will be translated from both the capped 5' end and the two internal IRES sequences of the polycistronic RNA molecule to thereby produce in the cell all different polypeptides. Alternatively, the construct can include several promoter sequences each linked to a different exogenous polynucleotide sequence.

The plant cell transformed with the construct including a plurality of different exogenous polynucleotides can be regenerated into a mature plant, using the methods described hereinabove.

Alternatively, expressing a plurality of exogenous polynucleotides can be effected by introducing different nucleic acid constructs, including different exogenous polynucleotides, into a plurality of plants. The regenerated transformed plants can then be cross-bred and resultant progeny selected for superior NUE, abiotic stress tolerance, yield as described above, using conventional plant breeding techniques.

As mentioned, expression (or reduction in a level of expression) of the target polynucleotides/polypeptides of the present invention can be qualified using methods which are well known in the art such as those involving gene amplification Western blotting, ELISA, or at the mRNA level involving e.g., PCR or RT-PCR or Northern blot or in-situ hybridization (in which one monitors the level of target gene expression).

According to some embodiments of the invention, the plant expressing the exogenous polynucleotide(s) is grown under stress (nitrogen or abiotic) or normal conditions (e.g., biotic conditions and/or conditions with sufficient water, nutrients such as nitrogen and fertilizer). Such conditions, which depend on the plant being grown, are known to those skilled in the art of agriculture, and are further, described above.

According to some embodiments of the invention, the method further comprises growing the plant expressing the exogenous polynucleotide(s) under abiotic stress or nitrogen limiting conditions. Non-limiting examples of abiotic stress conditions include, water deprivation, drought, excess of water (e.g., flood, waterlogging), freezing, low temperature, high temperature, strong winds, heavy metal toxicity, anaerobiosis, nutrient deficiency, nutrient excess, salinity, atmospheric pollution, intense light, insufficient light, or UV irradiation, etiolation and atmospheric pollution.

Thus, the invention encompasses plants exogenously expressing the polynucleotide(s), the nucleic acid constructs of the invention.

The sequence information and annotations uncovered by the present teachings can be harnessed in favor of classical breeding. Thus, sub-sequence data of those polynucleotides described above, can be used as markers for marker assisted selection (MAS), in which a marker is used for indirect selection of a genetic determinant or determinants of a trait of interest (e.g., tolerance to abiotic stress). Nucleic acid data of the present teachings (DNA or RNA sequence) may contain or be linked to polymorphic sites or genetic markers on the genome such as restriction fragment length polymorphism (RFLP), microsatellites and single nucleotide polymorphism (SNP), DNA fingerprinting (DFP), amplified fragment length polymorphism (AFLP), expression level polymorphism, and any other polymorphism at the DNA or RNA sequence.

Examples of marker assisted selections include, but are not limited to, selection for a morphological trait (e.g., a gene that affects form, coloration, male sterility or resistance such as the presence or absence of awn, leaf sheath coloration, height, grain color, aroma of rice); selection for a biochemical trait (e.g., a gene that encodes a protein that can be extracted and observed; for example, isozymes and storage proteins); selection for a biological trait (e.g., pathogen races or insect biotypes based on host pathogen or host parasite interaction can be used as a marker since the genetic constitution of an organism can affect its susceptibility to pathogens or parasites).

The polynucleotides described hereinabove can be used in a wide range of economical plants, in a safe and cost effective manner.

Plant lines exogenously expressing the polynucleotide of the invention can be screened to identify those that show the greatest increase of the desired plant trait.

Thus, according to an additional embodiment of the present invention, there is provided a method of evaluating a trait of a plant, the method comprising: (a) expressing in a plant or a portion thereof the nucleic acid construct; and (b) evaluating a trait of a plant as compared to a wild type plant of the same type; thereby evaluating the trait of the plant.

Thus, the effect of the transgene (the exogenous polynucleotide) on different plant characteristics may be determined any method known to one of ordinary skill in the art.

Thus, for example, tolerance to limiting nitrogen conditions may be compared in transformed plants {i.e., expressing the transgene) compared to non-transformed (wild type) plants exposed to the same stress conditions (other stress conditions are contemplated as well, e.g. water deprivation, salt stress e.g. salinity, suboptimal temperature, osmotic stress, and the like), using the following assays.

Methods of qualifying plants as being tolerant or having improved tolerance to abiotic stress or limiting nitrogen levels are well known in the art and are further described hereinbelow.

Fertilizer use efficiency—To analyze whether the transgenic plants are more responsive to fertilizers, plants are grown in agar plates or pots with a limited amount of fertilizer, as described, for example, in Yanagisawa et al (Proc Natl Acad Sci USA. 2004; 101:7833-8). The plants are analyzed for their overall size, time to flowering, yield, protein content of shoot and/or grain. The parameters checked are the overall size of the mature plant, its wet and dry weight, the weight of the seeds yielded, the average seed size and the number of seeds produced per plant. Other parameters that may be tested are: the chlorophyll content of leaves (as nitrogen plant status and the degree of leaf verdure is highly correlated), amino acid and the total protein content of the seeds or other plant parts such as leaves or shoots, oil content, etc. Similarly, instead of providing nitrogen at limiting amounts, phosphate or potassium can be added at increasing concentrations. Again, the same parameters measured are the same as listed above. In this way, nitrogen use efficiency (NUE), phosphate use efficiency (PUE) and potassium use efficiency (KUE) are assessed, checking the ability of the transgenic plants to thrive under nutrient restraining conditions.

Nitrogen use efficiency—To analyze whether the transgenic plants (e.g., *Arabidopsis* plants) are more responsive to nitrogen, plant are grown in 0.75-3 millimolar (mM, nitrogen deficient conditions) or 6-10 mM (optimal nitrogen concentration). Plants are allowed to grow for additional 25 days or until seed production. The plants are then analyzed for their overall size, time to flowering, yield, protein content of shoot and/or grain/seed production. The parameters checked can be the overall size of the plant, wet and dry weight, the weight of the seeds yielded, the average seed size and the number of seeds produced per plant. Other parameters that may be tested are: the chlorophyll content of leaves (as nitrogen plant status and the degree of leaf greenness is highly correlated), amino acid and the total protein content of the seeds or other plant parts such as leaves or shoots and oil content. Transformed plants not exhibiting substantial physiological and/or morphological effects, or exhibiting higher measured parameters levels than wild-type plants, are identified as nitrogen use efficient plants.

Nitrogen Use efficiency assay using plantlets—The assay is done according to Yanagisawa-S. et al. with minor modifications ("Metabolic engineering with Dof1 transcription factor in plants: Improved nitrogen assimilation and growth under low-nitrogen conditions" Proc. Natl. Acad. Sci. USA 101, 7833-7838). Briefly, transgenic plants which are grown for 7-10 days in 0.5×MS [Murashige-Skoog] supplemented with a selection agent are transferred to two nitrogen-limiting conditions: MS media in which the combined nitrogen concentration ($NH_4NO_3$ and $KNO_3$) was 0.75 mM (nitrogen deficient conditions) or 6-15 mM (optimal nitrogen concentration). Plants are allowed to grow for additional 30-40 days and then photographed, individually removed from the Agar (the shoot without the roots) and immediately weighed (fresh weight) for later statistical analysis. Constructs for which only T1 seeds are available are sown on selective media and at least 20 seedlings (each one representing an independent transformation event) are carefully transferred to the nitrogen-limiting media. For constructs for which T2 seeds are available, different transformation events are analyzed. Usually, 20 randomly selected plants from each event are transferred to the nitrogen-limiting media allowed to grow for 3-4 additional weeks and individually weighed at the end of that period. Transgenic plants are compared to control plants grown in parallel under the same conditions. Mock-transgenic plants expressing the uidA reporter gene (GUS) under the same promoter or transgenic plants carrying the same promoter but lacking a reporter gene are used as control.

Nitrogen determination—The procedure for N (nitrogen) concentration determination in the structural parts of the plants involves the potassium persulfate digestion method to convert organic N to $NO_3^-$ (Purcell and King 1996 Argon. J. 88:111-113, the modified $Cd^-$ mediated reduction of $NO_3^-$ to $NO_2^-$ (Vodovotz 1996 Biotechniques 20:390-394) and the measurement of nitrite by the Griess assay (Vodovotz 1996, supra). The absorbance values are measured at 550 nm against a standard curve of $NaNO_2$. The procedure is described in details in Samonte et al. 2006 Agron. J. 98:168-176.

Tolerance to abiotic stress (e.g. tolerance to drought or salinity) can be evaluated by determining the differences in physiological and/or physical condition, including but not limited to, vigor, growth, size, or root length, or specifically, leaf color or leaf area size of the transgenic plant compared to a non-modified plant of the same species grown under the same conditions. Other techniques for evaluating tolerance to abiotic stress include, but are not limited to, measuring chlorophyll fluorescence, photosynthetic rates and gas exchange rates. Further assays for evaluating tolerance to abiotic stress are provided hereinbelow and in the Examples section which follows.

Drought tolerance assay—Soil-based drought screens are performed with plants overexpressing the polynucleotides detailed above. Seeds from control *Arabidopsis* plants, or other transgenic plants overexpressing nucleic acid of the invention are germinated and transferred to pots. Drought stress is obtained after irrigation is ceased. Transgenic and control plants are compared to each other when the majority of the control plants develop severe wilting. Plants are re-watered after obtaining a significant fraction of the control plants displaying a severe wilting. Plants are ranked comparing to controls for each of two criteria: tolerance to the drought conditions and recovery (survival) following re-watering.

Quantitative parameters of tolerance measured include, but are not limited to, the average wet and dry weight, growth rate, leaf size, leaf coverage (overall leaf area), the weight of the seeds yielded, the average seed size and the number of seeds produced per plant. Transformed plants not exhibiting substantial physiological and/or morphological effects, or exhibiting higher biomass than wild-type plants, are identified as drought stress tolerant plants, Salinity tolerance assay—Transgenic plants with tolerance to high salt concentrations are expected to exhibit better germination, seedling vigor or growth in high salt. Salt stress can be effected in many ways such as, for example, by irrigating the plants with a hyperosmotic solution, by cultivating the plants hydroponically in a hyperosmotic growth solution (e.g., Hoagland solution with added salt), or by culturing the plants in a hyperosmotic growth medium [e.g., 50% Murashige-Skoog medium (MS medium) with added salt]. Since different plants vary considerably in their tolerance to salinity, the salt concentration in the irrigation water, growth solution, or growth medium can be adjusted according to the specific characteristics of the specific plant cultivar or variety, so as to inflict a mild or moderate effect on the physiology and/or morphology of the plants (for guidelines as to appropriate concentration see, Bernstein and Kafkafi, Root Growth Under Salinity Stress In: Plant Roots, The Hidden Half 3rd ed. Waisel Y, Eshel A and Kafkafi U. (editors) Marcel Dekker Inc., New York, 2002, and reference therein).

For example, a salinity tolerance test can be performed by irrigating plants at different developmental stages with increasing concentrations of sodium chloride (for example 50 mM, 150 mM, 300 mM NaCl) applied from the bottom and from above to ensure even dispersal of salt. Following exposure to the stress condition the plants are frequently monitored until substantial physiological and/or morphological effects appear in wild type plants. Thus, the external phenotypic appearance, degree of chlorosis and overall success to reach maturity and yield progeny are compared between control and transgenic plants. Quantitative parameters of tolerance measured include, but are not limited to, the average wet and dry weight, growth rate, leaf size, leaf coverage (overall leaf area), the weight of the seeds yielded, the average seed size and the number of seeds produced per plant. Transformed plants not exhibiting substantial physiological and/or morphological effects, or exhibiting higher biomass than wild-type plants, are identified as abiotic stress tolerant plants.

Osmotic tolerance test—Osmotic stress assays (including sodium chloride and PEG assays) are conducted to determine if an osmotic stress phenotype was sodium chloride-specific or if it was a general osmotic stress related phenotype. Plants which are tolerant to osmotic stress may have more tolerance to drought and/or freezing. For salt and osmotic stress experiments, the medium is supplemented for example with 50 mM, 100 mM, 200 mM NaCl or 15%, 20% or 25% PEG.

Cold stress tolerance—One way to analyze cold stress is as follows. Mature (25 day old) plants are transferred to 4° C. chambers for 1 or 2 weeks, with constitutive light. Later on plants are moved back to greenhouse. Two weeks later damages from chilling period, resulting in growth retardation and other phenotypes, are compared between control and transgenic plants, by measuring plant weight (wet and dry), and by comparing growth rates measured as time to flowering, plant size, yield, and the like.

Heat stress tolerance—One way to measure heat stress tolerance is by exposing the plants to temperatures above 34° C. for a certain period. Plant tolerance is examined after transferring the plants back to 22° C. for recovery and evaluation after 5 days relative to internal controls (non-transgenic plants) or plants not exposed to neither cold or heat stress.

The biomass, vigor and yield of the plant can also be evaluated using any method known to one of ordinary skill in the art. Thus, for example, plant vigor can be calculated by the increase in growth parameters such as leaf area, fiber length, rosette diameter, plant fresh weight and the like per time.

As mentioned, the increase of plant yield can be determined by various parameters. For example, increased yield of rice may be manifested by an increase in one or more of the following: number of plants per growing area, number of panicles per plant, number of spikelets per panicle, number of flowers per panicle, increase in the seed filling rate, increase in thousand kernel weight (1000-weight), increase oil content per seed, increase starch content per seed, among others. An increase in yield may also result in modified architecture, or may occur because of modified architecture. Similarly, increased yield of soybean may be manifested by an increase in one or more of the following: number of plants per growing area, number of pods per plant, number of seeds per pod, increase in the seed filling rate, increase in thousand seed weight (1000-weight), reduce pod shattering, increase oil content per seed, increase protein content per seed, among others. An increase in yield may also result in modified architecture, or may occur because of modified architecture.

Thus, the present invention is of high agricultural value for increasing tolerance of plants to nitrogen deficiency or abiotic stress as well as promoting the yield, biomass and vigor of commercially desired crops.

According to another embodiment of the present invention, there is provided a food or feed comprising the plants or a portion thereof of the present invention.

In a further aspect the invention, the transgenic plants of the present invention or parts thereof are comprised in a food or feed product (e.g., dry, liquid, paste). A food or feed product is any ingestible preparation containing the transgenic plants, or parts thereof, of the present invention, or preparations made from these plants. Thus, the plants or preparations are suitable for human (or animal) consumption, i.e. the transgenic plants or parts thereof are more readily digested. Feed products of the present invention further include a oil or a beverage adapted for animal consumption.

It will be appreciated that the transgenic plants, or parts thereof, of the present invention may be used directly as feed products or alternatively may be incorporated or mixed with feed products for consumption. Furthermore, the food or feed products may be processed or used as is. Exemplary feed products comprising the transgenic plants, or parts thereof, include, but are not limited to, grains, cereals, such as oats, e.g. black oats, barley, wheat, rye, *sorghum*, corn, vegetables, leguminous plants, especially soybeans, root vegetables and cabbage, or green forage, such as grass or hay.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Differential Expression of dsRNAs in Maize Plant Under Optimal Versus Deficient Nitrogen Conditions Experimental Procedures Plant Material Corn seeds were obtained from Galil seeds (Israel). Corn variety 5605 was used in all experiments. Plants were grown at 24° C. under a 16 hr light:8 hr dark regime.

Stress Induction

Corn seeds were germinated and grown on agar with defined growth media containing either optimal (100% $N_2$, 20.61 mM) or suboptimal nitrogen levels (1% or 10% $N_2$, 0.2 mM or 2.06 mM, respectively). Seedlings aged one or two weeks were used for tissue samples for RNA analysis, as described below.

Total RNA Extraction

Total RNA of leaf or root samples from four to eight biological repeats were extracted using the mirVana™ kit (Ambion, Austin, Tex.) by pooling 3-4 plants to one biological repeat.

Microarray Design

Custom microarrays were manufactured by Agilent Technologies by in situ synthesis. The first generation microarray consisted of a total of 13619 non-redundant DNA probes, the majority of which arose from deep sequencing data and includes different small RNA molecules (i.e. miRNAs, siRNA and predicted small RNA sequences), with each probe being printed once. An in-depth analysis of the first generation microarray, which included hybridization experiments as well as structure and orientation verifications on all its small RNAs, resulted in the formation of an improved, second generation, microarray. The second generation microarray consists of a total 4721 non-redundant DNA 45-nucleotide long probes for all known plant small RNAs, with 912 sequences (19.32%) from Sanger version 15 and the rest (3809), encompassing miRNAs (968=20.5%), siRNAs (1626=34.44%) and predicted small RNA sequences (1215=25.74%), from deep sequencing data accumulated by the inventors, with each probe being printed in triplicate.

Results

Wild type maize plants were allowed to grow at standard, optimal conditions or nitrogen deficient conditions for one or two weeks, at the end of which they were evaluated for NUE. Three to four plants from each group were used for reproducibility. Four to eight repeats were obtained for each group and RNA was extracted from leaf or root tissue. The expression level of the maize miRNAs was analyzed by high throughput microarray to identify miRNAs that were differentially expressed between the experimental groups.

Tables 1-4 below present dsRNA sequences that were found to be differentially expressed (upregulated=up; downregulated=down) in corn grown under low nitrogen conditions (nitrogen limiting conditions, as described above).

TABLE 1 miRNAs found upregulated in Plants Growing under Nitrogen Deficient Conditions versus Optimal conditions

| Mir Name | SEQ ID NO: | Stem Loop SEQ ID NO: | Direction | Fold Change Leaf | Fold Change Root |
| --- | --- | --- | --- | --- | --- |
| osa-miR1430 | TGGTGAGCCTTCCTGGCTAAG/1 | 196 | Up | | 3.99 |
| osa-miR1868 | TCACGGAAAACGAGGGAGCAGCCA/2 | 197 | Up | | 2.63 |
| osa-miR2096-3p | CCTGAGGGGAAATCGGCGGGA/3 | 198 | Up | 3.48 | 2.71 |
| zma-miR399f* | GGGCAACTTCTCCTTTGGCAGA/4 | 199 | Up | | 2.13 |
| Predicted folded 24-nts-long seq 50935 | AACTAAAACGAAACGGAAGGAGTA/5 | 200 | Up | 2.1 | |
| Predicted folded 24-nts-long seq 51052 | AAGGTGCTTTTAGGAGTAGGACGG/6 | 201 | Up | 2.08 | |
| Predicted folded 24-nts-long seq 51215 | ACAAAGGAATTAGAACGGAATGGC/7 | 202 | Up | 3.23 | 2.49 |
| Predicted folded 24-nts-long seq 51468 | AGAATCAGGAATGGAACGGCTCCG/8 | 203 | Up | | 1.54 |
| Predicted folded 24-nts-long seq 51469 | AGAATCAGGGATGGAACGGCTCTA/9 | 204 | Up | | 1.9 |
| Predicted folded 24-nts-long seq 51577 | AGAGTCACGGGCGAGAAGAGGACG/10 | 205 | Up | | 2.34 |
| Predicted folded 24-nts-long seq 51691 | AGGACCTAGATGAGCGGGCGGTTT/11 | 206 | Up | | 1.72 |
| Predicted folded 24-nts-long seq 51695 | AGGACGCTGCTGGAGACGGAGAAT/12 | 207 | Up | | 2.4 |

TABLE 1-continued miRNAs found upregulated in Plants Growing under Nitrogen
Deficient Conditions versus Optimal conditions

| Mir Name | SEQ ID NO: | Stem Loop SEQ ID NO: | Direction | Fold Change Leaf | Fold Change Root |
|---|---|---|---|---|---|
| Predicted folded 24-nts-long seq 51814 | AGGGCTTGTTCGGTTTG AAGGGGT/13 | 208 | Up | 2.52 | |
| Predicted folded 24-nts-long seq 52057 | ATCTTTCAACGGCTGCG AAGAAGG/14 | 209 | Up | | 2.11 |
| Predicted folded 24-nts-long seq 52327 | CTAGAATTAGGGATGG AACGGCTC/15 | 210 | Up | | 1.57 |
| Predicted folded 24-nts-long seq 52499 | GAGGGATAACTGGGGA CAACACGG/16 | 211 | Up | 2.97 | |
| Predicted folded 24-nts-long seq 52633 | GCGGAGTGGGATGGGG AGTGTTGC/17 | 212 | Up | | 1.51 |
| Predicted folded 24-nts-long seq 52688 | GGAGACGGATGCGGAG ACTGCTGG/18 | 213 | Up | | 1.51 |
| Predicted folded 24-nts-long seq 52805 | GGTTAGGAGTGGATTG AGGGGGAT/19 | 214 | Up | 3.77 | |
| Predicted folded 24-nts-long seq 52850 | GTCAAGTGACTAAGAG CATGTGGT/20 | 215 | Up | 4.93 | 10.17 |
| Predicted folded 24-nts-long seq 52882 | GTGGAATGGAGGAGAT TGAGGGA/21 | 216 | Up | 2.01 | |
| Predicted folded 24-nts-long seq 53118 | TGGCTGAAGGCAGAAC CAGGGGAG/22 | 217 | Up | | 4.45 |
| Predicted folded 24-nts-long seq 53149 | TGTGGTAGAGAGGAAG AACAGGAC/23 | 218 | Up | 3.25 | |
| Predicted folded 24-nts-long seq 53594 | AGGGACTCTCTTTATTT CCGACGG/24 | 219 | Up | | 1.83 |
| Predicted folded 24-nts-long seq 53604 | AGGGTTCGTTTCCTGGG AGCGCGG/25 | 220 | Up | | 1.66 |
| Predicted folded 24-nts-long seq 54081 | TCCTAGAATCAGGGAT GGAACGGC/26 | 221 | Up | | 1.6 |
| Predicted folded 24-nts-long seq 54132 | TGGGAGCTCTCTGTTCG ATGGCGC/27 | 222 | Up | | 3.47 |
| Predicted zma mir 48061 | AACGTCGTGTCGTGCTT GGGCT/28 | 223 | Up | | 1.62 |
| Predicted zma mir 48295 | ACCTGGACCAATACAT GAGATT/29 | 224 | Up | 2.58 | |
| Predicted zma mir 48350 | AGAAGCGACAATGGGA CGGAGT/30 | 225 | Up | 4.65 | |
| Predicted zma mir 48457 | AGGAAGGAACAAACGA GGATAAG/31 | 226 | Up | | 2.08 |

TABLE 1-continued miRNAs found upregulated in Plants Growing under Nitrogen Deficient Conditions versus Optimal conditions

| Mir Name | SEQ ID NO: | Stem Loop SEQ ID NO: | Direction | Fold Change Leaf | Fold Change Root |
|---|---|---|---|---|---|
| Predicted zma mir 48877 | CCAAGAGATGGAAGGG CAGAGC/32 | 227 | Up | 2 | |
| Predicted zma mir 48922 | CGACAACGGGACGGAG TTCAA/33 | 228 | Up | | 1.58 |
| Predicted zma mir 49123 | GAGGATGGAGAGGTAC GTCAGA/34 | 229 | Up | 2.02 | |
| Predicted zma mir 49161 | GATGGGTAGGAGAGCG TCGTGTG/35 | 230 | Up | 1.51 | 1.55 |
| Predicted zma mir 49162 | GATGGTTCATAGGTGA CGGTAG/36 | 231 | Up | | 4.2 |
| Predicted zma mir 49262 | GGGAGCCGAGACATAG AGATGT/37 | 232 | Up | | 2.64 |
| Predicted zma mir 49323 | GTGAGGAGTGATAATG AGACGG/38 | 233 | Up | | 2.17 |
| Predicted zma mir 49369 | GTTTGGGGCTTTAGCAG GTTTAT/39 | 234 | Up | 1.58 | |
| Predicted zma mir 49609 | TCCATAGCTGGGCGGA AGAGAT/40 | 235 | Up | | 5.52 |
| Predicted zma mir 49638 | TCGGCATGTGTAGGAT AGGTG/41 | 236 | Up | 3.24 ± 1.00 | 3.235 ± 0.205 |
| Predicted zma mir 49761 | TGATAGGCTGGGTGTG GAAGCG/42 | 237 | Up | 2.01 | 1.73 |
| Predicted zma mir 49787 | TGCAAACAGACTGGGG AGGCGA/43 | 238 | Up | | 3 |
| Predicted zma mir 50077 | TTTGGCTGACAGGATA AGGGAG/44 | 239 | Up | 2.44 | |
| Predicted zma mir 50095 | TTTTCATAGCTGGGCGG AAGAG/45 | 240 | Up | 19.94 | |
| Predicted zma mir 50110 | AACTTTAAATAGGTAG GACGGCGC/46 | 241 | Up | | 1.51 |
| Predicted zma mir 50204 | GGAATGTTGTCTGGTTC AAGG/47 | 242 | Up | 14.34 | |
| Predicted zma mir 50261 | TGTAATGTTCGCGGAA GGCCAC/48 | 243 | Up | | 1.7 |
| Predicted zma mir 50267 | TGTTGGCATGGCTCAAT CAAC/49 | 244 | Up | | 1.82 |
| Predicted zma mir 50460 | CGCTGACGCCGTGCCA CCTCAT/50 | 245 | Up | | 2.33 |
| Predicted zma mir 50545 | GCCTGGGCCTCTTTAGA CCT/51 | 246 | Up | | 1.5 |
| Predicted zma mir 50578 | GTAGGATGGATGGAGA GGGTTC/52 | 247 | Up | | 2.07 |
| Predicted zma mir 50611 | TCAACGGGCTGGCGGA TGTG/53 | 248 | Up | | 1.55 |

Table 1. provided are miRNAs that were found upregulated in Plants Growing under Nitrogen Deficient Conditions versus Optimal conditions.

TABLE 2 miRNAs found downregulated in Plants Growing under Nitrogen Deficient Conditions versus Optimal conditions

| Mir Name | Mature Sequence/seq id no: | Stem Loop Sequence/ seq id no: | Direction | Fold Change Leaf | Fold Change Root |
|---|---|---|---|---|---|
| aqc-miR529 | AGAAGAGAGAGAGCACAACCC/54 | 249 | Down | 1.53 | |
| ath-miR2936 | CTTGAGAGAGAGAACACAGACG/55 | 250 | Down | 1.54 | |
| mtr-miR169q | TGAGCCAGGATGACTTGCCGG/56 | 251 | Down | 3.04 | |
| peu-miR2911 | GGCCGGGGGACGGGCTGGGA/59 | 254 | Down | 1.66 | |
| Predicted folded 24-nts-long seq 50703 | AAAAAAGACTGAGCCGAATTGAAA/60 | 255 | Down | | 2.66 |
| Predicted folded 24-nts-long seq 51022 | AAGGAGTTTAATGAAGAAAGAGAG/61 | 256 | Down | 1.62 | |
| Predicted folded 24-nts-long seq 51381 | ACTGATGACGACACTGAGGAGGCT/62 | 257 | Down | 7.7 | |
| Predicted folded 24-nts-long seq 51542 | AGAGGAACCAGAGCCGAAGCCGTT/63 | 258 | Down | 1.52 | |
| Predicted folded 24-nts-long seq 51757 | AGGCAAGGTGGAGGACGTTGATGA/64 | 259 | Down | 2.07 | |
| Predicted folded 24-nts-long seq 51802 | AGGGCTGATTTGGTGACAAGGGGA/65 | 260 | Down | 3.7 | 2.04 |
| Predicted folded 24-nts-long seq 51966 | ATATAAAGGGAGGAGGTATGGACC/66 | 261 | Down | 2.1 | |
| Predicted folded 24-nts-long seq 52041 | ATCGGTCAGCTGGAGGAGACAGGT/67 | 262 | Down | 1.7 | |
| Predicted folded 24-nts-long seq 52109 | ATGGTAAGAGACTATGATCCAACT/68 | 263 | Down | | 1.62 |
| Predicted folded 24-nts-long seq 52212 | CAATTTTGTACTGGATCGGGGCAT/69 | 264 | Down | | 1.53 |
| Predicted folded 24-nts-long seq 52218 | CAGAGGAACCAGAGCCGAAGCCGT/70 | 265 | Down | 1.58 | |
| Predicted folded 24-nts-long seq 52299 | CGGCTGGACAGGGAAGAAGAGCAC/71 | 266 | Down | 1.63 | |

TABLE 2-continued miRNAs found downregulated in Plants Growing under Nitrogen Deficient Conditions versus Optimal conditions

| Mir Name | Mature Sequence/seq id no: | Stem Loop Sequence/ seq id no: | Direction | Fold Change Leaf | Fold Change Root |
|---|---|---|---|---|---|
| Predicted folded 24-nts-long seq 52347 | GAAACTTGGAGAGATGGAGGCTTT/72 | 267 | Down | | 1.7 |
| Predicted folded 24-nts-long seq 52452 | GAGAGAGAAGGGAGCGGATCTGGT/73 | 268 | Down | 3.25 | 2.52 |
| Predicted folded 24-nts-long seq 52648 | GCTGCACGGGATTGGTGGAGAGGT/74 | 269 | Down | 2.34 | |
| Predicted folded 24-nts-long seq 52739 | GGCTGCTGGAGAGCGTAGAGGACC/75 | 270 | Down | 2.13 | |
| Predicted folded 24-nts-long seq 52792 | GGGTTTTGAGAGCGAGTGAAGGGG/76 | 271 | Down | | 2.9 |
| Predicted folded 24-nts-long seq 52795 | GGTATTGGGGTGGATTGAGGTGGA/77 | 272 | Down | 1.59 | |
| Predicted folded 24-nts-long seq 52801 | GGTGGCGATGCAAGAGGAGCTCAA/78 | 273 | Down | 2.52 | 3.87 |
| Predicted folded 24-nts-long seq 52955 | GTTGCTGGAGAGAGTAGAGGACGT/79 | 274 | Down | | 2.35 |
| Predicted zma mir 47944 | AAAAGAGAAACCGAAGACACAT/80 | 275 | Down | | 1.78 |
| Predicted zma mir 47976 | AAAGAGGATGAGGAGTAGCATG/81 | 276 | Down | 4.09 | |
| Predicted zma mir 48185 | AATACACATGGGTTGAGGAGG/82 | 277 | Down | 1.85 | |
| Predicted zma mir 48351 | AGAAGCGGACTGCCAAGGAGGC/83 | 278 | Down | 3.18 | |
| Predicted zma mir 48397 | AGAGGGTTTGGGGATAGAGGGAC/84 | 279 | Down | | 8.95 |
| Predicted zma mir 48588 | TAAGGGATGAGGCAGAGCATG/85 | 280 | Down | | 2.1 |
| Predicted zma mir 48669 | ATGCTATTTGTACCCGTCACCG/86 | 281 | Down | | 1.67 |
| Predicted zma mir 48708 | ATGTGGATAAAAGGAGGGATGA/87 | 282 | Down | | 1.61 |

TABLE 2-continued miRNAs found downregulated in Plants Growing under Nitrogen Deficient Conditions versus Optimal conditions

| Mir Name | Mature Sequence/seq id no: | Stem Loop Sequence/ seq id no: | Direction | Fold Change Leaf | Fold Change Root |
|---|---|---|---|---|---|
| Predicted zma mir 48771 | CAACAGGAACAAGGAGGACCAT/88 | 283 | Down | 1.52 | |
| Predicted zma mir 49002 | CTCGAGTTGAGAAAGAGATGCT/89 | 284 | Down | | 1.51 |
| Predicted zma mir 49003 | CTCGATGGGAGGTGGAGTTGCAT/90 | 285 | Down | 1.61 | |
| Predicted zma mir 49011 | CTGGGAAGATGGAACATTTTGGT/91 | 286 | Down | | 1.64 |
| Predicted zma mir 49053 | GAAGATATACGATGATGAGGAG/92 | 287 | Down | 1.55 | |
| Predicted zma mir 49070 | GAATCTATCGTTTGGGCTCAT/93 | 288 | Down | 1.65 | 2.01 |
| Predicted zma mir 49082 | GAGCGAGCTACAAAAGGATTCG/94 | 289 | Down | 1.6 | |
| Predicted zma mir 49155 | GAGTGACGAGGAGTGAGAGTAGG/95 | 290 | Down | | 3.64 |
| Predicted zma mir 49269 | GGGCATCTTCTGGCAGGAGGACA/96 | 291 | Down | 1.64 | |
| Predicted zma mir 49435 | TACGGAAGAAGAGCAAGTTTT/97 | 292 | Down | 1.64 | |
| Predicted zma mir 49445 | TAGAAAGAGCGAGAGAACAAAG/98 | 293 | Down | | 1.55 |
| Predicted zma mir 49762 | TGATATTATGGACGACTGGTT/99 | 294 | Down | 1.54 | 1.57 |
| Predicted zma mir 49816 | TGGAAGGGCCATGCCGAGGAG/100 | 295 | Down | | 2.45 |
| Predicted zma mir 49985 | TTGAGCGCAGCGTTGATGAGC/101 | 296 | Down | | 2.93 |
| Predicted zma mir 50021 | TTGGATAACGGGTAGTTTGGAGT/102 | 297 | Down | | 1.79 |
| Predicted zma mir 50144 | AGCTGCCGACTCATTCACCCA/103 | 298 | Down | | 1.54 |
| Predicted zma mir 50263 | TGTACGATGATCAGGAGGAGGT/104 | 299 | Down | 1.53 | |
| Predicted zma mir 50266 | TGTGTTCTCAGGTCGCCCCCG/105 | 300 | Down | | 2.51 |

TABLE 2-continued miRNAs found downregulated in Plants Growing under Nitrogen Deficient Conditions versus Optimal conditions

| Mir Name | Mature Sequence/seq id no: | Stem Loop Sequence/seq id no: | Direction | Fold Change Leaf | Fold Change Root |
|---|---|---|---|---|---|
| Predicted zma mir 50318 | ACTAAAAAGAAACAGAGGGAG/106 | 301 | Down | 1.5 | |
| Predicted zma mir 50517 | GACCGGCTCGACCCTTCTGC/107 | 302 | Down | 1.55 | |
| Predicted zma mir 50670 | TGGTAGGATGGATGGAGAGGGT/108 | 303 | Down | 1.55 | |
| zma-miR166d* | GGAATGTTGTCTGGTTCAAGG/109 | 304 | Down | 1.73 | |
| zma-miR169c* | GGCAAGTCTGTCCTTGGCTACA/110 | 305 | Down | 2.41 | |
| zma-miR399g | TGCCAAAGGGGATTTGCCCGG/113 | 309 | Down | | 1.55 |

Table 2. provided are miRNAs that were found downregulated in Plants Growing under Nitrogen Deficient Conditions versus Optimal conditions.

TABLE 3 siRNAs found upregulated in Plants Growing under Nitrogen Deficient Conditions versus Optimal conditions

| Mir Name | Mature Sequence/SEQ ID NO: | Direction | Fold Change Leaf | Fold Change Root |
|---|---|---|---|---|
| Predicted siRNA 54339 | AAGAAACGGGGCAGTGAGATGGAC/114 | Up | | 1.51 |
| Predicted siRNA 54631 | AGAAAAGATTGAGCCGAATTGAATT/115 | Up | 2.02 | |
| Predicted siRNA 54991 | AGAGCCTGTAGCTAATGGTGGG/116 | Up | 1.95 | |
| Predicted siRNA 55111 | AGGTAGCGGCCTAAGAACGACACA/117 | Up | 2.36 | 1.67 |
| Predicted siRNA 55423 | CCTATATACTGGAACGGAACGGCT/118 | Up | | 1.57 |
| Predicted siRNA 55806 | CTATATACTGGAACGGAACGGCTT/119 | Up | | 2.23 |
| Predicted siRNA 56052 | GACGAGATCGAGTCTGGAGCGAGC/120 | Up | 1.86 | |
| Predicted siRNA 56106 | GAGTATGGGGAGGGACTAGGGA/121 | Up | | 2.3 |
| Predicted siRNA 56353 | GACGAAATAGAGGCTCAGGAGAGG/122 | Up | 2.08 | |
| Predicted siRNA 56388 | GGATTCGTGATTGGCGATGGGG/123 | Up | | 1.51 |
| Predicted siRNA 56406 | GGTGAGAAACGGAAAGGCAGGACA/124 | Up | 4.04 | |
| Predicted siRNA 56443 | GTGTCTGAGCAGGGTGAGAAGGCT/125 | Up | 1.53 | 1.58 |
| Predicted siRNA 56450 | GTTTTGGAGGCGTAGGCGAGGGAT/126 | Up | 3.04 | |

TABLE 3-continued siRNAs found upregulated in Plants Growing under Nitrogen Deficient Conditions versus Optimal conditions

| Mir Name | Mature Sequence/SEQ ID NO: | Direction | Fold Change Leaf | Fold Change Root |
|---|---|---|---|---|
| Predicted siRNA 56542 | TGGGACGCTGCATCTGTTGAT/127 | Up | 2.96 | |
| Predicted siRNA 56706 | TCTATATACTGGAACGGAACGGCT/128 | Up | | 1.76 |
| Predicted siRNA 56856 | GTTGTTGGAGGGGTAGAGGACGTC/129 | Up | 1.55 | |
| Predicted siRNA 57034 | AATGACAGGACGGGATGGGACGGG/130 | Up | | 2.87 |
| Predicted siRNA 57054 | ACGGAACGGCTTCATACCACAATA/131 | Up | | 2.43 |
| Predicted siRNA 57193 | GACGGGCCGACATTTAGAGCACGG/132 | Up | | 1.69 |
| Predicted siRNA 57884 | ACGGATAAAAGGTACTCT/133 | Up | | 2.82 |
| Predicted siRNA 58292 | AGTATGTCGAAAACTGGAGGGC/134 | Up | 4.54 | |
| Predicted siRNA 58362 | ATAAGCACCGGCTAACTCT/135 | Up | | 2.87 |
| Predicted siRNA 58665 | ATTCAGCGGGCGTGGTTATTGGCA/136 | Up | | 1.55 |
| Predicted siRNA 58872 | CAGCGGGTGCCATAGTCGAT/137 | Up | | 1.92 |
| Predicted siRNA 58940 | CATTGCGACGGTCCTCAA/138 | Up | | 1.57 |
| Predicted siRNA 59380 | CTCAACGGATAAAGGTAC/139 | Up | | 2.21 |
| Predicted siRNA 59626 | GACAGTCAGGATGTTGGCT/140 | Up | 2.68 | 2.12 |
| Predicted siRNA 59659 | GACTGATCCTTCGGTGTCGGCG/141 | Up | | 1.67 |
| Predicted siRNA 59846 | GCCGAAGATTAAAAGACGAGACGA/142 | Up | 1.64 | |
| Predicted siRNA 59867 | GCCTTTGCCGACCATCCTGA/143 | Up | | 1.6 |
| Predicted siRNA 59952 | GGAATCGCTAGTAATCGTGGAT/144 | Up | 1.87 | 1.76 |
| Predicted siRNA 59961 | GGAGCAGCTCTGGTCGTGGG/145 | Up | | 1.85 ± 0.007 |
| Predicted siRNA 59965 | GGAGGCTCGACTATGTTCAAA/146 | Up | | 2.97 |
| Predicted siRNA 59966 | GGAGGGATGTGAGAACATGGGC/147 | Up | | 1.62 |
| Predicted siRNA 60081 | GTCCCCTTCGTCTAGAGGC/148 | Up | | 2.82 |
| Predicted siRNA 60095 | GTCTGAGTGGTGTAGTTGGT/149 | Up | 2.12 | |
| Predicted siRNA 60188 | GTTGGTAGAGCAGTTGGC/150 | Up | | 4.11 |
| Predicted siRNA 60285 | TACGTTCCCGGGTCTTGTACA/151 | Up | | 1.95 |

TABLE 3-continued siRNAs found upregulated in Plants Growing under Nitrogen Deficient Conditions versus Optimal conditions

| Mir Name | Mature Sequence/SEQ ID NO: | Direction | Fold Change Leaf | Fold Change Root |
|---|---|---|---|---|
| Predicted siRNA 60387 | TATGGATGAAGATGGGGGTG/152 | Up | 3.68 | |
| Predicted siRNA 60434 | TCAACGGATAAAAGGTACTCCG/153 | Up | | 2.23 |
| Predicted siRNA 60837 | TGCCCAGTGCTTTGAATG/154 | Up | | 3.37 |
| Predicted siRNA 60850 | TGCGAGACCGACAAGTCGAGC/155 | Up | 1.64 | 1.86 |
| Predicted siRNA 61382 | TTTGCGACACGGGCTGCTCT/156 | Up | | 1.52 |

Table 3. Provided are siRNAs that were found upregulated in Plants Growing under Nitrogen Deficient Conditions versus Optimal conditions.

TABLE 4 siRNAs found downregulated in Plants Growing under Nitrogen Deficient Conditions versus Optimal conditions

| Mir Name | Mature Sequence/SEQ ID No: | Direction | Fold Change Leaf | Fold Change Root |
|---|---|---|---|---|
| Predicted siRNA 58924 | CATCGCTCAACGGACAAAAGGT/157 | Down | | 1.55 |
| Predicted siRNA 54240 | AAGACGAAGGTAGCAGCGCGATAT/158 | Down | 2.79 | |
| Predicted siRNA 54957 | AGCCAGACTGATGAGAGAAGGAGG/159 | Down | 1.51 | |
| Predicted siRNA 55081 | ACGTTGTTGGAAGGGTAGAGGACG/160 | Down | 1.56 | |
| Predicted siRNA 55393 | CAAGTTATGCAGTTGCTGCCT/161 | Down | | 5.98 |
| Predicted siRNA 55404 | CAGAATGGAGGAAGAGATGGTG/162 | Down | 3.49 | |
| Predicted siRNA 55472 | ATCTGTGGAGAGAGAAGGTTGCCC/163 | Down | 1.58 | |
| Predicted siRNA 55720 | ATGTCAGGGGGCCATGCAGTAT/164 | Down | 2.41 | |
| Predicted siRNA 55732 | ATCCTGACTGTGCCGGGCCGGCCC/165 | Down | 1.96 | |
| Predicted siRNA 56034 | CGAGTTCGCCGTAGAGAAAGCT/166 | Down | | 2.24 |
| Predicted siRNA 56162 | GACTGATTCGGACGAAGGAGGGTT/167 | Down | | 3.23 |
| Predicted siRNA 56205 | GTCTGAACACTAAACGAAGCACA/168 | Down | 1.87 | |
| Predicted siRNA 56277 | GACGTTGTTGGAAGGGTAGAGGAC/169 | Down | 3.94 | |
| Predicted siRNA 56307 | GCTACTGTAGTTCACGGGCCGGCC/170 | Down | 1.71 | |
| Predicted siRNA 56425 | GGTATTCGTGAGCCTGTTTCTGGTT/171 | Down | 1.67 | |

TABLE 4-continued siRNAs found downregulated in Plants Growing under Nitrogen Deficient Conditions versus Optimal conditions

| Mir Name | Mature Sequence/SEQ ID No: | Direction | Fold Change Leaf | Fold Change Root |
|---|---|---|---|---|
| Predicted siRNA 56837 | TGGAAGGAGCATGCATCTTGAG/172 | Down | | 2.68 |
| Predicted siRNA 56965 | TTCTTGACCTTGTAAGACCCA/173 | Down | | 3.66 |
| Predicted siRNA 57088 | AGCAGAATGGAGGAAGAGATGG/174 | Down | 1.53 | |
| Predicted siRNA 57179 | CTGGACACTGTTGCAGAAGGAGGA/175 | Down | 1.58 | |
| Predicted siRNA 57181 | GAAATAGGATAGGAGGAGGGATGA/176 | Down | 3.34 | 2.91 |
| Predicted siRNA 57228 | GGCACGACTAACAGACTCACGGGC/177 | Down | | 2.45 |
| Predicted siRNA 57685 | AATCCCGGTGGAACCTCCA/178 | Down | 3.6 | 2.7 |
| Predicted siRNA 57772 | ACACGACAAGACGAATGAGAGAGA/179 | Down | | 1.57 |
| Predicted siRNA 57863 | ACGACGAGGACTTCGAGACG/180 | Down | 1.53 | |
| Predicted siRNA 58721 | CAAAGTGGTCGTGCCGGAG/181 | Down | 1.61 | |
| Predicted siRNA 58877 | CAGCTTGAGAATCGGGCCGC/182 | Down | 3.8 | |
| Predicted siRNA 59032 | CCCTGTGACAAGAGGAGGA/183 | Down | 1.6 | |
| Predicted siRNA 59102 | CCTGCTAACTAGTTATGCGGAGC/184 | Down | 1.74 | |
| Predicted siRNA 59123 | CGAACTCAGAAGTGAAACC/185 | Down | 2.11 | 2.62 |
| Predicted siRNA 59235 | CGCTTCGTCAAGGAGAAGGGC/186 | Down | 1.59 | |
| Predicted siRNA 59485 | CTTAACTGGGCGTTAAGTTGCAGGGT/187 | Down | | 2.17 |
| Predicted siRNA 59954 | GGACGAACCTCTGGTGTACC/188 | Down | | 1.76 |
| Predicted siRNA 59993 | GGCGCTGGAGAACTGAGGG/189 | Down | | 2.58 |
| Predicted siRNA 60012 | GGGGGCCTAAATAAAGACT/190 | Down | 2.48 | |
| Predicted siRNA 60123 | GTGCTAACGTCCGTCGTGAA/191 | Down | | 3.15 |
| Predicted siRNA 60334 | TAGCTTAACCTTCGGGAGGG/192 | Down | | 1.9 |
| Predicted siRNA 60750 | TGAGAAAGAAAGAGAAGGCTCA/193 | Down | 1.64 | |
| Predicted siRNA 60803 | TGATGTCCTTAGATGTTCTGGGC/194 | Down | | 1.99 |

TABLE 4-continued siRNAs found downregulated in Plants Growing under Nitrogen Deficient Conditions versus Optimal conditions

| Mir Name | Mature Sequence/SEQ ID No: | Direction | Fold Change Leaf | Fold Change Root |
|---|---|---|---|---|
| Predicted siRNA 55413 | CATGTGTTCTCAGGTCGCCC C/195 | Down | | 2.55 |

Table 4. Provided are siRNAs that were found downregulated in Plants Growing under Nitrogen Deficient Conditions versus Optimal conditions.

Example 2

Target Prediction Using Bioinformatics Tools

A high throughput screening was performed on microarrays loaded with miRNAs/siRNAs that were found to be differentially expressed under multiple stress and optimal environmental conditions and in different plant tissues. The initial trait-associated miRNAs are later validated by quantitative Real Time PCR (qRT-PCR).

Target prediction—orthologous genes to the genes of interest in maize and/or *Arabidopsis* are found through a proprietary tool that analyzes publicly available genomic as well as expression and gene annotation databases from multiple plant species. Homologous as well as orthologous protein and nucleotide sequences of target genes of the small RNA sequences of the invention, were found using BLAST having at least 70% identity on at least 60% of the entire master gene length, and are summarized in Tables 5-8 below. BLAST version used was Version 2.2.25+, Released March 2011, at default parameters as follows: For step 1 using BlastX to find the master homolog: Word size 3, Gap open 11, gap extend 1. For step 2 using BlastN to find orthologs from other organisms: Word size 28, Gap open 0, Gap extend 0, Reward (match score) 1, Penalty (mismatch score)-2.

TABLE 5

Target Genes of miRNAs Associated with Increased NUE (Table 1)

| Mir name | Mir Bind. Pos. | Hom. NCBI Accession | Annotation/Organism | Identity | p.p. SEQ ID NO: | p.n. SEQ ID NO: |
|---|---|---|---|---|---|---|
| osa-miR2096-3p | 95-115 | XP_002468137 | hypothetical protein SORBIDRAFT_01g040220 [*Sorghum bicolor*] > gi|241921991|gb|EER95135.1| hypothetical protein SORBIDRAFT_01g040220 [*Sorghum bicolor*] | 1.00 | 311 | 515 |
| | | ACN26598 | unknown [*Zea mays*] | 0.95 | 312 | 516 |
| | | NP_001148956 | LOC100282576 [*Zea mays*] > gi|195623616|gb|ACG33638.1| CONSTANS interacting protein 4 [*Zea mays*] | 0.95 | 313 | 517 |
| | | ACG37488 | CONSTANS interacting protein 4 [*Zea mays*] | 0.96 | 314 | 518 |
| | | NP_001148721 | CONSTANS interacting protein 4 [*Zea mays*] > gi|195621640|gb|ACG32650.1| CONSTANS interacting protein 4 [*Zea mays*] | 0.96 | 315 | 519 |
| | | NP_001049637 | Os03g0263800 [*Oryza sativa Japonica* Group] > gi|29893607|gb|AAP06861.1| unknown protein [*Oryza sativa Japonica* Group] > gi|108707320|gb|ABF95115.1| S-ribonuclease binding protein SBP1, putative, expressed [*Oryza sativa Japonica* Group] > gi|113548108|dbj|BAF11551.1| Os03g0263800 [*Oryza sativa Japonica* Group] > gi|215696696|dbj|BAG88116.1| unnamed protein product [*Oryza sativa Japonica* Group] | 0.89 | 316 | 520 |

TABLE 5-continued

Target Genes of miRNAs Associated with Increased NUE (Table 1)

| Mir name | Mir Bind. Pos. | Hom. NCBI Accession | Annotation/Organism | Identity | p.p. SEQ ID NO: | p.n. SEQ ID NO: |
|---|---|---|---|---|---|---|
| | | | > gi|215704492|dbj|BAG93926.1| unnamed protein product [*Oryza sativa Japonica* Group] > gi|222624614|gb|EEE58746.1| hypothetical protein OsJ_10235 [*Oryza sativa Japonica* Group] | | | |
| | | EEC74912 | hypothetical protein OsI_10851 [*Oryza sativa Indica* Group] | 0.88 | 317 | |
| | | BAJ94154 | predicted protein [*Hordeum vulgare* subsp. *vulgare*] > gi|326493392|dbj|BAJ85157.1| predicted protein [*Hordeum vulgare* subsp. *vulgare*] | 0.85 | 318 | 521 |
| Predicted zma mir 49161 | 292-314 | NP_001169860 | hypothetical protein LOC100383754 [*Zea mays*] > gi|224032063|gb|ACN35107.1| unknown [*Zea mays*] | 1.00 | 319 | 522 |
| | | XP_002458357 | hypothetical protein SORBIDRAFT_03g031980 [*Sorghum bicolor*] > gi|241930332|gb|EES03477.1| hypothetical protein SORBIDRAFT_03g031980 [*Sorghum bicolor*] | 0.88 | 320 | 523 |
| | 282-304 | ACN34890 | unknown [*Zea mays*] | 1.00 | 321 | 524 |
| | | EEC71328 | hypothetical protein OsI_03374 [*Oryza sativa Indica* Group] > gi|222619103|gb|EEE55235.1| hypothetical protein OsJ_03112 [*Oryza sativa Japonica* Group] | 0.74 | 322 | |
| | | BAD81811 | hypothetical protein [*Oryza sativa Japonica* Group] | 0.74 | 323 | 525 |
| | | BAJ90295 | predicted protein [*Hordeum vulgare* subsp. *vulgare*] | 0.74 | 324 | 526 |
| | 353-375 | XP_002458357 | hypothetical protein SORBIDRAFT_03g031980 [*Sorghum bicolor*] > gi|241930332|gb|EES03477.1| hypothetical protein SORBIDRAFT_03g031980 [*Sorghum bicolor*] | 1.00 | 325 | 527 |
| | | NP_001169860 | hypothetical protein LOC100383754 [*Zea mays*] > gi|224032063|gb|ACN35107.1| unknown [*Zea mays*] | 0.88 | 326 | 528 |
| Predicted zma mir 50460 | 982-1003 | XP_002446326 | hypothetical protein SORBIDRAFT_06g014320 [*Sorghum bicolor*] > gi|241937509|gb|EES10654.1| hypothetical protein SORBIDRAFT_06g014320 [*Sorghum bicolor*] | 1.00 | 327 | 529 |
| | | NP_001169348 | hypothetical protein LOC100383215 [*Zea mays*] > gi|224028855|gb|ACN33503.1| unknown [*Zea mays*] | 0.84 | 328 | 530 |
| | | ACN25775 | unknown [*Zea mays*] | 0.75 | 329 | 531 |
| | 426-447 | NP_001136483 | hypothetical protein LOC100216597 [*Zea mays*] > gi|194695886|gb|ACF82027.1| unknown [*Zea mays*] | 1.00 | 330 | 532 |
| | 295-316 | ACG40990 | RING-H2 finger protein ATL5I [*Zea mays*] | 1.00 | 331 | 533 |
| | | NP_001159129 | hypothetical protein LOC100304207 [*Zea mays*] > gi|223942155|gb|ACN25161.1| unknown [*Zea mays*] | 0.85 | 332 | 534 |

TABLE 5-continued

Target Genes of miRNAs Associated with Increased NUE (Table 1)

| Mir name | Mir Bind. Pos. | Hom. NCBI Accession | Annotation/Organism | Identity | p.p. SEQ ID NO: | p.n. SEQ ID NO: |
|---|---|---|---|---|---|---|
| | | NP_001130949 | hypothetical protein LOC100192054 [*Zea mays*] > gi|194690534|gb|ACF79351.1| unknown [*Zea mays*] | 0.77 | 333 | 535 |
| | | BAJ92353 | predicted protein [*Hordeum vulgare* subsp. *vulgare*] | 0.76 | 334 | 536 |
| | | NP_001057231 | Os06g0233200 [*Oryza sativa Japonica* Group] > gi|51535192|dbj|BAD38165.1| putative RING finger 1 [*Oryza sativa Japonica* Group] > gi|113595271|dbj|BAF19145.1| Os06g0233200 [*Oryza sativa Japonica* Group] > gi|125554660|gb|EAZ00266.1| hypothetical protein OsI_22277 [*Oryza sativa Indica* Group] > gi|215766038|dbj|BAG98266.1| unnamed protein product [*Oryza sativa Japonica* Group] > gi|222635260|gb|EEE65392.1| hypothetical protein OsJ_20714 [*Oryza sativa Japonica* Group] | 0.76 | 335 | 537 |
| | 154-175 | NP_001183617 | hypothetical protein LOC100502211 [*Zea mays*] > gi|238013474|gb|ACR37772.1| unknown [*Zea mays*] | 1.00 | 336 | 538 |
| | | XP_002465702 | hypothetical protein SORBIDRAFT_01g044080 [*Sorghum bicolor*] > gi|241919556|gb|EER92700.1| hypothetical protein SORBIDRAFT_01g044080 [*Sorghum bicolor*] | 0.73 | 337 | 539 |
| | 93-114 | NP_001152266 | BHLH transcription factor [*Zea mays*] > gi|195654447|gb|ACG46691.1| BHLH transcription factor [*Zea mays*] | 1.00 | 338 | 540 |
| | 1159-1180 | ACN25775 | unknown [*Zea mays*] | 1.00 | 339 | 541 |
| | | NP_001169348 | hypothetical protein LOC100383215 [*Zea mays*] > gi|224028855|gb|ACN33503.1| unknown [*Zea mays*] | 1.00 | 340 | 542 |
| | | XP_002446326 | hypothetical protein SORBIDRAFT_06g014320 [*Sorghum bicolor*] > gi|241937509|gb|EES10654.1| hypothetical protein SORBIDRAFT_06g014320 [*Sorghum bicolor*] | 0.80 | 341 | 543 |
| Predicted folded 24-nts-long seq 51695 | 1984-2007 | XP_002444807 | hypothetical protein SORBIDRAFT_07g028330 [*Sorghum bicolor*] > gi|241941157|gb|EES14302.1| hypothetical protein SORBIDRAFT_07g028330 [*Sorghum bicolor*] | 1.00 | 342 | 544 |
| | | NP_001169681 | hypothetical protein LOC100383562 [*Zea mays*] > gi|224030801|gb|ACN34476.1| unknown [*Zea mays*] > gi|224030845|gb|ACN34498.1| unknown [*Zea mays*] | 0.90 | 343 | 545 |
| Predicted zma mir 48457 | 584-606 | NP_001161741 | hypothetical protein LOC100192929 isoform 3 [*Zea mays*] > gi|226713359|sp|B6UGG4.1| NNJA4_MAIZE | 1.00 | 344 | 546 |

TABLE 5-continued

Target Genes of miRNAs Associated with Increased NUE (Table 1)

| Mir name | Mir Bind. Pos. | Hom. NCBI Accession | Annotation/Organism | Identity | p.p. SEQ ID NO: | p.n. SEQ ID NO: |
|---|---|---|---|---|---|---|
| | | | RecName: Full = Ninja-family protein 4<br>> gi|195657959|gb|ACG48447.1| hypothetical protein [*Zea mays*] | | | |
| | | NP_001161740 | hypothetical protein LOC100192929 isoform 2 [*Zea mays*]<br>> gi|226713259|sp|B4FM28.1| NNJA2_MAIZE RecName: Full = Ninja-family protein 2<br>> gi|194698174|gb|ACF83171.1| unknown [*Zea mays*] | 1.00 | 345 | 547 |
| | | B6SLJ0 | RecName: Full = Ninja-family protein 3<br>> gi|195607786|gb|ACG25723.1| hypothetical protein [*Zea mays*] | 0.98 | 346 | |
| | | ACN33721 | unknown [*Zea mays*] | 0.97 | 347 | 548 |
| | 62-84 | B6SLJ0 | RecName: Full = Ninja-family protein 3<br>> gi|195607786|gb|ACG25723.1| hypothetical protein [*Zea mays*] | 1.00 | 348 | |
| | | NP_001161740 | hypothetical protein LOC100192929 isoform 2 [*Zea mays*]<br>> gi|226713259|sp|B4FM28.1| NNJA2_MAIZE RecName: Full = Ninja-family protein 2<br>> gi|194698174|gb|ACF83171.1| unknown [*Zea mays*] | 0.98 | 349 | 549 |
| | | ACN33721 | unknown [*Zea mays*] | 0.95 | 350 | 550 |
| | | NP_001161741 | hypothetical protein LOC100192929 isoform 3 [*Zea mays*]<br>> gi|226713359|sp|B6UGG4.1| NNJA4_MAIZE RecName: Full = Ninja-family protein 4<br>> gi|195657959|gb|ACG48447.1| hypothetical protein [*Zea mays*] | 0.97 | 351 | 551 |
| | 543-565 | NP_001161740 | hypothetical protein LOC100192929 isoform 2 [*Zea mays*]<br>> gi|226713259|sp|B4FM28.1| NNJA2_MAIZE RecName: Full = Ninja-family protein 2<br>> gi|194698174|gb|ACF83171.1| unknown [*Zea mays*] | 1.00 | 352 | 552 |
| | | ACN33721 | unknown [*Zea mays*] | 0.97 | 353 | 553 |
| | | NP_001161741 | hypothetical protein LOC100192929 isoform 3 [*Zea mays*]<br>> gi|226713359|sp|B6UGG4.1| NNJA4_MAIZE RecName: Full = Ninja-family protein 4<br>> gi|195657959|gb|ACG48447.1| hypothetical protein [*Zea mays*] | 0.99 | 354 | 554 |
| | | B6SLJ0 | RecName: Full = Ninja-family protein 3<br>> gi|195607786|gb|ACG25723.1| hypothetical protein [*Zea mays*] | 0.98 | 355 | |

TABLE 5-continued

Target Genes of miRNAs Associated with Increased NUE (Table 1)

| Mir name | Mir Bind. Pos. | Hom. NCBI Accession | Annotation/Organism | Identity | p.p. SEQ ID NO: | p.n. SEQ ID NO: |
|---|---|---|---|---|---|---|
| | 450-472 | NP_001131584 | hypothetical protein LOC100192929 isoform 1 [*Zea mays*] > gi|226713190|sp|B4FAF3.1| NNJA1_MAIZE RecName: Full = Ninja-family protein 1 > gi|194690024|gb|ACF79096.1| unknown [*Zea mays*] > gi|194691932|gb|ACF80050.1| unknown [*Zea mays*] > gi|195638284|gb|ACG38610.1| hypothetical protein [*Zea mays*] | 1.00 | 356 | 555 |
| | | XP_002465644 | hypothetical protein SORBIDRAFT_01g042880 [*Sorghum bicolor*] > gi|241919498|gb|EER92642.1| hypothetical protein SORBIDRAFT_01g042880 [*Sorghum bicolor*] | 0.83 | 357 | 556 |
| Predicted zma mir 50261 | 1313-1334 | NP_001182893 | hypothetical protein LOC100501172 [*Zea mays*] > gi|238008020|gb|ACR35045.1| unknown [*Zea mays*] | 1.00 | 358 | 557 |
| Predicted folded 24-nts-long seq 52805 | 86-109 | XP_002447337 | hypothetical protein SORBIDRAFT_06g033160 [*Sorghum bicolor*] > gi|241938520|gb|EES11665.1| hypothetical protein SORBIDRAFT_06g033160 [*Sorghum bicolor*] | 1.00 | 359 | 558 |
| | | NP_001142056 | hypothetical protein LOC100274212 [*Zea mays*] > gi|194706940|gb|ACF87554.1| unknown [*Zea mays*] > gi|223947485|gb|ACN27826.1| unknown [*Zea mays*] | 0.96 | 360 | 559 |
| | | ACG45259 | hypothetical protein [*Zea mays*] | 0.96 | 361 | 560 |
| | | EEC78262 | hypothetical protein OsI_17948 [*Oryza sativa* Indica Group] | 0.86 | 362 | |
| | | EEE61915 | hypothetical protein OsJ_16648 [*Oryza sativa* Japonica Group] | 0.86 | 363 | |
| | | BAJ96591 | predicted protein [*Hordeum vulgare* subsp. *vulgare*] | 0.86 | 364 | 561 |
| | | CAJ86266 | H0901F07.3 [*Oryza sativa* Indica Group] | 0.76 | 365 | 562 |
| | 596-619 | AAY57857 | cysteine proteinase inhibitor [*Zea mays* subsp. *parviglumis*] > gi|66866419|gb|AAY57858.1| cysteine proteinase inhibitor [*Zea mays* subsp. *parviglumis*] > gi|66866423|gb|AAY57860.1| cysteine proteinase inhibitor [*Zea mays* subsp. *parviglumis*] > gi|66866425|gb|AAY57861.1| cysteine proteinase inhibitor [*Zea mays* subsp. *parviglumis*] > gi|66866427|gb|AAY57862.1| cysteine proteinase inhibitor [*Zea mays* subsp. *parviglumis*] > gi|66866429|gb|AAY57863.1| cysteine proteinase inhibitor [*Zea mays* subsp. *parviglumis*] | 1.00 | 366 | 563 |

TABLE 5-continued

Target Genes of miRNAs Associated with Increased NUE (Table 1)

| Mir name | Mir Bind. Pos. | Hom. NCBI Accession | Annotation/Organism | Identity | p.p. SEQ ID NO: | p.n. SEQ ID NO: |
|---|---|---|---|---|---|---|
| | | | > gi|66866435|gb|AAY57866.1| cysteine proteinase inhibitor [*Zea mays* subsp. *parviglumis*] | | | |
| | | AAY57867 | cysteine proteinase inhibitor [*Zea mays* subsp. *parviglumis*] | 0.99 | 367 | 564 |
| | | ABQ32295 | cysteine protease inhibitor [*Zea mays*] | 0.99 | 368 | 565 |
| | | AAY57864 | cysteine proteinase inhibitor [*Zea mays* subsp. *parviglumis*] > gi|66866439|gb|AAY57868.1| cysteine proteinase inhibitor [*Zea mays* subsp. *parviglumis*] | 0.96 | 369 | 566 |
| | | AAY57859 | cysteine proteinase inhibitor [*Zea mays* subsp. *parviglumis*] | 0.98 | 370 | 567 |
| | | BAA09666 | cysteine proteinase inhibitor [*Zea mays*] > gi|66866433|gb|AAY57865.1| cysteine proteinase inhibitor [*Zea mays* subsp. *parviglumis*] > gi|71794635|emb|CAJ20024.1| putative cystatin [*Zea mays*] | 0.95 | 371 | 568 |
| | | CAA60610 | cysteine proteinase inhibitor [*Zea mays*] | 0.94 | 372 | 569 |
| | | NP_001106013 | cystatin2 [*Zea mays*] > gi|1008922|dbj|BAA07327.1| cystatin II [*Zea mays*] | 0.94 | 373 | 570 |
| | | BAB21558 | cystatin [*Coix lacryma-jobi*] | 0.86 | 374 | 571 |
| | | NP_001105295 | cystatin-1 precursor [*Zea mays*] > gi|399334|sp|P31726.1|CYT1_MAIZE RecName: Full = Cystatin-1; AltName: Full = Corn kernel cysteine proteinase inhibitor; AltName: Full = Cystatin I; Flags: Precursor > gi|217962|dbj|BAA01472.1| corn cystatin I [*Zea mays*] | 0.84 | 375 | 572 |
| | 2324-2347 | BAJ85758 | predicted protein [*Hordeum vulgare* subsp. *vulgare*] | 1.00 | 376 | 573 |
| | | NP_001044791 | Os01g0846600 [*Oryza sativa* Japonica Group] > gi|15408875|dbj|BAB64266.1| ankyrin-like protein [*Oryza sativa* Japonica Group] > gi|20160625|dbj|BAB89571.1| ankyrin-like protein [*Oryza sativa* Japonica Group] > gi|113534322|dbj|BAF06705.1| Os01g0846600 [*Oryza sativa* Japonica Group] > gi|215687255|dbj|BAG91820.1| unnamed protein product [*Oryza sativa* Japonica Group] > gi|222619533|gb|EEE55665.1| hypothetical protein OsJ_04065 [*Oryza sativa* Japonica Group] | 0.81 | 377 | 574 |
| | | XP_002458754 | hypothetical protein SORBIDRAFT_03g039680 [*Sorghum bicolor*] > gi|241930729|gb|EES03874.1| hypothetical protein | 0.81 | 378 | 575 |

TABLE 5-continued

Target Genes of miRNAs Associated with Increased NUE (Table 1)

| Mir name | Mir Bind. Pos. | Hom. NCBI Accession | Annotation/Organism | Identity | p.p. SEQ ID NO: | p.n. SEQ ID NO: |
|---|---|---|---|---|---|---|
| | | | SORBIDRAFT_03g039680 [*Sorghum bicolor*] | | | |
| | | ACR35053 | unknown [*Zea mays*] | 0.81 | 379 | 576 |
| | | NP_001147927 | LOC100281537 [*Zea mays*] > gi|195614640|gb|ACG29150.1| ankyrin-like protein [*Zea mays*] | 0.79 | 380 | 577 |
| Predicted folded 24-nts-long seq 51469 | 1320-1343 | XP_002457719 | hypothetical protein SORBIDRAFT_03g012350 [*Sorghum bicolor*] > gi|241929694|gb|EES02839.1| hypothetical protein SORBIDRAFT_03g012350 [*Sorghum bicolor*] | 1.00 | 381 | 578 |
| | | NP_001183022 | hypothetical protein LOC100501344 [*Zea mays*] > gi|238008824|gb|ACR35447.1| unknown [*Zea mays*] | 0.85 | 382 | 579 |
| | | XP_002457721 | hypothetical protein SORBIDRAFT_03g012360 [*Sorghum bicolor*] > gi|241929696|gb|EES02841.1| hypothetical protein SORBIDRAFT_03g012360 [*Sorghum bicolor*] | 0.77 | 383 | 580 |
| | | XP_002457722 | hypothetical protein SORBIDRAFT_03g012370 [*Sorghum bicolor*] > gi|241929697|gb|EES02842.1| hypothetical protein SORBIDRAFT_03g012370 [*Sorghum bicolor*] | 0.73 | 384 | 581 |
| zma-miR399f* | 158-179 | NP_001147885 | LOC100281495 [*Zea mays*] > gi|195611982|gb|ACG27821.1| citrate transporter family protein [*Zea mays*] > gi|195614372|gb|ACG29016.1| citrate transporter family protein [*Zea mays*] | 1.00 | 385 | 582 |
| | | ACF86945 | unknown [*Zea mays*] | 0.93 | 386 | 583 |
| | | ACG28034 | citrate transporter family protein [*Zea mays*] | 0.98 | 387 | 584 |
| | | NP_001048962 | Os03g0147400 [*Oryza sativa* Japonica Group] > gi|15451603|gb|AAK98727.1| AC090485_6 Putative anion transporter [*Oryza sativa* Japonica Group] > gi|108706182|gb|ABF93977.1| transmembrane protein, putative, expressed [*Oryza sativa* Japonica Group] > gi|108706183|gb|ABF93978.1| transmembrane protein, putative, expressed [*Oryza sativa* Japonica Group] > gi|108706184|gb|ABF93979.1| transmembrane protein, putative, expressed [*Oryza sativa* Japonica Group] > gi|108706185|gb|ABF93980.1| transmembrane protein, putative, expressed [*Oryza sativa* Japonica Group] > gi|13547433|dbj|BAF10876.1| Os03g0147400 [*Oryza sativa* Japonica Group] > gi|125542408|gb|EAY88547.1| hypothetical protein | 0.80 | 388 | 585 |

TABLE 5-continued

Target Genes of miRNAs Associated with Increased NUE (Table 1)

| Mir name | Mir Bind. Pos. | Hom. NCBI Accession | Annotation/Organism | Identity | p.p. SEQ ID NO: | p.n. SEQ ID NO: |
|---|---|---|---|---|---|---|
| | | EAY78724 | OsI_10021 [*Oryza sativa Indica* Group] > gi\|125584918\|gb\|EAZ25582.1\| hypothetical protein OsJ_09409 [*Oryza sativa Japonica* Group] hypothetical protein OsI_33828 [*Oryza sativa Indica* Group] > gi\|125574971\|gb\|EAZ16255.1\| hypothetical protein OsJ_31712 [*Oryza sativa Japonica* Group] | 0.83 | 389 | |
| | | NP_001151517 | LOC100285151 [*Zea mays*] > gi\|195647360\|gb\|ACG43148.1\| citrate transporter family protein [*Zea mays*] > gi\|223948219\|gb\|ACN28193.1\| unknown [*Zea mays*] > gi\|223974939\|gb\|ACN31657.1\| unknown [*Zea mays*] > gi\|238009364\|gb\|ACR35717.1\| unknown [*Zea mays*] | 0.80 | 390 | 586 |
| | | ACG43196 | citrate transporter family protein [*Zea mays*] | 0.80 | 391 | 587 |
| | | ACL54556 | unknown [*Zea mays*] | 0.77 | 392 | 588 |
| | | BAK05230 | predicted protein [*Hordeum vulgare* subsp. *vulgare*] | 0.78 | 393 | 589 |
| | | BAK06146 | predicted protein [*Hordeum vulgare* subsp. *vulgare*] | 0.78 | 394 | 590 |
| | 650-671 | XP_002460963 | hypothetical protein SORBIDRAFT_02g038300 [*Sorghum bicolor*] > gi\|241924340\|gb\|EER97484.1\| hypothetical protein SORBIDRAFT_02g038300 [*Sorghum bicolor*] | 1.00 | 395 | 591 |
| | | NP_001148467 | LOC100282082 [*Zea mays*] > gi\|195619570\|gb\|ACG31615.1\| saccharopine dehydrogenase [*Zea mays*] | 0.92 | 396 | 592 |
| | | EAZ04584 | hypothetical protein OsI_26734 [*Oryza sativa Indica* Group] | 0.79 | 397 | |
| | | BAJ97022 | predicted protein [*Hordeum vulgare* subsp. *vulgare*] | 0.79 | 398 | 593 |
| | | EAZ40532 | hypothetical protein OsJ_24988 [*Oryza sativa Japonica* Group] | 0.73 | 399 | |
| Predicted folded 24-nts-long seq 52499 | 2327-2350 | NP_001169325 | hypothetical protein LOC100383191 [*Zea mays*] > gi\|224028683\|gb\|ACN33417.1\| unknown [*Zea mays*] | 1.00 | 400 | 594 |
| | | XP_002447125 | hypothetical protein SORBIDRAFT_06g029090 [*Sorghum bicolor*] > gi\|241938308\|gb\|EES11453.1\| hypothetical protein SORBIDRAFT_06g029090 [*Sorghum bicolor*] | 0.98 | 401 | 595 |
| Predicted zma mir 50545 | 287-306 | XP_002447878 | hypothetical protein SORBIDRAFT_06g017360 [*Sorghum bicolor*] > gi\|241939061\|gb\|EES12206.1\| hypothetical protein SORBIDRAFT_06g017360 [*Sorghum bicolor*] | 1.00 | 402 | 596 |
| | | NP_001151469 | translocon Tic40 [*Zea mays*] > gi\|219887501\|gb\|ACL54125.1\| unknown [*Zea mays*] | 0.90 | 403 | 597 |

TABLE 5-continued

Target Genes of miRNAs Associated with Increased NUE (Table 1)

| Mir name | Mir Bind. Pos. | Hom. NCBI Accession | Annotation/Organism | Identity | p.p. SEQ ID NO: | p.n. SEQ ID NO: |
|---|---|---|---|---|---|---|
| | | ACG42966 | translocon Tic40 [*Zea mays*] | 0.90 | 404 | 598 |
| | | NP_001149949 | translocon Tic40 [*Zea mays*] > gi|195635683|gb|ACG37310.1| translocon Tic40 [*Zea mays*] | 0.90 | 405 | 599 |
| | | NP_001052871 | Os04g0439900 [*Oryza sativa Japonica* Group] > gi|113564442|dbj|BAF14785.1| Os04g0439900 [*Oryza sativa Japonica* Group] > gi|116309806|emb|CAH66845.1| H0525C06.8 [*Oryza sativa Indica* Group] > gi|215704350|dbj|BAG93784.1| unnamed protein product [*Oryza sativa Japonica* Group] > gi|218194904|gb|EEC77331.1| hypothetical protein OsI_16005 [*Oryza sativa Indica* Group] > gi|222628923|gb|EEE61055.1| hypothetical protein OsJ_14912 [*Oryza sativa Japonica* Group] | 0.81 | 406 | 600 |
| | | BAJ97578 | predicted protein [*Hordeum vulgare* subsp. *vulgare*] | 0.78 | 407 | 601 |
| | 46-65 | NP_001182915 | hypothetical protein LOC100501201 [*Zea mays*] > gi|238008164|gb|ACR35117.1| unknown [*Zea mays*] | 1.00 | 408 | 602 |
| | | ACN33347 | unknown [*Zea mays*] | 0.84 | 409 | 603 |
| | | NP_001150079 | CID11 [*Zea mays*] > gi|195636508|gb|ACG37722.1| CID11 [*Zea mays*] | 0.83 | 410 | 604 |
| | | XP_002444926 | hypothetical protein SORBIDRAFT_07g001560 [*Sorghum bicolor*] > gi|241941276|gb|EES14421.1| hypothetical protein SORBIDRAFT_07g001560 [*Sorghum bicolor*] | 0.78 | 411 | 605 |
| | | BAD33089 | putative RNA-binding protein RBP37 [*Oryza sativa Japonica* Group] > gi|182375457|dbj|BAG24017.1| RNA-binding protein [*Oryza sativa Japonica* Group] > gi|215736921|dbj|BAG95850.1| unnamed protein product [*Oryza sativa Japonica* Group] > gi|222639804|gb|EEE67936.1| hypothetical protein OsJ_25822 [*Oryza sativa Japonica* Group] | 0.74 | 412 | |
| | | EEC82815 | hypothetical protein OsI_27601 [*Oryza sativa Indica* Group] | 0.72 | 413 | |
| | | BAJ96189 | predicted protein [*Hordeum vulgare* subsp. *vulgare*] | 0.75 | 414 | 606 |
| | | XP_002518926 | RNA-binding protein, putative [*Ricinus communis*] > gi|223541913|gb|EEF43459.1| RNA-binding protein, putative [*Ricinus communis*] | 0.75 | 415 | 607 |
| | | XP_002272223 | PREDICTED: hypothetical protein [*Vitis vinifera*] > gi|302143972|emb|CBI23077.3| unnamed protein product [*Vitis vinifera*] | 0.75 | 416 | 608 |

TABLE 5-continued

Target Genes of miRNAs Associated with Increased NUE (Table 1)

| Mir name | Mir Bind. Pos. | Hom. NCBI Accession | Annotation/Organism | Identity | p.p. SEQ ID NO: | p.n. SEQ ID NO: |
|---|---|---|---|---|---|---|
| | 605-624 | NP_001142867 | hypothetical protein LOC100275266 [Zea mays] > gi|195610696|gb|ACG27178.1| hypothetical protein [Zea mays] | 1.00 | 417 | 609 |
| | | XP_002448750 | hypothetical protein SORBIDRAFT_06g032540 [Sorghum bicolor] > gi|241939933|gb|EES13078.1| hypothetical protein SORBIDRAFT_06g032540 [Sorghum bicolor] | 0.83 | 418 | 610 |
| | | NP_001143447 | hypothetical protein LOC100276102 [Zea mays] > gi|195620654|gb|ACG32157.1| hypothetical protein [Zea mays] | 0.78 | 419 | 611 |
| | | NP_001054225 | Os04g0672300 [Oryza sativa Japonica Group] > gi|90265231|emb|CAH67766.1| H0322F07.3 [Oryza sativa Indica Group] > gi|113565796|dbj|BAF16139.1| Os04g0672300 [Oryza sativa Japonica Group] > gi|215715224|dbj|BAG94975.1| unnamed protein product [Oryza sativa Japonica Group] | 0.72 | 420 | 612 |
| | 360-379 | NP_001043014 | Os01g0358300 [Oryza sativa Japonica Group] > gi|53791615|dbj|BAD52962.1| unknown protein [Oryza sativa Japonica Group] > gi|113532545|dbj|BAF04928.1| Os01g0358300 [Oryza sativa Japonica Group] > gi|215765732|dbj|BAG87429.1| unnamed protein product [Oryza sativa Japonica Group] > gi|218188197|gb|EEC70624.1| hypothetical protein OsI_01883 [Oryza sativa Indica Group] > gi|222618419|gb|EEE54551.1| hypothetical protein OsJ_01736 [Oryza sativa Japonica Group] | 1.00 | 421 | 613 |
| | | ACF87799 | unknown [Zea mays] | 0.86 | 422 | 614 |
| | | ACN30638 | unknown [Zea mays] | 0.85 | 423 | 615 |
| | | BAJ94646 | predicted protein [Hordeum vulgare subsp. vulgare] | 0.84 | 424 | 616 |
| | 557-576 | XP_002455496 | hypothetical protein SORBIDRAFT_03g011990 [Sorghum bicolor] > gi|241927471|gb|EES00616.1| hypothetical protein SORBIDRAFT_03g011990 [Sorghum bicolor] | 1.00 | 425 | 617 |
| | | XP_002457709 | hypothetical protein SORBIDRAFT_03g011980 [Sorghum bicolor] > gi|241929684|gb|EES02829.1| hypothetical protein SORBIDRAFT_03g011980 [Sorghum bicolor] | 0.98 | 426 | 618 |
| | | ACN26409 | unknown [Zea mays] | 0.93 | 427 | 619 |
| | | ACN27987 | unknown [Zea mays] | 0.93 | 428 | 620 |
| | | NP_001152255 | peroxidase 1 [Zea mays] > gi|195654333|gb|ACG46634.1| peroxidase 1 precursor [Zea mays] | 0.93 | 429 | 621 |

TABLE 5-continued

Target Genes of miRNAs Associated with Increased NUE (Table 1)

| Mir name | Mir Bind. Pos. | Hom. NCBI Accession | Annotation/Organism | Identity | p.p. SEQ ID NO: | p.n. SEQ ID NO: |
|---|---|---|---|---|---|---|
| | | EAY73614 | hypothetical protein OsI_01501 [*Oryza sativa Indica* Group] | 0.81 | 430 | |
| | | NP_001042800 | Os01g0294700 [*Oryza sativa Japonica* Group] > gi|9909174|dbj|BAB12033.1| putative peroxidase [*Oryza sativa Japonica* Group] > gi|55700889|tpe|CAH69254.1| TPA: class III peroxidase 11 precursor [*Oryza sativa Japonica* Group] > gi|113532331|dbj|BAF04714.1| Os01g0294700 [*Oryza sativa Japonica* Group] > gi|215697074|dbj|BAG91068.1| unnamed protein product [*Oryza sativa Japonica* Group] > gi|215737508|dbj|BAG96638.1| unnamed protein product [*Oryza sativa Japonica* Group] > gi|215740794|dbj|BAG96950.1| unnamed protein product [*Oryza sativa Japonica* Group] | 0.81 | 431 | 622 |
| | | EEE54389 | hypothetical protein OsJ_01407 [*Oryza sativa Japonica* Group] | 0.76 | 432 | |
| | 517-536 | ACN27987 | unknown [*Zea mays*] | 1.00 | 433 | 623 |
| | | NP_001152255 | peroxidase 1 [*Zea mays*] > gi|195654333|gb|ACG46634.1| peroxidase 1 precursor [*Zea mays*] | 1.00 | 434 | 624 |
| | | ACN26409 | unknown [*Zea mays*] | 0.94 | 435 | 625 |
| | | XP_002457709 | hypothetical protein SORBIDRAFT_03g011980 [*Sorghum bicolor*] > gi|241929684|gb|EES02829.1| hypothetical protein SORBIDRAFT_03g011980 [*Sorghum bicolor*] | 0.93 | 436 | 626 |
| | | XP_002455496 | hypothetical protein SORBIDRAFT_03g011990 [*Sorghum bicolor*] > gi|241927471|gb|EES00616.1| hypothetical protein SORBIDRAFT_03g011990 [*Sorghum bicolor*] | 0.93 | 437 | 627 |
| | | EAY73614 | hypothetical protein OsI_01501 [*Oryza sativa Indica* Group] | 0.81 | 438 | |
| | | NP_001042800 | Os01g0294700 [*Oryza sativa Japonica* Group] > gi|9909174|dbj|BAB12033.1| putative peroxidase [*Oryza sativa Japonica* Group] > gi|55700889|tpe|CAH69254.1| TPA: class III peroxidase 11 precursor [*Oryza sativa Japonica* Group] > gi|113532331|dbj|BAF04714.1| Os01g0294700 [*Oryza sativa Japonica* Group] > gi|215697074|dbj|BAG91068.1| unnamed protein product [*Oryza sativa Japonica* Group] | 0.81 | 439 | 628 |

TABLE 5-continued

Target Genes of miRNAs Associated with Increased NUE (Table 1)

| Mir name | Mir Bind. Pos. | Hom. NCBI Accession | Annotation/Organism | Identity | p.p. SEQ ID NO: | p.n. SEQ ID NO: |
|---|---|---|---|---|---|---|
| | | | > gi|215737508|dbj|BAG96638.1| unnamed protein product [Oryza sativa Japonica Group] > gi|215740794|dbj|BAG96950.1| unnamed protein product [Oryza sativa Japonica Group] | | | |
| | | EEE54389 | hypothetical protein OsJ_01407 [Oryza sativa Japonica Group] | 0.76 | 440 | |
| | 286-305 | ACG31680 | pepsin A [Zea mays] | 1.00 | 441 | 629 |
| | | NP_001141522 | hypothetical protein LOC100273634 [Zea mays] > gi|194704920|gb|ACF86544.1| unknown [Zea mays] > gi|223949445|gb|ACN28806.1| unknown [Zea mays] | 0.99 | 442 | 630 |
| | | ACL54367 | unknown [Zea mays] | 0.99 | 443 | 631 |
| | | NP_001132197 | hypothetical protein LOC100193625 [Zea mays] > gi|194693730|gb|ACF80949.1| unknown [Zea mays] > gi|195605492|gb|ACG24576.1| pepsin A [Zea mays] | 0.89 | 444 | 632 |
| | | NP_001048134 | Os02g0751100 [Oryza sativa Japonica Group] > gi|46390211|dbj|BAD15642.1| aspartyl protease-like [Oryza sativa Japonica Group] > gi|113537665|dbj|BAF10048.1| Os02g0751100 [Oryza sativa Japonica Group] > gi|222623681|gb|EEE57813.1| hypothetical protein OsJ_08401 [Oryza sativa Japonica Group] | 0.80 | 445 | 633 |
| | | EEC74016 | hypothetical protein OsI_08957 [Oryza sativa Indica Group] | 0.79 | 446 | |
| | | ACN27411 | unknown [Zea mays] | 0.77 | 447 | 634 |
| | | BAK05106 | predicted protein [Hordeum vulgare subsp. vulgare] | 0.75 | 448 | 635 |
| | 309-328 | NP_001143133 | hypothetical protein LOC100275611 [Zea mays] > gi|195614826|gb|ACG29243.1| hypothetical protein [Zea mays] | 1.00 | 449 | 636 |
| | | ACF83002 | unknown [Zea mays] | 0.99 | 450 | 637 |
| | | BAJ87435 | predicted protein [Hordeum vulgare subsp. vulgare] | 0.72 | 451 | 638 |
| | 46-65 | XP_002444926 | hypothetical protein SORBIDRAFT_07g001560 [Sorghum bicolor] > gi|241941276|gb|EES14421.1| hypothetical protein SORBIDRAFT_07g001560 [Sorghum bicolor] | 1.00 | 452 | 639 |
| | | ACN33347 | unknown [Zea mays] | 0.85 | 453 | 640 |
| | | NP_001182915 | hypothetical protein LOC100501201 [Zea mays] > gi|238008164|gb|ACR35117.1| unknown [Zea mays] | 0.87 | 454 | 641 |
| | | NP_001150079 | CID11 [Zea mays] > gi|195636508|gb|ACG37722.1| CID11 [Zea mays] | 0.86 | 455 | 642 |
| | | BAD33089 | putative RNA-binding protein RBP37 [Oryza sativa Japonica Group] > gi|182375457|dbj|BAG24017.1| | 0.75 | 456 | |

TABLE 5-continued

Target Genes of miRNAs Associated with Increased NUE (Table 1)

| Mir name | Mir Bind. Pos. | Hom. NCBI Accession | Annotation/Organism | Identity | p.p. SEQ ID NO: | p.n. SEQ ID NO: |
|---|---|---|---|---|---|---|
| | | | RNA-binding protein [*Oryza sativa Japonica* Group] > gi|215736921|dbj|BAG95850.1| unnamed protein product [*Oryza sativa Japonica* Group] > gi|222639804|gb|EEE67936.1| hypothetical protein OsJ_25822 [*Oryza sativa Japonica* Group] | | | |
| | | EEC82815 | hypothetical protein OsI_27601 [*Oryza sativa Indica* Group] | 0.72 | 457 | |
| | 40563 | NP_001059821 | Os07g0524100 [*Oryza sativa Japonica* Group] > gi|75118816|sp|Q69SA9.1| PDI54_ORYSJ RecName: Full = Protein disulfide isomerase-like 5-4; Short = OsPDIL5-4; AltName: Full = Protein disulfide isomerase-like 8-1; Short = OsPDIL8-1; Flags: Precursor > gi|50508559|dbj|BAD30858.1| thioredoxin family-like protein [*Oryza sativa Japonica* Group] > gi|113611357|dbj|BAF21735.1| Os07g0524100 [*Oryza sativa Japonica* Group] > gi|215704615|dbj|BAG94243.1| unnamed protein product [*Oryza sativa Japonica* Group] > gi|218199742|gb|EEC82169.1| hypothetical protein OsI_26259 [*Oryza sativa Indica* Group] > gi|222637167|gb|EEE67299.1| hypothetical protein OsJ_24505 [*Oryza sativa Japonica* Group] | 1.00 | 458 | 643 |
| | | BAJ86285 | predicted protein [*Hordeum vulgare* subsp. *vulgare*] | 0.93 | 459 | 644 |
| | | CBG91903 | putative PDI-like protein [*Triticum aestivum*] > gi|299469398|emb|CBG91917.1| putative PDI-like protein [*Triticum aestivum*] | 0.93 | 460 | |
| | | ACG39185 | PDIL5-4-*Zea mays* protein disulfide isomerase | 0.91 | 461 | 645 |
| | | NP_001105762 | protein disulfide isomerase12 [*Zea mays*] > gi|59861281|gb|AAX09970.1| protein disulfide isomerase [*Zea mays*] | 0.91 | 462 | 646 |
| | | ACN34146 | unknown [*Zea mays*] | 0.91 | 463 | 647 |
| | | XP_002522864 | thioredoxin domain-containing protein, putative [*Ricinus communis*] > gi|223537948|gb|EEF39562.1| thioredoxin domain-containing protein, putative [*Ricinus communis*] | 0.76 | 464 | 648 |
| | | XP_002281649 | PREDICTED: hypothetical protein [*Vitis vinifera*] > gi|297735969|emb|CBI23943.3| unnamed protein product [*Vitis vinifera*] | 0.74 | 465 | 649 |

TABLE 5-continued

Target Genes of miRNAs Associated with Increased NUE (Table 1)

| Mir name | Mir Bind. Pos. | Hom. NCBI Accession | Annotation/Organism | Identity | p.p. SEQ ID NO: | p.n. SEQ ID NO: |
|---|---|---|---|---|---|---|
| | | XP_002319814 | predicted protein [*Populus trichocarpa*] > gi|222858190|gb|EEE95737.1| predicted protein [*Populus trichocarpa*] | 0.74 | 466 | 650 |
| | | XP_002317580 | predicted protein [*Populus trichocarpa*] > gi|222860645|gb|EEE98192.1| predicted protein [*Populus trichocarpa*] | 0.74 | 467 | 651 |
| | 301-320 | ACF87799 | unknown [*Zea mays*] | 1.00 | 468 | 652 |
| | | ACN30638 | unknown [*Zea mays*] | 0.97 | 469 | 653 |
| | | NP_001043014 | Os01g0358300 [*Oryza sativa Japonica* Group] > gi|53791615|dbj|BAD52962.1| unknown protein [*Oryza sativa Japonica* Group] > gi|113532545|dbj|BAF04928.1| Os01g0358300 [*Oryza sativa Japonica* Group] > gi|215765732|dbj|BAG87429.1| unnamed protein product [*Oryza sativa Japonica* Group] > gi|218188197|gb|EEC70624.1| hypothetical protein OsI_01883 [*Oryza sativa Indica* Group] > gi|222618419|gb|EEE54551.1| hypothetical protein OsJ_01736 [*Oryza sativa Japonica* Group] | 0.87 | 470 | 654 |
| | | BAJ94646 | predicted protein [*Hordeum vulgare* subsp. *vulgare*] | 0.83 | 471 | 655 |
| Predicted zma mir 48350 | 40752 | ACF86440 | unknown [*Zea mays*] | 1.00 | 472 | 656 |
| | 22-43 | ABF67946 | putative Opie4 pol protein [*Zea mays*] | 1.00 | 473 | |
| | | AAC49502 | Pol [*Zea mays*] | 0.97 | 474 | 657 |
| | | ABF67947 | Opie2 pol protein [*Zea mays*] | 0.96 | 475 | |
| | | ABF67934 | Opie3 pol polyprotein [*Zea mays*] | 0.96 | 476 | |
| | | AAL35396 | Opie2a pol [*Zea mays*] > gi|168251075|gb|ACA21858.1| Opie2a pol protein [*Zea mays*] | 0.92 | 477 | |
| | | ABF67921 | Ji1 putative pol protein [*Zea mays*] | 0.79 | 478 | |
| | | AAD20307 | copia-type pol polyprotein [*Zea mays*] | 0.79 | 479 | |
| Predicted zma mir 49162 | 810-831 | XP_002455047 | hypothetical protein SORBIDRAFT_03g003530 [*Sorghum bicolor*] > gi|241927022|gb|EES00167.1| hypothetical protein SORBIDRAFT_03g003530 [*Sorghum bicolor*] | 1.00 | 480 | 658 |
| | | AAK51797 | small heat shock protein HSP17.8 [*Triticum aestivum*] | 0.83 | 481 | 659 |
| | | BAJ86365 | predicted protein [*Hordeum vulgare* subsp. *vulgare*] | 0.82 | 482 | 660 |
| | | NP_001105954 | 17.8 kDa class II heat shock protein [*Zea mays*] > gi|123553|sp|P24632.1|HSP22_MAIZE RecName: Full = 17.8 kDa class II heat shock protein > gi|22337|emb|CAA38012.1| 18 kDa heat shock protein [*Zea mays*] | 0.87 | 483 | 661 |

TABLE 5-continued

Target Genes of miRNAs Associated with Increased NUE (Table 1)

| Mir name | Mir Bind. Pos. | Hom. NCBI Accession | Annotation/Organism | Identity | p.p. SEQ ID NO: | p.n. SEQ ID NO: |
|---|---|---|---|---|---|---|
| | | | > gi|238009918|gb|ACR35994.1| unknown [*Zea mays*] > gi|238015198|gb|ACR38634.1| unknown [*Zea mays*] | | | |
| | | CAI96500 | 17.6 kDa heat-shock protein [*Triticum turgidum* subsp. *dicoccon*] | 0.83 | 484 | 662 |
| | | BAK07165 | predicted protein [*Hordeum vulgare* subsp. *vulgare*] | 0.81 | 485 | 663 |
| | | CAI96499 | 17.5 kDa heat-shock protein [*Triticum turgidum* subsp. *dicoccoides*] | 0.81 | 486 | 664 |
| | | CAI96501 | 17.6 kDa heat-shock protein [*Triticum turgidum* subsp. *durum*] | 0.82 | 487 | 665 |
| | | NP_001148454 | 17.5 kDa class II heat shock protein [*Zea mays*] > gi|195619384|gb|ACG31522.1| 17.5 kDa class II heat shock protein [*Zea mays*] | 0.87 | 488 | 666 |
| | | BAK05681 | predicted protein [*Hordeum vulgare* subsp. *vulgare*] | 0.80 | 489 | 667 |
| Predicted zma mir 48877 | 597-618 | XP_002456299 | hypothetical protein SORBIDRAFT_03g033710 [*Sorghum bicolor*] > gi|241928274|gb|EES01419.1| hypothetical protein SORBIDRAFT_03g033710 [*Sorghum bicolor*] | 1.00 | 490 | 668 |
| | | ACF79056 | unknown [*Zea mays*] > gi|194693496|gb|ACF80832.1| unknown [*Zea mays*] > gi|195626284|gb|ACG34972.1| GTP-binding protein [*Zea mays*] > gi|223946703|gb|ACN27435.1| unknown [*Zea mays*] | 0.92 | 491 | 669 |
| | | NP_001140242 | hypothetical protein LOC100272283 [*Zea mays*] > gi|194698666|gb|ACF8417.1| unknown [*Zea mays*] | 0.92 | 492 | 670 |
| | | NP_001044154 | Os01g0732200 [*Oryza sativa Japonica* Group] > gi|57899709|dbj|BAD87429.1| putative GTP-binding protein [*Oryza sativa Japonica* Group] > gi|113533685|dbj|BAF06068.1| Os01g0732200 [*Oryza sativa Japonica* Group] > gi|215695283|dbj|BAG90474.1| unnamed protein product [*Oryza sativa Japonica* Group] | 0.84 | 493 | 671 |
| | | EEC71435 | hypothetical protein OsI_03633 [*Oryza sativa Indica* Group] > gi|222619209|gb|EEE5541.1| hypothetical protein OsJ_03357 [*Oryza sativa Japonica* Group] | 0.84 | 494 | |
| | 218-239 | XP_002463058 | hypothetical protein SORBIDRAFT_02g036900 [*Sorghum bicolor*] > gi|241926435|gb|EER99579.1| hypothetical protein SORBIDRAFT_02g036900 [*Sorghum bicolor*] | 1.00 | 495 | 672 |
| | | NP_001142066 | hypothetical protein LOC100274223 [*Zea mays*] > gi|194706978|gb|ACF87573.1| unknown [*Zea mays*] | 0.90 | 496 | 673 |

TABLE 5-continued

Target Genes of miRNAs Associated with Increased NUE (Table 1)

| Mir name | Mir Bind. Pos. | Hom. NCBI Accession | Annotation/Organism | Identity | p.p. SEQ ID NO: | p.n. SEQ ID NO: |
|---|---|---|---|---|---|---|
| | | BAJ95349 | predicted protein [*Hordeum vulgare* subsp. *vulgare*] > gi\|326526013\|dbj\|BAJ93183.1\| predicted protein [*Hordeum vulgare* subsp. *vulgare*] | 0.75 | 497 | 674 |
| | | EAZ40364 | hypothetical protein OsJ_24810 [*Oryza sativa Japonica* Group] | 0.73 | 498 | |
| | | EAZ04406 | hypothetical protein OsI_26550 [*Oryza sativa Indica* Group] | 0.73 | 499 | |
| Predicted folded 24-nts-long seq 52057 | 63-86 | AAD11615 | prpol [*Zea mays*] | 1.00 | 500 | 675 |
| | | AAL76007 | prpol [*Zea mays*] | 0.97 | 501 | |
| | 907-930 | AAD11616 | prpol [*Zea mays*] | 1.00 | 502 | 676 |
| Predicted folded 24-nts-long seq 52633 | 387-410 | XP_002445682 | hypothetical protein SORBIDRAFT_07g024170 [*Sorghum bicolor*] > gi\|241942032\|gb\|EES15177.1\| hypothetical protein SORBIDRAFT_07g024170 [*Sorghum bicolor*] | 1.00 | 503 | 677 |
| | | ACF83553 | unknown [*Zea mays*] > gi\|195646380\|gb\|ACG42658.1\| glutathione S-transferase, N-terminal domain containing protein [*Zea mays*] | 0.90 | 504 | 678 |
| | | ACN26529 | unknown [*Zea mays*] | 0.89 | 505 | 679 |
| Predicted zma mir 48922 | 450-470 | NP_001141971 | hypothetical protein LOC100274121 [*Zea mays*] > gi\|194706630\|gb\|ACF87399.1\| unknown [*Zea mays*] | 1.00 | 506 | 680 |
| | | XP_002455881 | hypothetical protein SORBIDRAFT_03g026750 [*Sorghum bicolor*] > gi\|241927856\|gb\|EES01001.1\| hypothetical protein SORBIDRAFT_03g026750 [*Sorghum bicolor*] | 0.79 | 507 | 681 |
| Predicted zma mir 50077 | 1046-1067 | XP_002465053 | hypothetical protein SORBIDRAFT_01g031330 [*Sorghum bicolor*] > gi\|241918907\|gb\|EER92051.1\| hypothetical protein SORBIDRAFT_01g031330 [*Sorghum bicolor*] | 1.00 | 508 | 682 |
| | | NP_001137129 | hypothetical protein LOC100217311 [*Zea mays*] > gi\|194698486\|gb\|ACF83327.1\| unknown [*Zea mays*] | 0.90 | 509 | 683 |
| | | NP_001149312 | fas-associated factor 1-like protein [*Zea mays*] > gi\|195626306\|gb\|ACG34983.1\| fas-associated factor 1-like protein [*Zea mays*] > gi\|223975789\|gb\|ACN32082.1\| unknown [*Zea mays*] | 0.93 | 510 | 684 |
| | | BAJ89712 | predicted protein [*Hordeum vulgare* subsp. *vulgare*] > gi\|326495414\|dbj\|BAJ85803.1\| predicted protein [*Hordeum vulgare* subsp. *vulgare*] | 0.83 | 511 | 685 |
| | | AAG13433 | unknown protein [*Oryza sativa Japonica* Group] > gi\|31433109\|gb\|AAP54662.1\| | 0.85 | 512 | 686 |

TABLE 5-continued

Target Genes of miRNAs Associated with Increased NUE (Table 1)

| Mir name | Mir Bind. Pos. | Hom. NCBI Accession | Annotation/Organism | Identity | p.p. SEQ ID NO: | p.n. SEQ ID NO: |
|---|---|---|---|---|---|---|
| | | | UBX domain containing protein, expressed [*Oryza sativa Japonica* Group] > gi\|215678662\|dbj\|BAG92317.1\| unnamed protein product [*Oryza sativa Japonica* Group] | | | |
| | | EAY79232 | hypothetical protein OsI_34349 [*Oryza sativa Indica* Group] | 0.85 | 513 | |
| | | EAZ16707 | hypothetical protein OsJ_32183 [*Oryza sativa Japonica* Group] | 0.81 | 514 | |

Table 5: Provided are the target Genes of miRNAs Associated with Increased NUE (Table 1) along with their GenBank Accession numbers and sequence identifiers (SEQ ID NO:).
"bind" = binding;
"pos" = position;
"hom" = homologue;
"p.p." = polypeptide;
"p.n." = polynucleotide.

TABLE 6

Target Genes of down regulated miRNAs Associated with Increased NUE (Table 2)

| Mir name | Mir Bind. Pos. | Hom. NCBI Accession | Annotation/Organism | Identity | p.p. SEQ ID NO: | p.n. SEQ ID NO: |
|---|---|---|---|---|---|---|
| Predicted zma mir 50318 | 743-763 | NP_001148146 | terpene synthase 7 [*Zea mays*] > gi\|195616112\|gb\|ACG29886.1\| terpene synthase 7 [*Zea mays*] | 1.00 | 687 | 1392 |
| | | ACL54589 | unknown [*Zea mays*] | 0.99 | 688 | 1393 |
| | | XP_002447434 | hypothetical protein SORBIDRAFT_06g001020 [*Sorghum bicolor*] > gi\|241938617\|gb\|EES11762.1\| hypothetical protein SORBIDRAFT_06g001020 [*Sorghum bicolor*] | 0.71 | 689 | 1394 |
| | 776-796 | XP_002455470 | hypothetical protein SORBIDRAFT_03g011420 [*Sorghum bicolor*] > gi\|241927445\|gb\|EES00590.1\| hypothetical protein SORBIDRAFT_03g011420 [*Sorghum bicolor*] | 1.00 | 690 | 1395 |
| | | NP_001151624 | cyclin-like F-box [*Zea mays*] > gi\|195648178\|gb\|ACG43557.1\| cyclin-like F-box [*Zea mays*] | 0.90 | 691 | 1396 |
| | | BAJ88045 | predicted protein [*Hordeum vulgare* subsp. *vulgare*] > gi\|326521874\|dbj\|BAK04065.1\| predicted protein [*Hordeum vulgare* subsp. *vulgare*] | 0.79 | 692 | 1397 |
| | | NP_001042756 | Os01g0281000 [*Oryza sativa Japonica* Group] > gi\|6498442\|dbj\|BAA87845.1\| unknown protein [*Oryza sativa Japonica* Group] > gi\|11041564\|dbj\|BAB00648.2\| unnamed protein product [*Oryza sativa Japonica* Group] > gi\|11138071\|dbj\|BAB17744.1\| OSJNBa0036E02.18 [*Oryza sativa Japonica* Group] > gi\|13873014\|dbj\|BAB44118.1\| | 0.81 | 693 | 1398 |

TABLE 6-continued

Target Genes of down regulated miRNAs Associated with Increased NUE
(Table 2)

| Mir name | Mir Bind. Pos. | Hom. NCBI Accession | Annotation/Organism | Identity | p.p. SEQ ID NO: | p.n. SEQ ID NO: |
|---|---|---|---|---|---|---|
| | | | unknown protein [*Oryza sativa Japonica* Group] > gi|113532287|dbj|BAF04670.1| Os01g0281000 [*Oryza sativa Japonica* Group] > gi|215694300|dbj|BAG89293.1| unnamed protein product [*Oryza sativa Japonica* Group] | | | |
| | | EEE54342 | hypothetical protein OsJ_01321 [*Oryza sativa Japonica* Group] | 0.75 | 694 | |
| | | EEC70414 | hypothetical protein OsI_01411 [*Oryza sativa Indica* Group] | 0.75 | 695 | |
| | 2058-2078 | XP_002468633 | hypothetical protein SORBIDRAFT_01g049370 [*Sorghum bicolor*] > gi|241922487|gb|EER95631.1| hypothetical protein SORBIDRAFT_01g049370 [*Sorghum bicolor*] | 1.00 | 696 | 1399 |
| | | NP_001130361 | hypothetical protein LOC100191456 [*Zea mays*] > gi|194688936|gb|ACF78552.1| unknown [*Zea mays*] > gi|194707734|gb|ACF87951.1| unknown [*Zea mays*] | 0.98 | 697 | 1400 |
| | | NP_001167830 | hypothetical protein LOC100381530 [*Zea mays*] > gi|223944309|gb|ACN26238.1| unknown [*Zea mays*] | 0.96 | 698 | 1401 |
| | | NP_001046725 | Os02g0332200 [*Oryza sativa Japonica* Group] > gi|46390985|dbj|BAD16520.1| putative cytosolic chaperonin delta-subunit [*Oryza sativa Japonica* Group] > gi|113536256|dbj|BAF08639.1| Os02g0332200 [*Oryza sativa Japonica* Group] > gi|215695341|dbj|BAG90532.1| unnamed protein product [*Oryza sativa Japonica* Group] > gi|222636848|gb|EEE66980.1| hypothetical protein OsJ_23870 [*Oryza sativa Japonica* Group] | 0.95 | 699 | 1402 |
| | | EAZ06856 | hypothetical protein OsI_29091 [*Oryza sativa Indica* Group] | 0.95 | 700 | |
| | | BAJ97289 | predicted protein [*Hordeum vulgare* subsp. *vulgare*] | 0.92 | 701 | 1403 |
| | | NP_001065054 | Os10g0514600 [*Oryza sativa Japonica* Group] > gi|10140686|gb|AAG13521.1| AC068924_26 putative cytosolic chaperonin, delta-subunit [*Oryza sativa Japonica* Group] > gi|31433047|gb|AAP54607.1| T-complex protein 1, delta subunit, putative, expressed [*Oryza sativa Japonica* Group] > gi|113639663|dbj|BAF26968.1| Os10g0514600 [*Oryza sativa Japonica* Group] > gi|215687328|dbj|BAG91872.1| unnamed protein product [*Oryza sativa Japonica* Group] | 0.88 | 702 | 1404 |

TABLE 6-continued

Target Genes of down regulated miRNAs Associated with Increased NUE
(Table 2)

| Mir name | Mir Bind. Pos. | Hom. NCBI Accession | Annotation/Organism | Identity | p.p. SEQ ID NO: | p.n. SEQ ID NO: |
|---|---|---|---|---|---|---|
| | | XP_002322076 | predicted protein [*Populus trichocarpa*] > gi\|222869072\|gb\|EEF06203.1\| predicted protein [*Populus trichocarpa*] | 0.81 | 703 | 1405 |
| | | XP_002317895 | predicted protein [*Populus trichocarpa*] > gi\|222858568\|gb\|EEE96115.1\| predicted protein [*Populus trichocarpa*] | 0.80 | 704 | 1406 |
| | | CAN70636 | hypothetical protein VITISV_008621 [*Vitis vinifera*] | 0.82 | 705 | 1407 |
| | 554-574 | XP_002465983 | hypothetical protein SORBIDRAFT_01g049510 [*Sorghum bicolor*] > gi\|241919837\|gb\|EER92981.1\| hypothetical protein SORBIDRAFT_01g049510 [*Sorghum bicolor*] | 1.00 | 706 | 1408 |
| | | NP_001149716 | fusca homolog [*Zea mays*] > gi\|195629716\|gb\|ACG36499.1\| COP9 signalosome complex subunit 1 [*Zea mays*] | 0.95 | 707 | 1409 |
| | | NP_00148760 | Os03g0116500 [*Oryza sativa Japonica* Group] > gi\|108705858\|gb\|ABF93653.1\| COP9 signalosome complex subunit 1, putative, expressed [*Oryza sativa Japonica* Group] > gi\|113547231\|dbj\|BAF10674.1\| Os03g0116500 [*Oryza sativa Japonica* Group] > gi\|125542143\|gb\|EAY88282.1\| hypothetical protein OsI_09737 [*Oryza sativa Indica* Group] > gi\|125584695\|gb\|EAZ25359.1\| hypothetical protein OsJ_09174 [*Oryza sativa Japonica* Group] > gi\|215678827\|dbj\|BAG95264.1\| unnamed protein product [*Oryza sativa Japonica* Group] | 0.89 | 708 | 1410 |
| | | AAF40112 | constitutive photomorphogenic 11 [*Oryza sativa Indica* Group] | 0.88 | 709 | 1411 |
| | | AAG17476 | rCOP11 protein [*Oryza sativa Indica* Group] | 0.88 | 710 | 1412 |
| | | BAJ99160 | predicted protein [*Hordeum vulgare* subsp. *vulgare*] | 0.84 | 711 | 1413 |
| | | BAK01545 | predicted protein [*Hordeum vulgare* subsp. *vulgare*] | 0.78 | 712 | 1414 |
| | | XP_002275895 | PREDICTED: hypothetical protein [*Vitis vinifera*] > gi\|296089065\|emb\|CBI38768.3\| unnamed protein product [*Vitis vinifera*] | 0.72 | 713 | 1415 |
| | | CAN74681 | hypothetical protein VITISV_025856 [*Vitis vinifera*] | 0.72 | 714 | |
| | 372-392 | XP_002448372 | hypothetical protein SORBIDRAFT_06g026160 [*Sorghum bicolor*] > gi\|241939555\|gb\|EES12700.1\| hypothetical protein SORBIDRAFT_06g026160 [*Sorghum bicolor*] | 1.00 | 715 | 1416 |
| | | ADZ96243 | ACC synthase 1 [*Saccharum* hybrid cultivar SP80-3280] | 0.92 | 716 | 1417 |
| | | AAR25558 | acc synthase [*Zea mays*] | 0.92 | 717 | 1418 |
| | | AAR25559 | acc synthase [*Zea mays*] | 0.91 | 718 | 1419 |

TABLE 6-continued

Target Genes of down regulated miRNAs Associated with Increased NUE
(Table 2)

| Mir name | Mir Bind. Pos. | Hom. NCBI Accession | Annotation/Organism | Identity | p.p. SEQ ID NO: | p.n. SEQ ID NO: |
|---|---|---|---|---|---|---|
| | | NP_001146401 | 1-aminocyclopropane-1-carboxylate synthase7 [Zea mays] > gi|219886697|gb|ACL53723.1| unknown [Zea mays] | 0.91 | 719 | 1420 |
| | | ACN31344 | unknown [Zea mays] | 0.90 | 720 | 1421 |
| | | BAJ95898 | predicted protein [Hordeum vulgare subsp. vulgare] | 0.81 | 721 | 1422 |
| | | NP_001053637 | Os04g0578000 [Oryza sativa Japonica Group] > gi|32488497|emb|CAE03249.1| OSJNBa0011J08.4 [Oryza sativa Japonica Group] > gi|113565208|dbj|BAF15551.1| Os04g0578000 [Oryza sativa Japonica Group] > gi|215693849|dbj|BAG89048.1| unnamed protein product [Oryza sativa Japonica Group] | 0.80 | 722 | 1423 |
| | | CAH66732 | H0404F02.8 [Oryza sativa Indica Group] > gi|125549433|gb|EAY95255.1| hypothetical protein OsI_17075 [Oryza sativa Indica Group] | 0.80 | 723 | 1424 |
| | | AAB18416 | ACC synthase [Triticum aestivum] | 0.80 | 724 | 1425 |
| | 1204-1224 | ACN26771 | unknown [Zea mays] | 1.00 | 725 | 1426 |
| | | ACG31388 | F-box domain containing protein [Zea mays] | 1.00 | 726 | 1427 |
| | | ACG45892 | F-box domain containing protein [Zea mays] | 1.00 | 727 | 1428 |
| | | ACG25717 | F-box domain containing protein [Zea mays] | 0.99 | 728 | 1429 |
| | | NP_001152119 | F-box domain containing protein [Zea mays] > gi|195652827|gb|ACG45881.1| F-box domain containing protein [Zea mays] | 0.96 | 729 | 1430 |
| | | XP_002467684 | hypothetical protein SORBIDRAFT_01g032310 [Sorghum bicolor] > gi|241921538|gb|EER94682.1| hypothetical protein SORBIDRAFT_01g032310 [Sorghum bicolor] | 0.89 | 730 | 1431 |
| | | EAY90508 | hypothetical protein OsI_12108 [Oryza sativa Indica Group] | 0.82 | 731 | |
| | | NP_001050391 | Os03g0423000 [Oryza sativa Japonica Group] > gi|30089733|gb|AAP20837.1| expressed protein [Oryza sativa Japonica Group] > gi|108708889|gb|ABF96684.1| F-box domain containing protein, expressed [Oryza sativa Japonica Group] > gi|113548862|dbj|BAF12305.1| Os03g0423000 [Oryza sativa Japonica Group] > gi|125586708|gb|EAZ27372.1| hypothetical protein OsJ_11320 [Oryza sativa Japonica Group] > gi|215697584|dbj|BAG91578.1| unnamed protein product [Oryza sativa Japonica Group] | 0.82 | 732 | 1432 |

TABLE 6-continued

Target Genes of down regulated miRNAs Associated with Increased NUE
(Table 2)

| Mir name | Mir Bind. Pos. | Hom. NCBI Accession | Annotation/Organism | Identity | p.p. SEQ ID NO: | p.n. SEQ ID NO: |
|---|---|---|---|---|---|---|
| | 1019-1039 | XP_002464111 | hypothetical protein SORBIDRAFT_01g012470 [*Sorghum bicolor*] > gi|241917965|gb|EER91109.1| hypothetical protein SORBIDRAFT_01g012470 [*Sorghum bicolor*] | 1.00 | 733 | 1433 |
| | | NP_001140844 | hypothetical protein LOC100272920 [*Zea mays*] > gi|194701412|gb|ACF84790.1| unknown [*Zea mays*] > gi|223943945|gb|ACN26056.1| unknown [*Zea mays*] | 0.97 | 734 | 1434 |
| | | NP_001149791 | transmembrane protein 56 [*Zea mays*] > gi|195634693|gb|ACG36815.1| transmembrane protein 56 [*Zea mays*] | 0.94 | 735 | 1435 |
| | | NP_001050848 | Os03g0666700 [*Oryza sativa Japonica* Group] > gi|40538924|gb|AAR87181.1| expressed protein [*Oryza sativa Japonica* Group] > gi|108710279|gb|ABF98074.1| expressed protein [*Oryza sativa Japonica* Group] > gi|113549319|dbj|BAF12762.1| Os03g0666700 [*Oryza sativa Japonica* Group] > gi|215692429|dbj|BAG87849.1| unnamed protein product [*Oryza sativa Japonica* Group] > gi|215692647|dbj|BAG88067.1| unnamed protein product [*Oryza sativa Japonica* Group] > gi|215716974|dbj|BAG95337.1| unnamed protein product [*Oryza sativa Japonica* Group] | 0.90 | 736 | 1436 |
| | | BAJ94278 | predicted protein [*Hordeum vulgare* subsp. *vulgare*] > gi|326505624|dbj|BAJ95483.1| predicted protein [*Hordeum vulgare* subsp. *vulgare*] > gi|326513826|dbj|BAJ87931.1| predicted protein [*Hordeum vulgare* subsp. *vulgare*] > gi|326518414|dbj|BAJ88236.1| predicted protein [*Hordeum vulgare* subsp. *vulgare*] | 0.91 | 737 | 1437 |
| | | ACF84098 | unknown [*Zea mays*] | 0.93 | 738 | 1438 |
| | | EEE53990 | hypothetical protein OsJ_00621 [*Oryza sativa Japonica* Group] | 0.90 | 739 | |
| | 1917-1937 | XP_002453927 | hypothetical protein SORBIDRAFT_04g021570 [*Sorghum bicolor*] > gi|241933758|gb|EES06903.1| hypothetical protein SORBIDRAFT_04g021570 [*Sorghum bicolor*] | 1.00 | 740 | 1439 |
| | | NP_001105849 | putative glycosyltransferase [*Zea mays*] > gi|84794314|emb|CAJ57382.1| putative glycosyltransferase [*Zea mays*] | 0.96 | 741 | 1440 |
| | | BAK03947 | predicted protein [*Hordeum vulgare* subsp. *vulgare*] | 0.86 | 742 | 1441 |

TABLE 6-continued

Target Genes of down regulated miRNAs Associated with Increased NUE (Table 2)

| Mir name | Mir Bind. Pos. | Hom. NCBI Accession | Annotation/Organism | Identity | p.p. SEQ ID NO: | p.n. SEQ ID NO: |
|---|---|---|---|---|---|---|
| | | NP_001047014 | Os02g0529600 [*Oryza sativa Japonica* Group] > gi|49388322|dbj|BAD25434.1| putative galactomannan galactosyltransferase [*Oryza sativa Japonica* Group] > gi|113536545|dbj|BAF08928.1| Os02g0529600 [*Oryza sativa Japonica* Group] > gi|215704838|dbj|BAG94866.1| unnamed protein product [*Oryza sativa Japonica* Group] > gi|218190881|gb|EEC73308.1| hypothetical protein OsI_07488 [*Oryza sativa Indica* Group] > gi|222622984|gb|EEE57116.1| hypothetical protein OsJ_06989 [*Oryza sativa Japonica* Group] | 0.86 | 743 | 1442 |
| | 1590-1610 | NP_001131407 | hypothetical protein LOC100192736 [*Zea mays*] > gi|194691442|gb|ACF79805.1 unknown [*Zea mays*] | 1.00 | 744 | 1443 |
| | | NP_001141840 | hypothetical protein LOC100273982 [*Zea mays*] > gi|194706136|gb|ACF87152.1| unknown [*Zea mays*] | 0.78 | 745 | 1444 |
| | 510-530 | XP_002460574 | hypothetical protein SORBIDRAFT_02g031070 [*Sorghum bicolor*] > gi|241923951|gb|EER97095.1| hypothetical protein SORBIDRAFT_02g031070 [*Sorghum bicolor*] | 1.00 | 746 | 1445 |
| | | NP_001151754 | collagen, type IV, alpha 5 [*Zea mays*] > gi|195649521|gb|ACG44228.1 collagen, type IV, alpha 5 [*Zea mays*] | 0.87 | 747 | 1446 |
| | 876-896 | XP_002437709 | hypothetical protein SORBIDRAFT_10g001120 [*Sorghum bicolor*] > gi|241915932|gb|EER89076.1| hypothetical protein SORBIDRAFT_10g001120 [*Sorghum bicolor*] | 1.00 | 748 | 1447 |
| | | ACN34709 | unknown [*Zea mays*] | 0.99 | 749 | 1448 |
| | | ACN28096 | unknown [*Zea mays*] > gi|223948483|gb|ACN28325.1| unknown [*Zea mays*] | 0.99 | 750 | 1449 |
| | | NP_001056601 | Os06g0114000 [*Oryza sativa Japonica* Group] > gi|7248401|dbj|BAA92724.1| putative chaperonin 60 beta precursor [*Oryza sativa Japonica* Group] > gi|113594641|dbj|BAF18515.1| Os06g0114000 [*Oryza sativa Japonica* Group] > gi|164375533|gb|ABY52934.1| RuBisCo subunit binding-protein beta subunit [*Oryza sativa Japonica* Group] > gi|215715264|dbj|BAG95015.1| unnamed protein product [*Oryza sativa Japonica* Group] | 0.97 | 751 | 1450 |
| | | EEE64974 | hypothetical protein OsJ_19883 [*Oryza sativa Japonica* Group] | 0.93 | 752 | |

TABLE 6-continued

Target Genes of down regulated miRNAs Associated with Increased NUE
(Table 2)

| Mir name | Mir Bind. Pos. | Hom. NCBI Accession | Annotation/Organism | Identity | p.p. SEQ ID NO: | p.n. SEQ ID NO: |
|---|---|---|---|---|---|---|
| | | NP_001045601 | Os02g0102900 [*Oryza sativa Japonica* Group] > gi|41052909|dbj|BAD07821.1| putative RuBisCO subunit binding-protein beta subunit, chloroplast precursor [*Oryza sativa Japonica* Group] > gi|113535132|dbj|BAF07515.1| Os02g0102900 [*Oryza sativa Japonica* Group] > gi|218189867|gb|EEC72294.1| hypothetical protein OsI_05469 [*Oryza sativa Indica* Group] > gi|222621999|gb|EEE56131.1| hypothetical protein OsJ_05004 [*Oryza sativa Japonica* Group] > gi|313575775|gb|ADR66967.1| 60 kDa chaperonin beta subunit [*Oryza sativa Japonica* Group] | 0.87 | 753 | 1451 |
| | | XP_002285746 | PREDICTED: hypothetical protein [*Vitis vinifera*] > gi|297746501|emb|CBI16557.3| unnamed protein product [*Vitis vinifera*] | 0.88 | 754 | 1452 |
| | | XP_002303983 | predicted protein [*Populus trichocarpa*] > gi|222841415|gb|EEE78962.1| predicted protein [*Populus trichocarpa*] | 0.87 | 755 | 1453 |
| | | XP_002523404 | rubisco subunit binding-protein beta subunit, rubb, putative [*Ricinus communis*] > gi|223537354|gb|EEF38983.1| rubisco subunit binding-protein beta subunit, rubb, putative [*Ricinus communis*] | 0.87 | 756 | 1454 |
| | | XP_002894506 | CPN60B [*Arabidopsis lyrata* subsp. *lyrata*] > gi|297340348|gb|EFH70765.1| CPN60B [*Arabidopsis lyrata* subsp. *lyrata*] | 0.87 | 757 | 1455 |
| | 640-660 | XP_002456142 | hypothetical protein SORBIDRAFT_03g031180 [*Sorghum bicolor*] > gi|241928117|gb|EES01262.1| hypothetical protein SORBIDRAFT_03g031180 [*Sorghum bicolor*] | 1.00 | 758 | 1456 |
| | | NP_001148838 | LOC100282456 [*Zea mays*] > gi|195622536|gb|ACG33098.1| THAP domain-containing protein 4 [*Zea mays*] | 0.94 | 759 | 1457 |
| | | EEC71270 | hypothetical protein OsI_03268 [*Oryza sativa Indica* Group] | 0.87 | 760 | |
| | | CBH32601 | conserved hypothetical protein, expressed [*Triticum aestivum*] | 0.83 | 761 | 1458 |
| | | NP_001043867 | Os01g0679600 [*Oryza sativa Japonica* Group] > gi|56202146|dbj|BAD73479.1| unknown protein [*Oryza sativa Japonica* Group] > gi|255673554|dbj|BAF05781.2| Os01g0679600 [*Oryza sativa Japonica* Group] | 0.80 | 762 | 1459 |
| | | BAJ94714 | predicted protein [*Hordeum vulgare* subsp. *vulgare*] | 0.78 | 763 | 1460 |

TABLE 6-continued

Target Genes of down regulated miRNAs Associated with Increased NUE
(Table 2)

| Mir name | Mir Bind. Pos. | Hom. NCBI Accession | Annotation/Organism | Identity | p.p. SEQ ID NO: | p.n. SEQ ID NO: |
|---|---|---|---|---|---|---|
| | | BAD73478 | unknown protein [*Oryza sativa Japonica* Group] > gi|215693000|dbj|BAG88420.1| unnamed protein product [*Oryza sativa Japonica* Group] > gi|222619045|gb|EEE55177.1| hypothetical protein OsJ_03010 [*Oryza sativa Japonica* Group] | 0.78 | 764 | 1461 |
| | 1204-1224 | ACR38511 | unknown [*Zea mays*] | 1.00 | 765 | 1462 |
| | | ACG45146 | hypothetical protein [*Zea mays*] | 1.00 | 766 | 1463 |
| | | XP_002440220 | hypothetical protein SORBIDRAFT_09g027950 [*Sorghum bicolor*] > gi|241945505|gb|EES18650.1| hypothetical protein SORBIDRAFT_09g027950 [*Sorghum bicolor*] | 0.71 | 767 | 1464 |
| | | NP_001144829 | hypothetical protein LOC100277913 [*Zea mays*] > gi|195647628|gb|ACG43282.1| hypothetical protein [*Zea mays*] | 0.71 | 768 | 1465 |
| | 916-936 | NP_001143951 | hypothetical protein LOC100276764 [*Zea mays*] > gi|195631554|gb|ACG36672.1| hypothetical protein [*Zea mays*] | 1.00 | 769 | 1466 |
| | | NP_001169519 | hypothetical protein LOC100383393 [*Zea mays*] > gi|224029837|gb|ACN33994.1| unknown [*Zea mays*] | 0.81 | 770 | 1467 |
| | 1178-1198 | XP_002468109 | hypothetical protein SORBIDRAFT_01g039740 [*Sorghum bicolor*] > gi|241921963|gb|EER95107.1| hypothetical protein SORBIDRAFT_01g039740 [*Sorghum bicolor*] | 1.00 | 771 | 1468 |
| | | NP_001131833 | hypothetical protein LOC100193208 [*Zea mays*] > gi|194688576|gb|ACF78372.1| unknown [*Zea mays*] > gi|195627610|gb|ACG35635.1| protein binding protein [*Zea mays*] | 0.95 | 772 | 1469 |
| | | ACL53375 | unknown [*Zea mays*] | 0.94 | 773 | 1470 |
| | | NP_001147045 | protein binding protein [*Zea mays*] > gi|195606842|gb|ACG25251.1| protein binding protein [*Zea mays*] | 0.93 | 774 | 1471 |
| | | ABF95226 | zinc finger family protein, putative, expressed [*Oryza sativa Japonica* Group] > gi|108707432|gb|ABF95227.1| zinc finger family protein, putative, expressed [*Oryza sativa Japonica* Group] > gi|218192524|gb|EEC74951.1| hypothetical protein OsI_10935 [*Oryza sativa Indica* Group] > gi|222624650|gb|EEE58782.1| hypothetical protein OsJ_10309 [*Oryza sativa Japonica* Group] | 0.86 | 775 | |
| | | BAJ90599 | predicted protein [*Hordeum vulgare* subsp. *vulgare*] | 0.81 | 776 | 1472 |

TABLE 6-continued

Target Genes of down regulated miRNAs Associated with Increased NUE
(Table 2)

| Mir name | Mir Bind. Pos. | Hom. NCBI Accession | Annotation/Organism | Identity | p.p. SEQ ID NO: | p.n. SEQ ID NO: |
|---|---|---|---|---|---|---|
| | | ADX86798 | zinc-finger transcription factor [*Triticum aestivum*] | 0.79 | 777 | 1473 |
| | | ACN35095 | unknown [*Zea mays*] | 0.70 | 778 | 1474 |
| | | NP_001049696 | Os03g0272300 [*Oryza sativa Japonica* Group] > gi|108707430|gb|ABF95225.1| zinc finger family protein, putative, expressed [*Oryza sativa Japonica* Group] > gi|215765669|dbj|BAG87366.1| unnamed protein product [*Oryza sativa Japonica* Group] > gi|255674397|dbj|BAF11610.2| Os03g0272300 [*Oryza sativa Japonica* Group] | 0.70 | 779 | 1475 |
| | 1068-1088 | NP_001144727 | hypothetical protein LOC100277769 [*Zea mays*] > gi|195646260|gb|ACG42598.1| hypothetical protein [*Zea mays*] | 1.00 | 780 | 1476 |
| | | NP_001141817 | hypothetical protein LOC100273956 [*Zea mays*] > gi|194706038|gb|ACF87103.1| unknown [*Zea mays*] | 0.99 | 781 | 1477 |
| | | NP_001170260 | hypothetical protein LOC100384217 [*Zea mays*] > gi|224034675|gb|ACN36413.1| unknown [*Zea mays*] | 0.96 | 782 | 1478 |
| | | NP_001170241 | hypothetical protein LOC100384195 [*Zea mays*] > gi|224034547|gb|ACN36349.1| unknown [*Zea mays*] | 0.71 | 783 | 1479 |
| | 573-593 | XP_002454448 | hypothetical protein SORBIDRAFT_04g031260 [*Sorghum bicolor*] > gi|241934279|gb|EES07424.1| hypothetical protein SORBIDRAFT_04g031260 [*Sorghum bicolor*] | 1.00 | 784 | 1480 |
| | | NP_001149829 | LOC100283456 [*Zea mays*] > gi|195634913|gb|ACG36925.1| acetylornithine deacetylase [*Zea mays*] | 0.97 | 785 | 1481 |
| | | EEC73818 | hypothetical protein OsI_08537 [*Oryza sativa Indica* Group] | 0.85 | 786 | |
| | | NP_001047794 | Os02g0690800 [*Oryza sativa Japonica* Group] > gi|41053258|dbj|BAD07684.1| putative silverleaf whitefly-induced protein 1 [*Oryza sativa Japonica* Group] > gi|113537325|dbj|BAF09708.1| Os02g0690800 [*Oryza sativa Japonica* Group] > gi|215715374|dbj|BAG95125.1| unnamed protein product [*Oryza sativa Japonica* Group] > gi|215740943|dbj|BAG97438.1| unnamed protein product [*Oryza sativa Japonica* Group] > gi|222623478|gb|EEE57610.1| hypothetical protein OsJ_07995 [*Oryza sativa Japonica* Group] | 0.85 | 787 | 1482 |
| | 1820-1840 | XP_002456060 | hypothetical protein SORBIDRAFT_03g029660 [*Sorghum bicolor*] > gi|241928035|gb|EES01180.1| hypothetical protein | 1.00 | 788 | 1483 |

TABLE 6-continued

Target Genes of down regulated miRNAs Associated with Increased NUE
(Table 2)

| Mir name | Mir Bind. Pos. | Hom. NCBI Accession | Annotation/Organism | Identity | p.p. SEQ ID NO: | p.n. SEQ ID NO: |
|---|---|---|---|---|---|---|
| | | | SORBIDRAFT_03g029660 [*Sorghum bicolor*] | | | |
| | | ACG31412 | wax synthase isoform 3 [*Zea mays*] | 0.86 | 789 | 1484 |
| | | NP_001150127 | wax synthase [*Zea mays*] > gi|195636988|gb|ACG37962.1| wax synthase isoform 3 [*Zea mays*] | 0.86 | 790 | 1485 |
| | | NP_001043733 | Os01g0651500 [*Oryza sativa Japonica* Group] > gi|20146429|dbj|BAB89209.1| wax synthase-like [*Oryza sativa Japonica* Group] > gi|113533264|dbj|BAF05647.1| Os01g0651500 [*Oryza sativa Japonica* Group] > gi|125571401|gb|EAZ12916.1| hypothetical protein OsJ_02839 [*Oryza sativa Japonica* Group] | 0.73 | 791 | 1486 |
| | | EAY75194 | hypothetical protein OsI_03086 [*Oryza sativa Indica* Group] | 0.72 | 792 | |
| | | BAK07830 | predicted protein [*Hordeum vulgare* subsp. *vulgare*] | 0.70 | 793 | 1487 |
| | 1709-1729 | XP_002448959 | hypothetical protein SORBIDRAFT_05g002450 [*Sorghum bicolor*] > gi|241934802|gb|EES07947.1| hypothetical protein SORBIDRAFT_05g002450 [*Sorghum bicolor*] | 1.00 | 794 | 1488 |
| | | ACF84627 | unknown [*Zea mays*] > gi|223942887|gb|ACN25527.1| unknown [*Zea mays*] | 0.95 | 795 | 1489 |
| | | NP_001150994 | PP2A regulatory subunit TAP46 [*Zea mays*] > gi|195643460|gb|ACG41198.1| PP2A regulatory subunit TAP46 [*Zea mays*] | 0.95 | 796 | 1490 |
| | | ACF84366 | unknown [*Zea mays*] | 0.94 | 797 | 1491 |
| | | EAY79895 | hypothetical protein OsI_35058 [*Oryza sativa Indica* Group] | 0.89 | 798 | |
| | | NP_001066109 | Os12g0137500 [*Oryza sativa Japonica* Group] > gi|77552970|gb|ABA95766.1| TAP42-like family protein, expressed [*Oryza sativa Japonica* Group] > gi|113648616|dbj|BAF29128.1| Os12g0137500 [*Oryza sativa Japonica* Group] > gi|215769083|dbj|BAH01312.1| unnamed protein product [*Oryza sativa Japonica* Group] | 0.89 | 799 | 1492 |
| | | EAZ19586 | hypothetical protein OsJ_35163 [*Oryza sativa Japonica* Group] | 0.89 | 800 | |
| | | AAO72555 | PP2A regulatory subunit-like protein [*Oryza sativa Japonica* Group] | 0.89 | 801 | 1493 |
| | | ABA91420 | TAP42-like family protein, expressed [*Oryza sativa Japonica* Group] > gi|222615497|gb|EEE51629.1| hypothetical protein OsJ_32912 [*Oryza sativa Japonica* Group] | 0.88 | 802 | 1494 |
| | | NP_001148561 | PP2A regulatory subunit TAP46 [*Zea mays*] > gi|195620440|gb|ACG32050.1| | 0.86 | 803 | 1495 |

TABLE 6-continued

Target Genes of down regulated miRNAs Associated with Increased NUE
(Table 2)

| Mir name | Mir Bind. Pos. | Hom. NCBI Accession | Annotation/Organism | Identity | p.p. SEQ ID NO: | p.n. SEQ ID NO: |
|---|---|---|---|---|---|---|
| | 1417-1437 | XP_002465624 | PP2A regulatory subunit TAP46 [Zea mays] hypothetical protein SORBIDRAFT_01g042450 [Sorghum bicolor] > gi|194326198|emb|CAQ86599.1| glutamine synthetase [Sorghum bicolor] > gi|241919478|gb|EER92622.1| hypothetical protein SORBIDRAFT_01g042450 [Sorghum bicolor] | 1.00 | 804 | 1496 |
| | | AAW21274 | glutamine synthetase [Saccharum officinarum] | 0.98 | 805 | 1497 |
| | | NP_001105538 | glutamine synthetase root isozyme 1 [Zea mays] > gi|6996235|dbj|BAA03433.1| glutamine synthetase [Zea mays] > gi|194701040|gb|ACF84604.1| unknown [Zea mays] | 0.97 | 806 | 1498 |
| | | P38559 | RecName: Full = Glutamine synthetase root isozyme 1; AltName: Full = GS122; AltName: Full = Glutamate-- ammonia ligase > gi|434324|emb|CAA46719.1| glutamine synthetase [Zea mays] | 0.97 | 807 | |
| | | P38563 | RecName: Full = Glutamine synthetase root isozyme 5; AltName: Full = GS117; AltName: Full = Glutamate-- ammonia ligase | 0.96 | 808 | |
| | | NP_001105297 | glutamine synthetase root isozyme 5 [Zea mays] > gi|699621|dbj|BAA03432.1| glutamine synthetase [Zea mays] | 0.96 | 809 | 1499 |
| | | ACG47508 | glutamine synthetase root isozyme 5 [Zea mays] | 0.95 | 810 | 1500 |
| | | NP_001049424 | Os03g0223400 [Oryza sativa Japonica Group] > gi|121332|sp|P14654.1|GLN12_ORYSJ RecName: Full = Glutamine synthetase cytosolic isozyme 1-2; AltName: Full = Glutamate-- ammonia ligase GLN1; 2; Short = OsGLN1; 2; AltName: Full = Glutamine synthetase root isozyme; AltName: Full = OsGS1; 2 > gi|20358|emb|CAA32460.1| unnamed protein product [Oryza sativa Japonica Group] > gi|565414215|dbj|BAD77931.1| cytosolic glutamine synthetase 1; 2 [Oryza sativa Japonica Group] > gi|108706922|gb|ABF94717.1| Glutamine synthetase root isozyme 5, putative, expressed [Oryza sativa Japonica Group] > gi|1135478955|dbj|BAF11338.1| Os03g0223400 [Oryza sativa Japonica Group] > gi|215769188|dbj|BAH01417.1| unnamed protein | 0.91 | 811 | 1501 |

TABLE 6-continued

Target Genes of down regulated miRNAs Associated with Increased NUE
(Table 2)

| Mir name | Mir Bind. Pos. | Hom. NCBI Accession | Annotation/Organism | Identity | p.p. SEQ ID NO: | p.n. SEQ ID NO: |
|---|---|---|---|---|---|---|
| | | | product [*Oryza sativa Japonica* Group] > gi\|218192361\|gb\|EEC74788.1\| hypothetical protein OsI_10575 [*Oryza sativa Indica* Group] > gi\|222624488\|gb\|EEE58620.1\| hypothetical protein OsJ_09974 [*Oryza sativa Japonica* Group] | | | |
| | | AAR84347 | glutamine synthetase isoform GSr1 [*Triticum aestivum*] | 0.89 | 812 | 1502 |
| | | AAR84348 | glutamine synthetase isoform GSr2 [*Triticum aestivum*] | 0.89 | 813 | 1503 |
| | 1527-1547 | XP_002454761 | hypothetical protein SORBIDRAFT_04g036890 [*Sorghum bicolor*] > gi\|241934592\|gb\|EES07737.1\| hypothetical protein SORBIDRAFT_04g036890 [*Sorghum bicolor*] | 1.00 | 814 | 1504 |
| | | NP_001130621 | hypothetical protein LOC100191720 [*Zea mays*] > gi\|194689664\|gb\|ACF78916.1\| unknown [*Zea mays*] | 0.87 | 815 | 1505 |
| | | XP_002454762 | hypothetical protein SORBIDRAFT_04g036900 [*Sorghum bicolor*] > gi\|241934593\|gb\|EES07738.1\| hypothetical protein SORBIDRAFT_04g036900 [*Sorghum bicolor*] | 0.78 | 816 | 1506 |
| | | XP_002437453 | hypothetical protein SORBIDRAFT_10g027360 [*Sorghum bicolor*] > gi\|241915676\|gb\|EER88820.1\| hypothetical protein SORBIDRAFT_10g027360 [*Sorghum bicolor*] | 0.70 | 817 | 1507 |
| | | XP_002438878 | hypothetical protein SORBIDRAFT_10g027650 [*Sorghum bicolor*] > gi\|241917101\|gb\|EER90245.1\| hypothetical protein SORBIDRAFT_10g027650 [*Sorghum bicolor*] | 0.69 | 818 | 1508 |
| | | XP_002438877 | hypothetical protein SORBIDRAFT_10g027640 [*Sorghum bicolor*] > gi\|241917100\|gb\|EER90244.1\| hypothetical protein SORBIDRAFT_10g027640 [*Sorghum bicolor*] | 0.70 | 819 | 1509 |
| | 2363-2383 | XP_002436826 | hypothetical protein SORBIDRAFT_10g009530 [*Sorghum bicolor*] > gi\|241915049\|gb\|EER88193.1\| hypothetical protein SORBIDRAFT_10g009530 [*Sorghum bicolor*] | 1.00 | 820 | 1510 |
| | | ACN31818 | unknown [*Zea mays*] | 0.94 | 821 | 1511 |
| | | BAJ98035 | predicted protein [*Hordeum vulgare* subsp. *vulgare*] | 0.81 | 822 | 1512 |
| | | NP_001057335 | Os06g0264500 [*Oryza sativa Japonica* Group] > gi\|53793159\|dbj\|BAD54367.1\| putative nitrite transporter [*Oryza sativa Japonica* Group] > gi\|53793165\|dbj\|BAD54372.1\| putative nitrite transporter [*Oryza sativa* | 0.79 | 823 | 1513 |

TABLE 6-continued

Target Genes of down regulated miRNAs Associated with Increased NUE
(Table 2)

| Mir name | Mir Bind. Pos. | Hom. NCBI Accession | Annotation/Organism | Identity | p.p. SEQ ID NO: | p.n. SEQ ID NO: |
|---|---|---|---|---|---|---|
| | | | Japonica Group]<br>> gi|113595375|dbj|BAF19249.1|<br>Os06g0264500 [Oryza sativa Japonica Group]<br>> gi|215767857|dbj|BAH00086.1|<br>unnamed protein product [Oryza sativa Japonica Group]<br>> gi|218197932|gb|EEC80359.1|<br>hypothetical protein OsI_22454 [Oryza sativa Indica Group]<br>> gi|222635351|gb|EEE65483.1|<br>hypothetical protein OsJ_20894 [Oryza sativa Japonica Group] | | | |
| | 2309-2329 | XP_002446671 | hypothetical protein SORBIDRAFT_06g020190 [Sorghum bicolor]<br>> gi|241937854|gb|EES10999.1|<br>hypothetical protein SORBIDRAFT_06g020190 [Sorghum bicolor] | 1.00 | 824 | 1514 |
| | | NP_001151527 | ATSWI3A [Zea mays]<br>> gi|195647424|gb|ACG43180.1|<br>ATSWI3A [Zea mays] | 0.92 | 825 | 1515 |
| | | NP_001053100 | Os04g0480300 [Oryza sativa Japonica Group]<br>> gi|113564671|dbj|BAF15014.1|<br>Os04g0480300 [Oryza sativa Japonica Group]<br>> gi|215734840|dbj|BAG95562.1|<br>unnamed protein product [Oryza sativa Japonica Group] | 0.76 | 826 | 1516 |
| | | CAH66875 | OSIGBa0158F13.6 [Oryza sativa Indica Group] | 0.76 | 827 | 1517 |
| | | EEC77490 | hypothetical protein OsI_16334 [Oryza sativa Indica Group] | 0.73 | 828 | |
| | 1469-1489 | NP_001148712 | plant-specific domain TIGR01589 family protein [Zea mays]<br>> gi|195621580|gb|ACG32620.1|<br>plant-specific domain TIGR01589 family protein [Zea mays] | 1.00 | 829 | 1518 |
| | 2030-2050 | NP_001105116 | SBP-domain protein3 [Zea mays]<br>> gi|5931782|emb|CAB56629.1|<br>SBP-domain protein 3 [Zea mays] | 1.00 | 830 | 1519 |
| | | XP_002437398 | hypothetical protein SORBIDRAFT_10g026200 [Sorghum bicolor]<br>> gi|241915621|gb|EER88765.1|<br>hypothetical protein SORBIDRAFT_10g026200 [Sorghum bicolor] | 0.78 | 831 | 1520 |
| | | ACF78942 | unknown [Zea mays]<br>> gi|194690438|gb|ACF79303.1|<br>unknown [Zea mays]<br>> gi|223974801|gb|ACN31588.1|<br>unknown [Zea mays] | 0.70 | 832 | 1521 |
| | | NP_001105656 | SBP-domain protein4 [Zea mays]<br>> gi|5931784|emb|CAB56630.1|<br>SBP-domain protein 4 [Zea mays] | 0.69 | 833 | 1522 |
| | 1925-1945 | NP_001142263 | hypothetical protein LOC100274432 [Zea mays]<br>> gi|194707898|gb|ACF88033.1|<br>unknown [Zea mays] | 1.00 | 834 | 1523 |

TABLE 6-continued

Target Genes of down regulated miRNAs Associated with Increased NUE
(Table 2)

| Mir name | Mir Bind. Pos. | Hom. NCBI Accession | Annotation/Organism | Identity | p.p. SEQ ID NO: | p.n. SEQ ID NO: |
|---|---|---|---|---|---|---|
| | | XP_002468497 | hypothetical protein SORBIDRAFT_01g046950 [*Sorghum bicolor*] > gi|241922351|gb|EER95495.1| hypothetical protein SORBIDRAFT_01g046950 [*Sorghum bicolor*] | 0.81 | 835 | 1524 |
| | 88-108 | XP_002448249 | hypothetical protein SORBIDRAFT_06g023950 [*Sorghum bicolor*] > gi|241939432|gb|EES12577.1| hypothetical protein SORBIDRAFT_06g023950 [*Sorghum bicolor*] | 1.00 | 836 | 1525 |
| | | NP_001141834 | hypothetical protein LOC100273976 [*Zea mays*] > gi|194706118|gb|ACF87143.1| unknown [*Zea mays*] | 0.92 | 837 | 1526 |
| | | BAJ88132 | predicted protein [*Hordeum vulgare* subsp. *vulgare*] | 0.86 | 838 | 1527 |
| | | CAE02784 | OSJNBa0011L07.8 [*Oryza sativa Japonica* Group] > gi|116310379|emb|CAH67390.1| H0115B09.2 [*Oryza sativa Indica* Group] > gi|215768681|dbj|BAH00910.1| unnamed protein product [*Oryza sativa Japonica* Group] > gi|218195296|gb|EEC77723.1| hypothetical protein OsI_16815 [*Oryza sativa Indica* Group] > gi|222629289|gb|EEE61421.1| hypothetical protein OsJ_15623 [*Oryza sativa Japonica* Group] | 0.87 | 839 | 1528 |
| | | ACF88110 | unknown [*Zea mays*] | 0.76 | 840 | 1529 |
| | | NP_001065045 | Os10g0512700 [*Oryza sativa Japonica* Group] > gi|78708906|gb|ABB47881.1| SH3 domain-containing protein 3, putative, expressed [*Oryza sativa Japonica* Group] > gi|113639654|dbj|BAF26959.1| Os10g0512700 [*Oryza sativa Japonica* Group] > gi|218184876|gb|EEC67303.1| hypothetical protein OsI_34298 [*Oryza sativa Indica* Group] > gi|222613131|gb|EEE51263.1| hypothetical protein OsJ_32141 [*Oryza sativa Japonica* Group] | 0.73 | 841 | 1530 |
| | | BAJ89635 | predicted protein [*Hordeum vulgare* subsp. *vulgare*] | 0.72 | 842 | 1531 |
| | | ACG28140 | clathrin binding protein [*Zea mays*] | 0.72 | 843 | 1532 |
| | | NP_001130175 | hypothetical protein LOC100191269 [*Zea mays*] > gi|194688470|gb|ACF78319.1| unknown [*Zea mays*] | 0.72 | 844 | 1533 |
| | | XP_002464381 | hypothetical protein SORBIDRAFT_01g017250 [*Sorghum bicolor*] > gi|241918235|gb|EER91379.1| hypothetical protein SORBIDRAFT_01g017250 [*Sorghum bicolor*] | 0.71 | 845 | 1534 |

TABLE 6-continued

Target Genes of down regulated miRNAs Associated with Increased NUE
(Table 2)

| Mir name | Mir Bind. Pos. | Hom. NCBI Accession | Annotation/Organism | Identity | p.p. SEQ ID NO: | p.n. SEQ ID NO: |
|---|---|---|---|---|---|---|
| | 2810-2830 | XP_002458234 | hypothetical protein SORBIDRAFT_03g029520 [Sorghum bicolor] > gi|241930209|gb|EES03354.1| hypothetical protein SORBIDRAFT_03g029520 [Sorghum bicolor] | 1.00 | 846 | 1535 |
| | | CAI77627 | potassium uptake channel [Zea mays] | 0.93 | 847 | |
| | | NP_001105480 | potassium channel5 [Zea mays] > gi|2104908|emb|CAA68912.1| potassium channel [Zea mays] | 0.91 | 848 | 1536 |
| | | NP_001043713 | Os01g0648000 [Oryza sativa Japonica Group] > gi|122241153|sp|Q0JKV1.1| AKT1_ORYSJ RecName: Full = Potassium channel AKT1; Short = OsAKT1 > gi|113533244|dbj|BAF05627.1| Os01g0648000 [Oryza sativa Japonica Group] | 0.82 | 849 | 1537 |
| | | P0C550 | RecName: Full = Potassium channel AKT1; Short = OsAKT1 | 0.82 | 850 | |
| | | ABE99810 | inwardly rectifying potassium channel AKT1 [Hordeum vulgare] > gi|326519172|dbj|BAJ96585.1| predicted protein [Hordeum vulgare subsp. vulgare] | 0.81 | 851 | 1538 |
| | | AAF36832 | AKT1-like potassium channel [Triticum aestivum] | 0.81 | 852 | 1539 |
| | | AAL40894 | AKT1-like potassium channel [Oryza sativa] | 0.78 | 853 | 1540 |
| | | ADK93728 | inward-rectifying potassium channel [Puccinellia tenuiflora] | 0.79 | 854 | 1541 |
| | | EEE55080 | hypothetical protein OsJ_02815 [Oryza sativa Japonica Group] | 0.78 | 855 | |
| | 1465-1485 | NP_001151754 | collagen, type IV, alpha 5 [Zea mays] > gi|195649521|gb|ACG44228.1| collagen, type IV, alpha 5 [Zea mays] | 1.00 | 856 | 1542 |
| | | XP_002460574 | hypothetical protein SORBIDRAFT_02g031070 [Sorghum bicolor] > gi|241923951|gb|EER97095.1| hypothetical protein SORBIDRAFT_02g031070 [Sorghum bicolor] | 0.87 | 857 | 1543 |
| | 1702-1722 | XP_002460183 | hypothetical protein SORBIDRAFT_02g024090 [Sorghum bicolor] > gi|241923560|gb|EER96704.1| hypothetical protein SORBIDRAFT_02g024090 [Sorghum bicolor] | 1.00 | 858 | 1544 |
| | | NP_001149599 | LOC100283225 [Zea mays] > gi|194705944|gb|ACF87056.1| unknown [Zea mays] > gi|195628360|gb|ACG36010.1| annexin A4 [Zea mays] | 0.96 | 859 | 1545 |
| | | ACG40326 | annexin A4 [Zea mays] | 0.95 | 860 | 1546 |
| | | NP_001063096 | Os09g0394900 [Oryza sativa Japonica Group] > gi|49389155|dbj|BAD26449.1| putative annexin [Oryza sativa Japonica Group] | 0.89 | 861 | 1547 |

TABLE 6-continued

Target Genes of down regulated miRNAs Associated with Increased NUE
(Table 2)

| Mir name | Mir Bind. Pos. | Hom. NCBI Accession | Annotation/Organism | Identity | p.p. SEQ ID NO: | p.n. SEQ ID NO: |
|---|---|---|---|---|---|---|
| | | | > gi|49389211|dbj|BAD26499.1| putative annexin [*Oryza sativa Japonica* Group] > gi|113631329|dbj|BAF25010.1| Os09g0394900 [*Oryza sativa Japonica* Group] > gi|215692709|dbj|BAG88129.1| unnamed protein product [*Oryza sativa Japonica* Group] > gi|215704491|dbj|BAG93925.1| unnamed protein product [*Oryza sativa Japonica* Group] > gi|222641513|gb|EEE69645.1| hypothetical protein OsJ_29255 [*Oryza sativa Japonica* Group] | | | |
| | | EEC84533 | hypothetical protein OsI_31267 [*Oryza sativa Indica* Group] | 0.89 | 862 | |
| | | NP_001132118 | hypothetical protein LOC100193535 [*Zea mays*] > gi|238908661|gb|ACF80822.2| unknown [*Zea mays*] | 0.86 | 863 | 1548 |
| | | BAJ85227 | predicted protein [*Hordeum vulgare* subsp. *vulgare*] > gi|326510845|dbj|BAJ91770.1| predicted protein [*Hordeum vulgare* subsp. *vulgare*] | 0.73 | 864 | 1549 |
| | | NP_001147343 | annexin A4 [*Zea mays*] > gi|195610314|gb|ACG26987.1| annexin A4 [*Zea mays*] > gi|219887403|gb|ACL54076.1| unknown [*Zea mays*] | 0.72 | 865 | 1550 |
| | | AAR25142 | annexin [*Triticum aestivum*] | 0.73 | 866 | 1551 |
| | | ACF06448 | annexin [*Elaeis guineensis*] | 0.74 | 867 | 1552 |
| Predicted folded 24-nts-long seq 51802 | 891-914 | ACG34432 | L-allo-threonine aldolase [*Zea mays*] | 1.00 | 868 | 1553 |
| | | ACG33933 | L-allo-threonine aldolase [*Zea mays*] | 0.99 | 869 | 1554 |
| | | NP_001149239 | L-allo-threonine aldolase [*Zea mays*] > gi|195625716|gb|ACG34688.1| L-allo-threonine aldolase [*Zea mays*] | 0.98 | 870 | 1555 |
| | | NP_001053314 | Os04g0516600 [*Oryza sativa Japonica* Group] > gi|38344656|emb|CAD4182.21| OSJNBb0072M01.18 [*Oryza sativa Japonica* Group] > gi|113564885|dbj|BAF15228.1| Os04g0516600 [*Oryza sativa Japonica* Group] > gi|116310209|emb|CAH67219.1| OSIGBa0145M07.1 [*Oryza sativa Indica* Group] > gi|215708770|dbj|BAG94039.1| unnamed protein product [*Oryza sativa Japonica* Group] > gi|215765369|dbj|BAG87066.1| unnamed protein product [*Oryza sativa Japonica* Group] > gi|218195217|gb|EEC77644.1| hypothetical protein | 0.79 | 871 | 1556 |

TABLE 6-continued

Target Genes of down regulated miRNAs Associated with Increased NUE
(Table 2)

| Mir name | Mir Bind. Pos. | Hom. NCBI Accession | Annotation/Organism | Identity | p.p. SEQ ID NO: | p.n. SEQ ID NO: |
|---|---|---|---|---|---|---|
| | | | OsI_16646 [*Oryza sativa Indica* Group] > gi|222629209|gb|EEE61341.1| hypothetical protein OsJ_15466 [*Oryza sativa Japonica* Group] | | | |
| | | CAE05443 | OSJNBa0073E02.3 [*Oryza sativa Japonica* Group] | 0.75 | 872 | 1557 |
| | | XP_002448187 | hypothetical protein SORBIDRAFT_06g022630 [*Sorghum bicolor*] > gi|241939370|gb|EES12515.1| hypothetical protein SORBIDRAFT_06g022630 [*Sorghum bicolor*] | 0.79 | 873 | 1558 |
| | | ACG36649 | L-allo-threonine aldolase [*Zea mays*] | 0.80 | 874 | 1559 |
| | | BAK03835 | predicted protein [*Hordeum vulgare* subsp. *vulgare*] | 0.79 | 875 | 1560 |
| | | BAJ93201 | predicted protein [*Hordeum vulgare* subsp. *vulgare*] | 0.76 | 876 | 1561 |
| | | NP_001140767 | hypothetical protein LOC100272842 [*Zea mays*] > gi|194700996|gb|ACF84582.1| unknown [*Zea mays*] | 0.72 | 877 | 1562 |
| | 700-723 | AAS47590 | phospholipid-hydroperoxide glutathione peroxidase [*Setaria italica*] | 1.00 | 878 | 1563 |
| | | XP_002446921 | hypothetical protein SORBIDRAFT_06g024920 [*Sorghum bicolor*] > gi|48374968|gb|AAT42166.1| putative glutathione peroxidase [*Sorghum bicolor*] > gi|241938104|gb|EES11249.1| hypothetical protein SORBIDRAFT_06g024920 [*Sorghum bicolor*] | 0.99 | 879 | 1564 |
| | | NP_001141210 | hypothetical protein LOC100273297 [*Zea mays*] > gi|48374955|gb|AAT42154.1| putative glutathione peroxidase [*Zea mays*] > gi|194703274|gb|ACF85721.1| unknown [*Zea mays*] > gi|195622840|gb|ACG33250.1| phospholipid hydroperoxide glutathione peroxidase [*Zea mays*] > gi|223975959|gb|ACN32167.1| unknown [*Zea mays*] | 0.96 | 880 | 1565 |
| | | ACG39625 | phospholipid hydroperoxide glutathione peroxidase [*Zea mays*] | 0.96 | 881 | 1566 |
| | | EEC77777 | hypothetical protein OsI_16938 [*Oryza sativa Indica* Group] | 0.95 | 882 | |
| | | NP_001146472 | hypothetical protein LOC100280060 [*Zea mays*] > gi|219887431|gb|ACL54090.1| unknown [*Zea mays*] | 0.94 | 883 | 1567 |
| | | NP_001147681 | phospholipid hydroperoxide glutathione peroxidase [*Zea mays*] > gi|195613068|gb|ACG28364.1| phospholipid hydroperoxide glutathione peroxidase [*Zea mays*] | 0.94 | 884 | 1568 |

TABLE 6-continued

Target Genes of down regulated miRNAs Associated with Increased NUE
(Table 2)

| Mir name | Mir Bind. Pos. | Hom. NCBI Accession | Annotation/Organism | Identity | p.p. SEQ ID NO: | p.n. SEQ ID NO: |
|---|---|---|---|---|---|---|
| | | NP_001053524 | Os04g0556300 [*Oryza sativa Japonica* Group] > gi|21360380|gb|AAM47493.1| glutathione peroxidase 1 [*Oryza sativa*] > gi|113565095|dbj|BAF15438.1| Os04g0556300 [*Oryza sativa Japonica* Group] > gi|215693018|dbj|BAG88438.1| unnamed protein product [*Oryza sativa Japonica* Group] > gi|222629338|gb|EEE61470.1| hypothetical protein OsJ_15735 [*Oryza sativa Japonica* Group] | 0.94 | 885 | 1569 |
| | | NP_001105091 | GP protein [*Zea mays*] > gi|22268405|gb|AAM88847.2| AF520911_1 putative glutathione peroxidase [*Zea mays*] | 0.94 | 886 | 1570 |
| | | AAQ64633 | cytosolic glutathione peroxidase [*Triticum monococcum*] | 0.93 | 887 | 1571 |
| | 714-737 | XP_002446921 | hypothetical protein SORBIDRAFT_06g024920 [*Sorghum bicolor*] > gi|48374968|gb|AAT42166.1| putative glutathione peroxidase [*Sorghum bicolor*] > gi|241938104|gb|EES11249.1| hypothetical protein SORBIDRAFT_06g024920 [*Sorghum bicolor*] | 1.00 | 888 | 1572 |
| | | AAS47590 | phospholipid-hydroperoxide glutathione peroxidase [*Setaria italica*] | 0.99 | 889 | 1573 |
| | | NP_001141210 | hypothetical protein LOC100273297 [*Zea mays*] > gi|48374955|gb|AAT42154.1| putative glutathione peroxidase [*Zea mays*] > gi|194703274|gb|ACF85721.1| unknown [*Zea mays*] > gi|195622840|gb|ACG33250.1| phospholipid hydroperoxide glutathione peroxidase [*Zea mays*] > gi|223975959|gb|ACN32167.1| unknown [*Zea mays*] | 0.98 | 890 | 1574 |
| | | ACG39625 | phospholipid hydroperoxide glutathione peroxidase [*Zea mays*] | 0.97 | 891 | 1575 |
| | | EEC77777 | hypothetical protein OsI_16938 [*Oryza sativa Indica* Group] | 0.96 | 892 | |
| | | NP_001146472 | hypothetical protein LOC100280060 [*Zea mays*] > gi|219887431|gb|ACL54090.1| unknown [*Zea mays*] | 0.95 | 893 | 1576 |
| | | NP_001147681 | phospholipid hydroperoxide glutathione peroxidase [*Zea mays*] > gi|195613068|gb|ACG28364.1| phospholipid hydroperoxide glutathione peroxidase [*Zea mays*] | 0.95 | 894 | 1577 |
| | | NP_001053524 | Os04g0556300 [*Oryza sativa Japonica* Group] > gi|21360380|gb|AAM47493.1| glutathione peroxidase 1 | 0.95 | 895 | 1578 |

TABLE 6-continued

Target Genes of down regulated miRNAs Associated with Increased NUE
(Table 2)

| Mir name | Mir Bind. Pos. | Hom. NCBI Accession | Annotation/Organism | Identity | p.p. SEQ ID NO: | p.n. SEQ ID NO: |
|---|---|---|---|---|---|---|
| | | | [*Oryza sativa*] > gi|113565095|dbj|BAF15438.1| Os04g0556300 [*Oryza sativa Japonica* Group] > gi|215693018|dbj|BAG88438.1| unnamed protein product [*Oryza sativa Japonica* Group] > gi|222629338|gb|EEE61470.1| hypothetical protein OsJ_15735 [*Oryza sativa Japonica* Group] | | | |
| | | NP_001105091 | GP protein [*Zea mays*] > gi|22268405|gb|AAM88847.2| AF520911_1 putative glutathione peroxidase [*Zea mays*] | 0.95 | 896 | 1579 |
| | | AAQ64633 | cytosolic glutathione peroxidase [*Triticum monococcum*] | 0.95 | 897 | 1580 |
| | 160-183 | NP_001159179 | hypothetical protein LOC100304264 [*Zea mays*] > gi|223942501|gb|ACN25334.1| unknown [*Zea mays*] | 1.00 | 898 | 1581 |
| | | NP_001105290 | LOC542207 [*Zea mays*] > gi|57791232|gb|AAW56446.1| methyl-binding domain protein MBD113 [*Zea mays*] | 0.74 | 899 | 1582 |
| | 1054-1077 | XP_002450144 | hypothetical protein SORBIDRAFT_05g001160 [*Sorghum bicolor*] > gi|241935987|gb|EES09132.1| hypothetical protein SORBIDRAFT_05g001160 [*Sorghum bicolor*] | 1.00 | 900 | 1583 |
| | | NP_001065992 | Os12g0116000 [*Oryza sativa Japonica* Group] > gi|108862099|gb|ABA96293.2| Vacuolar sorting receptor 1 precursor, putative, expressed [*Oryza sativa Japonica* Group] > gi|113648499|dbj|BAF29011.1| Os12g0116000 [*Oryza sativa Japonica* Group] > gi|215694863|dbj|BAG90054.1| unnamed protein product [*Oryza sativa Japonica* Group] | 0.89 | 901 | 1584 |
| | | EEC68730 | hypothetical protein OsI_37233 [*Oryza sativa Indica* Group] | 0.89 | 902 | |
| | | EEE51529 | hypothetical protein OsJ_32728 [*Oryza sativa Japonica* Group] | 0.89 | 903 | |
| | | EEC67546 | hypothetical protein OsI_34875 [*Oryza sativa Indica* Group] | 0.89 | 904 | |
| | | BAK03786 | predicted protein [*Hordeum vulgare* subsp. *vulgare*] | 0.87 | 905 | 1585 |
| | | BAK00302 | predicted protein [*Hordeum vulgare* subsp. *vulgare*] | 0.87 | 906 | 1586 |
| | | CBI18031 | unnamed protein product [*Vitis vinifera*] | 0.78 | 907 | |
| | | XP_002267833 | PREDICTED: hypothetical protein [*Vitis vinifera*] | 0.78 | 908 | 1587 |
| | | XP_002309184 | predicted protein [*Populus trichocarpa*] > gi|222855160|gb|EEE92707.1| predicted protein [*Populus trichocarpa*] | 0.78 | 909 | 1588 |

TABLE 6-continued

Target Genes of down regulated miRNAs Associated with Increased NUE
(Table 2)

| Mir name | Mir Bind. Pos. | Hom. NCBI Accession | Annotation/Organism | Identity | p.p. SEQ ID NO: | p.n. SEQ ID NO: |
|---|---|---|---|---|---|---|
| | 1792-1815 | NP_001140790 | hypothetical protein LOC100272865 [Zea mays] > gi|194701088|gb|ACF84628.1| unknown [Zea mays] | 1.00 | 910 | 1589 |
| | | XP_002464219 | hypothetical protein SORBIDRAFT_01g014350 [Sorghum bicolor] > gi|241918073|gb|EER91217.1| hypothetical protein SORBIDRAFT_01g014350 [Sorghum bicolor] | 0.85 | 911 | 1590 |
| | | XP_002464218 | hypothetical protein SORBIDRAFT_01g014340 [Sorghum bicolor] > gi|241918072|gb|EER91216.1| hypothetical protein SORBIDRAFT_01g014340 [Sorghum bicolor] | 0.84 | 912 | 1591 |
| | | AAL73972 | putative cytochrome P450-like protein [Sorghum bicolor] | 0.73 | 913 | 1592 |
| | 2477-2500 | XP_002454227 | hypothetical protein SORBIDRAFT_04g027100 [Sorghum bicolor] > gi|241934058|gb|EES07203.1| hypothetical protein SORBIDRAFT_04g027100 [Sorghum bicolor] | 1.00 | 914 | 1593 |
| | | NP_001169751 | hypothetical protein LOC100383632 [Zea mays] > gi|224031415|gb|ACN34783.1| unknown [Zea mays] | 0.93 | 915 | 1594 |
| | | BAJ95386 | predicted protein [Hordeum vulgare subsp. vulgare] | 0.78 | 916 | 1595 |
| | | EEC73665 | hypothetical protein OsI_08209 [Oryza sativa Indica Group] | 0.77 | 917 | |
| | | NP_001047529 | Os02g0637800 [Oryza sativa Japonica Group] > gi|49387984|dbj|BAD25092.1| unknown protein [Oryza sativa Japonica Group] > gi|49388709|dbj|BAD25890.1| unknown protein [Oryza sativa Japonica Group] > gi|113537060|dbj|BAF09443.1| Os02g0637800 [Oryza sativa Japonica Group] > gi|215704166|dbj|BAG93006.1| unnamed protein product [Oryza sativa Japonica Group] > gi|222623311|gb|EEE57443.1| hypothetical protein OsJ_07658 [Oryza sativa Japonica Group] | 0.77 | 918 | 1596 |
| | 3108-3131 | NP_001169691 | hypothetical protein LOC100383572 [Zea mays] > gi|224030935|gb|ACN34543.1| unknown [Zea mays] | 1.00 | 919 | 1597 |
| | | ACN33688 | unknown [Zea mays] | 0.96 | 920 | 1598 |
| | | NP_001131248 | hypothetical protein LOC100192560 [Zea mays] > gi|195656461|gb|ACG47698.1| nucleic acid binding protein [Zea mays] | 0.81 | 921 | 1599 |
| | | XP_002441761 | hypothetical protein SORBIDRAFT_08g001980 [Sorghum bicolor] > gi|241942454|gb|EES15599.1| hypothetical protein SORBIDRAFT_08g001980 [Sorghum bicolor] | 0.80 | 922 | 1600 |

TABLE 6-continued

Target Genes of down regulated miRNAs Associated with Increased NUE
(Table 2)

| Mir name | Mir Bind. Pos. | Hom. NCBI Accession | Annotation/Organism | Identity | p.p. SEQ ID NO: | p.n. SEQ ID NO: |
|---|---|---|---|---|---|---|
| | 2192-2215 | NP_001150353 | LOC100283983 [Zea mays] > gi\|195638608\|gb\|ACG38772.1\| ubiquilin-1 [Zea mays] > gi\|195644430\|gb\|ACG41683.1\| ubiquilin-1 [Zea mays] > gi\|224029247\|gb\|ACN33699.1\| unknown [Zea mays] | 1.00 | 923 | 1601 |
| | | XP_002465921 | hypothetical protein SORBIDRAFT_01g048260 [Sorghum bicolor] > gi\|241919775\|gb\|EER92919.1\| hypothetical protein SORBIDRAFT_01g048260 [Sorghum bicolor] | 0.92 | 924 | 1602 |
| | | NP_001048862 | Os03g0131300 [Oryza sativa Japonica Group] > gi\|108706017\|gb\|ABF93812.1\| Ubiquitin family protein, expressed [Oryza sativa Japonica Group] > gi\|113547333\|dbj\|BAF10776.1\| Os03g0131300 [Oryza sativa Japonica Group] > gi\|215713564\|dbj\|BAG94701.1\| unnamed protein product [Oryza sativa Japonica Group] > gi\|222624144\|gb\|EEE58276.1\| hypothetical protein OsJ_09294 [Oryza sativa Japonica Group] | 0.78 | 925 | 1603 |
| | | EEC74450 | hypothetical protein OsI_09858 [Oryza sativa Indica Group] | 0.78 | 926 | |
| | | NP_001169509 | hypothetical protein LOC100383383 [Zea mays] > gi\|224029753\|gb\|ACN33952.1\| unknown [Zea mays] | 0.78 | 927 | 1604 |
| | | EAY79386 | hypothetical protein OsI_34513 [Oryza sativa Indica Group] | 0.71 | 928 | |
| | | N_001065193 | Os10g0542200 [Oryza sativa Japonica Group] > gi\|10140758\|gb\|AAG13589.1\| AC051633_5 putative ubiquitin protein [Oryza sativa Japonica Group] > gi\|31433330\|gb\|AAP54859.1\| Ubiquitin family protein, expressed [Oryza sativa Japonica Group] > gi\|113639802\|dbj\|BAF27107.1\| Os10g0542200 [Oryza sativa Japonica Group] | 0.71 | 929 | 1605 |
| | | EEE51337 | hypothetical protein OsJ_32327 [Oryza sativa Japonica Group] | 0.71 | 930 | |
| | | BAJ87273 | predicted protein [Hordeum vulgare subsp. vulgare] | 0.73 | 931 | 1606 |
| | | BAK06552 | predicted protein [Hordeum vulgare subsp. vulgare] | 0.74 | 932 | 1607 |
| | 1289-1312 | NP_001046031 | Os02g0171100 [Oryza sativa Japonica Group] > gi\|49387565\|dbj\|BAD25496.1\| putative glyceraldehyde-3-phosphate dehydrogenase [Oryza sativa Japonica Group] > gi\|49388082\|dbj\|BAD25194.1\| putative glyceraldehyde-3-phosphate dehydrogenase | 1.00 | 933 | 1608 |

TABLE 6-continued

Target Genes of down regulated miRNAs Associated with Increased NUE
(Table 2)

| Mir name | Mir Bind. Pos. | Hom. NCBI Accession | Annotation/Organism | Identity | p.p. SEQ ID NO: | p.n. SEQ ID NO: |
|---|---|---|---|---|---|---|
| | | | [*Oryza sativa Japonica* Group] > gi\|113535562\|dbj\|BAF07945.1\| Os02g0171100 [*Oryza sativa Japonica* Group] > gi\|215697739\|dbj\|BAG91733.1\| unnamed protein product [*Oryza sativa Japonica* Group] > gi\|218190154\|gb\|EEC72581.1\| hypothetical protein OsI_06028 [*Oryza sativa Indica* Group] > gi\|222622270\|gb\|EEE56402.1\| hypothetical protein OsJ_05558 [*Oryza sativa Japonica* Group] | | | |
| | | NP_001149357 | LOC100282981 [*Zea mays*] > gi\|195626622\|gb\|ACG35141.1\| glyceraldehyde-3-phosphate dehydrogenase, cytosolic [*Zea mays*] > gi\|195641440\|gb\|ACG40188.1\| glyceraldehyde-3-phosphate dehydrogenase, cytosolic [*Zea mays*] | 0.92 | 934 | 1609 |
| | | ACL54292 | unknown [*Zea mays*] | 0.92 | 935 | 1610 |
| | | XP_002451619 | hypothetical protein SORBIDRAFT_04g004750 [*Sorghum bicolor*] > gi\|241931450\|gb\|EES04595.1\| hypothetical protein SORBIDRAFT_04g004750 [*Sorghum bicolor*] | 0.90 | 936 | 1611 |
| | | NP_001130796 | hypothetical protein LOC100191900 [*Zea mays*] > gi\|194690136\|gb\|ACF79152.1\| unknown [*Zea mays*] > gi\|195622606\|gb\|ACG33133.1\| glyceraldehyde-3-phosphate dehydrogenase, cytosolic [*Zea mays*] > gi\|195625996\|gb\|ACG34828.1\| glyceraldehyde-3-phosphate dehydrogenase, cytosolic [*Zea mays*] | 0.88 | 937 | 1612 |
| | | NP_001058309 | Os06g0666600 [*Oryza sativa Japonica* Group] > gi\|52076528\|dbj\|BAD45405.1\| putative glyceraldehyde-3-phosphate dehydrogenase [*Oryza sativa Japonica* Group] > gi\|113596349\|dbj\|BAF20223.1\| Os06g0666600 [*Oryza sativa Japonica* Group] > gi\|125556399\|gb\|EAZ02005.1\| hypothetical protein OsI_24036 [*Oryza sativa Indica* Group] > gi\|215741351\|dbj\|BAG97846.1\| unnamed protein product [*Oryza sativa Japonica* Group] | 0.85 | 938 | 1613 |
| | | BAJ86344 | predicted protein [*Hordeum vulgare* subsp. *vulgare*] > gi\|326520716\|dbj\|BAJ92721.1\| predicted protein [*Hordeum vulgare* subsp. *vulgare*] | 0.82 | 939 | 1614 |
| | | ADJ96634 | glyceraldehyde-3-phosphate dehydrogenase [*Guzmania wittmackii* x *Guzmania lingulata*] | 0.82 | 940 | 1615 |

TABLE 6-continued

Target Genes of down regulated miRNAs Associated with Increased NUE
(Table 2)

| Mir name | Mir Bind. Pos. | Hom. NCBI Accession | Annotation/Organism | Identity | p.p. SEQ ID NO: | p.n. SEQ ID NO: |
|---|---|---|---|---|---|---|
| | | CAC80377 | glyceraldehyde-3-phosphate dehydrogenase [*Capsicum annuum*] > gi|26986729|emb|CAC88118.1| glyceraldehyde-3-phosphate dehydrogenase [*Capsicum annuum*] | 0.77 | 941 | 1616 |
| | | XP_002263263 | PREDICTED: hypothetical protein [*Vitis vinifera*] > gi|297736130|emb|CBI24168.3| unnamed protein product [*Vitis vinifera*] | 0.75 | 942 | 1617 |
| Predicted folded 24-nts-long seq 52801 | 173-196 | AAL76004 | putative gag-pol polyprotein [*Zea mays*] | 1.00 | 943 | |
| | | AAN40035 | putative gag-pol polyprotein [*Zea mays*] | 0.90 | 944 | |
| | | AAN40025 | putative gag-pol polyprotein [*Zea mays*] | 0.85 | 945 | |
| | | AAL66753 | putative copia-type pol polyprotein [*Zea mays*] | 0.81 | 946 | |
| | | AAP94599 | putative copia-type pol polyprotein [*Zea mays*] | 0.81 | 947 | |
| Predicted folded 24-nts-long seq 52452 | 14-37 | XP_002458660 | hypothetical protein SORBIDRAFT_03g037610 [*Sorghum bicolor*] > gi|241930635|gb|EES03780.1| hypothetical protein SORBIDRAFT_03g037610 [*Sorghum bicolor*] | 1.00 | 948 | 1618 |
| | | NP_001106055 | ribonuclease III domain protein1 [*Zea mays*] > gi|149980667|gb|ABR53724.1| chloroplast ribonuclease III domain protein [*Zea mays*] > gi|194704042|gb|ACF86105.1| unknown [*Zea mays*] > gi|195647406|gb|ACG43171.1| RNA binding protein [*Zea mays*] > gi|223950477|gb|ACN29322.1| unknown [*Zea mays*] | 0.98 | 949 | 1619 |
| | | BAJ85766 | predicted protein [*Hordeum vulgare* subsp. *vulgare*] > gi|326503490|dbj|BAJ86251.1| predicted protein [*Hordeum vulgare* subsp. *vulgare*] > gi|326520661|dbj|BAJ92694.1| predicted protein [*Hordeum vulgare* subsp. *vulgare*] | 0.91 | 950 | 1620 |
| | | EEE55556 | hypothetical protein OsJ_03820 [*Oryza sativa Japonica* Group] | 0.89 | 951 | |
| | | NP_001044581 | Os01g0810100 [*Oryza sativa Japonica* Group] > gi|20160696|dbj|BAB89639.1| unknown protein [*Oryza sativa Japonica* Group] > gi|113534112|dbj|BAF06495.1| Os01g0810100 [*Oryza sativa Japonica* Group] > gi|215701330|dbj|BAG92754.1| unnamed protein product [*Oryza sativa Japonica* Group] > gi|215704464|dbj|BAG93898.1| unnamed protein product [*Oryza sativa Japonica* Group] | 0.92 | 952 | 1621 |

TABLE 6-continued

Target Genes of down regulated miRNAs Associated with Increased NUE
(Table 2)

| Mir name | Mir Bind. Pos. | Hom. NCBI Accession | Annotation/Organism | Identity | p.p. SEQ ID NO: | p.n. SEQ ID NO: |
|---|---|---|---|---|---|---|
| | | EEC71679 | hypothetical protein OsI__04153 [*Oryza sativa Indica* Group] | 0.86 | 953 | |
| | | BAJ91324 | predicted protein [*Hordeum vulgare* subsp. *vulgare*] | 0.85 | 954 | 1622 |
| | | XP__002533159 | RNA binding protein, putative [*Ricinus communis*] > gi|223527031|gb|EEF29218.1| RNA binding protein, putative [*Ricinus communis*] | 0.75 | 955 | 1623 |
| | | NP__195467 | Ribonuclease III family protein [*Arabidopsis thaliana*] > gi|4468817|emb|CAB38218.1| putative protein [*Arabidopsis thaliana*] > gi|7270733|emb|CAB80416.1| putative protein [*Arabidopsis thaliana*] > gi|95147308|gb|ABF57289.1| At4g37510 [*Arabidopsis thaliana*] > gi|332661403|gb|AEE86803.1| Ribonuclease III family protein [*Arabidopsis thaliana*] | 0.74 | 956 | 1624 |
| | | XP__002866942 | ribonuclease III family protein [*Arabidopsis lyrata* subsp. *lyrata*] > gi|297312778|gb|EFH43201.1| ribonuclease III family protein [*Arabidopsis lyrata* subsp. *lyrata*] | 0.74 | 957 | 1625 |
| | 86-109 | NP__001169273 | hypothetical protein LOC100383136 [*Zea mays*] > gi|224028313|gb|ACN33232.1| unknown [*Zea mays*] | 1.00 | 958 | 1626 |
| | | XP__022462951 | hypothetical protein SORBIDRAFT__02g035180 [*Sorghum bicolor*] > gi|241926328|gb|EER99472.1| hypothetical protein SORBIDRAFT__02g035180 [*Sorghum bicolor*] | 0.94 | 959 | 1627 |
| | | BAK06716 | predicted protein [*Hordeum vulgare* subsp. *vulgare*] | 0.82 | 960 | 1628 |
| | | EEC82174 | hypothetical protein OsI__26284 [*Oryza sativa Indica* Group] | 0.81 | 961 | |
| | | NP__001059844 | Os07g0530100 [*Oryza sativa Japonica* Group] > gi|33146648|dbj|BAC79984.1| putative tyrosyl-DNA phosphodiesterase [*Oryza sativa Japonica* Group] > gi|113611380|dbj|BAF21758.1| Os07g0530100 [*Oryza sativa Japonica* Group] > gi|215697362|dbj|BAG91356.1| unnamed protein product [*Oryza sativa Japonica* Group] > gi|222637174|gb|EEE67306.1| hypothetical protein OsJ__24533 [*Oryza sativa Japonica* Group] | 0.81 | 962 | 1629 |
| Predicted zma mir 48588 | 69-89 | NP__001167972 | hypothetical protein LOC100381689 [*Zea mays*] > gi|223945237|gb|ACN26702.1| unknown [*Zea mays*] | 1.00 | | |
| zma-miR166d* | 1395-1415 | NP__001151161 | riboflavin kinase family protein [*Zea mays*] > gi|195644710|gb|ACG41823.1| riboflavin kinase family protein [*Zea mays*] | 1.00 | 963 | 1630 |

TABLE 6-continued

Target Genes of down regulated miRNAs Associated with Increased NUE
(Table 2)

| Mir name | Mir Bind. Pos. | Hom. NCBI Accession | Annotation/Organism | Identity | p.p. SEQ ID NO: | p.n. SEQ ID NO: |
|---|---|---|---|---|---|---|
| | | EEC76352 | hypothetical protein OsI__13934 [*Oryza sativa Indica* Group] | 0.78 | 964 | |
| | | ABF99395 | riboflavin biosynthesis protein, putative, expressed [*Oryza sativa Japonica* Group] | 0.77 | 965 | 1631 |
| | | NP__001051594 | Os03g0801700 [*Oryza sativa Japonica* Group] > gi|108711599|gb|ABF99394.1| riboflavin biosynthesis protein, putative, expressed [*Oryza sativa Japonica* Group] > gi|113550065|dbj|BAF13508.1| Os03g0801700 [*Oryza sativa Japonica* Group] > gi|222625981|gb|EEE60113.1| hypothetical protein OsJ__12987 [*Oryza sativa Japonica* Group] | 0.77 | 966 | 1632 |
| | | BAK03408 | predicted protein [*Hordeum vulgare* subsp. *vulgare*] | 0.73 | 967 | 1633 |
| | | BAJ90790 | predicted protein [*Hordeum vulgare* subsp. *vulgare*] | 0.72 | 968 | 1634 |
| Predicted folded 24-nts-long seq 52795 | 923-946 | XP__002461133 | hypothetical protein SORBIDRAFT__02g041270 [*Sorghum bicolor*] > gi|241924510|gb|EER97654.1| hypothetical protein SORBIDRAFT__02g041270 [*Sorghum bicolor*] | 1.00 | 969 | 1635 |
| | | ACR36108 | unknown [*Zea mays*] | 0.97 | 970 | 1636 |
| | | NP__001149600 | protein SFT2 [*Zea mays*] > gi|195628366|gb|ACG36013.1| protein SFT2 [*Zea mays*] | 0.96 | 971 | 1637 |
| | | BAJ93024 | predicted protein [*Hordeum vulgare* subsp. *vulgare*] | 0.90 | 972 | 1638 |
| | | BAJ93185 | predicted protein [*Hordeum vulgare* subsp. *vulgare*] | 0.90 | 973 | 1639 |
| | | NP__001057449 | Os06g0300300 [*Oryza sativa Japonica* Group] > gi|53792521|dbj|BAD53485.1| unknown protein [*Oryza sativa Japonica* Group] > gi|113595489|dbj|BAF19363.1| Os06g0300300 [*Oryza sativa Japonica* Group] > gi|215697111|dbj|BAG91105.1| unnamed protein product [*Oryza sativa Japonica* Group] > gi|215766579|dbj|BAG98738.1| unnamed protein product [*Oryza sativa Japonica* Group] > gi|218198021|gb|EEC80448.1| hypothetical protein OsI__22649 [*Oryza sativa Indica* Group] > gi|222635438|gb|EEE65570.1| hypothetical protein OsJ__21068 [*Oryza sativa Japonica* Group] | 0.89 | 974 | 1640 |
| | | XP__002532175 | Protein transport protein SFT2, putative [*Ricinus communis*] > gi|223528143|gb|EEF30212.1| Protein transport protein SFT2, putative [*Ricinus communis*] | 0.73 | 975 | 1641 |
| | | XP__002264182 | PREDICTED: hypothetical protein [*Vitis vinifera*] > gi|296085064|emb|CBI28479.3| unnamed protein product [*Vitis vinifera*] | 0.70 | 976 | 1642 |

TABLE 6-continued

Target Genes of down regulated miRNAs Associated with Increased NUE
(Table 2)

| Mir name | Mir Bind. Pos. | Hom. NCBI Accession | Annotation/Organism | Identity | p.p. SEQ ID NO: | p.n. SEQ ID NO: |
|---|---|---|---|---|---|---|
| | 149-172 | XP_002445951 | hypothetical protein SORBIDRAFT_07g028610 [Sorghum bicolor] > gi|241942301|gb|EES15446.1| hypothetical protein SORBIDRAFT_07g028610 [Sorghum bicolor] | 1.00 | 977 | 1643 |
| | | NP_001131191 | hypothetical protein LOC100192499 [Zea mays] > gi|194690830|gb|ACF79499.1| unknown [Zea mays] | 0.92 | 978 | 1644 |
| | | BAK06465 | predicted protein [Hordeum vulgare subsp. vulgare] > gi|326515200|dbj|BAK03513.1| predicted protein [Hordeum vulgare subsp. vulgare] | 0.83 | 979 | 1645 |
| | | EAZ07476 | hypothetical protein OsI_29735 [Oryza sativa Indica Group] > gi|125603873|gb|EAZ43198.1| hypothetical protein OsJ_27795 [Oryza sativa Japonica Group] | 0.83 | 980 | |
| | | NP_001062134 | Os08g0496000 [Oryza sativa Japonica Group] > gi|42408865|dbj|BAD10124.1| putative cytochrome c oxidase subunit 15(COX15) homolog isoform 1 precursor [Oryza sativa Japonica Group] > gi|113624103|dbj|BAF24048.1| Os08g0496000 [Oryza sativa Japonica Group] > gi|215737013|dbj|BAG95942.1| unnamed protein product [Oryza sativa Japonica Group] | 0.83 | 981 | 1646 |
| zma-miR169c* | 107-128 | XP_002451684 | hypothetical protein SORBIDRAFT_04g005850 [Sorghum bicolor] > gi|241931515|gb|EES04660.1| hypothetical protein SORBIDRAFT_04g005850 [Sorghum bicolor] | 1.00 | 992 | 1655 |
| | | NP_001169303 | hypothetical protein LOC100383167 [Zea mays] > gi|195627360|gb|ACG35510.1| cytochrome P450 CYP71K14 [Zea mays] | 0.85 | 993 | 1656 |
| | | ACN33338 | unknown [Zea mays] | 0.76 | 994 | 1657 |
| | 1135-1156 | NP_001169303 | hypothetical protein LOC100383167 [Zea mays] > gi|195627360|gb|ACG35510.1| cytochrome P450 CYP71K14 [Zea mays] | 1.00 | 995 | 1658 |
| | | ACN33338 | unknown [Zea mays] | 0.88 | 996 | 1659 |
| | | XP_002451684 | hypothetical protein SORBIDRAFT_04g005850 [Sorghum bicolor] > gi|241931515|gb|EES04660.1| hypothetical protein SORBIDRAFT_04g005850 [Sorghum bicolor] | 0.85 | 997 | 1660 |
| Predicted zma mir 50517 | 606-625 | XP_002436376 | hypothetical protein SORBIDRAFT_10g001390 [Sorghum bicolor] > gi|241914599|gb|EER87743.1| hypothetical protein SORBIDRAFT_10g001390 [Sorghum bicolor] | 1.00 | 998 | 1661 |

TABLE 6-continued

Target Genes of down regulated miRNAs Associated with Increased NUE
(Table 2)

| Mir name | Mir Bind. Pos. | Hom. NCBI Accession | Annotation/Organism | Identity | p.p. SEQ ID NO: | p.n. SEQ ID NO: |
|---|---|---|---|---|---|---|
| | | NP_001150208 | DAG protein [Zea mays] > gi|195637572|gb|ACG38254.1| DAG protein [Zea mays] > gi|223947219|gb|ACN27693.1| unknown [Zea mays] | 0.81 | 999 | 1662 |
| | | BAC22214 | putative plastid protein [Oryza sativa Japonica Group] | 0.81 | 1000 | 1663 |
| | | BAK01694 | predicted protein [Hordeum vulgare subsp. vulgare] | 0.80 | 1001 | 1664 |
| | | BAJ87670 | predicted protein [Hordeum vulgare subsp. vulgare] | 0.76 | 1002 | 1665 |
| | 560-579 | NP_001056622 | Os06g0116600 [Oryza sativa Japonica Group] > gi|55296199|dbj|BAD67917.1| putative DAL1 protein [Oryza sativa Japonica Group] > gi|113594662|dbj|BAF18536.1| Os06g0116600 [Oryza sativa Japonica Group] > gi|218197457|gb|EEC79884.1| hypothetical protein OsI_21391 [Oryza sativa Indica Group] > gi|222634859|gb|EEE64991.1| hypothetical protein OsJ_19911 [Oryza sativa Japonica Group] | 1.00 | 1003 | 1666 |
| | 3352-3371 | NP_001170545 | hypothetical protein LOC100384563 [Zea mays] > gi|238005944|gb|ACR34007.1| unknown [Zea mays] | 1.00 | 1004 | 1667 |
| | | XP_002436375 | hypothetical protein SORBIDRAFT_10g001380 [Sorghum bicolor] > gi|241914598|gb|EER87742.1| hypothetical protein SORBIDRAFT_10g001380 [Sorghum bicolor] | 0.85 | 1005 | 1668 |
| | | EEC79883 | hypothetical protein OsI_21390 [Oryza sativa Indica Group] | 0.81 | 1006 | |
| | | EEE64990 | hypothetical protein OsJ_19910 [Oryza sativa Japonica Group] | 0.78 | 1007 | |
| | | NP_001045600 | Os02g0102800 [Oryza sativa Japonica Group] > gi|41052906|dbj|BAD07818.1| unknown protein [Oryza sativa Japonica Group] > gi|41053240|dbj|BAD08201.1| unknown protein [Oryza sativa Japonica Group] > gi|113535131|dbj|BAF07514.1| Os02g0102800 [Oryza sativa Japonica Group] | 0.75 | 1008 | 1669 |
| Predicted zma mir 49435 | 965-985 | NP_001141527 | hypothetical protein LOC100273639 [Zea mays] > gi|194704936|gb|ACF86552.1| unknown [Zea mays] > gi|195642904|gb|ACG40920.1| hypothetical protein [Zea mays] | 1.00 | 1009 | 1670 |
| | | XP_002440488 | hypothetical protein SORBIDRAFT_09g001840 [Sorghum bicolor] > gi|241945773|gb|EES18918.1| hypothetical protein SORBIDRAFT_09g001840 [Sorghum bicolor] | 0.85 | 1010 | 1671 |

TABLE 6-continued

Target Genes of down regulated miRNAs Associated with Increased NUE
(Table 2)

| Mir name | Mir Bind. Pos. | Hom. NCBI Accession | Annotation/Organism | Identity | p.p. SEQ ID NO: | p.n. SEQ ID NO: |
|---|---|---|---|---|---|---|
| | 358-378 | ACF85023 | unknown [*Zea mays*] | 1.00 | 1011 | 1672 |
| | | NP_001151177 | transposon protein [*Zea mays*] > gi|195644822|gb|ACG41879.1| transposon protein [*Zea mays*] | 0.99 | 1012 | 1673 |
| | | XP_002452722 | hypothetical protein SORBIDRAFT_04g031370 [*Sorghum bicolor*] > gi|241932553|gb|EES05698.1| hypothetical protein SORBIDRAFT_04g031370 [*Sorghum bicolor*] | 0.86 | 1013 | 1674 |
| | | NP_001047784 | Os02g0689500 [*Oryza sativa Japonica* Group] > gi|41052806|dbj|BAD07674.1| unknown protein [*Oryza sativa Japonica* Group] > gi|113537315|dbj|BAF09698.1| Os02g0689500 [*Oryza sativa Japonica* Group] > gi|125540730|gb|EAY87125.1| hypothetical protein OsI_08527 [*Oryza sativa Indica* Group] > gi|215704259|dbj|BAG93099.1| unnamed protein product [*Oryza sativa Japonica* Group] | 0.77 | 1014 | 1675 |
| mtr-miR169q | 174-194 | XP_002468544 | hypothetical protein SORBIDRAFT_01g047710 [*Sorghum bicolor*] > gi|241922398|gb|EER95542.1| hypothetical protein SORBIDRAFT_01g047710 [*Sorghum bicolor*] | 1.00 | 1015 | 1676 |
| | | NP_001142595 | hypothetical protein LOC100274862 [*Zea mays*] > gi|195607096|gb|ACG25378.1| hypothetical protein [*Zea mays*] | 0.85 | 1016 | 1677 |
| | | ACN31627 | unknown [*Zea mays*] | 0.85 | 1017 | 1678 |
| | | ACR38267 | unknown [*Zea mays*] | 0.85 | 1018 | 1679 |
| | | NP_001144209 | hypothetical protein LOC100277070 [*Zea mays*] > gi|195638456|gb|ACG38696.1| hypothetical protein [*Zea mays*] | 0.85 | 1019 | 1680 |
| | | NP_001048909 | Os03g0138500 [*Oryza sativa Japonica* Group] > gi|108706085|gb|ABF93880.1| expressed protein [*Oryza sativa Japonica* Group] > gi|113547380|dbj|BAF10823.1| Os03g0138500 [*Oryza sativa Japonica* Group] | 0.72 | 1020 | 1681 |
| | | EAZ25513 | hypothetical protein OsJ_09336 [*Oryza sativa Japonica* Group] | 0.71 | 1021 | |
| | | EAY88465 | hypothetical protein OsI_09934 [*Oryza sativa Indica* Group] | 0.71 | 1022 | |
| | 1074-1094 | NP_001150090 | PIT1 [*Zea mays*] > gi|195636634|gb|ACG37785.1| PIT1 [*Zea mays*] | 1.00 | 1023 | 1682 |
| | | NP_001042834 | Os01g0303600 [*Oryza sativa Japonica* Group] > gi|52075677|dbj|BAD44897.1| zinc finger protein-like [*Oryza sativa Japonica* Group] > gi|52077476|dbj|BAD45040.1| zinc finger protein-like [*Oryza sativa Japonica* Group] > gi|218188061|dbj|EEC70488.1| | 0.76 | 1024 | 1683 |

TABLE 6-continued

Target Genes of down regulated miRNAs Associated with Increased NUE
(Table 2)

| Mir name | Mir Bind. Pos. | Hom. NCBI Accession | Annotation/Organism | Identity | p.p. SEQ ID NO: | p.n. SEQ ID NO: |
|---|---|---|---|---|---|---|
| | | | hypothetical protein OsI_01559 [*Oryza sativa Indica* Group] > gi|255673151|dbj|BAF04748.2| Os01g0303600 [*Oryza sativa Japonica* Group] | | | |
| Predicted zma mir 49003 | 71-92 | XP_002437560 | hypothetical protein SORBIDRAFT_10g029400 [*Sorghum bicolor*] > gi|241915783|gb|EER88927.1| hypothetical protein SORBIDRAFT_10g029400 [*Sorghum bicolor*] | 1.00 | 1025 | 1684 |
| | | ACL53917 | unknown [*Zea mays*] | 0.97 | 1026 | 1685 |
| | | NP_001152313 | LOC100285952 [*Zea mays*] > gi|195654989|gb|ACG46962.1| MPK17-1-putative MAPK [*Zea mays*] | 0.97 | 1027 | 1686 |
| | | NP_001146196 | LOC100279766 [*Zea mays*] > gi|219886151|gb|ACL53450.1| unknown [*Zea mays*] > gi|297595201|gb|ADI48121.1| putative mitogen-activated protein kinase 17-3 [*Zea mays*] | 0.95 | 1028 | 1687 |
| | | EEC81289 | hypothetical protein OsI_24409 [*Oryza sativa Indica* Group] | 0.91 | 1029 | |
| | | NP_001058530 | Os06g0708000 [*Oryza sativa Japonica* Group] > gi|108860803|sp|Q5Z9J0.2| MPK12_ORYSJ RecName: Full = Mitogen-activated protein kinase 12; Short = MAP kinase 12; AltName: Full = Blast- and wound-induced MAP kinase 1; AltName: Full = MAP kinase 1; AltName: Full = OsBWMK1; AltName: Full = OsMAPK1 > gi|53792601|dbj|BAD53616.1| putative MAP kinase [*Oryza sativa Japonica* Group] > gi|113596570|dbj|BAF20444.1| Os06g0708000 [*Oryza sativa Japonica* Group] | 0.91 | 1030 | 1688 |
| | | AAX20165 | putative MAPK protein kinase [*Triticum aestivum*] > gi|84795226|gb|ABC65849.1| mitogen-activated protein kinase MAPK1e [*Triticum aestivum*] | 0.86 | 1031 | 1689 |
| | | ABC54587 | mitogen-activated protein kinase [*Triticum aestivum*] | 0.86 | 1032 | 1690 |
| | | AAX20166 | putative MAPK protein kinase [*Triticum aestivum*] | 0.86 | 1033 | 1691 |
| | | ABD97883 | mitogen-activated protein kinase [*Triticum aestivum*] | 0.86 | 1034 | 1692 |
| | 53-74 | EAY76957 | hypothetical protein OsI_04915 [*Oryza sativa Indica* Group] | 1.00 | 1035 | |
| | | NP_001045192 | Os01g0916200 [*Oryza sativa Japonica* Group] > gi|19386749|dbj|BAB86130.1| putative adapter-related protein complex 4 epsilon 1 subunit [*Oryza sativa Japonica* Group] > gi|20805003|dbj|BAB92679.1| putative adapter-related protein complex 4 epsilon 1 subunit [*Oryza sativa Japonica* Group] | 1.00 | 1036 | 1693 |

TABLE 6-continued

Target Genes of down regulated miRNAs Associated with Increased NUE
(Table 2)

| Mir name | Mir Bind. Pos. | Hom. NCBI Accession | Annotation/Organism | Identity | p.p. SEQ ID NO: | p.n. SEQ ID NO: |
|---|---|---|---|---|---|---|
| | | | > gi|113534723|dbj|BAF07106.1| Os01g0916200 [*Oryza sativa Japonica* Group] > gi|215707205|dbj|BAG93665.1| unnamed protein product [*Oryza sativa Japonica* Group] | | | |
| | | EAZ14613 | hypothetical protein OsJ_04538 [*Oryza sativa Japonica* Group] | 0.93 | 1037 | |
| | | XP_002458982 | hypothetical protein SORBIDRAFT_03g043730 [*Sorghum bicolor*] > gi|241930957|gb|EES04102.1| hypothetical protein SORBIDRAFT_03g043730 [*Sorghum bicolor*] | 0.91 | 1038 | 1694 |
| | | NP_001169710 | hypothetical protein LOC100383591 [*Zea mays*] > gi|224031083|gb|ACN34617.1| unknown [*Zea mays*] | 0.90 | 1039 | 1695 |
| | | BAJ89128 | predicted protein [*Hordeum vulgare* subsp. *vulgare*] | 0.88 | 1040 | 1696 |
| | | XP_002328755 | predicted protein [*Populus trichocarpa*] > gi|222839053|gb|EEE77404.1| predicted protein [*Populus trichocarpa*] | 0.70 | 1041 | 1697 |
| | | XP_002519936 | AP-1 complex subunit gamma-2, putative [*Ricinus communis*] > gi|223540982|gb|EEF42540.1| AP-1 complex subunit gamma-2, putative [*Ricinus communis*] | 0.71 | 1042 | 1698 |
| zma-miR399g | 897-917 | NP_001105061 | Hageman factor inhibitor [*Zea mays*] > gi|16305146|gb|AAL16995.1| Hageman factor inhibitor [*Zea mays*] | 1.00 | 1043 | 1699 |
| | | NP_001106233 | trypsin/factor XIIA inhibitor precursor [*Zea mays*] > gi|266398|sp|P01088.2|ITRF_MAIZE RecName: Full = Trypsin/factor XIIA inhibitor; AltName: Full = CHFI; AltName: Full = Hageman factor inhibitor; Flags: Precursor > gi|22327|emb|CAA37998.1| corn Hageman factor inhibitor [*Zea mays*] > gi|75994173|gb|ABA34122.1| hageman factor inhibitor [*Zea mays* subsp. *parviglumis*] > gi|75994177|gb|ABA34124.1| hageman factor inhibitor [*Zea mays* subsp. *parviglumis*] > gi|75994189|gb|ABA34130.1| hageman factor inhibitor [*Zea mays* subsp. *parviglumis*] > gi|75994193|gb|ABA34132.1| hageman factor inhibitor [*Zea mays* subsp. *parviglumis*] > gi|195658559|gb|ACG48747.1| trypsin/factor XIIA inhibitor precursor [*Zea mays*] > gi|195658619|gb|ACG48777.1| trypsin/factor XIIA inhibitor precursor [*Zea mays*] > gi|214014768|gb|ACJ62034.1| | 0.84 | 1044 | 1700 |

TABLE 6-continued

Target Genes of down regulated miRNAs Associated with Increased NUE
(Table 2)

| Mir name | Mir Bind. Pos. | Hom. NCBI Accession | Annotation/Organism | Identity | p.p. SEQ ID NO: | p.n. SEQ ID NO: |
|---|---|---|---|---|---|---|
| | | | Hageman factor inhibitor [*Zea mays* subsp. *parviglumis*] > gi|214014812|gb|ACJ62056.1| Hageman factor inhibitor [*Zea mays* subsp. *parviglumis*] > gi|214014814|gb|ACJ62057.1| Hageman factor inhibitor [*Zea mays* subsp. *parviglumis*] > gi|214014820|gb|ACJ62060.1| Hageman factor inhibitor [*Zea mays* subsp. *parviglumis*] > gi|214014826|gb|ACJ62063.1| Hageman factor inhibitor [*Zea mays* subsp. *parviglumis*] > gi|214014828|gb|ACJ62064.1| Hageman factor inhibitor [*Zea mays* subsp. *parviglumis*] > gi|214014862|gb|ACJ62081.1| Hageman factor inhibitor [*Zea mays* subsp. *parviglumis*] > gi|214014864|gb|ACJ62082.1| Hageman factor inhibitor [*Zea mays* subsp. *parviglumis*] > gi|214014870|gb|ACJ62085.1| Hageman factor inhibitor [*Zea mays* subsp. *parviglumis*] > gi|238014562|gb|ACR38316.1| unknown [*Zea mays*] | | | |
| | | ABA34135 | hageman factor inhibitor [*Zea mays* subsp. *parviglumis*] > gi|214014790|gb|ACJ62045.1| Hageman factor inhibitor [*Zea mays* subsp. *parviglumis*] > gi|214014796|gb|ACJ62048.1| Hageman factor inhibitor [*Zea mays* subsp. *parviglumis*] | 0.83 | 1045 | 1701 |
| | | ACJ62011 | Hageman factor inhibitor [*Zea mays* subsp. *parviglumis*] > gi|214014726|gb|ACJ62013.1| Hageman factor inhibitor [*Zea mays* subsp. *parviglumis*] > gi|214014728|gb|ACJ62014.1| Hageman factor inhibitor [*Zea mays* subsp. *parviglumis*] > gi|214014730|gb|ACJ62015.1| Hageman factor inhibitor [*Zea mays* subsp. *parviglumis*] > gi|214014732|gb|ACJ62016.1| Hageman factor inhibitor [*Zea mays* subsp. *parviglumis*] > gi|214014734|gb|ACJ62017.1| Hageman factor inhibitor [*Zea mays* subsp. *parviglumis*] > gi|214014744|gb|ACJ62022.1| Hageman factor inhibitor [*Zea mays* subsp. *parviglumis*] > gi|214014746|gb|ACJ62023.1| Hageman factor inhibitor [*Zea mays* subsp. *parviglumis*] > gi|214014748|gb|ACJ62024.1| Hageman factor inhibitor [*Zea mays* subsp. *parviglumis*] | 0.83 | 1046 | 1702 |
| | | ABA34133 | hageman factor inhibitor [*Zea mays* subsp. *parviglumis*] | 0.83 | 1047 | 1703 |
| | | ACJ62080 | Hageman factor inhibitor [*Zea mays* subsp. *parviglumis*] | 0.83 | 1048 | 1704 |
| | | ABA34137 | hageman factor inhibitor [*Zea diploperennis*] > gi|75994207|gb|ABA34139.1| hageman factor inhibitor [*Zea diploperennis*] > gi|75994211|gb|ABA34141.1| hageman factor inhibitor | 0.83 | 1049 | 1705 |

TABLE 6-continued

Target Genes of down regulated miRNAs Associated with Increased NUE
(Table 2)

| Mir name | Mir Bind. Pos. | Hom. NCBI Accession | Annotation/Organism | Identity | p.p. SEQ ID NO: | p.n. SEQ ID NO: |
|---|---|---|---|---|---|---|
| | | | [Zea diploperennis] > gi\|75994213\|gb\|ABA34142.1\| hageman factor inhibitor [Zea diploperennis] > gi\|75994215\|gb\|ABA34143.1\| hageman factor inhibitor [Zea diploperennis] > gi\|75994217\|gb\|ABA34144.1\| hageman factor inhibitor [Zea diploperennis] | | | |
| | | ACG48546 | trypsin/factor XIIA inhibitor precursor [Zea mays] | 0.83 | 1050 | 1706 |
| | | ABA34129 | hageman factor inhibitor [Zea mays subsp. parviglumis] | 0.83 | 1051 | 1707 |
| | | ABA34125 | hageman factor inhibitor [Zea mays subsp. parviglumis] > gi\|75994185\|gb\|ABA34128.1\| hageman factor inhibitor [Zea mays subsp. parviglumis] > gi\|214014736\|gb\|ACJ62018.1\| Hageman factor inhibitor [Zea mays subsp. parviglumis] > gi\|214014752\|gb\|ACJ62026.1\| Hageman factor inhibitor [Zea mays subsp. parviglumis] > gi\|214014822\|gb\|ACJ62061.1\| Hageman factor inhibitor [Zea mays subsp. parviglumis] | 0.83 | 1052 | 1708 |
| Predicted zma mir 49985 | 379-399 | XP_002454327 | hypothetical protein SORBIDRAFT_04g028730 [Sorghum bicolor] > gi\|241934158\|gb\|EES07303.1\| hypothetical protein SORBIDRAFT_04g028730 [Sorghum bicolor] | 1.00 | 1053 | 1709 |
| | | ACG36841 | caleosin related protein [Zea mays] | 0.81 | 1054 | 1710 |
| | | ACN31536 | unknown [Zea mays] | 0.78 | 1055 | 1711 |
| | | NP_001142815 | hypothetical protein LOC100275194 [Zea mays] > gi\|195610158\|gb\|ACG26909.1\| hypothetical protein [Zea mays] | 0.79 | 1056 | 1712 |
| | | NP_001148700 | caleosin related protein [Zea mays] > gi\|195621488\|gb\|ACG32574.1\| caleosin related protein [Zea mays] | 0.77 | 1057 | 1713 |
| | 632-652 | XP_002448765 | hypothetical protein SORBIDRAFT_06g032800 [Sorghum bicolor] > gi\|241939948\|gb\|EES13093.1\| hypothetical protein SORBIDRAFT_06g032800 [Sorghum bicolor] | 1.00 | 1058 | 1714 |
| | | NP_001131374 | hypothetical protein LOC100192699 [Zea mays] > gi\|195620734\|gb\|ACG32197.1\| oligosaccharyl transferase STT3 subunit [Zea mays] | 0.99 | 1059 | 1715 |
| | | NP_001168720 | hypothetical protein LOC100382512 [Zea mays] > gi\|223950395\|gb\|ACN29281.1\| unknown [Zea mays] | 0.98 | 1060 | 1716 |
| | | NP_001054248 | Os04g0675500 [Oryza sativa Japonica Group] > gi\|38344929\|emb\|CAE03245.2\| OSJNBa0018M05.20 [Oryza sativa Japonica Group] > gi\|90399055\|emb\|CAJ86104.1\| H0103C06.8 [Oryza sativa Indica Group] | 0.96 | 1061 | 1717 |

TABLE 6-continued

Target Genes of down regulated miRNAs Associated with Increased NUE
(Table 2)

| Mir name | Mir Bind. Pos. | Hom. NCBI Accession | Annotation/Organism | Identity | p.p. SEQ ID NO: | p.n. SEQ ID NO: |
|---|---|---|---|---|---|---|
| | | | > gi|113565819|dbj|BAF16162.1| Os04g0675500 [*Oryza sativa Japonica* Group] > gi|125550210|gb|EAY96032.1| hypothetical protein OsI_17905 [*Oryza sativa Indica* Group] > gi|125592048|gb|EAZ32398.1| hypothetical protein OsJ_16609 [*Oryza sativa Japonica* Group] > gi|215708677|dbj|BAG93946.1| unnamed protein product [*Oryza sativa Japonica* Group] | | | |
| | | BAJ87792 | predicted protein [*Hordeum vulgare* subsp. *vulgare*] | 0.95 | 1062 | 1718 |
| | | CBG76274 | OO__Ba0005L10-OO__Ba0081K17.25 [*Oryza officinalis*] | 0.93 | 1063 | 1719 |
| | | XP_002269119 | PREDICTED: hypothetical protein [*Vitis vinifera*] | 0.86 | 1064 | 1720 |
| | | XP_002318345 | predicted protein [*Populus trichocarpa*] > gi|222859018|gb|EEE96565.1| predicted protein [*Populus trichocarpa*] | 0.86 | 1065 | 1721 |
| | | XP_002891078 | hypothetical protein ARALYDRAFT_891007 [*Arabidopsis lyrata* subsp. *lyrata*] > gi|297336920|gb|EFH67337.1| hypothetical protein ARALYDRAFT_891007 [*Arabidopsis lyrata* subsp. *lyrata*] | 0.85 | 1066 | 1722 |
| | | XP_002329687 | predicted protein [*Populus trichocarpa*] > gi|222870595|gb|EEF07726.1| predicted protein [*Populus trichocarpa*] | 0.85 | 1067 | 1723 |
| | 795-815 | XP_002458747 | hypothetical protein SORBIDRAFT_03g039530 [*Sorghum bicolor*] > gi|241930722|gb|EES03867.1| hypothetical protein SORBIDRAFT_03g039530 [*Sorghum bicolor*] | 1.00 | 1068 | 1724 |
| | | NP_001147942 | L-ascorbate oxidase [*Zea mays*] > gi|195614732|gb|ACG29196.1| L-ascorbate oxidase precursor [*Zea mays*] | 0.96 | 1069 | 1725 |
| | | ACN34362 | unknown [*Zea mays*] | 0.96 | 1070 | 1726 |
| | | EEC71780 | hypothetical protein OsI_04394 [*Oryza sativa Indica* Group] | 0.86 | 1071 | |
| | | NP_001044773 | Os01g0842500 [*Oryza sativa Japonica* Group] > gi|19571025|dbj|BAB86452.1| putative laccase LAC5-6 [*Oryza sativa Japonica* Group] > gi|113534304|dbj|BAF06687.1| Os01g0842500 [*Oryza sativa Japonica* Group] > gi|125572601|gb|EAZ14116.1| hypothetical protein OsJ_04040 [*Oryza sativa Japonica* Group] > gi|215694814|dbj|BAG90005.1| unnamed protein product [*Oryza sativa Japonica* Group] | 0.86 | 1072 | 1727 |

TABLE 6-continued

Target Genes of down regulated miRNAs Associated with Increased NUE
(Table 2)

| Mir name | Mir Bind. Pos. | Hom. NCBI Accession | Annotation/Organism | Identity | p.p. SEQ ID NO: | p.n. SEQ ID NO: |
|---|---|---|---|---|---|---|
| | | BAJ84890 | predicted protein [*Hordeum vulgare* subsp. *vulgare*] | 0.84 | 1073 | 1728 |
| | | BAJ96691 | predicted protein [*Hordeum vulgare* subsp. *vulgare*] | 0.84 | 1074 | 1729 |
| | | NP_001105875 | putative laccase [*Zea mays*] > gi|84618781|emb|CAJ30500.1| putative laccase [*Zea mays*] | 0.79 | 1075 | 1730 |
| | | ACN28855 | unknown [*Zea mays*] | 0.79 | 1076 | 1731 |
| | | XP_002458746 | hypothetical protein SORBIDRAFT_03g039520 [*Sorghum bicolor*] > gi|241930721|gb|EES03866.1| hypothetical protein SORBIDRAFT_03g039520 [*Sorghum bicolor*] | 0.78 | 1077 | 1732 |
| | 198-218 | XP_002458746 | hypothetical protein SORBIDRAFT_03g039520 [*Sorghum bicolor*] > gi|241930721|gb|EES03866.1| hypothetical protein SORBIDRAFT_03g039520 [*Sorghum bicolor*] | 1.00 | 1078 | 1733 |
| | | NP_001105875 | putative laccase [*Zea mays*] > gi|84618781|emb|CAJ30500.1| putative laccase [*Zea mays*] | 0.94 | 1079 | 1734 |
| | | NP_001146658 | hypothetical protein LOC100280258 [*Zea mays*] > gi|219888209|gb|ACL54479.1| unknown [*Zea mays*] | 0.93 | 1080 | 1735 |
| | | ACN28855 | unknown [*Zea mays*] | 0.94 | 1081 | 1736 |
| | | NP_001044772 | Os01g0842400 [*Oryza sativa Japonica* Group] > gi|75321217|sp|Q5N9X2.1| LAC4_ORYSJ RecName: Full = Laccase-4; AltName: Full = Benzenediol:oxygen oxidoreductase 4; AltName: Full = Diphenol oxidase 4; AltName: Full = Urishiol oxidase 4; Flags: Precursor > gi|56784239|dbj|BAD81734.1| putative laccase LAC5-6 [*Oryza sativa Japonica* Group] > gi|113534303|dbj|BAF06686.1| Os01g0842400 [*Oryza sativa Japonica* Group] > gi|215697155|dbj|BAG91149.1| unnamed protein product [*Oryza sativa Japonica* Group] | 0.80 | 1082 | 1737 |
| | | EAZ14115 | hypothetical protein OsJ_04039 [*Oryza sativa Japonica* Group] | 0.80 | 1083 | |
| | | EEC71777 | hypothetical protein OsI_04389 [*Oryza sativa Indica* Group] | 0.80 | 1084 | |
| | | BAJ99773 | predicted protein [*Hordeum vulgare* subsp. *vulgare*] | 0.78 | 1085 | 1738 |
| | | XP_002458747 | hypothetical protein SORBIDRAFT_03g039530 [*Sorghum bicolor*] > gi|241930722|gb|EES03867.1| hypothetical protein SORBIDRAFT_03g039530 [*Sorghum bicolor*] | 0.78 | 1086 | 1739 |
| | | AAC04576 | putative high-pI laccase [*Oryza sativa Japonica* Group] | 0.79 | 1087 | 1740 |
| | 751-771 | XP_002456566 | hypothetical protein SORBIDRAFT_03g038550 [*Sorghum bicolor*] > gi|241928541|gb|EES01686.1| | 1.00 | 1088 | 1741 |

TABLE 6-continued

Target Genes of down regulated miRNAs Associated with Increased NUE
(Table 2)

| Mir name | Mir Bind. Pos. | Hom. NCBI Accession | Annotation/Organism | Identity | p.p. SEQ ID NO: | p.n. SEQ ID NO: |
|---|---|---|---|---|---|---|
| | | | hypothetical protein SORBIDRAFT_03g038550 [*Sorghum bicolor*] | | | |
| | | NP_001148479 | L-ascorbate oxidase [*Zea mays*] > gi|195619672|gb|ACG31666.1| L-ascorbate oxidase precursor [*Zea mays*] | 0.92 | 1089 | 1742 |
| | | NP_001183899 | hypothetical protein LOC100502492 [*Zea mays*] > gi|223948465|gb|ACN28316.1| unknown [*Zea mays*] > gi|238015342|gb|ACR38706.1| unknown [*Zea mays*] | 0.90 | 1090 | 1743 |
| | | NP_001044679 | Os01g0827300 [*Oryza sativa Japonica* Group] > gi|75331868|sp|Q941X2.1| LAC3_ORYSJ RecName: Full = Benzenediol: oxygen oxidoreductase 3; AltName: Full = Diphenol oxidase 3; AltName: Full = Urishiol oxidase 3; Flags: Precursor > gi|15624045|dbj|BAB68098.1| putative laccase [*Oryza sativa Japonica* Group] > gi|113534210|dbj|BAF06593.1| Os01g0827300 [*Oryza sativa Japonica* Group] > gi|215701334|dbj|BAG92758.1| unnamed protein product [*Oryza sativa Japonica* Group] > gi|222619479|gb|EEE55611.1| hypothetical protein OsJ_03932 [*Oryza sativa Japonica* Group] | 0.84 | 1091 | 1744 |
| | | ACN27868 | unknown [*Zea mays*] | 0.82 | 1092 | 1745 |
| | | XP_002315131 | laccase 90c [*Populus trichocarpa*] > gi|222864171|gb|EEF01302.1| laccase 90c [*Populus trichocarpa*] | 0.71 | 1093 | 1746 |
| | | ABK92474 | unknown [*Populus trichocarpa*] | 0.70 | 1094 | 1747 |
| | | XP_002312186 | laccase 90a [*Populus trichocarpa*] > gi|222852006|gb|EEE89553.1| laccase 90a [*Populus trichocarpa*] | 0.70 | 1095 | 1748 |
| | 868-888 | NP_001141205 | hypothetical protein LOC100273292 [*Zea mays*] > gi|223944003|gb|ACN26085.1| unknown [*Zea mays*] | 1.00 | 1096 | 1749 |
| | | ACF85713 | unknown [*Zea mays*] | 0.91 | 1097 | 1750 |
| | | XP_002446013 | hypothetical protein SORBIDRAFT_06g000500 [*Sorghum bicolor*] > gi|241937196|gb|EES10341.1| hypothetical protein SORBIDRAFT_06g000500 [*Sorghum bicolor*] | 0.84 | 1098 | 1751 |
| | | XP_002446014 | hypothetical protein SORBIDRAFT_06g000510 [*Sorghum bicolor*] > gi|241937197|gb|EES10342.1| hypothetical protein SORBIDRAFT_06g000510 [*Sorghum bicolor*] | 0.81 | 1099 | 1752 |
| | | CAH67827 | B0616E02-H0507E05.3 [*Oryza sativa Indica* Group] > gi|125546940|gb|EAY92762.1| hypothetical protein | 0.80 | 1100 | 1753 |

TABLE 6-continued

Target Genes of down regulated miRNAs Associated with Increased NUE
(Table 2)

| Mir name | Mir Bind. Pos. | Hom. NCBI Accession | Annotation/Organism | Identity | p.p. SEQ ID NO: | p.n. SEQ ID NO: |
|---|---|---|---|---|---|---|
| | | | OsI_14564 [*Oryza sativa Indica* Group] > gi\|125589087\|gb\|EAZ29437.1\| hypothetical protein OsJ_13511 [*Oryza sativa Japonica* Group] | | | |
| | | BAJ88131 | predicted protein [*Hordeum vulgare* subsp. *vulgare*] | 0.83 | 1101 | 1754 |
| | 172-192 | NP_001148700 | caleosin related protein [*Zea mays*] > gi\|195621488\|gb\|ACG32574.1\| caleosin related protein [*Zea mays*] | 1.00 | 1102 | 1755 |
| | | ACN31536 | unknown [*Zea mays*] | 0.99 | 1103 | 1756 |
| | | ACG36841 | caleosin related protein [*Zea mays*] | 0.83 | 1104 | 1757 |
| | | NP_001142815 | hypothetical protein LOC100275194 [*Zea mays*] > gi\|195610158\|gb\|ACG26909.1\| hypothetical protein [*Zea mays*] | 0.82 | 1105 | 1758 |
| | | XP_002454327 | hypothetical protein SORBIDRAFT_04g028730 [*Sorghum bicolor*] > gi\|241934158\|gb\|EES07303.1\| hypothetical protein SORBIDRAFT_04g028730 [*Sorghum bicolor*] | 0.76 | 1106 | 1759 |
| | 782-802 | XP_002465485 | hypothetical protein SORBIDRAFT_01g039690 [*Sorghum bicolor*] > gi\|241919339\|gb\|EER92483.1\| hypothetical protein SORBIDRAFT_01g039690 [*Sorghum bicolor*] | 1.00 | 1107 | 1760 |
| | | NP_001131665 | hypothetical protein LOC100193025 [*Zea mays*] > gi\|194692196\|gb\|ACF80182.1\| unknown [*Zea mays*] | 0.92 | 1108 | 1761 |
| | | NP_001049699 | Os03g0273200 [*Oryza sativa Japonica* Group] > gi\|122247226\|sp\|Q10ND7.1\| LAC10_ORYSJ RecName: Full = Laccase-10; AltName: Full = Benzenediol:oxygen oxidoreductase 10; AltName: Full = Diphenol oxidase 10; AltName: Full = Urishiol oxidase 10; Flags: Precursor > gi\|108707435\|gb\|ABF95230.1\| laccase, putative, expressed [*Oryza sativa Japonica* Group] > gi\|113548170\|dbj\|BAF11613.1\| Os03g0273200 [*Oryza sativa Japonica* Group] > gi\|215704111\|dbj\|BAG92951.1\| unnamed protein product [*Oryza sativa Japonica* Group] > gi\|215765805\|dbj\|BAG87502.1\| unnamed protein product [*Oryza sativa Japonica* Group] > gi\|222624652\|gb\|EEE58784.1\| hypothetical protein OsJ_10313 [*Oryza sativa Japonica* Group] | 0.82 | 1109 | 1762 |
| | | XP_002531824 | laccase, putative [*Ricinus communis*] > gi\|223528520\|gb\|EEF30544.1\| laccase, putative [*Ricinus communis*] | 0.73 | 1110 | 1763 |

TABLE 6-continued

Target Genes of down regulated miRNAs Associated with Increased NUE
(Table 2)

| Mir name | Mir Bind. Pos. | Hom. NCBI Accession | Annotation/Organism | Identity | p.p. SEQ ID NO: | p.n. SEQ ID NO: |
|---|---|---|---|---|---|---|
| | | XP_002278215 | PREDICTED: hypothetical protein [*Vitis vinifera*] | 0.73 | 1111 | 1764 |
| | | CBI16199 | unnamed protein product [*Vitis vinifera*] | 0.72 | 1112 | |
| | | XP_002278232 | PREDICTED: hypothetical protein [*Vitis vinifera*] | 0.73 | 1113 | 1765 |
| | | XP_002282823 | PREDICTED: hypothetical protein [*Vitis vinifera*] | 0.74 | 1114 | 1766 |
| | 943-963 | NP_001183899 | hypothetical protein LOC100502492 [*Zea mays*] > gi|223948465|gb|ACN28316.1| unknown [*Zea mays*] > gi|238015342|gb|ACR38706.1| unknown [*Zea mays*] | 1.00 | 1115 | 1767 |
| | | NP_001148479 | L-ascorbate oxidase [*Zea mays*] > gi|195619672|gb|ACG31666.1| L-ascorbate oxidase precursor [*Zea mays*] | 0.90 | 1116 | 1768 |
| | | XP_002456566 | hypothetical protein SORBIDRAFT_03g038550 [*Sorghum bicolor*] > gi|241928541|gb|EES01686.1| hypothetical protein SORBIDRAFT_03g038550 [*Sorghum bicolor*] | 0.89 | 1117 | 1769 |
| | | NP_001044679 | Os01g0827300 [*Oryza sativa Japonica* Group] > gi|75331868|sp|Q941X2.1| LAC3_ORYSJ RecName: Full = Laccase-3; AltName: Full = Benzenediol:oxygen oxidoreductase 3; AltName: Full = Diphenol oxidase 3; AltName: Full = Urishiol oxidase 3; Flags: Precursor > gi|15624045|dbj|BAB68098.1| putative laccase [*Oryza sativa Japonica* Group] > gi|113534210|dbj|BAF06593.1| Os01g0827300 [*Oryza sativa Japonica* Group] > gi|215701334|dbj|BAG92758.1| unnamed protein product [*Oryza sativa Japonica* Group] > gi|222619479|gb|EEE55611.1| hypothetical protein OsJ_03932 [*Oryza sativa Japonica* Group] | 0.83 | 1118 | 1770 |
| | | ACN27868 | unknown [*Zea mays*] | 0.80 | 1119 | 1771 |
| | | XP_002315131 | laccase 90c [*Populus trichocarpa*] > gi|222864171|gb|EEF01302.1| laccase 90c [*Populus trichocarpa*] | 0.70 | 1120 | 1772 |
| | | CBI25418 | unnamed protein product [*Vitis vinifera*] | 0.71 | 1121 | 1773 |
| | | XP_002273875 | PREDICTED: hypothetical protein [*Vitis vinifera*] | 0.71 | 1122 | 1774 |
| | 852-872 | NP_001105875 | putative laccase [*Zea mays*] > gi|84618781|emb|CAJ30500.1| putative laccase [*Zea mays*] | 1.00 | 1123 | 1775 |
| | | ACN28855 | unknown [*Zea mays*] | 0.98 | 1124 | 1776 |
| | | NP_001146658 | hypothetical protein LOC100280258 [*Zea mays*] > gi|219888209|gb|ACL54479.1| unknown [*Zea mays*] | 0.94 | 1125 | 1777 |
| | | XP_002458746 | hypothetical protein SORBIDRAFT_03g039520 [*Sorghum bicolor*] > gi|241930721|gb|EES03866.1| | 0.91 | 1126 | 1778 |

TABLE 6-continued

Target Genes of down regulated miRNAs Associated with Increased NUE
(Table 2)

| Mir name | Mir Bind. Pos. | Hom. NCBI Accession | Annotation/Organism | Identity | p.p. SEQ ID NO: | p.n. SEQ ID NO: |
|---|---|---|---|---|---|---|
| | | NP_001044772 | hypothetical protein SORBIDRAFT_03g039520 [Sorghum bicolor] Os01g0842400 [Oryza sativa Japonica Group] > gi|75321217|sp|Q5N9X2.1| LAC4_ORYSJ RecName: Full = Laccase-4; AltName: Full = Benzenediol:oxygen oxidoreductase 4; AltName: Full = Diphenol oxidase 4; AltName: Full = Urishiol oxidase 4; Flags: Precursor > gi|56784239|dbj|BAD81734.1| putative laccase LAC5-6 [Oryza sativa Japonica Group] > gi|113534303|dbj|BAF06686.1| Os01g0842400 [Oryza sativa Japonica Group] > gi|215697155|dbj|BAG91149.1| unnamed protein product [Oryza sativa Japonica Group] | 0.80 | 1127 | 1779 |
| | | EAZ14115 | hypothetical protein OsJ_04039 [Oryza sativa Japonica Group] | 0.80 | 1128 | |
| | | EEC71777 | hypothetical protein OsI_04389 [Oryza sativa Indica Group] | 0.80 | 1129 | |
| | | AAC04576 | putative high-pI laccase [Oryza sativa Japonica Group] | 0.79 | 1130 | 1780 |
| | | BAJ99773 | predicted protein [Hordeum vulgare subsp. vulgare] | 0.77 | 1131 | 1781 |
| | | XP_002458747 | hypothetical protein SORBIDRAFT_03g039530 [Sorghum bicolor] > gi|241930722|gb|EES03867.1| hypothetical protein SORBIDRAFT_03g039530 [Sorghum bicolor] | 0.78 | 1132 | 1782 |
| | 801-821 | XP_002441216 | hypothetical protein SORBIDRAFT_09g022460 [Sorghum bicolor] > gi|241946501|gb|EES19646.1| hypothetical protein SORBIDRAFT_09g022460 [Sorghum bicolor] | 1.00 | 1133 | 1783 |
| | | NP_001105874 | putative laccase [Zea mays] > gi|84618777|emb|CAJ30498.1| putative laccase [Zea mays] | 0.89 | 1134 | 1784 |
| | | Q0DHL5 | RecName: Full = Putative laccase-11; AltName: Full = Benzenediol:oxygen oxidoreductase 11; AltName: Full = Diphenol ocidase 11; AltName: Full = Urishiol oxidase 11 > gi|222631843|gb|EEE63975.1| hypothetical protein OsJ_18801 [Oryza sativa Japonica Group] | 0.88 | 1135 | |
| | | NP_001055744 | Os05g0458300 [Oryza sativa Japonica Group] > gi|113579295|dbj|BAF17658.1| Os05g0458300 [Oryza sativa Japonica Group] | 0.81 | 1136 | 1785 |
| | | XP_002456622 | hypothetical protein SORBIDRAFT_03g039570 [Sorghum bicolor] > gi|241928597|gb|EES01742.1| hypothetical protein | 0.76 | 1137 | 1786 |

TABLE 6-continued

Target Genes of down regulated miRNAs Associated with Increased NUE
(Table 2)

| Mir name | Mir Bind. Pos. | Hom. NCBI Accession | Annotation/Organism | Identity | p.p. SEQ ID NO: | p.n. SEQ ID NO: |
|---|---|---|---|---|---|---|
| | | | SORBIDRAFT_03g039570 [*Sorghum bicolor*] | | | |
| | | ACG47007 | L-ascorbate oxidase precursor [*Zea mays*] | 0.76 | 1138 | 1787 |
| | | NP_001105921 | putative laccase [*Zea mays*] > gi|84618783|emb|CAJ30497.1| putative laccase [*Zea mays*] | 0.74 | 1139 | 1788 |
| | 673-693 | NP_001168720 | hypothetical protein LOC100382512 [*Zea mays*] > gi|223950395|gb|ACN29281.1| unknown [*Zea mays*] | 1.00 | 1140 | 1789 |
| | | XP_002448765 | hypothetical protein SORBIDRAFT_06g032800 [*Sorghum bicolor*] > gi|241939948|gb|EES13093.1| hypothetical protein SORBIDRAFT_06g032800 [*Sorghum bicolor*] | 0.98 | 1141 | 1790 |
| | | NP_001131374 | hypothetical protein LOC100192699 [*Zea mays*] > gi|195620734|gb|ACG32197.1| oligosaccharyl transferase STT3 subunit [*Zea mays*] | 0.98 | 1142 | 1791 |
| | | NP_001054248 | Os04g0675500 [*Oryza sativa Japonica* Group] > gi|38344929|emb|CAE03245.2| OSJNBa0018M05.20 [*Oryza sativa Japonica* Group] > gi|90399055|emb|CAJ86104.1| H0103C06.8 [*Oryza sativa Indica* Group] > gi|113565819|dbj|BAF16162.1| Os04g0675500 [*Oryza sativa Japonica* Group] > gi|125550210|gb|EAY96032.1| hypothetical protein OsI_17905 [*Oryza sativa Indica* Group] > gi|125592048|gb|EAZ32398.1| hypothetical protein OsJ_16609 [*Oryza sativa Japonica* Group] > gi|215708677|dbj|BAG93946.1| unnamed protein product [*Oryza sativa Japonica* Group] | 0.96 | 1143 | 1792 |
| | | BAJ87792 | predicted protein [*Hordeum vulgare* subsp. *vulgare*] | 0.94 | 1144 | 1793 |
| | | XP_002269119 | PREDICTED: hypothetical protein [*Vitis vinifera*] | 0.86 | 1145 | 1794 |
| | | CBG76274 | OO_Ba0005L10-OO_Ba0081K17.25 [*Oryza officinalis*] | 0.93 | 1146 | 1795 |
| | | XP_002318345 | predicted protein [*Populus trichocarpa*] > gi|222859018|gb|EEE96565.1| predicted protein [*Populus trichocarpa*] | 0.86 | 1147 | 1796 |
| | | XP_002891078 | hypothetical protein ARALYDRAFT_891007 [*Arabidopsis lyrata* subsp. *lyrata*] > gi|297336920|gb|EFH67337.1| hypothetical protein ARALYDRAFT_891007 [*Arabidopsis lyrata* subsp. *lyrata*] | 0.86 | 1148 | 1797 |
| | | XP_002329687 | predicted protein [*Populus trichocarpa*] | 0.85 | 1149 | 1798 |

TABLE 6-continued

Target Genes of down regulated miRNAs Associated with Increased NUE
(Table 2)

| Mir name | Mir Bind. Pos. | Hom. NCBI Accession | Annotation/Organism | Identity | p.p. SEQ ID NO: | p.n. SEQ ID NO: |
|---|---|---|---|---|---|---|
| | | | > gi|222870595|gb|EEF07726.1| predicted protein [*Populus trichocarpa*] | | | |
| | 1539-1559 | XP_002462694 | hypothetical protein SORBIDRAFT_02g030360 [*Sorghum bicolor*] > gi|241926071|gb|EER99215.1| hypothetical protein SORBIDRAFT_02g030360 [*Sorghum bicolor*] | 1.00 | 1150 | 1799 |
| | | NP_001168360 | hypothetical protein LOC100382128 [*Zea mays*] > gi|223947749|gb|ACN27958.1| unknown [*Zea mays*] | 0.92 | 1151 | 1800 |
| | | NP_001063714 | Os09g0524300 [*Oryza sativa Japonica* Group] > gi|52076031|dbj|BAD46484.1| ethionine resistance protein-like [*Oryza sativa Japonica* Group] > gi|255679074|dbj|BAF25628.2| Os09g0524300 [*Oryza sativa Japonica* Group] | 0.80 | 1152 | 1801 |
| | | ABG73448 | MATE efflux family protein [*Oryza brachyantha*] | 0.80 | 1153 | 1802 |
| | | EAZ09807 | hypothetical protein OsI_32095 [*Oryza sativa Indica* Group] | 0.80 | 1154 | |
| | | XP_002444635 | hypothetical protein SORBIDRAFT_07g025190 [*Sorghum bicolor*] > gi|241940985|gb|EES14130.1| hypothetical protein SORBIDRAFT_07g025190 [*Sorghum bicolor*] | 0.73 | 1155 | 1803 |
| | | BAD09230 | putative ripening regulated protein DDTFR18 [*Oryza sativa Japonica* Group] | 0.70 | 1156 | 1804 |
| | 1198-1218 | NP_001146658 | hypothetical protein LOC100280258 [*Zea mays*] > gi|219888209|gb|ACL54479.1| unknown [*Zea mays*] | 1.00 | 1157 | 1805 |
| | | NP_001105875 | putative laccase [*Zea mays*] > gi|84618781|emb|CAJ30500.1| putative laccase [*Zea mays*] | 0.95 | 1158 | 1806 |
| | | ACN28855 | unknown [*Zea mays*] | 0.92 | 1159 | 1807 |
| | | XP_002458746 | hypothetical protein SORBIDRAFT_03g039520 [*Sorghum bicolor*] > gi|241930721|gb|EES03866.1| hypothetical protein SORBIDRAFT_03g039520 [*Sorghum bicolor*] | 0.91 | 1160 | 1808 |
| | | NP_001044772 | Os01g0842400 [*Oryza sativa Japonica* Group] > gi|75321217|sp|Q5N9X2.1| LAC4_ORYSJ RecName: Full = Laccase-4; AltName: Full = Benzenediol:oxygen oxidoreductase 4; AltName: Full = Diphenol oxidase 4; AltName: Full = Urishiol oxidase 4; Flags: Precursor > gi|56784239|dbj|BAD81734.1| putative laccase LAC5-6 [*Oryza sativa Japonica* Group] > gi|113534303|dbj|BAF06686.1| Os01g0842400 [*Oryza sativa Japonica* Group] > gi|215697155|dbj|BAG91149.1| unnamed protein | 0.80 | 1161 | 1809 |

TABLE 6-continued

Target Genes of down regulated miRNAs Associated with Increased NUE
(Table 2)

| Mir name | Mir Bind. Pos. | Hom. NCBI Accession | Annotation/Organism | Identity | p.p. SEQ ID NO: | p.n. SEQ ID NO: |
|---|---|---|---|---|---|---|
| | | EAZ14115 | product [*Oryza sativa Japonica* Group] hypothetical protein OsJ_04039 [*Oryza sativa Japonica* Group] | 0.80 | 1162 | |
| | | EEC71777 | hypothetical protein OsI_04389 [*Oryza sativa Indica* Group] | 0.80 | 1163 | |
| | | BAJ99773 | predicted protein [*Hordeum vulgare* subsp. *vulgare*] | 0.78 | 1164 | 1810 |
| | | AAC04576 | putative high-pI laccase [*Oryza sativa Japonica* Group] | 0.78 | 1165 | 1811 |
| | | XP_002458747 | hypothetical protein SORBIDRAFT_03g039530 [*Sorghum bicolor*] > gi|241930722|gb|EES03867.1| hypothetical protein SORBIDRAFT_03g039530 [*Sorghum bicolor*] | 0.77 | 1166 | 1812 |
| | 934-954 | ACN27868 | unknown [*Zea mays*] | 1.00 | 1167 | 1813 |
| | | NP_001148479 | L-ascorbate oxidase [*Zea mays*] > gi|195619672|gb|ACG31666.1| L-ascorbate oxidase precursor [*Zea mays*] | 0.94 | 1168 | 1814 |
| | | XP_002456566 | hypothetical protein SORBIDRAFT_03g038550 [*Sorghum bicolor*] > gi|241928541|gb|EES01686.1| hypothetical protein SORBIDRAFT_03g038550 [*Sorghum bicolor*] | 0.90 | 1169 | 1815 |
| | | NP_001183899 | hypothetical protein LOC100502492 [*Zea mays*] > gi|223948465|gb|ACN28316.1| unknown [*Zea mays*] > gi|238015342|gb|ACR38706.1| unknown [*Zea mays*] | 0.88 | 1170 | 1816 |
| | | NP_001044679 | Os01g0827300 [*Oryza sativa Japonica* Group] > gi|75331868|sp|Q941X2.1| LAC3_ORYSJ RecName: Full = Laccase-3; AltName: Full = Benzenediol:oxygen oxidoreductase 3; AltName: Full = Diphenol oxidase 3; AltName: Full = Urishiol oxidase 3; Flags: Precursor > gi|15624045|dbj|BAB68098.1| putative laccase [*Oryza sativa Japonica* Group] > gi|113534210|dbj|BAF06593.1| Os01g0827300 [*Oryza sativa Japonica* Group] > gi|215701334|dbj|BAG92758.1| unnamed protein product [*Oryza sativa Japonica* Group] > gi|222619479|gb|EEE55611.1| hypothetical protein OsJ_03932 [*Oryza sativa Japonica* Group] | 0.81 | 1171 | 1817 |
| Predicted folded 24-nts-long seq 52739 | 1620-1643 | NP_001137083 | hypothetical protein LOC100217256 [*Zea mays*] > gi|194698278|gb|ACF83223.1| unknown [*Zea mays*] | 1.00 | 1172 | 1818 |
| | | XP_002446946 | hypothetical protein SORBIDRAFT_06g025600 [*Sorghum bicolor*] > gi|241938129|gb|EES11274.1| hypothetical protein | 0.75 | 1173 | 1819 |

TABLE 6-continued

Target Genes of down regulated miRNAs Associated with Increased NUE
(Table 2)

| Mir name | Mir Bind. Pos. | Hom. NCBI Accession | Annotation/Organism | Identity | p.p. SEQ ID NO: | p.n. SEQ ID NO: |
|---|---|---|---|---|---|---|
| Predicted zma mir 49816 | 334-354 | XP_002459032 | SORBIDRAFT_06g025600 [*Sorghum bicolor*] hypothetical protein SORBIDRAFT_03g044830 [*Sorghum bicolor*] > gi\|241931007\|gb\|EES04152.1\| hypothetical protein SORBIDRAFT_03g044830 [*Sorghum bicolor*] | 1.00 | 1174 | 1820 |
| | | NP_001131974 | hypothetical protein LOC100193372 [*Zea mays*] > gi\|194693076\|gb\|ACF80622.1\| unknown [*Zea mays*] | 0.90 | 1175 | 1821 |
| | | BAJ85237 | predicted protein [*Hordeum vulgare* subsp. *vulgare*] > gi\|326511587\|dbj\|BAJ91938.1\| predicted protein [*Hordeum vulgare* subsp. *vulgare*] | 0.84 | 1176 | 1822 |
| | | NP_001045294 | Os01g0931100 [*Oryza sativa Japonica* Group] > gi\|57899654\|dbj\|BAD87323.1\| unknown protein [*Oryza sativa Japonica* Group] > gi\|57900117\|dbj\|BAD88179.1\| unknown protein [*Oryza sativa Japonica* Group] > gi\|113534825\|dbj\|BAF07208.1\| Os01g0931100 [*Oryza sativa Japonica* Group] > gi\|215697092\|dbj\|BAG91086.1\| unnamed protein product [*Oryza sativa Japonica* Group] | 0.85 | 1177 | 1823 |
| | 116-136 | CAE04743 | OSJNBb0060E08.6 [*Oryza sativa Japonica* Group] > gi\|116309791\|emb\|CAH66831.1\| OSIGBa0148A10.8 [*Oryza sativa Indica* Group] | 1.00 | 1178 | 1824 |
| | | NP_001053941 | 0s04g0625800 [*Oryza sativa Japonica* Group] > gi\|113565512\|dbj\|BAF15855.1\| Os04g0625800 [*Oryza sativa Japonica* Group] > gi\|215767966\|dbj\|BAH00195.1\| unnamed protein product [*Oryza sativa Japonica* Group] | 1.00 | 1179 | 1825 |
| | | EAY95645 | hypothetical protein OsI_17510 [*Oryza sativa Indica* Group] | 1.00 | 1180 | |
| | | NP_001131852 | hypothetical protein LOC100193230 [*Zea mays*] > gi\|194692726\|gb\|ACF80447.1\| unknown [*Zea mays*] | 0.79 | 1181 | 1826 |
| | | BAK03410 | predicted protein [*Hordeum vulgare* subsp. *vulgare*] > gi\|326525779\|dbj\|BAJ88936.1\| predicted protein [*Hordeum vulgare* subsp. *vulgare*] | 0.81 | 1182 | 1827 |
| | | XP_002447134 | hypothetical protein SORBIDRAFT_06g029180 [*Sorghum bicolor*] > gi\|241938317\|gb\|EES11462.1\| hypothetical protein SORBIDRAFT_06g029180 [*Sorghum bicolor*] | 0.78 | 1183 | 1828 |
| | | NP_001168401 | hypothetical protein LOC100382170 [*Zea mays*] > gi\|223948043\|gb\|ACN28105.1\| unknown [*Zea mays*] | 0.77 | 1184 | 1829 |

TABLE 6-continued

Target Genes of down regulated miRNAs Associated with Increased NUE
(Table 2)

| Mir name | Mir Bind. Pos. | Hom. NCBI Accession | Annotation/Organism | Identity | p.p. SEQ ID NO: | p.n. SEQ ID NO: |
|---|---|---|---|---|---|---|
| | | ACF85557 | unknown [Zea mays] | 0.74 | 1185 | 1830 |
| | | NP_001141359 | hypothetical protein LOC100273450 [Zea mays] > gi|194704160|gb|ACF86164.1| unknown [Zea mays] | 0.74 | 1186 | 1831 |
| | 81-101 | XP_002463519 | hypothetical protein SORBIDRAFT_01g001270 [Sorghum bicolor] > gi|241917373|gb|EER90517.1| hypothetical protein SORBIDRAFT_01g001270 [Sorghum bicolor] | 1.00 | 1187 | 1832 |
| | | BAK01513 | predicted protein [Hordeum vulgare subsp. vulgare] | 0.86 | 1188 | 1833 |
| | | NP_001051898 | Os03g0849600 [Oryza sativa Japonica Group] > gi|28269403|gb|AAO37946.1| putative conserved oligomeric Golgi complex component [Oryza sativa Japonica Group] > gi|108712114|gb|ABF99909.1| brefeldin A-sensitive Golgi protein, putative, expressed [Oryza sativa Japonica Group] > gi|113550369|dbj|BAF13812.1| Os03g0849600 [Oryza sativa Japonica Group] > gi|125588645|gb|EAZ29309.1| hypothetical protein OsJ_13370 [Oryza sativa Japonica Group] | 0.85 | 1189 | 1834 |
| | | EEC76534 | hypothetical protein OsI_14326 [Oryza sativa Indica Group] | 0.85 | 1190 | |
| | 322-342 | NP_001168448 | hypothetical protein LOC100382221 [Zea mays] > gi|223948365|gb|ACN28266.1| unknown [Zea mays] | 1.00 | 1191 | 1835 |
| | 98-118 | BAD05744 | putative RNA Binding Protein 45 [Oryza sativa Japonica Group] > gi|40253847|dbj|BAD05783.1| putative RNA Binding Protein 45 [Oryza sativa Japonica Group] | 1.00 | 1192 | 1836 |
| | | EEE68172 | hypothetical protein OSJ_26296 [Oryza sativa Japonica Group] | 0.75 | 1193 | |
| | | ACF85557 | unknown [Zea mays] | 0.78 | 1194 | 1837 |
| | | NP_001141359 | hypothetical protein LOC100273450 [Zea mays] > gi|194704160|gb|ACF86164.1| unknown [Zea mays] | 0.78 | 1195 | 1838 |
| aqc-miR529 | 955-975 | AAX83875 | teosinte glume architecture 1 [Zea mays subsp. mays] | 1.00 | 1196 | 1839 |
| | | AAX83872 | teosinte glume architecture 1 [Zea mays subsp. mays] | 0.99 | 1197 | 1840 |
| | | AAX83873 | teosinte glume architecture 1 [Zea mays subsp. mays] > gi|62467440|gb|AAX83874.1| teosinte glume architecture 1 [Zea mays subsp. mays] | 0.99 | 1198 | 1841 |
| | | XP_002445815 | hypothetical protein SORBIDRAFT_07g026220 [Sorghum bicolor] > gi|241942165|gb|EES15310.1| hypothetical protein SORBIDRAFT_07g026220 [Sorghum bicolor] | 0.80 | 1199 | 1842 |

TABLE 6-continued

Target Genes of down regulated miRNAs Associated with Increased NUE
(Table 2)

| Mir name | Mir Bind. Pos. | Hom. NCBI Accession | Annotation/Organism | Identity | p.p. SEQ ID NO: | p.n. SEQ ID NO: |
|---|---|---|---|---|---|---|
| | 831-851 | ADX60108 | SBP transcription factor [*Zea mays*] | 1.00 | 1200 | 1843 |
| | | XP_002446904 | hypothetical protein SORBIDRAFT_06g024630 [*Sorghum bicolor*] > gi|241938087|gb|EES11232.1| hypothetical protein SORBIDRAFT_06g024630 [*Sorghum bicolor*] | 0.72 | 1201 | 1844 |
| | 882-902 | ACN30570 | unknown [*Zea mays*] > gi|223973927|gb|ACN31151.1| unknown [*Zea mays*] > gi|323388595|gb|ADX60102.1| SBP transcription factor [*Zea mays*] | 1.00 | 1202 | 1845 |
| | | NP_001145445 | hypothetical protein LOC100278824 [*Zea mays*] > gi|195656399|gb|ACG47667.1| hypothetical protein [*Zea mays*] | 0.98 | 1203 | 1846 |
| | | XP_002450775 | hypothetical protein SORBIDRAFT_05g017510 [*Sorghum bicolor*] > gi|241936618|gb|EES09763.1| hypothetical protein SORBIDRAFT_05g017510 [*Sorghum bicolor*] | 0.87 | 1204 | 1847 |
| | 656-676 | NP_001137049 | hypothetical protein LOC100217221 [*Zea mays*] > gi|194698154|gb|ACF83161.1| unknown [*Zea mays*] | 1.00 | 1205 | 1848 |
| | 1248-1268 | XP_002447211 | hypothetical protein SORBIDRAFT_06g030520 [*Sorghum bicolor*] > gi|241938394|gb|EES11539.1| hypothetical protein SORBIDRAFT_06g030520 [*Sorghum bicolor*] | 1.00 | 1206 | 1849 |
| | | NP_001132831 | hypothetical protein LOC100194321 [*Zea mays*] > gi|194695516|gb|ACF81842.1| unknown [*Zea mays*] | 0.90 | 1207 | 1850 |
| | | NP_001054060 | Os04g0644700 [*Oryza sativa Japonica* Group] > gi|148886836|sp|P0C541.1| COPE2_ORYSJ RecName: Full = Coatomer subunit epsilon-2; AltName: Full = Epsilon-coat protein 2; Short = Epsilon-COP 2 > gi|38344895|emb|CAD41918.2| OSJNBa0033G05.19 [*Oryza sativa Japonica* Group] > gi|113565631|dbj|BAF15974.1| Os04g0644700 [*Oryza sativa Japonica* Group] > gi|125591839|gb|EAZ32189.1| hypothetical protein OsJ_16395 [*Oryza sativa Japonica* Group] | 0.80 | 1208 | 1851 |
| | | A2XY73 | RecName: Full = Coatomer subunit epsilon-2; AltName: Full = Epsilon-coat protein 2; Short = Epsilon-COP 2 > gi|90399097|emb|CAJ86157.1| H0413E07.10 [*Oryza sativa Indica* Group] | 0.80 | 1209 | |
| | | EAY95783 | hypothetical protein OsI_17658 [*Oryza sativa Indica* Group] | 0.80 | 1210 | |
| | 82-102 | ACR34442 | unknown [*Zea mays*] | 1.00 | 1211 | 1852 |
| | 82-102 | NP_00145733 | hypothetical protein LOC100279240 [*Zea mays*] | 1.00 | 1212 | 1853 |

TABLE 6-continued

Target Genes of down regulated miRNAs Associated with Increased NUE
(Table 2)

| Mir name | Mir Bind. Pos. | Hom. NCBI Accession | Annotation/Organism | Identity | p.p. SEQ ID NO: | p.n. SEQ ID NO: |
|---|---|---|---|---|---|---|
| | | XP_002460490 | > gi|219884215|gb|ACL52482.1| unknown [Zea mays] hypothetical protein SORBIDRAFT_02g029300 [Sorghum bicolor] > gi|241923867|gb|EER97011.1| hypothetical protein SORBIDRAFT_02g029300 [Sorghum bicolor] | 0.87 | 1213 | 1854 |
| | | NP_001063612 | Os09g0507100 [Oryza sativa Japonica Group] > gi|122234416|sp|Q0JOK1.1| SPL18_ORYSJ RecName: Full = Squamosa promoter-binding-like protein 18 > gi|113631845|dbj|BAF25526.1| Os09g0507100 [Oryza sativa Japonica Group] | 0.71 | 1214 | 1855 |
| | 996-1016 | ACF86782 | unknown [Zea mays] > gi|323388573|gb|ADX60091.1| SBP transcription factor [Zea mays] | 1.00 | 1215 | 1856 |
| | | ACG45113 | squamosa promoter-binding-like protein 9 [Zea mays] | 1.00 | 1216 | 1857 |
| | | XP_002462571 | hypothetical protein SORBIDRAFT_02g028420 [Sorghum bicolor] > gi|241925948|gb|EER99092.1| hypothetical protein SORBIDRAFT_02g028420 [Sorghum bicolor] | 0.83 | 1217 | 1858 |
| | | NP_001136945 | hypothetical protein LOC100217104 [Zea mays] > gi|194697718|gb|ACF82943.1| unknown [Zea mays] | 0.76 | 1218 | 1859 |
| | 1120-1140 | ACL52941 | unknown [Zea mays] | 1.00 | 1219 | 1860 |
| | | XP_002444771 | hypothetical protein SORBIDRAFT_07g027740 [Sorghum bicolor] > gi|241941121|gb|EES14266.1| hypothetical protein SORBIDRAFT_07g027740 [Sorghum bicolor] | 0.76 | 1220 | 1861 |
| | 1348-1368 | XP_002438971 | hypothetical protein SORBIDRAFT_10g029190 [Sorghum bicolor] > gi|241917194|gb|EER90338.1| hypothetical protein SORBIDRAFT_10g029190 [Sorghum bicolor] | 1.00 | 1221 | 1862 |
| | | NP_001149534 | squamosa promoter-binding-like protein 11 [Zea mays] > gi|195627850|gb|ACG35755.1| squamosa promoter-binding-like protein 11 [Zea mays] > gi|195644948|gb|ACG41942.1| squamosa promoter-binding-like protein 11 [Zea mays] | 0.88 | 1222 | 1863 |
| | 221-241 | XP_002447219 | hypothetical protein SORBIDRAFT_06g030650 [Sorghum bicolor] > gi|241938402|gb|EES11547.1| hypothetical protein SORBIDRAFT_06g030650 [Sorghum bicolor] | 1.00 | 1223 | 1864 |
| | | NP_001169344 | hypothetical protein LOC100383211 [Zea mays] > gi|224028835|gb|ACN33493.1| unknown [Zea mays] | 0.92 | 1224 | 1865 |

TABLE 6-continued

Target Genes of down regulated miRNAs Associated with Increased NUE
(Table 2)

| Mir name | Mir Bind. Pos. | Hom. NCBI Accession | Annotation/Organism | Identity | p.p. SEQ ID NO: | p.n. SEQ ID NO: |
|---|---|---|---|---|---|---|
| | | NP_001147890 | LOC100281500 [*Zea mays*] > gi\|195614420\|gb\|ACG29040.1\| zinc finger, C3HC4 type family protein [*Zea mays*] | 0.90 | 1225 | 1866 |
| | | CAD41707 | OSJNBa0010D21.9 [*Oryza sativa Japonica* Group] > gi\|125549990\|gb\|EAY95812.1\| hypothetical protein OsI_17683 [*Oryza sativa Indica* Group] > gi\|125591860\|gb\|EAZ32210.1\| hypothetical protein OsJ_16417 [*Oryza sativa Japonica* Group] > gi\|215701084\|dbj\|BAG92508.1\| unnamed protein product [*Oryza sativa Japonica* Group] | 0.74 | 1226 | 1867 |
| | 973-993 | NP_001136945 | hypothetical protein LOC100217104 [*Zea mays*] > gi\|194697718\|gb\|ACF82943.1\| unknown [*Zea mays*] | 1.00 | 1227 | 1868 |
| | | XP_002462571 | hypothetical protein SORBIDRAFT_02g028420 [*Sorghum bicolor*] > gi\|241925948\|gb\|EER99092.1\| hypothetical protein SORBIDRAFT_02g028420 [*Sorghum bicolor*] | 0.82 | 1228 | 1869 |
| | | ACF86782 | unknown [*Zea mays*] > gi\|323388573\|gb\|ADX60091.1\| SBP transcription factor [*Zea mays*] | 0.76 | 1229 | 1870 |
| | | ACG45113 | squamosa promoter-binding-like protein 9 [*Zea mays*] | 0.76 | 1230 | 1871 |
| | 558-578 | CAB56631 | SBP-domain protein 5 [*Zea mays*] | 1.00 | 1231 | 1872 |
| | | XP_002444771 | hypothetical protein SORBIDRAFT_07g027740 [*Sorghum bicolor*] > gi\|241941121\|gb\|EES14266.1\| hypothetical protein SORBIDRAFT_07g027740 [*Sorghum bicolor*] | 0.85 | 1232 | 1873 |
| | | ACL52941 | unknown [*Zea mays*] | 0.78 | 1233 | 1874 |
| | 1410-1430 | NP_001152658 | MTA/SAH nucleosidase [*Zea mays*] > gi\|195658647\|gb\|ACG48791.1\| MTA/SAH nucleosidase [*Zea mays*] > gi\|223973627\|gb\|ACN31001.1\| unknown [*Zea mays*] | 1.00 | 1234 | 1875 |
| | | ACF83838 | unknown [*Zea mays*] | 0.88 | 1235 | 1876 |
| | | ACG39594 | MTA/SAH nucleosidase [*Zea mays*] | 0.88 | 1236 | 1877 |
| | | XP_002445813 | hypothetical protein SORBIDRAFT_07g026190 [*Sorghum bicolor*] > gi\|241942163\|gb\|EES15308.1\| hypothetical protein SORBIDRAFT_07g026190 [*Sorghum bicolor*] | 0.88 | 1237 | 1878 |
| | | ACN31483 | unknown [*Zea mays*] | 0.90 | 1238 | 1879 |
| | | NP_001056592 | Os06g0112200 [*Oryza sativa Japonica* Group] > gi\|7363290\|dbj\|BAA93034.1\| methylthioadenosine/S-adenosyl homocysteine nucleosidase [*Oryza sativa Japonica* Group] > gi\|32352128\|dbj\|BAC78557.1\| hypothetical protein [*Oryza sativa Japonica* Group] | 0.80 | 1239 | 1880 |

TABLE 6-continued

Target Genes of down regulated miRNAs Associated with Increased NUE
(Table 2)

| Mir name | Mir Bind. Pos. | Hom. NCBI Accession | Annotation/Organism | Identity | p.p. SEQ ID NO: | p.n. SEQ ID NO: |
|---|---|---|---|---|---|---|
| | | | > gi|113594632|dbj|BAF18506.1| Os06g0112200 [*Oryza sativa Japonica* Group] > gi|125595804|gb|EAZ35584.1| hypothetical protein OsJ_19870 [*Oryza sativa Japonica* Group] > gi|215694661|dbj|BAG89852.1| unnamed protein product [*Oryza sativa Japonica* Group] > gi|215740802|dbj|BAG96958.1| unnamed protein product [*Oryza sativa Japonica* Group] | | | |
| | | AAL58883 | methylthioadenosine/S-adenosyl homocysteine nucleosidase [*Oryza sativa*] | 0.79 | 1240 | 1881 |
| | | ABR25495 | mta/sah nucleosidase [*Oryza sativa Indica* Group] | 0.79 | 1241 | 1882 |
| | | BAK03317 | predicted protein [*Hordeum vulgare* subsp. *vulgare*] > gi|326534118|dbj|BAJ89409.1| predicted protein [*Hordeum vulgare* subsp. *vulgare*] | 0.78 | 1242 | 1883 |
| | | EAY99382 | hypothetical protein OsI_21350 [*Oryza sativa Indica* Group] | 0.78 | 1243 | |
| | 1197-1217 | AAX83872 | teosinte glume architecture 1 [*Zea mays* subsp. *mays*] | 1.00 | 1244 | 1884 |
| | | AAX83875 | teosinte glume architecture 1 [*Zea mays* subsp. *mays*] | 0.98 | 1245 | 1885 |
| | | AAX83873 | teosinte glume architecture 1 [*Zea mays* subsp. *mays*] > gi|62467440|gb|AAX83874.1| teosinte glume architecture 1 [*Zea mays* subsp. *mays*] | 0.99 | 1246 | 1886 |
| | | XP_002445815 | hypothetical protein SORBIDRAFT_07g026220 [*Sorghum bicolor*] > gi|241942165|gb|EES15310.1| hypothetical protein SORBIDRAFT_07g026220 [*Sorghum bicolor*] | 0.80 | 1247 | 1887 |
| | | BAK05794 | predicted protein [*Hordeum vulgare* subsp. *vulgare*] | 0.63 | 1248 | 1888 |
| Predicted folded 24-nts-long seq 52792 | 748-771 | NP_001143705 | hypothetical protein LOC100276442 [*Zea mays*] > gi|195625088|gb|ACG34374.1| hypothetical protein [*Zea mays*] | 1.00 | 1281 | 1911 |
| | | ACF83056 | unknown [*Zea mays*] | 0.95 | 1282 | 1912 |
| | 1078-1101 | ACF83056 | unknown [*Zea mays*] | 1.00 | 1283 | 1913 |
| | | NP_001143705 | hypothetical protein LOC100276442 [*Zea mays*] > gi|195625088|gb|ACG34374.1| hypothetical protein [*Zea mays*] | 0.88 | 1284 | 1914 |
| Predicted folded 24-nts-long seq 51757 | 278-301 | XP_002458944 | hypothetical protein SORBIDRAFT_03g043140 [*Sorghum bicolor*] > gi|241930919|gb|EES04064.1| hypothetical protein SORBIDRAFT_03g043140 [*Sorghum bicolor*] | 1.00 | 1285 | 1915 |
| | | ACF79162 | unknown [*Zea mays*] > gi|194703646|gb|ACF85907.1| unknown [*Zea mays*] | 0.98 | 1286 | 1916 |
| | | NP_001105336 | fructose-bisphosphate aldolase, cytoplasmic isozyme [*Zea mays*] | 0.98 | 1287 | 1917 |

TABLE 6-continued

Target Genes of down regulated miRNAs Associated with Increased NUE
(Table 2)

| Mir name | Mir Bind. Pos. | Hom. NCBI Accession | Annotation/Organism | Identity | p.p. SEQ ID NO: | p.n. SEQ ID NO: |
|---|---|---|---|---|---|---|
| | | | > gi|113621|sp|P08440.1|ALF_MAIZE RecName: Full = Fructose-bisphosphate aldolase, cytoplasmic isozyme > gi|168420|gb|AAA33435.1| aldolase [*Zea mays*] > gi|295850|emb|CAA31366.1| fructose bisphosphate aldolase [*Zea mays*] > gi|225624|prf||1307278A cytoplasmic aldolase | | | |
| | | NP_001150049 | fructose-bisphosphate aldolase cytoplasmic isozyme [*Zea mays*] > gi|194704898|gb|ACF86533.1| unknown [*Zea mays*] > gi|195636310|gb|ACG37623.1| fructose-bisphosphate aldolase cytoplasmic isozyme [*Zea mays*] | 0.98 | 1288 | 1918 |
| | | XP_002453822 | hypothetical protein SORBIDRAFT_04g019020 [*Sorghum bicolor*] > gi|241933653|gb|EES06798.1| hypothetical protein SORBIDRAFT_04g019020 [*Sorghum bicolor*] | 0.95 | 1289 | 1919 |
| | | P17784 | RecName: Full = Fructose-bisphosphate aldolase cytoplasmic isozyme; AltName: Full = Gravity-specific protein GSC 233 > gi|41398198|gb|AAS05825.1| fructose 1,6-bisphosphate aldolase [*Oryza sativa Japonica* Group] > gi|50878379|gb|AAT85154.1| putative fructose-bisphosphate aldolase [*Oryza sativa Japonica* Group] > gi|50878433|gb|AAT85207.1| putative fructose-bisphosphate aldolase [*Oryza sativa Japonica* Group] > gi|169244417|gb|ACA50482.1| fructose-bisphosphate aldolase [*Oryza sativa Japonica* Group] > gi|306415953|gb|ADM86851.1| fructose-bisphosphate aldolase [*Oryza sativa Japonica* Group] | 0.94 | 1290 | |
| | | BAI59774 | aldolase C-1 [*Phyllostachys edulis*] | 0.94 | 1291 | 1920 |
| | | EAY94426 | hypothetical protein OsI_16195 [*Oryza sativa Indica* Group] | 0.93 | 1292 | |
| | | CAA37290 | unnamed protein product [*Oryza sativa Japonica* Group] | 0.93 | 1293 | 1921 |
| | | ABG65931 | Fructose-bisphosphate aldolase, cytoplasmic isozyme, putative, expressed [*Oryza sativa Japonica* Group] > gi|125574121|gb|EAZ15405.1| hypothetical protein OsJ_30817 [*Oryza sativa Japonica* Group] > gi|215701125|dbj|BAG92549.1| unnamed protein product [*Oryza sativa Japonica* Group] > gi|215708712|dbj|BAG93981.1| unnamed protein | 0.92 | 1294 | 1922 |

TABLE 6-continued

Target Genes of down regulated miRNAs Associated with Increased NUE
(Table 2)

| Mir name | Mir Bind. Pos. | Hom. NCBI Accession | Annotation/Organism | Identity | p.p. SEQ ID NO: | p.n. SEQ ID NO: |
|---|---|---|---|---|---|---|
| | | | product [*Oryza sativa Japonica* Group] | | | |
| | 686-709 | NP_001145778 | hypothetical protein LOC100279285 [*Zea mays*] > gi|219884395|gb|ACL52572.1| unknown [*Zea mays*] | 1.00 | 1295 | 1923 |
| | | ACF87373 | unknown [*Zea mays*] | 1.00 | 1296 | 1924 |
| | | ACG25535 | ribosomal RNA apurinic site specific lyase [*Zea mays*] | 0.99 | 1297 | 1925 |
| | | XP_002455890 | hypothetical protein SORBIDRAFT_03g026880 [*Sorghum bicolor*] > gi|241927865|gb|EES01010.1| hypothetical protein SORBIDRAFT_03g026880 [*Sorghum bicolor*] | 0.79 | 1298 | 1926 |
| | 365-388 | ACR36335 | unknown [*Zea mays*] | 1.00 | 1299 | 1927 |
| | | ACR35742 | unknown [*Zea mays*] | 0.75 | 1300 | 1928 |
| | 512-535 | XP_002458102 | hypothetical protein SORBIDRAFT_03g026990 [*Sorghum bicolor*] > gi|241930077|gb|EES03222.1| hypothetical protein SORBIDRAFT_03g026990 [*Sorghum bicolor*] | 1.00 | 1301 | 1929 |
| | | NP_001151540 | hydrogen-transporting ATP synthase, rotational mechanism [*Zea mays*] > gi|195605790|gb|ACG24725.1| hydrogen-transporting ATP synthase, rotational mechanism [*Zea mays*] > gi|195608344|gb|ACG26002.1| hydrogen-transporting ATP synthase, rotational mechanism [*Zea mays*] > gi|195647528|gb|ACG43232.1| hydrogen-transporting ATP synthase, rotational mechanism [*Zea mays*] > gi|195658703|gb|ACG48819.1| hydrogen-transporting ATP synthase, rotational mechanism [*Zea mays*] | 0.93 | 1302 | 1930 |
| | | ACF82609 | unknown [*Zea mays*] | 0.93 | 1303 | 1931 |
| | | NP_001149611 | LOC100283237 [*Zea mays*] > gi|194696248|gb|ACF82208.1| unknown [*Zea mays*] > gi|195605550|gb|ACG24605.1| hydrogen-transporting ATP synthase, rotational mechanism [*Zea mays*] > gi|195619622|gb|ACG31641.1| hydrogen-transporting ATP synthase, rotational mechanism [*Zea mays*] > gi|195628500|gb|ACG36080.1| hydrogen-transporting ATP synthase, rotational mechanism [*Zea mays*] > gi|195637444|gb|ACG38190.1| hydrogen-transporting ATP synthase, rotational mechanism [*Zea mays*] > gi|195644406|gb|ACG41671.1| hydrogen-transporting ATP synthase, rotational mechanism [*Zea mays*] | 0.93 | 1304 | 1932 |
| | | BAJ87122 | predicted protein [*Hordeum vulgare* subsp. *vulgare*] | 0.89 | 1305 | 1933 |
| | | NP_001043488 | Os01g0600000 [*Oryza sativa Japonica* Group] > gi|113533019|dbj|BAF05402.1| | 0.88 | 1306 | 1934 |

TABLE 6-continued

Target Genes of down regulated miRNAs Associated with Increased NUE
(Table 2)

| Mir name | Mir Bind. Pos. | Hom. NCBI Accession | Annotation/Organism | Identity | p.p. SEQ ID NO: | p.n. SEQ ID NO: |
|---|---|---|---|---|---|---|
| | | | Os01g0600000 [*Oryza sativa Japonica* Group] > gi\|125571065\|gb\|EAZ12580.1\| hypothetical protein OsJ_02485 [*Oryza sativa Japonica* Group] > gi\|215768142\|dbj\|BAH00371.1\| unnamed protein product [*Oryza sativa Japonica* Group] > gi\|218188591\|gb\|EEC71018.1\| hypothetical protein OsI_02711 [*Oryza sativa Indica* Group] | | | |
| | | ABF70110 | mitochondrial ATP synthase g subunit family protein [*Musabalbisiana*] | 0.78 | 1307 | 1935 |
| | | ABA40451 | unknown [*Solanum tuberosum*] | 0.72 | 1308 | 1936 |
| | | NP_001056144 | Os05g0533800 [*Oryza sativa Japonica* Group] > gi\|48843828\|gb\|AAT47087.1\| unknown protein [*Oryza sativa Japonica* Group] > gi\|113579695\|dbj\|BAF18058.1\| Os05g0533800 [*Oryza sativa Japonica* Group] > gi\|222632347\|gb\|EEE64479.1\| hypothetical protein OsJ_19329 [*Oryza sativa Japonica* Group] | 0.73 | 1309 | 1937 |
| | | BAJ90534 | predicted protein [*Hordeum vulgare* subsp. *vulgare*] | 0.74 | 1310 | 1938 |
| ath-miR2936 | 742-763 | ACN26323 | unknown [*Zea mays*] > gi\|223944533\|gb\|ACN26350.1\| unknown [*Zea mays*] | 1.00 | 1389 | 2005 |
| | | BAC01259 | glycosylphosphatidylinositol anchor attachment 1-like [*Oryza sativa Japonica* Group] > gi\|125571593\|gb\|EAZ13108.1\| hypothetical protein OsJ_03027 [*Oryza sativa Japonica* Group] | 0.78 | 1390 | 2006 |
| | | EAY75389 | hypothetical protein OsI_03287 [*Oryza sativa Indica* Group] | 0.78 | 1391 | |

Table 6: Provided are the target Genes of miRNAs Associated with Increased NUE (Table 2) along with their GenBank Accession numbers and sequence identifiers (SEQ ID NO:).
"bind" = binding;
"pos" = position;
"hom" = homologue;
"p.p." = polypeptide;
"p.n." = polynucleotide.

TABLE 7

Target genes of up regulated siRNA sequences associated with NUE
(Table 3)

| Mir name | Mir Bind. Pos. | Hom. NCBI Accession | Annotation/organism | Identity | p.p. SEQ ID NO: | p.n. SEQ ID NO: |
|---|---|---|---|---|---|---|
| Predicted siRNA 59952 | 1180-1201 | XP_002439783 | hypothetical protein SORBIDRAFT_09g019980 [*Sorghum bicolor*] > gi\|241945068\|gb\|EES18213.1\| hypothetical protein SORBIDRAFT_09g019980 [*Sorghum bicolor*] | 1.00 | 2007 | 2437 |

TABLE 7-continued

Target genes of up regulated siRNA sequences associated with NUE
(Table 3)

| Mir name | Mir Bind. Pos. | Hom. NCBI Accession | Annotation/organism | Identity | p.p. SEQ ID NO: | p.n. SEQ ID NO: |
|---|---|---|---|---|---|---|
| | | NP_001140772 | hypothetical protein LOC100272847 [*Zea mays*] > gi\|194701020\|gb\|ACF84594.1\| unknown [*Zea mays*] | 0.87 | 2008 | 2438 |
| | | ACG40649 | hypothetical protein [*Zea mays*] | 0.87 | 2009 | 2439 |
| | | NP_001140587 | hypothetical protein LOC100272657 [*Zea mays*] > gi\|194700088\|gb\|ACF84128.1\| unknown [*Zea mays*] | 0.85 | 2010 | 2440 |
| | | ACG28586 | hypothetical protein [*Zea mays*] | 0.83 | 2011 | 2441 |
| | | EEC79208 | hypothetical protein OsI_19925 [*Oryza sativa Indica* Group] | 0.73 | 2012 | |
| | 2775-2796 | NP_001146628 | hypothetical protein LOC100280226 [*Zea mays*] > gi\|219888087\|gb\|ACL54418.1\| unknown [*Zea mays*] | 1.00 | 2013 | 2442 |
| | | EEE65008 | hypothetical protein OsJ_19956 [*Oryza sativa Japonica* Group] | 0.71 | 2014 | |
| | | BAA90807 | putative SEU1 protein [*Oryza sativa Japonica* Group] > gi\|215704489\|dbj\|BAG93923.1\| unnamed protein product [*Oryza sativa Japonica* Group] | 0.71 | 2015 | 2443 |
| Predicted siRNA 59626 | 220-238 | ACR33998 | unknown [*Zea mays*] | 1.00 | 2016 | 2444 |
| | | NP_001141472 | hypothetical protein LOC100273582 [*Zea mays*] > gi\|194704716\|gb\|ACF86442.1\| unknown [*Zea mays*] | 1.00 | 2017 | 2445 |
| | 1435-1453 | XP_002446603 | hypothetical protein SORBIDRAFT_06g018770 [*Sorghum bicolor*] > gi\|241937786\|gb\|EES10931.1\| hypothetical protein SORBIDRAFT_06g018770 [*Sorghum bicolor*] | 1.00 | 2018 | 2446 |
| | | NP_001159223 | hypothetical protein LOC100304309 [*Zea mays*] > gi\|223942807\|gb\|ACN25487.1\| unknown [*Zea mays*] | 0.92 | 2019 | 2447 |
| | | BAJ94860 | predicted protein [*Hordeum vulgare* subsp. *vulgare*] | 0.79 | 2020 | 2448 |
| | | CAE03375 | OSJNBa0036B21.17 [*Oryza sativa Japonica* Group] | 0.80 | 2021 | |
| | | EEE61116 | hypothetical protein OsJ_15040 [*Oryza sativa Japonica* Group] | 0.80 | 2022 | |
| | | CBW45773 | ORW1943Ba0077G13.1 [*Oryza rufipogon*] | 0.80 | 2023 | |
| | | NP_001052976 | Os04g0458200 [*Oryza sativa Japonica* Group] > gi\|215715295\|dbj\|BAG95046.1\| unnamed protein product [*Oryza sativa Japonica* Group] > gi\|218194967\|gb\|EEC77394.1\| hypothetical protein OsI_16151 [*Oryza sativa Indica* Group] > gi\|255675525\|dbj\|BAF14890.2\| Os04g0458200 [*Oryza sativa Japonica* Group] | 0.80 | 2024 | 2449 |
| | | CAH67071 | OSIGBa0097P08.1 [*Oryza sativa Indica* Group] | 0.79 | 2025 | 2450 |
| | 1613-1631 | NP_001141472 | hypothetical protein LOC100273582 [*Zea mays*] > gi\|194704716\|gb\|ACF86442.1\| unknown [*Zea mays*] | 1.00 | 2026 | 2451 |
| | | ACR33998 | unknown [*Zea mays*] | 0.85 | 2027 | 2452 |
| Predicted siRNA 60850 | 408-428 | NP_001131645 | hypothetical protein LOC100193004 [*Zea mays*] > gi\|194692138\|gb\|ACF80153.1\| unknown [*Zea mays*] | 1.00 | 2028 | 2453 |

TABLE 7-continued

Target genes of up regulated siRNA sequences associated with NUE
(Table 3)

| Mir name | Mir Bind. Pos. | Hom. NCBI Accession | Annotation/organism | Identity | p.p. SEQ ID NO: | p.n. SEQ ID NO: |
|---|---|---|---|---|---|---|
| | 481-501 | ACG31592 | hypothetical protein [*Zea mays*] | 1.00 | 2029 | 2454 |
| | | NP_001132267 | hypothetical protein LOC100193703 [*Zea mays*] > gi\|194693920\|gb\|ACF81044.1\| unknown [*Zea mays*] | 1.00 | 2030 | 2455 |
| Predicted siRNA 59961 | 1611-1630 | XP_002463038 | hypothetical protein SORBIDRAFT_02g036610 [*Sorghum bicolor*] > gi\|241926415\|gb\|EER99559.1\| hypothetical protein SORBIDRAFT_02g036610 [*Sorghum bicolor*] | 1.00 | 2031 | 2456 |
| | | NP_001130320 | hypothetical protein LOC100191414 [*Zea mays*] > gi\|194688838\|gb\|ACF78503.1\| unknown [*Zea mays*] | 0.96 | 2032 | 2457 |
| | | BAJ88611 | predicted protein [*Hordeum vulgare* subsp. *vulgare*] | 0.87 | 2033 | 2458 |
| | | NP_001060016 | Os07g0566200 [*Oryza sativa* Japonica Group] > gi\|75152457\|sp\|Q8H4S6.2\|P2C64_ORYSJ RecName: Full = Probable protein phosphatase 2C 64; Short = OsPP2C64 > gi\|33146759\|dbj\|BAC79670.1\| putative protein phosphatase 2C [*Oryza sativa* Japonica Group] > gi\|113611552\|dbj\|BAF21930.1\| Os07g0566200 [*Oryza sativa* Japonica Group] > gi\|125600752\|gb\|EAZ40328.1\| hypothetical protein OsJ_24776 [*Oryza sativa* Japonica Group] | 0.89 | 2034 | 2459 |
| | | NP_001150759 | LOC100284392 [*Zea mays*] > gi\|195641568\|gb\|ACG40252.1\| catalytic/protein phosphatase type 2C [*Zea mays*] | 0.92 | 2035 | 2460 |
| | | ACR38208 | unknown [*Zea mays*] | 0.92 | 2036 | 2461 |
| | | EAZ04367 | hypothetical protein OsI_26509 [*Oryza sativa* Indica Group] | 0.88 | 2037 | |
| | | ACN30598 | unknown [*Zea mays*] | 0.87 | 2038 | 2462 |
| | | ACF84784 | unknown [*Zea mays*] | 0.80 | 2039 | 2463 |
| | 802-821 | XP_002462759 | hypothetical protein SORBIDRAFT_02g031500 [*Sorghum bicolor*] > gi\|241926136\|gb\|EER99280.1\| hypothetical protein SORBIDRAFT_02g031500 [*Sorghum bicolor*] | 1.00 | 2040 | 2464 |
| | | NP_001151289 | RING-H2 finger protein ATL2B [*Zea mays*] > gi\|195645562\|gb\|ACG42249.1\| RING-H2 finger protein ATL2B [*Zea mays*] > gi\|223946553\|gb\|ACN27360.1\| unknown [*Zea mays*] | 0.80 | 2041 | 2465 |
| | 540-559 | XP_002438439 | hypothetical protein SORBIDRAFT_10g019640 [*Sorghum bicolor*] > gi\|241916662\|gb\|EER89806.1\| hypothetical protein SORBIDRAFT_10g019640 [*Sorghum bicolor*] | 1.00 | 2042 | 2466 |
| | | ACN33733 | unknown [*Zea mays*] | 0.89 | 2043 | 2467 |
| | | NP_001150669 | amino acid permease [*Zea mays*] > gi\|195640964\|gb\|ACG39950.1\| amino acid permease [*Zea mays*] | 0.89 | 2044 | 2468 |
| | | XP_002453115 | hypothetical protein SORBIDRAFT_04g000290 [*Sorghum bicolor*] | 0.82 | 2045 | 2469 |

TABLE 7-continued

Target genes of up regulated siRNA sequences associated with NUE
(Table 3)

| Mir name | Mir Bind. Pos. | Hom. NCBI Accession | Annotation/organism | Identity | p.p. SEQ ID NO: | p.n. SEQ ID NO: |
|---|---|---|---|---|---|---|
| | | | > gi|241932946|gb|EES06091.1| hypothetical protein SORBIDRAFT_04g000290 [*Sorghum bicolor*] | | | |
| | | NP_001136459 | hypothetical protein LOC100216569 [*Zea mays*] > gi|194695786|gb|ACF81977.1| unknown [*Zea mays*] | 0.80 | 2046 | 2470 |
| | | NP_001045585 | Os02g0101000 [*Oryza sativa Japonica* Group] > gi|41053220|dbj|BAD08181.1| putative amino acid transport protein [*Oryza sativa Japonica* Group] > gi|113535116|dbj|BAF07499.1| Os02g0101000 [*Oryza sativa Japonica* Group] > gi|215704334|dbj|BAG93768.1| unnamed protein product [*Oryza sativa Japonica* Group] > gi|218189857|gb|EEC72284.1| hypothetical protein OsI_05452 [*Oryza sativa Indica* Group] > gi|222621988|gb|EEE56120.1| hypothetical protein OsJ_04987 [*Oryza sativa Japonica* Group] | 0.78 | 2047 | 2471 |
| | | BAJ96557 | predicted protein [*Hordeum vulgare* subsp. *vulgare*] > gi|326523625|dbj|BAJ92983.1| predicted protein [*Hordeum vulgare* subsp. *vulgare*] | 0.73 | 2048 | 2472 |
| | | XP_002446139 | hypothetical protein SORBIDRAFT_06g002240 [*Sorghum bicolor*] > gi|241937322|gb|EES10467.1| hypothetical protein SORBIDRAFT_06g002240 [*Sorghum bicolor*] | 0.72 | 2049 | 2473 |
| | | NP_001147785 | amino acid permease [*Zea mays*] > gi|195613758|gb|ACG28709.1| amino acid permease [*Zea mays*] | 0.71 | 2050 | 2474 |
| | 987-1006 | NP_001132785 | hypothetical protein LOC100194274 [*Zea mays*] > gi|194695392|gb|ACF81780.1| unknown [*Zea mays*] | 1.00 | 2051 | 2475 |
| | | NP_001150926 | bHLH transcription factor GBOF-1 [*Zea mays*] > gi|195642998|gb|ACG40967.1| bHLH transcription factor GBOF-1 [*Zea mays*] | 0.96 | 2052 | 2476 |
| | | XP_002462650 | hypothetical protein SORBIDRAFT_02g029530 [*Sorghum bicolor*] > gi|241926027|gb|EER99171.1| hypothetical protein SORBIDRAFT_02g029530 [*Sorghum bicolor*] | 0.79 | 2053 | 2477 |
| | | NP_001149110 | LOC100282732 [*Zea mays*] > gi|195624818|gb|ACG34239.1| bHLH transcription factor GBOF-1 [*Zea mays*] | 0.76 | 2054 | 2478 |
| | | ACR35934 | unknown [*Zea mays*] | 0.75 | 2055 | 2479 |
| | 235-254 | NP_001065691 | Os11g0136600 [*Oryza sativa Japonica* Group] > gi|33340240|gb|AAQ14593.1| AF319480_1 calcium-dependent calmodulin-independent protein kinase [*Oryza sativa*] > gi|33340242|gb|AAQ14594.1| AF319481_1 calcium-dependent calmodulin-independent protein | 1.00 | | 2480 |

TABLE 7-continued

Target genes of up regulated siRNA sequences associated with NUE
(Table 3)

| Mir name | Mir Bind. Pos. | Hom. NCBI Accession | Annotation/organism | Identity | p.p. SEQ ID NO: | p.n. SEQ ID NO: |
|---|---|---|---|---|---|---|
| | | | kinase [*Oryza sativa*] > gi\|77548548\|gb\|ABA91345.1\| Calcium-dependent protein kinase, isoform 2, putative, expressed [*Oryza sativa Japonica* Group] > gi\|113644395\|dbj\|BAF27536.1\| Os11g0136600 [*Oryza sativa Japonica* Group] | | | |
| Predicted siRNA 56542 | 452-472 | XP_002465086 | hypothetical protein SORBIDRAFT_01g031850 [*Sorghum bicolor*] > gi\|241918940\|gb\|EER92084.1\| hypothetical protein SORBIDRAFT_01g031850 [*Sorghum bicolor*] | 1.00 | 2056 | 2481 |
| | | NP_001145189 | hypothetical protein LOC100278439 [*Zea mays*] > gi\|195652469\|gb\|ACG45702.1\| hypothetical protein [*Zea mays*] | 0.92 | 2057 | 2482 |
| | | NP_001050454 | Os03g0439700 [*Oryza sativa Japonica* Group] > gi\|108709042\|gb\|ABF96837.1\| expressed protein [*Oryza sativa Japonica* Group] > gi\|113548925\|dbj\|BAF12368.1\| Os03g0439700 [*Oryza sativa Japonica* Group] > gi\|222625197\|gb\|EEE59329.1\| hypothetical protein OsJ_11404 [*Oryza sativa Japonica* Group] | 0.78 | 2058 | 2483 |
| | | AAR89010 | expressed protein [*Oryza sativa Japonica* Group] | 0.77 | 2059 | |
| | | BAJ96331 | predicted protein [*Hordeum vulgare* subsp. *vulgare*] | 0.77 | 2060 | 2484 |
| Predicted siRNA 56353 | 585-608 | NP_001183654 | hypothetical protein LOC100502248 [*Zea mays*] > gi\|238013682\|gb\|ACR37876.1\| unknown [*Zea mays*] | 1.00 | 2061 | 2485 |
| | | XP_002464467 | hypothetical protein SORBIDRAFT_01g018940 [*Sorghum bicolor*] > gi\|241918321\|gb\|EER91465.1\| hypothetical protein SORBIDRAFT_01g018940 [*Sorghum bicolor*] | 0.94 | 2062 | 2486 |
| | | AAL59033 | hypothetical protein [*Oryza sativa Japonica* Group] > gi\|31432747\|gb\|AAP54340.1\| expressed protein [*Oryza sativa Japonica* Group] | 0.78 | 2063 | |
| | | BAJ89715 | predicted protein [*Hordeum vulgare* subsp. *vulgare*] > gi\|326505214\|dbj\|BAK02994.1\| predicted protein [*Hordeum vulgare* subsp. *vulgare*] | 0.77 | 2064 | 2487 |
| | | BAK03788 | predicted protein [*Hordeum vulgare* subsp. *vulgare*] | 0.75 | 2065 | 2488 |
| | | NP_001064892 | Os10g0484900 [*Oryza sativa Japonica* Group] > gi\|255679504\|dbj\|BAF26806.2\| Os10g0484900 [*Oryza sativa Japonica* Group] | 0.76 | 2066 | 2489 |
| | 23-46 | XP_002463222 | hypothetical protein SORBIDRAFT_02g040060 [*Sorghum bicolor*] > gi\|241926599\|gb\|EER99743.1\| hypothetical protein SORBIDRAFT_02g040060 [*Sorghum bicolor*] | 1.00 | 2067 | 2490 |

TABLE 7-continued

Target genes of up regulated siRNA sequences associated with NUE
(Table 3)

| Mir name | Mir Bind. Pos. | Hom. NCBI Accession | Annotation/organism | Identity | p.p. SEQ ID NO: | p.n. SEQ ID NO: |
|---|---|---|---|---|---|---|
| | | NP_001105697 | thiazole biosynthetic enzyme 1-2, chloroplastic precursor [Zea mays] > gi\|2501190\|sp\|Q41739.1\|THI42_MAIZE RecName: Full = Thiazole biosynthetic enzyme 1-2, chloroplastic; Flags: Precursor > gi\|596080\|gb\|AAA96739.1\| thiamine biosynthetic enzyme [Zea mays] | 0.93 | 2068 | 2491 |
| | | ACF87708 | unknown [Zea mays] > gi\|224033955\|gb\|ACN36053.1\| unknown [Zea mays] | 0.93 | 2069 | 2492 |
| | | NP_001105696 | thiazole biosynthetic enzyme 1-1, chloroplastic precursor [Zea mays] > gi\|2501189\|sp\|Q41738.1\|THI41_MAIZE RecName: Full = Thiazole biosynthetic enzyme 1-1, chloroplastic; Flags: Precursor > gi\|596078\|gb\|AAA96738.1\| thiamine biosynthetic enzyme [Zea mays] > gi\|194704634\|gb\|ACF86401.1\| unknown [Zea mays] | 0.92 | 2070 | 2493 |
| | | NP_001059841 | Os07g0529600 [Oryza sativa Japonica Group] > gi\|32352138\|dbj\|BAC78562.1\| thiamine biosynthetic enzyme [Oryza sativa Japonica Group] > gi\|113611377\|dbj\|BAF21755.1\| Os07g0529600 [Oryza sativa Japonica Group] > gi\|215712225\|dbj\|BAG94352.1\| unnamed protein product [Oryza sativa Japonica Group] | 0.87 | 2071 | 2494 |
| | | BAC45141 | putative thiamine biosynthesis protein [Oryza sativa Japonica Group] > gi\|125600511\|gb\|EAZ40087.1\| hypothetical protein OsJ_24530 [Oryza sativa Japonica Group] | 0.87 | 2072 | 2495 |
| | | EAZ04139 | hypothetical protein OsI_26282 [Oryza sativa Indica Group] | 0.87 | 2073 | |
| | | XP_002458014 | hypothetical protein SORBIDRAFT_03g025520 [Sorghum bicolor] > gi\|241929989\|gb\|EES03134.1\| hypothetical protein SORBIDRAFT_03g025520 [Sorghum bicolor] | 0.91 | 2074 | 2496 |
| | | ACF85034 | unknown [Zea mays] | 0.84 | 2075 | 2497 |
| | | AAZ93636 | pathogen-induced defense-responsive protein 8 [Oryza sativa Indica Group] | 0.84 | 2076 | 2498 |
| | 71-94 | ACG31888 | ubiquitin-conjugating enzyme E2 W [Zea mays] | 1.00 | 2077 | 2499 |
| | | NP_001050906 | Os03g0681400 [Oryza sativa Japonica Group] > gi\|57164486\|gb\|AAK00965.2\| AC079736_5 putative ubiquitin-conjugating enzyme E2 [Oryza sativa Japonica Group] > gi\|108710422\|gb\|ABF98217.1\| Ubiquitin-conjugating enzyme family protein, expressed [Oryza sativa Japonica Group] > gi\|113549377\|dbj\|BAF12820.1\| Os03g0681400 [Oryza sativa Japonica Group] | 0.71 | 2078 | 2500 |

TABLE 7-continued

Target genes of up regulated siRNA sequences associated with NUE
(Table 3)

| Mir name | Mir Bind. Pos. | Hom. NCBI Accession | Annotation/organism | Identity | p.p. SEQ ID NO: | p.n. SEQ ID NO: |
|---|---|---|---|---|---|---|
| | | XP_002464080 | > gi\|215737341\|dbj\|BAG96270.1\| unnamed protein product [*Oryza sativa Japonica* Group] > gi\|222625566\|gb\|EEE59698.1\| hypothetical protein OsJ_12122 [*Oryza sativa Japonica* Group] hypothetical protein SORBIDRAFT_01g011940 [*Sorghum bicolor*] > gi\|241917934\|gb\|EER91078.1\| hypothetical protein SORBIDRAFT_01g011940 [*Sorghum bicolor*] | 0.72 | 2079 | 2501 |
| | | XP_002443656 | hypothetical protein SORBIDRAFT_08g022990 [*Sorghum bicolor*] > gi\|241944349\|gb\|EES17494.1\| hypothetical protein SORBIDRAFT_08g022990 [*Sorghum bicolor*] | 0.71 | 2080 | 2502 |
| | | NP_001146940 | ubiquitin-conjugating enzyme E2 W [*Zea mays*] > gi\|195605468\|gb\|ACG24564.1\| ubiquitin-conjugating enzyme E2 W [*Zea mays*] | 0.70 | 2081 | 2503 |
| Predicted siRNA 59965 | 614-634 | NP_001047323 | Os02g0596900 [*Oryza sativa Japonica* Group] > gi\|75291091\|sp\|Q6K908.1\|ARP3_ORYSJ RecName: Full = Actin-related protein 3 > gi\|190356069\|sp\|A2X6S3.2\|ARP3_ORYSI RecName: Full = Actin-related protein 3 > gi\|47847830\|dbj\|BAD21625.1\| putative arp3 [*Oryza sativa Japonica* Group] > gi\|113536854\|dbj\|BAF09237.1\| Os02g0596900 [*Oryza sativa Japonica* Group] > gi\|218191098\|gb\|EEC73525.1\| hypothetical protein OsI_07915 [*Oryza sativa Indica* Group] > gi\|222623169\|gb\|EEE57301.1\| hypothetical protein OsJ_07378 [*Oryza sativa Japonica* Group] | 1.00 | 2082 | 2504 |
| | | ACF87749 | unknown [*Zea mays*] > gi\|223972725\|gb\|ACN30550.1\| unknown [*Zea mays*] | 0.92 | 2083 | 2505 |
| | | XP_002285370 | PREDICTED: hypothetical protein [*Vitis vinifera*] | 0.86 | 2084 | 2506 |
| | | NP_001147580 | LOC100281189 [*Zea mays*] > gi\|195612296\|gb\|ACG27978.1\| actin-like protein 3 [*Zea mays*] | 0.92 | 2085 | 2507 |
| | | NP_001170315 | hypothetical protein LOC100384280 [*Zea mays*] > gi\|224034999\|gb\|ACN36575.1\| unknown [*Zea mays*] | 0.90 | 2086 | 2508 |
| | | XP_002315648 | predicted protein [*Populus trichocarpa*] > gi\|222864688\|gb\|EEF01819.1\| predicted protein [*Populus trichocarpa*] | 0.84 | 2087 | 2509 |
| | | XP_002515041 | protein binding protein, putative [*Ricinus communis*] > gi\|223546092\|gb\|EEF47595.1\| protein binding protein, putative [*Ricinus communis*] | 0.85 | 2088 | 2510 |
| | | XP_002312654 | predicted protein [*Populus trichocarpa*] > gi\|222852474\|gb\|EEE90021.1\| predicted protein [*Populus trichocarpa*] | 0.84 | 2089 | 2511 |

TABLE 7-continued

Target genes of up regulated siRNA sequences associated with NUE
(Table 3)

| Mir name | Mir Bind. Pos. | Hom. NCBI Accession | Annotation/organism | Identity | p.p. SEQ ID NO: | p.n. SEQ ID NO: |
|---|---|---|---|---|---|---|
| | | CAM97883 | actin-related protein 3 [*Nicotiana tabacum*] | 0.83 | 2090 | 2512 |
| | | NP_172777 | actin-related protein 3 [*Arabidopsis thaliana*] > gi|75313139|sp|Q9SAF1.1|ARP3_ARATH RecName: Full = Actin-related protein 3; AltName: Full = Protein DISTORTED TRICHOMES 1 > gi|4850401|gb|AAD31071.1| AC007357_20 Strong similarity to gb|U29610 Actin-like protein (Arp3) from *Acanthamoeba castellanii* and is a member of the PF|00022 Actin family [*Arabidopsis thaliana*] > gi|21427461|gb|AAM53243.1| AF507911_1 actin-related protein 3 [*Arabidopsis thaliana*] > gi|20260500|gb|AAM13148.1| similar to actin-like protein [*Arabidopsis thaliana*] > gi|21489929|tpg|DAA00033.1| TPA_exp: actin-related protein 3; AtARP3 [*Arabidopsis thaliana*] > gi|30387525|gb|AAP31928.1| At1g13180 [*Arabidopsis thaliana*] > gi|332190859|gb|AEE28980.1| actin-related protein 3 [*Arabidopsis thaliana*] | 0.81 | 2091 | 2513 |
| Predicted siRNA 58872 | 632-651 | ACR34392 | unknown [*Zea mays*] | 1.00 | 2092 | 2514 |
| | 315-334 | NP_001004443 | beta-hexosaminidase subunit alpha precursor [*Rattus norvegicus*] > gi|85701350|sp|Q641X3.1|HEXA_RAT RecName: Full = Beta-hexosaminidase subunit alpha; AltName: Full = Beta-N-acetylhexosaminidase subunit alpha; Short = Hexosaminidase subunit A; AltName: Full = N-acetyl-beta-glucosaminidase subunit alpha; Flags: Precursor > gi|51980341|gb|AAH82097.1| Hexosaminidase A [*Rattus norvegicus*] > gi|149041858|gb|EDL95699.1| hexosaminidase A, isoform CRA_a [*Rattus norvegicus*] | 1.00 | 2093 | 2515 |
| | | NP_034551 | beta-hexosaminidase subunit alpha precursor [*Mus musculus*] > gi|497174|gb|AAA18775.1| beta-hexosaminidase [*Mus musculus*] > gi|497196|gb|AAA18777.1| beta-hexosaminidase alpha-subunit [*Mus musculus*] > gi|14789650|gb|AAH10755.1| Hexosaminidase A [*Mus musculus*] > gi|26344774|dbj|BAC36036.1| unnamed protein product [*Mus musculus*] > gi|26344800|dbj|BAC36049.1| unnamed protein product [*Mus musculus*] > gi|74184438|dbj|BAE25744.1| unnamed protein product [*Mus musculus*] | 0.94 | 2094 | 2516 |

TABLE 7-continued

Target genes of up regulated siRNA sequences associated with NUE
(Table 3)

| Mir name | Mir Bind. Pos. | Hom. NCBI Accession | Annotation/organism | Identity | p.p. SEQ ID NO: | p.n. SEQ ID NO: |
|---|---|---|---|---|---|---|
| | | | > gi\|74204649\|dbj\|BAE35394.1\| unnamed protein product [*Mus musculus*] > gi\|148694024\|gb\|EDL25971.1\| hexosaminidase A [*Mus musculus*] | | | |
| | | BAE35636 | unnamed protein product [*Mus musculus*] | 0.94 | 2095 | 2517 |
| | | BAE29566 | unnamed protein product [*Mus musculus*] | 0.94 | 2096 | 2518 |
| | | BAE30831 | unnamed protein product [*Mus musculus*] | 0.94 | 2097 | 2519 |
| | | BAE35457 | unnamed protein product [*Mus musculus*] | 0.94 | 2098 | 2520 |
| | | P29416 | RecName: Full = Beta-hexosaminidase subunit alpha; AltName: Full = Beta-N-acetylhexosaminidase subunit alpha; Short = Hexosaminidase subunit A; AltName: Full = N-acetyl-beta-glucosaminidase subunit alpha; Flags: Precursor > gi\|51265\|emb\|CAA45615.1\| beta-N-acetylhexosaminidase [*Mus musculus*] > gi\|577688\|gb\|AAC53246.1\| beta-N-acetylhexosaminidase, alpha-subunit [*Mus musculus*] | 0.94 | 2099 | |
| | | BAC38018 | unnamed protein product [*Mus musculus*] | 0.94 | 2100 | 2521 |
| | | BAE39189 | unnamed protein product [*Mus musculus*] | 0.94 | 2101 | 2522 |
| | | BAE40146 | unnamed protein product [*Mus musculus*] | 0.94 | 2102 | 2523 |
| | 535-554 | XP-002526446 | heat shock protein, putative [*Ricinus communis*] > gi\|223534226\|gb\|EEF35941.1\| heat shock protein, putative [*Ricinus communis*] | 1.00 | 2103 | 2524 |
| | | XP_002328713 | predicted protein [*Populus trichocarpa*] > gi\|222839011\|gb\|EEE77362.1\| predicted protein [*Populus trichocarpa*] | 0.92 | 2104 | 2525 |
| | | XP_002331133 | predicted protein [*Populus trichocarpa*] > gi\|222872861\|gb\|EEF09992.1\| predicted protein [*Populus trichocarpa*] | 0.92 | 2105 | 2526 |
| | | XP_002279101 | PREDICTED: hypothetical protein [*Vitis vinifera*] | 0.93 | 2106 | 2527 |
| | | ABZ04081 | chloroplast heat shock protein 70-2 [*Ipomoea nil*] | 0.90 | 2107 | 2528 |
| | | ABM92419 | chloroplast HSP70 [*Cucumis sativus*] | 0.90 | 2108 | 2529 |
| | | ABE79560 | Chaperone DnaK [*Medicago truncatula*] | 0.90 | 2109 | 2530 |
| | | CAA52149 | heat shock protein 70 [*Cucumis sativus*] | 0.89 | 2110 | 2531 |
| | | Q02028 | RecName: Full = Stromal 70 kDa heat shock-related protein, chloroplastic; Flags: Precursor > gi\|169023\|gb\|AAA33637.1\| 70 kDa heat shock protein [*Pisum sativum*] > gi\|871515\|emb\|CAA49147.1\| Psst70 (stress 70 protein) [*Pisum sativum*] | 0.90 | 2111 | |
| | | CAN81065 | hypothetical protein VITISV_000728 [*Vitis vinifera*] | 0.91 | 2112 | 2532 |

TABLE 7-continued

Target genes of up regulated siRNA sequences associated with NUE
(Table 3)

| Mir name | Mir Bind. Pos. | Hom. NCBI Accession | Annotation/organism | Identity | p.p. SEQ ID NO: | p.n. SEQ ID NO: |
|---|---|---|---|---|---|---|
| Predicted siRNA 54631 | 1842-1866 | YP_024387 | ribulose-1,5-bisphosphate carboxylase/oxygenase large subunit [*Saccharum* hybrid cultivar SP-80-3280] > gi|50812536|ref|YP_054639.1| ribulose-1,5-bisphosphate carboxylase/oxygenase large subunit [*Saccharum officinarum*] > gi|118614500|ref|YP_899415.1| ribulose 1,5-bisphosphate carboxylase/oxygenase large subunit [*Sorghum bicolor*] > gi|75290174|sp|Q6ENV5.1|RBL_SACOF RecName: Full = Ribulose bisphosphate carboxylase large chain; Short = RuBisCO large subunit; Flags: Precursor > gi|75291223|sp|Q6L391.1|RBL_SACHY RecName: Full = Ribulose bisphosphate carboxylase large chain; Short = RuBisCO large subunit; Flags: Precursor > gi|125987520|sp|A1E9T2.1|RBL_SORBI RecName: Full = Ribulose bisphosphate carboxylase large chain; Short = RuBisCO large subunit; Flags: Precursor > gi|48478681|gb|AAT44701.1| RuBisCO large chain [*Saccharum* hybrid cultivar SP80-3280] > gi|49659520|dbj|BAD27301.1| RuBisCO large subunit [*Saccharum* hybrid cultivar NCo 310] > gi|118201134|gb|ABK79504.1| ribulose-1,5-bisphosphate carboxylase/oxygenase large subunit [*Sorghum bicolor*] | 1.00 | 2113 | 2533 |
| | | NP_043033 | ribulose-1,5-bisphosphate carboxylase/oxygenase large subunit [*Zea mays*] > gi|1172861|sp|P00874.2|RBL_MAIZE RecName: Full = Ribulose bisphosphate carboxylase large chain; Short = RuBisCO large subunit; Flags: Precursor > gi|18036|emb|CAA78027.1| Ribulose bisphosphate carboxylase [*Zea mays*] > gi|902230|emb|CAA60294.1| ribulose-1,5-bisphosphate carboxylase/oxygenase large subunit [*Zea mays*] | 0.99 | 2114 | 2534 |
| | | ABP01447 | ribulose-1,5-bisphosphate carboxylase/oxygenase large subunit [*Sorghastrum nutans*] | 0.99 | 2115 | 2535 |
| | | YP_003208195 | ribulose-1,5-bisphosphate carboxylase/oxygenase large subunit [*Coix lacryma-jobi*] > gi|209361365|gb|ACI43280.1| ribulose-1,5-bisphosphate carboxylase/oxygenase large subunit [*Coix lacryma-jobi*] | 0.98 | 2116 | 2536 |
| | | ABP01443 | ribulose-1,5-bisphosphate carboxylase/oxygenase large subunit [*Cymbopogon citratus*] | 0.98 | 2117 | 2537 |

TABLE 7-continued

Target genes of up regulated siRNA sequences associated with NUE
(Table 3)

| Mir name | Mir Bind. Pos. | Hom. NCBI Accession | Annotation/organism | Identity | p.p. SEQ ID NO: | p.n. SEQ ID NO: |
|---|---|---|---|---|---|---|
| | | ABP01445 | ribulose-1,5-bisphosphate carboxylase/oxygenase large subunit [*Pogonatherum* sp. Hodkinson 21] | 0.98 | 2118 | 2538 |
| | | ABP01442 | ribulose-1,5-bisphosphate carboxylase/oxygenase large subunit [*Coix lacryma-jobi*] | 0.97 | 2119 | 2539 |
| | | ABP01448 | ribulose-1,5-bisphosphate carboxylase/oxygenase large subunit [*Sorghum halepense*] | 0.96 | 2120 | 2540 |
| | | CAG34130 | ribulose-1,5-bisphosphate carboxylase/oxygenase large subunit [*Arthraxon* sp. Hodkinson 111] | 0.96 | 2121 | 2541 |
| | | AAA31678 | ribulose 1,5-bisphosphate carboxylase/oxygenase [*Cenchrus setiger*] > gi|294104|gb|AAA32020.1| ribulosebiphosphate carboxylase, large subunit [*Pennisetum glaucum*] | 0.97 | 2122 | 2542 |
| | 884-908 | ABP01449 | ribulose-1,5-bisphosphate carboxylase/oxygenase large subunit [*Trachypogon spicatus*] | 1.00 | 2123 | 2543 |
| | | ABP01447 | ribulose-1,5-bisphosphate carboxylase/oxygenase large subunit [*Sorghastrum nutans*] | 1.00 | 2124 | 2544 |
| | | NP_043033 | ribulose-1,5-bisphosphate carboxylase/oxygenase large subunit [*Zea mays*] > gi|1172861|sp|P00874.2|RBL_MAIZE RecName: Full = Ribulose bisphosphate carboxylase large chain; Short = RuBisCO large subunit; Flags: Precursor > gi|18036|emb|CAA78027.1| Ribulose bisphosphate carboxylase [*Zea mays*] > gi|902230|emb|CAA60294.1| ribulose-1,5-bisphosphate carboxylase/oxygenase subunit [*Zea mays*] | 0.99 | 2125 | 2545 |
| | | YP_024387 | ribulose-1,5-bisphosphate carboxylase/oxygenase large subunit [*Saccharum* hybrid cultivar SP-80-3280] > gi|50812536|ref|YP_054639.1| ribulose-1,5-bisphosphate carboxylase/oxygenase large subunit [*Saccharum officinarum*] > gi|118614500|ref|YP_899415.1| ribulose 1,5-bisphosphate carboxylase/oxygenase large subunit [*Sorghum bicolor*] > gi|75290174|sp|Q6ENV5.1|RBL_SACOF RecName: Full = Ribulose bisphosphate carboxylase large chain; Short = RuBisCO large subunit; Flags: Precursor > gi|75291223|sp|Q6L391.1|RBL_SACHY RecName: Full = Ribulose bisphosphate carboxylase large chain; Short = RuBisCO large subunit; Flags: Precursor > gi|125987520|sp|A1E9T2.1|RBL_SORBI RecName: Full = Ribulose bisphosphate carboxylase large chain; | 1.00 | 2126 | 2546 |

TABLE 7-continued

Target genes of up regulated siRNA sequences associated with NUE
(Table 3)

| Mir name | Mir Bind. Pos. | Hom. NCBI Accession | Annotation/organism | p.p. Identity | p.p. SEQ ID NO: | p.n. SEQ ID NO: |
|---|---|---|---|---|---|---|
| | | | Short = RuBisCO large subunit; Flags: Precursor<br>> gi|48478681|gb|AAT44701.1| RuBisCO large chain [*Saccharum* hybrid cultivar SP80-3280]<br>> gi|49659520|dbj|BAD27301.1| RuBisCO large subunit [*Saccharum* hybrid cultivar NCo 310]<br>> gi|118201134|gb|ABK79504.1| ribulose-1,5-bisphosphate carboxylase/oxygenase large subunit [*Sorghum bicolor*] | | | |
| | | ABP01443 | ribulose-1,5-bisphosphate carboxylase/oxygenase large subunit [*Cymbopogon citratus*] | 1.00 | 2127 | 2547 |
| | | ABP01445 | ribulose-1,5-bisphosphate carboxylase/oxygenase large subunit [*Pogonatherum* sp. Hodkinson 21] | 0.99 | 2128 | 2548 |
| | | ABP01442 | ribulose-1,5-bisphosphate carboxylase/oxygenase large subunit [*Coix lacryma-jobi*] | 0.98 | 2129 | 2549 |
| | | YP_003208195 | ribulose-1,5-bisphosphate carboxylase/oxygenase large subunit [*Coix lacryma-jobi*]<br>> gi|209361365|gb|ACI43280.1| ribulose-1,5-bisphosphate carboxylase/oxygenase large subunit [*Coix lacryma-jobi*] | 0.98 | 2130 | 2550 |
| | | ABP01441 | ribulose-1,5-bisphosphate carboxylase/oxygenase large subunit [*Bothriochloa ischaemum*] | 0.98 | 2131 | 2551 |
| | | CAG34130 | ribulose-1,5-bisphosphate carboxylase/oxygenase large subunit [*Arthraxon* sp. Hodkinson 111] | 0.96 | 2132 | 2552 |
| Predicted siRNA 59846 | 69-92 | XP_002458082 | hypothetical protein SORBIDRAFT_03g026670 [*Sorghum bicolor*]<br>> gi|241930057|gb|EES03202.1| hypothetical protein SORBIDRAFT_03g026670 [*Sorghum bicolor*] | 1.00 | 2133 | 2553 |
| | | EEC70994 | hypothetical protein OsI_02661 [*Oryza sativa* Indica Group] | 0.83 | 2134 | |
| | | NP_001152397 | regulator of telomere elongation helicase 1 [*Zea mays*]<br>> gi|195655863|gb|ACG47399.1| regulator of telomere elongation helicase 1 [*Zea mays*] | 0.78 | 2135 | 2554 |
| | | NP_001043456 | Os01g0592900 [*Oryza sativa Japonica* Group]<br>> gi|53791584|dbj|BAD52706.1| DEAH helicase isoform 5-like [*Oryza sativa Japonica* Group]<br>> gi|255673416|dbj|BAF05370.2| Os01g0592900 [*Oryza sativa Japonica* Group] | 0.70 | 2136 | 2555 |
| | 85-108 | ACR34511 | unknown [*Zea mays*] | 1.00 | 2137 | 2556 |
| | | NP_001105187 | histone acetyltransferase1 [*Zea mays*]<br>> gi|20977602|gb|AAM28228.1| histone acetyl transferase [*Zea mays*]<br>> gi|223975399|gb|ACN31887.1| unknown [*Zea mays*] | 0.99 | 2138 | 2557 |
| | | Q8LPU4 | RecName: Full = Histone acetyltransferase type B catalytic subunit; AltName: Full = Histone acetyltransferase HAT B; | 0.99 | 2139 | |

TABLE 7-continued

Target genes of up regulated siRNA sequences associated with NUE
(Table 3)

| Mir name | Mir Bind. Pos. | Hom. NCBI Accession | Annotation/organism | Identity | p.p. SEQ ID NO: | p.n. SEQ ID NO: |
|---|---|---|---|---|---|---|
| | | | AltName: Full = Histone acetyltransferase HAT-B-p50 > gi|6288802|gb|AAF06742.1| AF171927_1 histone acetyltransferase HAT-B-p50 [*Zea mays*] > gi|5579441|gb|AAC03423.2| histone acetyltransferase HAT B [*Zea mays*] | | | |
| | | XP_002460092 | hypothetical protein SORBIDRAFT_02g022640 [*Sorghum bicolor*] > gi|241923469|gb|EER96613.1| hypothetical protein SORBIDRAFT_02g022640 [*Sorghum bicolor*] | 0.89 | 2140 | 2558 |
| | | NP_001062946 | Os09g0347800 [*Oryza sativa Japonica* Group] > gi|75121858|sp|Q6ES10.1|HAT1_ORYSJ RecName: Full = Probable acetyltransferase type B catalytic subunit; AltName: Full = HAT B > gi|50252375|dbj|BAD28482.1| putative histone acetyltransferase HAT B [*Oryza sativa Japonica* Group] > gi|50252405|dbj|BAD28560.1| putative histone acetyltransferase HAT B [*Oryza sativa Japonica* Group] > gi|113631179|dbj|BAF24860.1| Os09g0347800 [*Oryza sativa Japonica* Group] > gi|215678892|dbj|BAG95329.1| unnamed protein product [*Oryza sativa Japonica* Group] | 0.77 | 2141 | 2559 |
| | | EEC84410 | hypothetical protein OsI_30998 [*Oryza sativa Indica* Group] | 0.77 | 2142 | |
| | | EEE69531 | hypothetical protein OsJ_29003 [*Oryza sativa Japonica* Group] | 0.77 | 2143 | |
| | | BAK05443 | predicted protein [*Hordeum vulgare* subsp. *vulgare*] | 0.75 | 2144 | 2560 |
| | 85-108 | XP_002460092 | hypothetical protein SORBIDRAFT_02g022640 [*Sorghum bicolor*] > gi|241923469|gb|EER96613.1| hypothetical protein SORBIDRAFT_02g022640 [*Sorghum bicolor*] | 1.00 | 2145 | 2561 |
| | | NP_001105187 | histone acetyltransferase1 [*Zea mays*] > gi|20977602|gb|AAM28228.1| histone acetyl transferase [*Zea mays*] > gi|223975399|gb|ACN31887.1| unknown [*Zea mays*] | 0.90 | 2146 | 2562 |
| | | Q8LPU4 | RecName: Full = Histone acetyltransferase type B catalytic subunit; AltName: Full = Histone acetyltransferase HAT B; AltName: Full = Histone acetyltransferase HAT-B-p50 > gi|6288802|gb|AAF06742.1| AF171927_1 histone acetyltransferase HAT-B-p50 [*Zea mays*] > gi|5579441|gb|AAC03423.2| histone acetyltransferase HAT B [*Zea mays*] | 0.90 | 2147 | |

TABLE 7-continued

Target genes of up regulated siRNA sequences associated with NUE
(Table 3)

| Mir name | Mir Bind. Pos. | Hom. NCBI Accession | Annotation/organism | Identity | p.p. SEQ ID NO: | p.n. SEQ ID NO: |
|---|---|---|---|---|---|---|
| | | NP_001062946 | Os09g0347800 [*Oryza sativa Japonica* Group] > gi|75121858|sp|Q6ES10.1|HAT1_ORYSJ RecName: Full = Probable acetyltransferase type B catalytic subunit; AltName: Full = HAT B > gi|50252375|dbj|BAD28482.1| putative histone acetyltransferase HAT B [*Oryza sativa Japonica* Group] > gi|50252405|dbj|BAD28560.1| putative histone acetyltransferase HAT B [*Oryza sativa Japonica* Group] > gi|113631179|dbj|BAF24860.1| Os09g0347800 [*Oryza sativa Japonica* Group] > gi|215678892|dbj|BAG95329.1| unnamed protein product [*Oryza sativa Japonica* Group] | 0.81 | 2148 | 2563 |
| | | EEC84410 | hypothetical protein OsI_30998 [*Oryza sativa Indica* Group] | 0.81 | 2149 | |
| | | EEE69531 | hypothetical protein OsJ_29003 [*Oryza sativa Japonica* Group] | 0.81 | 2150 | |
| | | BAK05443 | predicted protein [*Hordeum vulgare* subsp. *vulgare*] | 0.78 | 2151 | 2564 |
| | | ACR34511 | unknown [*Zea mays*] | 0.79 | 2152 | 2565 |
| Predicted siRNA 60081 | 293-311 | XP_002460816 | hypothetical protein SORBIDRAFT_02g035420 [*Sorghum bicolor*] > gi|241924193|gb|EER97337.1| hypothetical protein SORBIDRAFT_02g035420 [*Sorghum bicolor*] | 1.00 | 2153 | 2566 |
| | | NP_001147287 | receptor-like serine-threonine protein kinase [*Zea mays*] > gi|195609532|gb|ACG26596.1| receptor-like serine-threonine protein kinase [*Zea mays*] | 0.87 | 2154 | 2567 |
| | | BAK06110 | predicted protein [*Hordeum vulgare* subsp. *vulgare*] | 0.73 | 2155 | 2568 |
| | 564-582 | ACN27203 | unknown [*Zea mays*] | 1.00 | 2156 | 2569 |
| | | NP_001150572 | RING-H2 finger protein ATL1R [*Zea mays*] > gi|195640284|gb|ACG39610.1| RING-H2 finger protein ATL1R [*Zea mays*] | 1.00 | 2157 | 2570 |
| | | XP_002448400 | hypothetical protein SORBIDRAFT_06g026580 [*Sorghum bicolor*] > gi|241939583|gb|EES12728.1| hypothetical protein SORBIDRAFT_06g026580 [*Sorghum bicolor*] | 0.80 | 2158 | 2571 |
| | 374-392 | NP_001151643 | DNA binding protein [*Zea mays*] > gi|195648318|gb|ACG43627.1| DNA binding protein [*Zea mays*] | 1.00 | 2159 | 2572 |
| | | XP_002468594 | hypothetical protein SORBIDRAFT_01g048710 [*Sorghum bicolor*] > gi|241922448|gb|EER95592.1| hypothetical protein SORBIDRAFT_01g048710 [*Sorghum bicolor*] | 0.83 | 2160 | 2573 |
| | | NP_001048832 | Os03g0127500 [*Oryza sativa Japonica* Group] > gi|20330751|gb|AAM19114.1| | 0.73 | 2161 | 2574 |

TABLE 7-continued

Target genes of up regulated siRNA sequences associated with NUE
(Table 3)

| Mir name | Mir Bind. Pos. | Hom. NCBI Accession | Annotation/organism | Identity | p.p. SEQ ID NO: | p.n. SEQ ID NO: |
|---|---|---|---|---|---|---|
| | | | AC104427_12 Putative bZIP transcription factor [*Oryza sativa Japonica* Group] > gi|108705971|gb|ABF93766.1| bZIP family transcription factor, putative, expressed [*Oryza sativa Japonica* Group] > gi|113547303|dbj|BAF10746.1| Os03g0127500 [*Oryza sativa Japonica* Group] | | | |
| | | EAZ25438 | hypothetical protein OsJ_09254 [*Oryza sativa Japonica* Group] | 0.73 | 2162 | |
| | | EAY88362 | hypothetical protein OsI_09817 [*Oryza sativa Indica* Group] | 0.73 | 2163 | |
| | 365-383 | XP_002446810 | hypothetical protein SORBIDRAFT_06g023020 [*Sorghum bicolor*] > gi|241937993|gb|EES11138.1| hypothetical protein SORBIDRAFT_06g023020 [*Sorghum bicolor*] | 1.00 | 2164 | 2575 |
| | | NP_001185810 | yellow stripe-like transporter 11 [*Zea mays*] > gi|308210134|gb|ADO20998.1| yellow stripe-like transporter 11 [*Zea mays*] | 0.90 | 2165 | 2576 |
| | | CAH67887 | OSIGBa0153E02-OSIGBa0093I20.16 [*Oryza sativa Indica* Group] > gi|125549079|gb|EAY94901.1| hypothetical protein OsI_16701 [*Oryza sativa Indica* Group] | 0.79 | 2166 | |
| | | Q7X660 | RecName: Full = Probable metal-nicotianamine transporter YSL11; AltName: Full = Protein YELLOW STRIPE LIKE 11; Short = OsYSL11 > gi|32487645|emb|CAE05635.1| OSJNBa0038O10.1 [*Oryza sativa Japonica* Group] > gi|57834127|emb|CAI44638.1| OSJNBb0065J09.18 [*Oryza sativa Japonica* Group] > gi|125591037|gb|EAZ31387.1| hypothetical protein OsJ_15515 [*Oryza sativa Japonica* Group] | 0.79 | 2167 | |
| | | BAE91891 | hypothetical protein [*Oryza sativa Japonica* Group] | 0.79 | 2168 | 2577 |
| | | Q5JQD7 | RecName: Full = Probable metal-nicotianamine transporter YSL12; AltName: Full = Protein YELLOW STRIPE LIKE 12; Short = OsYSL12 > gi|116310949|emb|CAH67886.1| OSIGBa0153E02-OSIGBa0093I20.15 [*Oryza sativa Indica* Group] | 0.74 | 2169 | |
| | | NP_001185468 | yellow stripe-like transporter 12 [*Zea mays*] > gi|308210136|gb|ADO20999.1| yellow stripe-like transporter 12 [*Zea mays*] | 0.73 | 2170 | 2578 |
| | | XP_002452492 | hypothetical protein SORBIDRAFT_04g026840 [*Sorghum bicolor*] > gi|241932323|gb|EES05468.1| hypothetical protein SORBIDRAFT_04g026840 [*Sorghum bicolor*] | 0.71 | 2171 | 2579 |
| | | BAE91892 | hypothetical protein [*Oryza sativa Japonica* Group] | 0.73 | 2172 | 2580 |

TABLE 7-continued

Target genes of up regulated siRNA sequences associated with NUE
(Table 3)

| Mir name | Mir Bind. Pos. | Hom. NCBI Accession | Annotation/organism | Identity | p.p. SEQ ID NO: | p.n. SEQ ID NO: |
|---|---|---|---|---|---|---|
| | | XP_002446809 | hypothetical protein SORBIDRAFT_06g023010 [*Sorghum bicolor*] > gi\|241937992\|gb\|EES11137.1\| hypothetical protein SORBIDRAFT_06g023010 [*Sorghum bicolor*] | 0.72 | 2173 | 2581 |
| | 529-547 | XP_002464238 | hypothetical protein SORBIDRAFT_01g014760 [*Sorghum bicolor*] > gi\|241918092\|gb\|EER91236.1\| hypothetical protein SORBIDRAFT_01g014760 [*Sorghum bicolor*] | 1.00 | 2174 | 2582 |
| | | NP_001146578 | hypothetical protein LOC100280174 [*Zea mays*] > gi\|219887889\|gb\|ACL54319.1\| unknown [*Zea mays*] | 0.92 | 2175 | 2583 |
| | | ACN27618 | unknown [*Zea mays*] | 0.91 | 2176 | 2584 |
| | | EAY90980 | hypothetical protein OsI_12589 [*Oryza sativa Indica* Group] | 0.83 | 2177 | |
| | | NP_001050649 | Os03g0609800 [*Oryza sativa Japonica* Group] > gi\|37700299\|gb\|AAR00589.1\| putative NPH3 family protein [*Oryza sativa Japonica* Group] > gi\|40539093\|gb\|AAR87349.1\| transposon protein, putative, mutator sub-class [*Oryza sativa Japonica* Group] > gi\|62733727\|gb\|AAX95837.1\| transposon protein, putative, mutator sub-class [*Oryza sativa Japonica* Group] > gi\|108709776\|gb\|ABF97571.1\| transposon protein, putative, Mutator sub-class, expressed [*Oryza sativa Japonica* Group] > gi\|108709777\|gb\|ABF97572.1\| transposon protein, putative, Mutator sub-class, expressed [*Oryza sativa Japonica* Group] > gi\|113549120\|dbj\|BAF12563.1\| Os03g0609800 [*Oryza sativa Japonica* Group] > gi\|125587097\|gb\|EAZ27761.1\| hypothetical protein OsJ_11706 [*Oryza sativa Japonica* Group] > gi\|215686957\|dbj\|BAG89762.1\| unnamed protein product [*Oryza sativa Japonica* Group] | 0.83 | 2178 | 2585 |
| | | EAZ21022 | hypothetical protein OsJ_36671 [*Oryza sativa Japonica* Group] | 0.73 | 2179 | |
| | | NP_001067147 | Os12g0583500 [*Oryza sativa Japonica* Group] > gi\|77556906\|gb\|ABA99702.1\| transposon protein, putative, Mutator sub-class, expressed [*Oryza sativa Japonica* Group] > gi\|113649654\|dbj\|BAF30166.1\| Os12g0583500 [*Oryza sativa Japonica* Group] | 0.73 | 2180 | 2586 |
| | | EAY83679 | hypothetical protein OsI_38903 [*Oryza sativa Indica* Group] | 0.73 | 2181 | |
| | | BAJ87350 | predicted protein [*Hordeum vulgare* subsp. *vulgare*] | 0.71 | 2182 | 2587 |
| | 3078-3096 | NP_001185468 | yellow stripe-like transporter 12 [*Zea mays*] > gi\|308210136\|gb\|ADO20999.1\| yellow stripe-like transporter 12 [*Zea mays*] | 1.00 | 2183 | 2588 |

TABLE 7-continued

Target genes of up regulated siRNA sequences associated with NUE
(Table 3)

| Mir name | Mir Bind. Pos. | Hom. NCBI Accession | Annotation/organism | Identity | p.p. SEQ ID NO: | p.n. SEQ ID NO: |
|---|---|---|---|---|---|---|
| | | XP_002446809 | hypothetical protein SORBIDRAFT_06g023010 [*Sorghum bicolor*] > gi|241937992|gb|EES11137.1| hypothetical protein SORBIDRAFT_06g023010 [*Sorghum bicolor*] | 0.93 | 2184 | 2589 |
| | | Q5JQD7 | RecName: Full = Probable metal-nicotianamine transporter YSL12; AltName: Full = Protein YELLOW STRIPE LIKE 12; Short = OsYSL12 > gi|116310949|emb|CAH67886.1| OSIGBa0153E02-OSIGBa0093I20.15 [*Oryza sativa Indica* Group] | 0.88 | 2185 | |
| | | BAE91892 | hypothetical protein [*Oryza sativa Japonica* Group] | 0.87 | 2186 | 2590 |
| | | XP_002452492 | hypothetical protein SORBIDRAFT_04g026840 [*Sorghum bicolor*] > gi|241932323|gb|EES05468.1| hypothetical protein SORBIDRAFT_04g026840 [*Sorghum bicolor*] | 0.82 | 2187 | 2591 |
| | | BAE44205 | hypothetical protein [*Oryza sativa Japonica* Group] | 0.81 | 2188 | 2592 |
| | | Q6H7J6 | RecName: Full = Probable metal-nicotianamine transporter YSL14; AltName: Full = Protein YELLOW STRIPE LIKE 14; Short = OsYSL14 > gi|49388177|dbj|BAD25303.1| oligopeptide transporter OPT-like [*Oryza sativa Japonica* Group] | 0.81 | 2189 | |
| | | BAJ89062 | predicted protein [*Hordeum vulgare* subsp. *vulgare*] | 0.80 | 2190 | 2593 |
| | | BAJ92335 | predicted protein [*Hordeum vulgare* subsp. *vulgare*] | 0.80 | 2191 | 2594 |
| | | ACN34648 | unknown [*Zea mays*] > gi|295441975|gb|ADG21035.1| oligopeptide transporter [*Zea mays*] > gi|308210138|gb|ADO21000.1| yellow stripe-like transporter 14A [*Zea mays*] | 0.81 | 2192 | 2595 |
| Predicted siRNA 59380 | 1927-1945 | XP_002450269 | hypothetical protein SORBIDRAFT_05g002900 [*Sorghum bicolor*] > gi|241936112|gb|EES09257.1| hypothetical protein SORBIDRAFT_05g002900 [*Sorghum bicolor*] | 1.00 | 2193 | 2596 |
| | | NP_001130515 | hypothetical protein LOC100191614 [*Zea mays*] > gi|194689354|gb|ACF78761.1| unknown [*Zea mays*] > gi|195635013|gb|ACG36975.1| pyruvate kinase, cytosolic isozyme [*Zea mays*] > gi|223947285|gb|ACN27726.1| unknown [*Zea mays*] > gi|238009496|gb|ACR35783.1| unknown [*Zea mays*] | 0.98 | 2194 | 2597 |
| | | NP_001149198 | LOC100282820 [*Zea mays*] > gi|195625378|gb|ACG34519.1| pyruvate kinase, cytosolic isozyme [*Zea mays*] | 0.97 | 2195 | 2598 |
| | | BAJ87403 | predicted protein [*Hordeum vulgare* subsp. *vulgare*] | 0.95 | 2196 | 2599 |

TABLE 7-continued

Target genes of up regulated siRNA sequences associated with NUE
(Table 3)

| Mir name | Mir Bind. Pos. | Hom. NCBI Accession | Annotation/organism | Identity | p.p. SEQ ID NO: | p.n. SEQ ID NO: |
|---|---|---|---|---|---|---|
| | | BAJ94667 | predicted protein [*Hordeum vulgare* subsp. *vulgare*] | 0.95 | 2197 | 2600 |
| | | NP_001065749 | Os11g0148500 [*Oryza sativa Japonica* Group] > gi\|77548686\|gb\|ABA91483.1\| pyruvate kinase family protein, expressed [*Oryza sativa Japonica* Group] > gi\|113644453\|dbj\|BAF27594.1\| Os11g0148500 [*Oryza sativa Japonica* Group] > gi\|215692631\|dbj\|BAG88051.1\| unnamed protein product [*Oryza sativa Japonica* Group] > gi\|218185248\|gb\|EEC67675.1\| hypothetical protein OsI_35105 [*Oryza sativa Indica* Group] > gi\|222615524\|gb\|EEE51656.1\| hypothetical protein OsJ_32969 [*Oryza sativa Japonica* Group] | 0.95 | 2198 | 2601 |
| | | NP_001066148 | Os12g0145700 [*Oryza sativa Japonica* Group] > gi\|77553678\|gb\|ABA96474.1\| pyruvate kinase family protein, expressed [*Oryza sativa Japonica* Group] > gi\|113648655\|dbj\|BAF29167.1\| Os12g0145700 [*Oryza sativa Japonica* Group] > gi\|215701048\|dbj\|BAG92472.1\| unnamed protein product [*Oryza sativa Japonica* Group] > gi\|218186432\|gb\|EEC68859.1\| hypothetical protein OsI_37456 [*Oryza sativa Indica* Group] > gi\|222616632\|gb\|EEE52764.1\| hypothetical protein OsJ_35209 [*Oryza sativa Japonica* Group] | 0.94 | 2199 | 2602 |
| | | XP_002283911 | PREDICTED: hypothetical protein [*Vitis vinifera*] | 0.89 | 2200 | 2603 |
| | | AAM22747 | pyruvate kinase-like [*Deschampsia antarctica*] | 0.88 | 2201 | 2604 |
| | | ABE80121 | Pyruvate kinase [*Medicago truncatula*] | 0.89 | 2202 | |
| Predicted siRNA 55806 | 43-66 | NP_001052992 | Os04g0460600 [*Oryza sativa Japonica* Group] > gi\|38344965\|emb\|CAD40985.2\| OSJNBa0072F16.10 [*Oryza sativa Japonica* Group] > gi\|108947442\|gb\|ABF47345.2\| NAC domain protein [*Oryza sativa Japonica* Group] > gi\|113564563\|dbj\|BAF14906.1\| Os04g0460600 [*Oryza sativa Japonica* Group] > gi\|116310448\|emb\|CAH67453.1\| H0219H12.10 [*Oryza sativa Indica* Group] > gi\|215692665\|dbj\|BAG88085.1\| unnamed protein product [*Oryza sativa Japonica* Group] > gi\|215737715\|dbj\|BAG96845.1\| unnamed protein product [*Oryza sativa Japonica* Group] > gi\|218194979\|gb\|EEC77406.1\| hypothetical protein OsI_16171 [*Oryza sativa Indica* Group] > gi\|222628996\|gb\|EEE61128.1\| hypothetical protein OsJ_15058 [*Oryza sativa Japonica* Group] | 1.00 | 2203 | 2605 |

TABLE 7-continued

Target genes of up regulated siRNA sequences associated with NUE
(Table 3)

| Mir name | Mir Bind. Pos. | Hom. NCBI Accession | Annotation/organism | Identity | p.p. SEQ ID NO: | p.n. SEQ ID NO: |
|---|---|---|---|---|---|---|
| | | BAC53811 | OsNAC2 protein [*Oryza sativa*] | 0.97 | 2204 | 2606 |
| | | XP_002446618 | hypothetical protein SORBIDRAFT_06g019010 [*Sorghum bicolor*] > gi|241937801|gb|EES10946.1| hypothetical protein SORBIDRAFT_06g019010 [*Sorghum bicolor*] | 0.71 | 2205 | 2607 |
| Predicted siRNA 57034 | 2555-2578 | NP_001141674 | hypothetical protein LOC100273800 [*Zea mays*] > gi|194705506|gb|ACF86837.1| unknown [*Zea mays*] | 1.00 | 2206 | 2608 |
| | | XP_002451554 | hypothetical protein SORBIDRAFT_04g003650 [*Sorghum bicolor*] > gi|241931385|gb|EES04530.1| hypothetical protein SORBIDRAFT_04g003650 [*Sorghum bicolor*] | 0.74 | 2207 | 2609 |
| | 95-115 | YP_874773 | ribosomal protein L14 [*Agrostis stolonifera*] > gi|118430423|ref|YP_874689.1| ribosomal protein L14 [*Hordeum vulgare* subsp. *vulgare*] > gi|159106900|ref|YP_001531318.1| ribosomal protein L14 [*Lolium perenne*] > gi|125987532|sp|A1EA45.1|RK14_AGRST RecName: Full = 50S ribosomal protein L14, chloroplastic > gi|218546804|sp|A1E9M7.1| RK14_HORVU RecName: Full = 50S ribosomal protein L14, chloroplastic > gi|218546811|sp|A8Y9C3.1|RK14_LOLPR RecName: Full = 50S ribosomal protein L14, chloroplastic > gi|118201077|gb|ABK79448.1| ribosomal protein L14 [*Hordeum vulgare* subsp. *vulgare*] > gi|118201247|gb|ABK79616.1| ribosomal protein L14 [*Agrostis stolonifera*] > gi|158934434|emb|CAO86012.1| ribosomal protein L14 [*Lolium perenne*] | 1.00 | 2208 | 2610 |
| | | YP_002364534 | ribosomal protein L14 [*Festuca arundinacea*] > gi|215882361|gb|ACJ70791.1| ribosomal protein L14 [*Festuca arundinacea*] | 0.99 | 2209 | 2611 |
| | | NP_114294 | ribosomal protein L14 [*Triticum aestivum*] > gi|45477200|sp|Q95H51.1|RK14_WHEAT RecName: Full = 50S ribosomal protein L14, chloroplastic > gi|13928241|dbj|BAB47070.1| ribosomal protein L14 [*Triticum aestivum*] | 0.99 | 2210 | 2612 |
| | | NP_039422 | ribosomal protein L14 [*Oryza sativa Japonica* Group] > gi|50234008|ref|YP_052786.1| ribosomal protein L14 [*Oryza nivara*] > gi|109156621|ref|YP_654240.1| ribosomal protein L14 [*Oryza sativa Indica* Group] > gi|253729591|ref|YP_003029775.1| ribosomal protein L14 | 0.98 | 2211 | 2613 |

TABLE 7-continued

Target genes of up regulated siRNA sequences associated with NUE
(Table 3)

| Mir name | Mir Bind. Pos. | Hom. NCBI Accession | Annotation/organism | Identity | p.p. SEQ ID NO: | p.n. SEQ ID NO: |
|---|---|---|---|---|---|---|
| | | | [*Bambusa oldhamii*]<br>> gi\|255961418\|ref\|YP_003097611.1\|<br>ribosomal protein L14<br>[*Dendrocalamus latiflorus*]<br>> gi\|297723921\|ref\|NP_001174324.1\|<br>Os05g0292700 [*Oryza sativa Japonica* Group]<br>> gi\|68565732\|sp\|Q6END7.1\|RK14_ORYNI<br>RecName:<br>Full = 50S ribosomal protein L14, chloroplastic<br>> gi\|148839610\|sp\|P0C438.1\|RK14_ORYSA<br>RecName:<br>Full = 50S ribosomal protein L14, chloroplastic<br>> gi\|148839611\|sp\|P0C439.1\|RK14_ORYSI<br>RecName: Full = 50S ribosomal protein L14, chloroplastic<br>> gi\|148839612\|sp\|P0C440.1\|RK14_ORYSJ<br>RecName: Full = 50S ribosomal protein L14, chloroplastic<br>> gi\|12023\|emb\|CAA33932.1\|<br>ribosomal protein L14 [*Oryza sativa Japonica* Group]<br>> gi\|20160833\|dbj\|BAB89773.1\|<br>Chloroplast ribosomal protein L14 [*Oryza sativa Japonica* Group]<br>> gi\|40253571\|dbj\|BAD05517.1\|<br>ribosomal protein L14 [*Oryza sativa Japonica* Group]<br>> gi\|42795513\|gb\|AAS46080.1\|<br>ribosomal protein L14 [*Oryza sativa Indica* Group]<br>> gi\|49615032\|dbj\|BAD26815.1\|<br>ribosomal protein L14 [*Oryza nivara*]<br>> gi\|246367101\|gb\|ACS94712.1\|<br>ribosomal protein L14 [*Bambusa oldhamii*]<br>> gi\|255040295\|gb\|ACT99955.1\|<br>ribosomal protein L14 [*Dendrocalamus latiflorus*]<br>> gi\|255676212\|dbj\|BAH93052.1\|<br>Os05g0292700 [*Oryza sativa Japonica* Group]<br>> gi\|307133922\|gb\|ADN32927.1\|<br>ribosomal protein L14 [*Phyllostachys nigra* var. *henonis*]<br>> gi\|309321653\|gb\|ADO65178.1\|<br>ribosomal protein L14 [*Acidosasa purpurea*]<br>> gi\|309321737\|gb\|ADO65261.1\|<br>ribosomal protein L14 [*Ferrocalamus rimosivaginus*]<br>> gi\|309321821\|gb\|ADO65344.1\|<br>ribosomal protein L14 [*Indocalamus longiauritus*]<br>> gi\|309321904\|gb\|ADO65426.1\|<br>ribosomal protein L14 [*Phyllostachys edulis*]<br>> gi\|309321989\|gb\|ADO65510.1\|<br>ribosomal protein L14 [*Bambusa emeiensis*]<br>> gi\|226644\|prf\|1603356BU | | | |
| | | YP_00200522 | ribosomal protein L14 [*Brachypodium distachyon*]<br>> gi\|218546902\|sp\|B3TN86.1\|RK14_BRADI<br>RecName: Full = 50S | 0.98 | 2212 | 2614 |

TABLE 7-continued

Target genes of up regulated siRNA sequences associated with NUE
(Table 3)

| Mir name | Mir Bind. Pos. | Hom. NCBI Accession | Annotation/organism | Identity | p.p. SEQ ID NO: | p.n. SEQ ID NO: |
|---|---|---|---|---|---|---|
| | | | ribosomal protein L14, chloroplastic > gi\|193075591\|gb\|ACF08674.1\| ribosomal protein L14 [*Brachypodium distachyon*] | | | |
| | | ABJ52167 | ribosomal protein L14 [*Phyllostachys edulis*] | 0.98 | 2213 | 2615 |
| | | BAC10087 | Chloroplast 50S ribosomal protein L14 [*Oryza sativa Japonica* Group] > gi\|50510231\|dbj\|BAD31429.1\| Chloroplast 50S ribosomal protein L14 [*Oryza sativa Japonica* Group] | 0.98 | 2214 | 2616 |
| | | YP_003587704 | ribosomal protein L14 [*Anomochloa marantoidea*] > gi\|251765288\|gb\|ACT15442.1\| ribosomal protein L14 [*Anomochloa marantoidea*] | 0.95 | 2215 | 2617 |
| | | BAD33446 | putative ribosomal protein L14 [*Oryza sativa Japonica* Group] > gi\|50726203\|dbj\|BAD33722.1\| putative ribosomal protein L14 [*Oryza sativa Japonica* Group] | 0.96 | 2216 | 2618 |
| | | AAT85078 | putative 50S ribosomal protein L14 [*Oryza sativa Japonica* Group] > gi\|50878445\|gb\|AAT85219.1\| putative 50S ribosomal protein L14 [*Oryza sativa Japonica* Group] | 0.94 | 2217 | 2619 |
| Predicted siRNA 60387 | 403-422 | XP_002439358 | hypothetical protein SORBIDRAFT_09g005070 [*Sorghum bicolor*] > gi\|241944643\|gb\|EES17788.1\| hypothetical protein SORBIDRAFT_09g005070 [*Sorghum bicolor*] | 1.00 | 2218 | 2620 |
| | | NP_001140641 | hypothetical protein LOC100272716 [*Zea mays*] > gi\|194700306\|gb\|ACF84237.1\| unknown [*Zea mays*] | 0.88 | 2219 | 2621 |
| | | ACG56678 | tryptophan aminotransferase [*Zea mays*] | 0.88 | 2220 | 2622 |
| | | NP_001151869 | alliin lyase 2 [*Zea mays*] > gi\|195650459\|gb\|ACG44697.1\| alliin lyase 2 precursor [*Zea mays*] | 0.79 | 2221 | 2623 |
| | 374-393 | NP_001140641 | hypothetical protein LOC100272716 [*Zea mays*] > gi\|194700306\|gb\|ACF84237.1\| unknown [*Zea mays*] | 1.00 | 2222 | 2624 |
| | | ACG56678 | tryptophan aminotransferase [*Zea mays*] | 1.00 | 2223 | 2625 |
| | | XP_002439358 | hypothetical protein SORBIDRAFT_09g005070 [*Sorghum bicolor*] > gi\|241944643\|gb\|EES17788.1\| hypothetical protein SORBIDRAFT_09g005070 [*Sorghum bicolor*] | 0.89 | 2224 | 2626 |
| | | NP_001151869 | alliin lyase 2 [*Zea mays*] > gi\|195650459\|gb\|ACG44697.1\| alliin lyase 2 precursor [*Zea mays*] | 0.77 | 2225 | 2627 |
| | 155-174 | XP_002446287 | hypothetical protein SORBIDRAFT_06g013470 [*Sorghum bicolor*] > gi\|241937470\|gb\|EES10615.1\| hypothetical protein SORBIDRAFT_06g013470 [*Sorghum bicolor*] | 1.00 | 2226 | 2628 |

TABLE 7-continued

Target genes of up regulated siRNA sequences associated with NUE
(Table 3)

| Mir name | Mir Bind. Pos. | Hom. NCBI Accession | Annotation/organism | Identity | p.p. SEQ ID NO: | p.n. SEQ ID NO: |
|---|---|---|---|---|---|---|
| | | NP_001132422 | hypothetical protein LOC100193871 [Zea mays] > gi|194694338|gb|ACF81253.1| unknown [Zea mays] | 0.89 | 2227 | 2629 |
| | | ACN36503 | unknown [Zea mays] | 0.89 | 2228 | 2630 |
| | | NP_001144520 | hypothetical protein LOC100277514 [Zea mays] > gi|195643396|gb|ACG41166.1| hypothetical protein [Zea mays] | 0.89 | 2229 | 2631 |
| | | ACN25444 | unknown [Zea mays] | 0.89 | 2230 | 2632 |
| | | XP_002454376 | hypothetical protein SORBIDRAFT_04g029660 [Sorghum bicolor] > gi|241934207|gb|EES07352.1| hypothetical protein SORBIDRAFT_04g029660 [Sorghum bicolor] | 0.83 | 2231 | 2633 |
| | 302-321 | XP_002445712 | hypothetical protein SORBIDRAFT_07g024570 [Sorghum bicolor] > gi|241942062|gb|EES15207.1| hypothetical protein SORBIDRAFT_07g024570 [Sorghum bicolor] | 1.00 | 2232 | 2634 |
| | | NP_001148095 | auxin-independent growth promoter [Zea mays] > gi|195615748|gb|ACG29704.1| auxin-independent growth promoter [Zea mays] | 0.95 | 2233 | 2635 |
| | | BAD10226 | putative auxin-independent growth promoter [Oryza sativa Japonica Group] > gi|50725540|dbj|BAD33009.1| putative auxin-independent growth promoter [Oryza sativa Japonica Group] | 0.82 | 2234 | 2636 |
| | | XP_002460613 | hypothetical protein SORBIDRAFT_02g031900 [Sorghum bicolor] > gi|241923990|gb|EER97134.1| hypothetical protein SORBIDRAFT_02g031900 [Sorghum bicolor] | 0.71 | 2235 | 2637 |
| | 151-170 | NP_001144386 | hypothetical protein LOC100277314 [Zea mays] > gi|195641382|gb|ACG40159.1| hypothetical protein [Zea mays] | 1.00 | 2236 | 2638 |
| | 781-800 | NP_001151955 | senescence-associated protein 15 [Zea mays] > gi|195651331|gb|ACG45133.1| senescence-associated protein 15 [Zea mays] | 1.00 | 2237 | 2639 |
| | 46-65 | XP_002465563 | hypothetical protein SORBIDRAFT_01g041190 [Sorghum bicolor] > gi|241919417|gb|EER92561.1| hypothetical protein SORBIDRAFT_01g041190 [Sorghum bicolor] | 1.00 | 2238 | 2640 |
| | | NP_001049540 | Os03g0245700 [Oryza sativa Japonica Group] > gi|108707147|gb|ABF94942.1| senescence-associated protein 15, putative, expressed [Oryza sativa Japonica Group] > gi|113548011|dbj|BAF11454.1| Os03g0245700 [Oryza sativa Japonica Group] > gi|125543096|gb|EAY89235.1| hypothetical protein OsI_10732 [Oryza sativa Indica Group] > gi|125585589|gb|EAZ26253.1| | 0.88 | 2239 | 2641 |

TABLE 7-continued

Target genes of up regulated siRNA sequences associated with NUE (Table 3)

| Mir name | Mir Bind. Pos. | Hom. NCBI Accession | Annotation/organism | Identity | p.p. SEQ ID NO: | p.n. SEQ ID NO: |
|---|---|---|---|---|---|---|
| | | BAJ85769 | hypothetical protein OsJ_10120 [*Oryza sativa Japonica* Group] predicted protein [*Hordeum vulgare* subsp. *vulgare*] > gi|326514266|dbj|BAJ92283.1| predicted protein [*Hordeum vulgare* subsp. *vulgare*] | 0.86 | 2240 | 2642 |
| | | XP_002464724 | hypothetical protein SORBIDRAFT_01g025820 [*Sorghum bicolor*] > gi|241918578|gb|EER91722.1| hypothetical protein SORBIDRAFT_01g025820 [*Sorghum bicolor*] | 0.76 | 2241 | 2643 |
| | | AAC34858 | senescence-associated protein 15 [*Hemerocallis* hybrid cultivar] | 0.70 | 2242 | 2644 |
| | | EEC66585 | hypothetical protein OsI_32794 [*Oryza sativa Indica* Group] | 0.74 | 2243 | |
| | | EEE50594 | hypothetical protein OsJ_30776 [*Oryza sativa Japonica* Group] | 0.74 | 2244 | |
| | | NP_001064196 | Os10g0158100 [*Oryza sativa Japonica* Group] > gi|255679225|dbj|BAF26110.2| Os10g0158100 [*Oryza sativa Japonica* Group] | 0.73 | 2245 | 2645 |
| | 400-419 | NP_001149275 | DNA polymerase epsilon subunit 3 [*Zea mays*] > gi|195625970|gb|ACG34815.1| DNA polymerase epsilon subunit 3 [*Zea mays*] > gi|195628668|gb|ACG36164.1| DNA polymerase epsilon subunit 3 [*Zea mays*] > gi|223942345|gb|ACN25256.1| unknown [*Zea mays*] | 1.00 | 2246 | 2646 |
| | | XP_002461994 | hypothetical protein SORBIDRAFT_02g012030 [*Sorghum bicolor*] > gi|241925371|gb|EER98515.1| hypothetical protein SORBIDRAFT_02g012030 [*Sorghum bicolor*] | 0.71 | 2247 | 2647 |
| | 71-90 | NP_001141681 | hypothetical protein LOC100273808 [*Zea mays*] > gi|238908879|gb|ACF86850.2| unknown [*Zea mays*] | 1.00 | 2248 | 2648 |
| | 106-125 | XP_002468642 | hypothetical protein SORBIDRAFT_01g049490 [*Sorghum bicolor*] > gi|241922496|gb|EER95640.1| hypothetical protein SORBIDRAFT_01g049490 [*Sorghum bicolor*] | 1.00 | 2249 | 2649 |
| | | ACG46521 | F-box protein [*Zea mays*] | 0.83 | 2250 | 2650 |
| | 670-689 | XP_002444258 | hypothetical protein SORBIDRAFT_07g019090 [*Sorghum bicolor*] > gi|241940608|gb|EES13753.1| hypothetical protein SORBIDRAFT_07g019090 [*Sorghum bicolor*] | 1.00 | 2251 | 2651 |
| | | NP_001131520 | hypothetical protein LOC100192859 [*Zea mays*] > gi|194691750|gb|ACF79959.1| unknown [*Zea mays*] | 0.95 | 2252 | 2652 |
| | | ACG32608 | peroxisomal coenzyme A diphosphatase NUDT7 [*Zea mays*] | 0.95 | 2253 | 2653 |

TABLE 7-continued

Target genes of up regulated siRNA sequences associated with NUE
(Table 3)

| Mir name | Mir Bind. Pos. | Hom. NCBI Accession | Annotation/organism | Identity | p.p. SEQ ID NO: | p.n. SEQ ID NO: |
|---|---|---|---|---|---|---|
| | | EAZ06644 | hypothetical protein OsI_28893 [*Oryza sativa Indica* Group] > gi|125561356|gb|EAZ06804.1| hypothetical protein OsI_29048 [*Oryza sativa Indica* Group] | 0.74 | 2254 | |
| | | EAZ42551 | hypothetical protein OsJ_27117 [*Oryza sativa Japonica* Group] | 0.74 | 2255 | |
| | | EAZ06802 | hypothetical protein OsI_29046 [*Oryza sativa Indica* Group] | 0.72 | 2256 | |
| | | NP_001061674 | Os08g0375900 [*Oryza sativa Japonica* Group] > gi|40253324|dbj|BAD05258.1| putative phosphohydrolase [*Oryza sativa Japonica* Group] > gi|40253358|dbj|BAD05290.1| putative phosphohydrolase [*Oryza sativa Japonica* Group] > gi|113623643|dbj|BAF23588.1| Os08g0375900 [*Oryza sativa Japonica* Group] | 0.72 | 2257 | 2654 |
| | | XP_002444259 | hypothetical protein SORBIDRAFT_07g019110 [*Sorghum bicolor*] > gi|241940609|gb|EES13754.1| hypothetical protein SORBIDRAFT_07g019110 [*Sorghum bicolor*] | 0.71 | 2258 | 2655 |
| | 2195-2214 | XP_002440313 | hypothetical protein SORBIDRAFT_09g029610 [*Sorghum bicolor*] > gi|241945598|gb|EES18743.1| hypothetical protein SORBIDRAFT_09g029610 [*Sorghum bicolor*] | 1.00 | 2259 | 2656 |
| | | ACG34981 | glucose-1-phosphate adenylyltransferase large subunit [*Zea mays*] > gi|223948357|gb|ACN28262.1| unknown [*Zea mays*] | 0.97 | 2260 | 2657 |
| | | NP_001056424 | Os05g0580000 [*Oryza sativa Japonica* Group] > gi|51854319|gb|AAU10700.1| putative glucose-1-phosphate adenylyltransferase [*Oryza sativa Japonica* Group] > gi|125553462|gb|EAY99171.1| hypothetical protein OsI_21129 [*Oryza sativa Indica* Group] > gi|169244411|gb|ACA50479.1| ADP-glucose pyrophosphorylase large subunit [*Oryza sativa Japonica* Group] > gi|215704797|dbj|BAG94825.1| unnamed protein product [*Oryza sativa Japonica* Group] > gi|222632685|gb|EEE64817.1| hypothetical protein OsJ_19673 [*Oryza sativa Japonica* Group] > gi|255676601|dbj|BAF18338.2| Os05g0580000 [*Oryza sativa Japonica* Group] > gi|262344368|gb|ACY56044.1| ADP-glucose pyrophosphorylase large subunit [*Oryza sativa Japonica* Group] > gi|262344370|gb|ACY56045.1| ADP-glucose pyrophosphorylase large subunit [*Oryza sativa Japonica* Group] > gi|262344372|gb|ACY56046.1| ADP-glucose pyrophosphorylase large subunit | 0.93 | 2261 | 2658 |

TABLE 7-continued

Target genes of up regulated siRNA sequences associated with NUE
(Table 3)

| Mir name | Mir Bind. Pos. | Hom. NCBI Accession | Annotation/organism | Identity | p.p. SEQ ID NO: | p.n. SEQ ID NO: |
|---|---|---|---|---|---|---|
| | | | [*Oryza sativa Japonica* Group] > gi|262344374|gb|ACY56047.1| ADP-glucose pyrophosphorylase large subunit [*Oryza sativa Japonica* Group] > gi|262344376|gb|ACY56048.1| ADP-glucose pyrophosphorylase large subunit [*Oryza sativa Japonica* Group] > gi|262344378|gb|ACY56049.1| ADP-glucose pyrophosphorylase large subunit [*Oryza sativa Japonica* Group] > gi|262344380|gb|ACY56050.1| ADP-glucose pyrophosphorylase large subunit [*Oryza sativa Indica* Group] > gi|262344382|gb|ACY56051.1| ADP-glucose pyrophosphorylase large subunit [*Oryza sativa Indica* Group] > gi|262344384|gb|ACY56052.1| ADP-glucose pyrophosphorylase large subunit [*Oryza sativa Indica* Group] > gi|262344386|gb|ACY56053.1| ADP-glucose pyrophosphorylase large subunit [*Oryza sativa Indica* Group] > gi|262344388|gb|ACY56054.1| ADP-glucose pyrophosphorylase large subunit [*Oryza sativa Indica* Group] > gi|262344390|gb|ACY56055.1| ADP-glucose pyrophosphorylase large subunit [*Oryza sativa Indica* Group] > gi|262344392|gb|ACY56056.1| ADP-glucose pyrophosphorylase large subunit [*Oryza sativa Indica* Group] > gi|262344394|gb|ACY56057.1| ADP-glucose pyrophosphorylase large subunit [*Oryza sativa Indica* Group] | | | |
| | | BAA23490 | ADP glucose pyrophosphorylase large subunit [*Oryza sativa Japonica* Group] | 0.92 | 2262 | 2659 |
| | | AAD39597 | 10A19I.12 [*Oryza sativa Japonica* Group] | 0.93 | 2263 | 2660 |
| | | P12299 | RecName: Full = Glucose-1-phosphate adenylyltransferase large subunit, chloroplastic/amyloplastic; AltName: Full = ADP-glucose pyrophosphorylase; AltName: Full = ADP-glucose synthase; AltName: Full = AGPase S; AltName: Full = Alpha-D-glucose-1-phosphate adenyl transferase; Flags: Precursor > gi|995746|emb|CAA79980.1| ADP-glucose pyrophosphorylase large subunit [*Triticum aestivum*] > gi|110729318|gb|ABG88200.1| ADP-glucose pyrophosphorylase large subunit [*Triticum aestivum*] | 0.91 | 2264 | |
| | | P30524 | RecName: Full = Glucose-1-phosphate adenylyltransferase large subunit 1, chloroplastic/amyloplastic; | 0.91 | 2265 | |

TABLE 7-continued

Target genes of up regulated siRNA sequences associated with NUE
(Table 3)

| Mir name | Mir Bind. Pos. | Hom. NCBI Accession | Annotation/organism | Identity | p.p. SEQ ID NO: | p.n. SEQ ID NO: |
|---|---|---|---|---|---|---|
| | | | AltName: Full = ADP-glucose pyrophosphorylase; AltName: Full = ADP-glucose synthase; AltName: Full = AGPase S; AltName: Full = Alpha-D-glucose-1-phosphate adenyl transferase; AltName: Full = BEPL; Flags: Precursor > gi|1279513|emb|CAA47626.1| glucose-1-phosphate adenylyltransferase [Hordeum vulgare subsp. vulgare] > gi|229610847|emb|CAX51355.1| large subunit of ADP-glucose pyrophosphorylase [Hordeum vulgare subsp. vulgare] > gi|326527375|dbj|BAK04629.1| predicted protein [Hordeum vulgare subsp. vulgare] > gi|326528409|dbj|BAJ93393.1| predicted protein [Hordeum vulgare subsp. vulgare] > gi|326528511|dbj|BAJ93437.1| predicted protein [Hordeum vulgare subsp. vulgare] | | | |
| | | CAD98749 | ADP-glucose pyrophosphorylase large subunit [Triticum aestivum] | 0.89 | 2266 | 2661 |
| | | NP_001105717 | glucose-1-phosphate adenylyltransferase large subunit 2, chloroplastic/amyloplastic [Zea mays] >gi|707928|sp|p55234.1|GLG L2_MAIZE RecName: Full = Glucose-1-phosphate adenylyltransferase large subunit 2, chloroplastic/amyloplastic; AltName: Full = ADP-glucose pyrophosphorylase; AltName: Full = synthase AltName: Full = AGPase S; AltName: Full = Alpha-D-glucose-1-phosphate adenyl transferase; Flags: Precursor >gi|558365|emb|CAA86227.1| ADP-glucose pyrophosphorylase [Zea mays] | 0.92 | 2267 | 2662 |
| | | 1909370A | ADP glucose | 0.87 | 2268 | |
| Predicted siRNA 60837 | 154-171 | XP_001545081 | hypothetical protie BC1G_16418 [Botryotinia fuckeliana B05.10 ] >gi|150854146|gb|EDN29338.1| hypothetical protein BC1G_16418[Botryotinia fuckeliana B05.10 | 1.00 | 2269 | 2663 |
| | 629-646 | XP_002441128 | hypothetical protein SORBIDRAFT_09g020930 [Sorghum bicolor] >g1|241946413|gb|EES19558.1| hypothetical protein SORBIDRAFT_09g020930 [Sorghum bicolor] | 1.00 | 2270 | 2664 |
| | | ACR35990 | unknown [Zea mays] | 0.91 | 2271 | 2665 |
| | | NP_001152387 | LOC100286027 [Zea mays] >gi|195655783|gb|ACG47359.1| secondary cell wall-related glycosyltransferase family 8 [Zea mays] | 0.92 | 2272 | 2666 |
| | | BAJ85213 | predicted protein [Hordeum vulgare subsp. vulgare] >gi|326515442|dbj|BAK03634.1| predicted protein [Hordeum vulgare subsp. vulgare] | 0.86 | 2273 | 2667 |

TABLE 7-continued

Target genes of up regulated siRNA sequences associated with NUE
(Table 3)

| Mir name | Mir Bind. Pos. | Hom. NCBI Accession | Annotation/organism | Identity | p.p. SEQ ID NO: | p.n. SEQ ID NO: |
|---|---|---|---|---|---|---|
| | | AAS90653 | putative glycogenin [*Oryza sativa Japonica* Group] | 0.84 | 2274 | 2668 |
| | | EEC79261 | hypothetical protein OsI_20036 [*Oryza sativa Indica* Group] | 0.84 | 2275 | |
| | | EEE63788 | hypothetical protein OsJ_18611 [*Oryza sativa Japonica* Group] | 0.83 | 2276 | |
| | | NP_00104491 | Os01g0880200 [*Oryza sativa Japonica* Group] >gi\|56784626\|dbj\|BAD81673.1\| glycogenin-like protein [*Oryza sativa Japonica* Group] > gi\|113534522\|dbj\|BAF06905.1\| Os01g0880200 [*Oryza sativa Japonica* Group] | 0.84 | 2277 | 2669 |
| | | EEC71899 | hypothetical protein OsI_04661 [*Oryza sativa Indica* Group] | 0.84 | 2278 | |
| | | BAJ87677 | predicted protein [*Hordeum vulgare* subsp. *vulgare*] | 0.82 | 2279 | 2670 |
| | 687-704 | EEC83357 | hypothetical protein OsI_28763 [*Oryza sativa Indica* Group] > gi\|222623167\|gb\|EEE57299.1\| hypothetical protein OsJ_07374 [*Oryza sativa Japonica* Group] | 1.00 | 2280 | |
| | | NP_001060995 | Os08g0150800 [*Oryza sativa Japonica* Group] > gi\|37573038\|dbj\|BAC98550.1\| putative tyrosyl-tRNA synthetase [*Oryza sativa Japonica* Group] > gi\|113622964\|dbj\|BAF22909.1\| Os08g0150800 [*Oryza sativa Japonica* Group] > gi\|222639916\|gb\|EEE68048.1\| hypothetical protein OsJ_26046 [*Oryza sativa Japonica* Group] | 0.94 | 2281 | 2671 |
| | | ACF82652 | unknown [*Zea mays*] | 0.87 | 2282 | 2672 |
| | | NP_001149217 | LOC100282839 [*Zea mays*] > gi\|195625536\|gb\|ACG34598.1\| tyrosyl-tRNA synthetase [*Zea mays*] | 0.86 | 2283 | 2673 |
| | | NP_001148699 | tyrosyl-tRNA synthetase [*Zea mays*] > gi\|195621482\|gb\|ACG32571.1\| tyrosyl-tRNA synthetase [*Zea mays*] | 0.83 | 2284 | 2674 |
| | | BAK05692 | predicted protein [*Hordeum vulgare* subsp. *vulgare*] > gi\|326527699\|dbj\|BAK08124.1\| predicted protein [*Hordeum vulgare* subsp. *vulgare*] > gi\|326533322\|dbj\|BAJ93633.1\| predicted protein [*Hordeum vulgare* subsp. *vulgare*] | 0.83 | 2285 | 2675 |
| | | CAA71881 | Tyrosyl-tRNA synthetase [*Nicotiana tabacum*] | 0.69 | 2286 | 2676 |
| | | XP_002517485 | tyrosyl-tRNA synthetase, putative [*Ricinus communis*] > gi\|223543496\|gb\|EEF45027.1\| tyrosyl-tRNA synthetase, putative [*Ricinus communis*] | 0.71 | 2287 | 2677 |
| | | XP_002274369 | PREDICTED: hypothetical protein [*Vitis vinifera*] > gi\|297742518\|emb\|CBI34667.3\| unnamed protein product [*Vitis vinifera*] | 0.71 | 2288 | 2678 |
| | | CAN65657 | hypothetical protein VITISV_000951 [*Vitis vinifera*] | 0.71 | 2289 | 2679 |

TABLE 7-continued

Target genes of up regulated siRNA sequences associated with NUE
(Table 3)

| Mir name | Mir Bind. Pos. | Hom. NCBI Accession | Annotation/organism | Identity | p.p. SEQ ID NO: | p.n. SEQ ID NO: |
|---|---|---|---|---|---|---|
| | 796-813 | ACG35054 | THO complex subunit 4 [*Zea mays*] | 1.00 | 2290 | 2680 |
| | | NP_001146734 | hypothetical protein LOC100280336 [*Zea mays*] > gi|194704900|gb|ACF86534.1| unknown [*Zea mays*] > gi|219888533|gb|ACL54641.1| unknown [*Zea mays*] | 0.99 | 2291 | 2681 |
| | | XP_002438180 | hypothetical protein SORBIDRAFT_10g009240 [*Sorghum bicolor*] > gi|241916403|gb|EER89547.1| hypothetical protein SORBIDRAFT_10g009240 [*Sorghum bicolor*] | 0.87 | 2292 | 2682 |
| | 310-327 | NP_001168358 | hypothetical protein LOC100382126 [*Zea mays*] > gi|223947741|gb|ACN27954.1| unknown [*Zea mays*] | 1.00 | 2293 | 2683 |
| | | BAD54151 | putative poly(A) polymerase [*Oryza sativa Japonica* Group] | 0.81 | 2294 | |
| | | BAJ95542 | predicted protein [*Hordeum vulgare* subsp. *vulgare*] | 0.80 | 2295 | 2684 |
| | | NP_001174846 | Os06g0558700 [*Oryza sativa Japonica* Group] > gi|255677141|dbj|BAH93574.1| Os06g0558700 [*Oryza sativa Japonica* Group] | 0.80 | 2296 | 2685 |
| | | AAW68015 | putative polynucleotide adenylyltransferase [*Oryza sativa Indica* Group] | 0.80 | 2297 | 2686 |
| | | EAZ37348 | hypothetical protein OsJ_21686 [*Oryza sativa Japonica* Group] | 0.78 | 2298 | |
| | | EAZ01335 | hypothetical protein OsI_23369 [*Oryza sativa Indica* Group] | 0.78 | 2299 | |
| | 576-593 | XP_002466644 | hypothetical protein SORBIDRAFT_01g011560 [*Sorghum bicolor*] > gi|241920498|gb|EER93642.1| hypothetical protein SORBIDRAFT_01g011560 [*Sorghum bicolor*] | 1.00 | 2300 | 2687 |
| | | NP_001169332 | hypothetical protein LOC100383199 [*Zea mays*] > gi|224028751|gb|ACN33451.1| unknown [*Zea mays*] | 0.96 | 2301 | 2688 |
| | | NP_001130678 | hypothetical protein LOC100191781 [*Zea mays*] > gi|194688930|gb|ACF78549.1| unknown [*Zea mays*] | 0.95 | 2302 | 2689 |
| | | EEC81302 | hypothetical protein OsI_24438 [*Oryza sativa Indica* Group] > gi|222636212|gb|EEE66344.1| hypothetical protein OsJ_22634 [*Oryza sativa Japonica* Group] | 0.87 | 2303 | |
| | | BAJ99110 | predicted protein [*Hordeum vulgare* subsp. *vulgare*] | 0.86 | 2304 | 2690 |
| | | BAJ86220 | predicted protein [*Hordeum vulgare* subsp. *vulgare*] | 0.75 | 2305 | 2691 |
| | | NP_001063757 | Os09g0531900 [*Oryza sativa Japonica* Group] > gi|52075938|dbj|BAD46018.1| glycosyl transferase family 8 protein-like [*Oryza sativa Japonica* Group] > gi|52077221|dbj|BAD46265.1| glycosyl transferase family 8 protein-like [*Oryza sativa Japonica* Group] > gi|113631990|dbj|BAF25671.1| | 0.74 | 2306 | 2692 |

TABLE 7-continued

Target genes of up regulated siRNA sequences associated with NUE
(Table 3)

| Mir name | Mir Bind. Pos. | Hom. NCBI Accession | Annotation/organism | Identity | p.p. SEQ ID NO: | p.n. SEQ ID NO: |
|---|---|---|---|---|---|---|
| | | | Os09g0531900 [*Oryza sativa Japonica* Group] > gi\|222641970\|gb\|EEE70102.1\| hypothetical protein OsJ_30110 [*Oryza sativa Japonica* Group] | | | |
| | | EEC84934 | hypothetical protein OsI_32147 [*Oryza sativa Indica* Group] | 0.74 | 2307 | |
| | | XP_002462717 | hypothetical protein SORBIDRAFT_02g030820 [*Sorghum bicolor*] > gi\|241926094\|gb\|EER99238.1\| hypothetical protein SORBIDRAFT_02g030820 [*Sorghum bicolor*] | 0.75 | 2308 | 2693 |
| | | CBI38820 | unnamed protein product [*Vitis vinifera*] | 0.72 | 2309 | |
| Predicted siRNA 61382 | 70-89 | XP_002446795 | hypothetical protein SORBIDRAFT_06g022830 [*Sorghum bicolor*] > gi\|241937978\|gb\|EES11123.1\| hypothetical protein SORBIDRAFT_06g022830 [*Sorghum bicolor*] | 1.00 | 2310 | 2694 |
| | | NP_001143685 | hypothetical protein LOC100276413 [*Zea mays*] > gi\|195624570\|gb\|ACG34115.1\| hypothetical protein [*Zea mays*] | 0.86 | 2311 | 2695 |
| | | ACN29321 | unknown [*Zea mays*] | 0.86 | 2312 | 2696 |
| | | NP_001053334 | Os04g0520900 [*Oryza sativa Japonica* Group] > gi\|21741854\|emb\|CAD41444.1\| OSJNBa0019D11.15 [*Oryza sativa Japonica* Group] > gi\|113564905\|dbj\|BAF15248.1\| Os04g0520900 [*Oryza sativa Japonica* Group] > gi\|116310729\|emb\|CAH67525.1\| OSIGBa0131L05.6 [*Oryza sativa Indica* Group] > gi\|125549050\|gb\|EAY94872.1\| hypothetical protein OsI_16672 [*Oryza sativa Indica* Group] > gi\|125591012\|gb\|EAZ31362.1\| hypothetical protein OsJ_15488 [*Oryza sativa Japonica* Group] > gi\|215697100\|dbj\|BAG91094.1\| unnamed protein product [*Oryza sativa Japonica* Group] | 0.72 | 2313 | 2697 |
| | 682-701 | NP_001143685 | hypothetical protein LOC100276413 [*Zea mays*] > gi\|195624570\|gb\|ACG34115.1\| hypothetical protein [*Zea mays*] | 1.00 | 2314 | 2698 |
| | | ACN29321 | unknown [*Zea mays*] | 0.95 | 2315 | 2699 |
| | | XP_002446795 | hypothetical protein SORBIDRAFT_06g022830 [*Sorghum bicolor*] > gi\|241937978\|gb\|EES11123.1\| hypothetical protein SORBIDRAFT_06g022830 [*Sorghum bicolor*] | 0.90 | 2316 | 2700 |
| | | NP_001053334 | Os04g0520900 [*Oryza sativa Japonica* Group] > gi\|21741854\|emb\|CAD41444.1\| OSJNBa0019D11.15 [*Oryza sativa Japonica* Group] > gi\|113564905\|dbj\|BAF15248.1\| Os04g0520900 [*Oryza sativa Japonica* Group] > gi\|116310729\|emb\|CAH67525.1\| | 0.70 | 2317 | 2701 |

TABLE 7-continued

Target genes of up regulated siRNA sequences associated with NUE
(Table 3)

| Mir name | Mir Bind. Pos. | Hom. NCBI Accession | Annotation/organism | Identity | p.p. SEQ ID NO: | p.n. SEQ ID NO: |
|---|---|---|---|---|---|---|
| Predicted siRNA 60188 | 237-254 | XP_002459573 | OSIGBa0131L05.6 [*Oryza sativa Indica* Group] > gi\|125549050\|gb\|EAY94872.1\| hypothetical protein OsI_16672 [*Oryza sativa Indica* Group] > gi\|125591012\|gb\|EAZ31362.1\| hypothetical protein OsJ_15488 [*Oryza sativa Japonica* Group] > gi\|215697100\|dbj\|BAG91094.1\| unnamed protein product [*Oryza sativa Japonica* Group] hypothetical protein SORBIDRAFT_02g006770 [*Sorghum bicolor*] > gi\|241922950\|gb\|EER96094.1\| hypothetical protein SORBIDRAFT_02g006770 [*Sorghum bicolor*] | 1.00 | 2318 | 2702 |
| | | NP_001150031 | nucleic acid binding protein [*Zea mays*] > gi\|194699002\|gb\|ACF83585.1\| unknown [*Zea mays*] > gi\|195636208\|gb\|ACG37572.1\| nucleic acid binding protein [*Zea mays*] | 0.98 | 2319 | 2703 |
| | | NP_001140438 | hypothetical protein LOC100272497 [*Zea mays*] > gi\|194699514\|gb\|ACF83841.1\| unknown [*Zea mays*] | 0.96 | 2320 | 2704 |
| | | NP_001059216 | Os07g0227400 [*Oryza sativa Japonica* Group] > gi\|24060154\|dbj\|BAC21599.1\| KH domain-like protein [*Oryza sativa Japonica* Group] > gi\|113610752\|dbj\|BAF21130.1\| Os07g0227400 [*Oryza sativa Japonica* Group] > gi\|215697533\|dbj\|BAG91527.1\| unnamed protein product [*Oryza sativa Japonica* Group] | 0.91 | 2321 | 2705 |
| | | EAZ39172 | hypothetical protein OsJ_23597 [*Oryza sativa Japonica* Group] > gi\|218199326\|gb\|EEC81753.1\| hypothetical protein OsI_25419 [*Oryza sativa Indica* Group] | 0.91 | 2322 | |
| | | NP_001148920 | nucleic acid binding protein [*Zea mays*] > gi\|195623320\|gb\|ACG33490.1\| nucleic acid binding protein [*Zea mays*] | 0.85 | 2323 | 2706 |
| | | XP_002466215 | hypothetical protein SORBIDRAFT_01g003680 [*Sorghum bicolor*] > gi\|241920069\|gb\|EER93213.1\| hypothetical protein SORBIDRAFT_01g003680 [*Sorghum bicolor*] | 0.85 | 2324 | 2707 |
| | | NP_001051685 | Os03g0815700 [*Oryza sativa Japonica* Group] > gi\|75226290\|sp\|Q75GR5.1\|SPIN1_ORYSJ RecName: Full = KH domain-containing protein SPIN1; AltName: Full = SPL11-interacting protein 1 > gi\|37718879\|gb\|AAR01750.1\| expressed protein [*Oryza sativa Japonica* Group] > gi\|108711745\|gb\|ABF99540.1\| KH domain-containing protein, putative, expressed [*Oryza sativa Japonica* Group] > gi\|113550156\|dbj\|BAF13599.1\| | 0.86 | 2325 | 2708 |

TABLE 7-continued

Target genes of up regulated siRNA sequences associated with NUE
(Table 3)

| Mir name | Mir Bind. Pos. | Hom. NCBI Accession | Annotation/organism | Identity | p.p. SEQ ID NO: | p.n. SEQ ID NO: |
|---|---|---|---|---|---|---|
| | | | Os03g0815700 [*Oryza sativa Japonica* Group] > gi\|215694514\|dbj\|BAG89507.1\| unnamed protein product [*Oryza sativa Japonica* Group] > gi\|218193980\|gb\|EEC76407.1\| hypothetical protein OsI_14057 [*Oryza sativa Indica* Group] > gi\|222626037\|gb\|EEE60169.1\| hypothetical protein OsJ_13097 [*Oryza sativa Japonica* Group] | | | |
| | | NP_001130116 | hypothetical protein LOC100191210 [*Zea mays*] > gi\|194688334\|gb\|ACF78251.1\| unknown [*Zea mays*] | 0.84 | 2326 | 2709 |
| | | BAJ96236 | predicted protein [*Hordeum vulgare* subsp. *vulgare*] | 0.83 | 2327 | 2710 |
| | 362-379 | XP_002448500 | hypothetical protein SORBIDRAFT_06g028030 [*Sorghum bicolor*] > gi\|241939683\|gb\|EES12828.1\| hypothetical protein SORBIDRAFT_06g028030 [*Sorghum bicolor*] | 1.00 | 2328 | 2711 |
| | | NP_001148728 | protein phosphatase 2C [*Zea mays*] > gi\|195621678\|gb\|ACG32669.1\| protein phosphatase 2C [*Zea mays*] > gi\|238007398\|gb\|ACR34734.1\| unknown [*Zea mays*] | 0.93 | 2329 | 2712 |
| | | NP_001053823 | Os04g0609600 [*Oryza sativa Japonica* Group] > gi\|122240832\|sp\|Q0JAA0.1\|P2C44_ORYSJ RecName: Full = Probable protein phosphatase 2C 44; Short = OsPP2C44 > gi\|113565394\|dbj\|BAF15737.1\| Os04g0609600 [*Oryza sativa Japonica* Group] | 0.91 | 2330 | 2713 |
| | | 5 | [*Oryza sativa Japonica* Group] | | | |
| | | EEC71777 | hypothetical protein OsI_04389 [*Oryza sativa Indica* Group] | 0.80 | 2339 | |
| | | BAJ99773 | predicted protein [*Hordeum vulgare* subsp. *vulgare*] | 0.78 | 2340 | 2721 |
| | | XP_002458747 | hypothetical protein SORBIDRAFT_03g039530 [*Sorghum bicolor*] > gi\|241930722\|gb\|EES03867.1\| hypothetical protein SORBIDRAFT_03g039530 [*Sorghum bicolor*] | 0.78 | 2341 | 2722 |
| | | AAC04576 | putative high-pI laccase [*Oryza sativa Japonica* Group] | 0.79 | 2342 | 2723 |
| | 725-742 | CAE03557 | OSJNBa0085I10.2 [*Oryza sativa Japonica* Group] > gi\|90265077\|emb\|CAH67750.1\| H0702G05.9 [*Oryza sativa Indica* Group] | 1.00 | 2343 | 2724 |
| | | NP_001053823 | Os04g0609600 [*Oryza sativa Japonica* Group] > gi\|122240832\|sp\|Q0JAA0.1\|P2C44_ORYSJ RecName: Full = Probable protein phosphatase 2C 44; Short = OsPP2C44 > gi\|113565394\|dbj\|BAF15737.1\| Os04g0609600 [*Oryza sativa Japonica* Group] > gi\|218195541\|gb\|EEC77968.1\| hypothetical protein OsI_17335 | 1.00 | 2344 | 2725 |

TABLE 7-continued

Target genes of up regulated siRNA sequences associated with NUE
(Table 3)

| Mir name | Mir Bind. Pos. | Hom. NCBI Accession | Annotation/organism | Identity | p.p. SEQ ID NO: | p.n. SEQ ID NO: |
|---|---|---|---|---|---|---|
| | | XP_002448500 | [Oryza sativa Indica Group] > gi\|222629521\|gb\|EEE61653.1\| hypothetical protein OsJ_16105 [Oryza sativa Japonica Group] hypothetical protein SORBIDRAFT_06g028030 [Sorghum bicolor] > gi\|241939683\|gb\|EES12828.1\| hypothetical protein SORBIDRAFT_06g028030 [Sorghum bicolor] | 0.91 | 2345 | 2726 |
| | | NP_001148728 | protein phosphatase 2C [Zea mays] > gi\|195621678\|gb\|ACG32669.1\| protein phosphatase 2C [Zea mays] > gi\|238007398\|gb\|ACR34734.1\| unknown [Zea mays] | 0.90 | 2346 | 2727 |
| | | CAE03658 | OSJNBa0060NO3.23 [Oryza sativa Japonica Group] | 0.75 | 2347 | 2728 |
| | | XP_002274944 | PREDICTED: hypothetical protein isoform 1 [Vitis vinifera] > gi\|297745124\|emb\|CB138963.3\| unnamed protein product [Vitis vinifera] | 0.74 | 2348 | 2729 |
| | | XP_002514493 | protein phosphatase 2c, putative [Ricinus communis] > gi\|223546392\|gb\|EEF47893.1\| protein phosphatase 2c, putative [Ricinus communis] | 0.76 | 2349 | 2730 |
| | | XP_002274981 | PREDICTED: hypothetical protein isoform 2 [Vitis vinifera] | 0.71 | 2350 | 2731 |
| | 879-896 | NP_001054756 | Os05g0168700 [Oryza sativa Japonica Group] > gi\|53982148\|gb\|AAV25244.1\| putative phosphate translocator [Oryza sativa Japonica Group] > gi\|113578307\|dbj\|BAF16670.1\| Os05g0168700 [Oryza sativa Japonica Group] > gi\|215686739\|dbj\|BAG89589.1\| unnamed protein product [Oryza sativa Japonica Group] > gi\|218196167\|gb\|EEC78594.1\| hypothetical protein OsI_18612 [Oryza sativa Indica Group] > gi\|222630341\|gb\|EEE62473.1\| hypothetical protein OsJ_17270 [Oryza sativa Japonica Group] | 1.00 | 2351 | 2732 |
| | | BAB41206 | putative glucose-6-phosphate/phosphate-tranlocat or [Oryza sativa (japonica cultivar-group)] | 0.99 | 2352 | 2733 |
| | | ACN32013 | unknown [Zea mays] | 0.96 | 2353 | 2734 |
| | | XP_002440680 | hypothetical protein SORBIDRAFT_09g005010 [Sorghum bicolor] > gi\|241945965\|gb\|EES19110.1\| hypothetical protein SORBIDRAFT_09g005010 [Sorghum bicolor] | 0.96 | 2354 | 2735 |
| | | NP_001142411 | hypothetical protein LOC100274586 [Zea mays] > gi\|194707946\|gb\|ACF88057.1\| unknown [Zea mays] > gi\|194708688\|gb\|ACF88428.1\| unknown [Zea mays] > gi\|195620476\|gb\|ACG32068.1\| integral membrane protein like [Zea mays] | 0.95 | 2355 | 2736 |

TABLE 7-continued

Target genes of up regulated siRNA sequences associated with NUE
(Table 3)

| Mir name | Mir Bind. Pos. | Hom. NCBI Accession | Annotation/organism | Identity | p.p. SEQ ID NO: | p.n. SEQ ID NO: |
|---|---|---|---|---|---|---|
| | | BAK03308 | predicted protein [*Hordeum vulgare* subsp. *vulgare*] | 0.95 | 2356 | 2737 |
| | | NP_001148556 | integral membrane protein like [*Zea mays*] > gi|195620390|gb|ACG32025.1| integral membrane protein like [*Zea mays*] | 0.87 | 2357 | 2738 |
| | | NP_001042121 | Os01g0167500 [*Oryza sativa Japonica* Group] > gi|13486667|dbj|BAB39904.1| P0028E10.8 [*Oryza sativa Japonica* Group] > gi|15528768|dbj|BAB64810.1| putative glucose-6-phosphate/phosphate-tranlocator [*Oryza sativa Japonica* Group] > gi|20804811|dbj|BAB92494.1| putative glucose-6-phosphate/phosphate-tranlocator [*Oryza sativa Japonica* Group] > gi|113531652|dbj|BAF04035.1| Os01g0167500 [*Oryza sativa Japonica* Group] > gi|215767361|dbj|BAG99589.1| unnamed protein product [*Oryza sativa Japonica* Group] > gi|218187579|gb|EEC70006.1| hypothetical protein OsI_00550 [*Oryza sativa Indica* Group] > gi|222617800|gb|EEE53932.1| hypothetical protein OsJ_00515 [*Oryza sativa Japonica* Group] | 0.92 | 2358 | 2739 |
| | | NP_001142171 | hypothetical protein LOC100274338 [*Zea mays*] > gi|194707458|gb|ACF87813.1| unknown [*Zea mays*] | 0.93 | 2359 | 2740 |
| | | ACN34739 | unknown [*Zea mays*] | 0.92 | 2360 | 2741 |
| | 130-147 | XP_002448782 | hypothetical protein SORBIDRAFT_06g033075 [*Sorghum bicolor*] > gi|241939965|gb|EES13110.1| hypothetical protein SORBIDRAFT_06g033075 [*Sorghum bicolor*] | 1.00 | 2361 | 2742 |
| | | NP_001151057 | LOC100284690 [*Zea mays*] > gi|195643970|gb|ACG41453.1| ATP binding protein [*Zea mays*] | 0.92 | 2362 | 2743 |
| | | EAZ32429 | hypothetical protein OsJ_16639 [*Oryza sativa Japonica* Group] | 0.82 | 2363 | |
| | | NP_001054279 | Os04g0679200 [*Oryza sativa Japonica* Group] > gi|38344039|emb|CAE05726.2| OSJNBb0017I01.6 [*Oryza sativa Japonica* Group] > gi|113565850|dbj|BAF16193.1| Os04g0679200 [*Oryza sativa Japonica* Group] > gi|215712397|dbj|BAG94524.1| unnamed protein product [*Oryza sativa Japonica* Group] > gi|215740866|dbj|BAG97022.1| unnamed protein product [*Oryza sativa Japonica*Group] | 0.82 | 2364 | 2744 |
| | | CAJ86254 | H0801D08.12 [*Oryza sativa Indica* Group] > gi|125550244|gb|EAY96066.1| hypothetical protein OsI_17939 [*Oryza sativa Indica* Group] | 0.82 | 2365 | 2745 |
| | | BAJ93433 | predicted protein [*Hordeum vulgare* subsp. *vulgare*] | 0.80 | 2366 | 2746 |

TABLE 7-continued

Target genes of up regulated siRNA sequences associated with NUE
(Table 3)

| Mir name | Mir Bind. Pos. | Hom. NCBI Accession | Annotation/organism | Identity | p.p. SEQ ID NO: | p.n. SEQ ID NO: |
|---|---|---|---|---|---|---|
| | 99-116 | XP_002452000 | hypothetical protein SORBIDRAFT_04g014390 [*Sorghum bicolor*] > gi\|241931831\|gb\|EES04976.1\| hypothetical protein SORBIDRAFT_04g014390 [*Sorghum bicolor*] | 1.00 | 2367 | 2747 |
| | | ACR36123 | unknown [*Zea mays*] | 0.93 | 2368 | 2748 |
| | | NP_001145206 | hypothetical protein LOC100278461 [*Zea mays*] > gi\|195652631\|gb\|ACG45783.1\| hypothetical protein [*Zea mays*] | 0.92 | 2369 | 2749 |
| | | NP_001046716 | Os02g0329300 [*Oryza sativa Japonica* Group] > gi\|46389946\|dbj\|BAD15798.1\| unknown protein [*Oryza sativa Japonica* Group] > gi\|113536247\|dbj\|BAF08630.1\| Os02g0329300 [*Oryza sativa Japonica* Group] > gi\|222622747\|gb\|EEE56879.1\| hypothetical protein OsJ_06518 [*Oryza sativa Japonica* Group] | 0.86 | 2370 | 2750 |
| | | EEC73063 | hypothetical protein OsI_07020 [*Oryza sativa Indica* Group] | 0.85 | 2371 | |
| | | BAK07073 | predicted protein [*Hordeum vulgare* subsp. *vulgare*] | 0.81 | 2372 | 2751 |
| | 736-753 | ACN28855 | unknown [*Zea mays*] | 1.00 | 2373 | 2752 |
| | | NP_001105875 | putative laccase [*Zea mays*] > gi\|84618781\|emb\|CAJ30500.1\| putative laccase [*Zea mays*] | 0.99 | 2374 | 2753 |
| | | NP_001146658 | hypothetical protein LOC100280258 [*Zea mays*] > gi\|219888209\|gb\|ACL54479.1\| unknown [*Zea mays*] | 0.93 | 2375 | 2754 |
| | | XP_002458746 | hypothetical protein SORBIDRAFT_03g039520 [*Sorghum bicolor*] > gi\|241930721\|gb\|EES03866.1\| hypothetical protein SORBIDRAFT_03g039520 [*Sorghum bicolor*] | 0.93 | 2376 | 2755 |
| | | NP_001044772 | Os01g0842400 [*Oryza sativa Japonica* Group] > gi\|75321217\|sp\|Q5N9X2.1\|LAC4_ORYSJ RecName: Full = Laccase-4; AltName: Full = Benzenediol:oxygen oxidoreductase 4; AltName: Full = Diphenol oxidase 4; AltName: Full = Urishiol oxidase 4; Flags: Precursor > gi\|56784239\|dbj\|BAD81734.1\| putative laccase LAC5-6 [*Oryza sativa Japonica* Group] > gi\|113534303\|dbj\|BAF06686.1\| Os01g0842400 [*Oryza sativa Japonica* Group] > gi\|215697155\|dbj\|BAG91149.1\| unnamed protein product [*Oryza sativa Japonica* Group] | 0.81 | 2377 | 2756 |
| | | EAZ14115 | hypothetical protein OsJ_04039 [*Oryza sativa Japonica* Group] | 0.81 | 2378 | |
| | | EEC71777 | hypothetical protein OsI_04389 [*Oryza sativa Indica* Group] | 0.80 | 2379 | |
| | | BAJ99773 | predicted protein [*Hordeum vulgare* subsp. *vulgare*] | 0.78 | 2380 | 2757 |
| | | XP_002458747 | hypothetical protein SORBIDRAFT_03g039530 [*Sorghum bicolor*] > gi\|241930722\|gb\|EES03867.1\| hypothetical protein | 0.78 | 2381 | 2758 |

TABLE 7-continued

Target genes of up regulated siRNA sequences associated with NUE (Table 3)

| Mir name | Mir Bind. Pos. | Hom. NCBI Accession | Annotation/organism | Identity | p.p. SEQ ID NO: | p.n. SEQ ID NO: |
|---|---|---|---|---|---|---|
| | | | SORBIDRAFT_03g039530 [*Sorghum bicolor*] | | | |
| | | AAC04576 | putative high-pI laccase [*Oryza sativa Japonica* Group] | 0.79 | 2382 | 2759 |
| | 0-17 | NP_001132686 | hypothetical protein LOC100194164 [*Zea mays*] > gi|194695090|gb|ACF81629.1| unknown [*Zea mays*] | 1.00 | 2383 | 2760 |
| | | XP_002457397 | hypothetical protein SORBIDRAFT_03g006690 [*Sorghum bicolor*] > gi|241929372|gb|EES02517.1| hypothetical protein SORBIDRAFT_03g006690 [*Sorghum bicolor*] | 0.81 | 2384 | 2761 |
| | 1000-1017 | NP_001136742 | hypothetical protein LOC100216883 [*Zea mays*] > gi|194696868|gb|ACF82518.1| unknown [*Zea mays*] > gi|195648274|gb|ACG43605.1| monoglyceride lipase [*Zea mays*] | 1.00 | 2385 | 2762 |
| | | XP_002450081 | hypothetical protein SORBIDRAFT_05g000200 [*Sorghum bicolor*] > gi|241935924|gb|EES09069.1| hypothetical protein SORBIDRAFT_05g000200 [*Sorghum bicolor*] | 0.80 | 2386 | 2763 |
| | | XP_002442631 | hypothetical protein SORBIDRAFT_08g000200 [*Sorghum bicolor*] > gi|241943324|gb|EES16469.1| hypothetical protein SORBIDRAFT_08g000200 [*Sorghum bicolor*] | 0.80 | 2387 | 2764 |
| | 296-313 | XP_002440680 | hypothetical protein SORBIDRAFT_09g005010 [*Sorghum bicolor*] > gi|241945965|gb|EES19110.1| hypothetical protein SORBIDRAFT_09g005010 [*Sorghum bicolor*] | 1.00 | 2388 | 2765 |
| | | ACN32013 | unknown [*Zea mays*] | 0.99 | 2389 | 2766 |
| | | NP_001142411 | hypothetical protein LOC100274586 [*Zea mays*] > gi|194707946|gb|ACF88057.1| unknown [*Zea mays*] > gi|194708688|gb|ACF88428.1| unknown [*Zea mays*] > gi|195620476|gb|ACG32068.1| integral membrane protein like [*Zea mays*] | 0.98 | 2390 | 2767 |
| | | NP_001054756 | Os05g0168700 [*Oryza sativa Japonica* Group] > gi|53982148|gb|AAV25244.1| putative phosphate translocator [*Oryza sativa Japonica* Group] > gi|113578307|dbj|BAF16670.1| Os05g0168700 [*Oryza sativa Japonica* Group] > gi|215686739|dbj|BAG89589.1| unnamed protein product [*Oryza sativa Japonica* Group] > gi|218196167|gb|EEC78594.1| hypothetical protein OsI_18612 [*Oryza sativa Indica* Group] > gi|222630341|gb|EEE62473.1| hypothetical protein OsJ_17270 [*Oryza sativa Japonica* Group] | 0.96 | 2391 | 2768 |

TABLE 7-continued

Target genes of up regulated siRNA sequences associated with NUE (Table 3)

| Mir name | Mir Bind. Pos. | Hom. NCBI Accession | Annotation/organism | Identity | p.p. SEQ ID NO: | p.n. SEQ ID NO: |
|---|---|---|---|---|---|---|
| | | BAB41206 | putative glucose-6-phosphate/phosphate-tranlocat or [*Oryza sativa* (*japonica* cultivar-group)] | 0.95 | 2392 | 2769 |
| | | BAK03308 | predicted protein [*Hordeum vulgare* subsp. *vulgare*] | 0.94 | 2393 | 2770 |
| | | NP_001148556 | integral membrane protein like [*Zea mays*] > gi|195620390|gb|ACG32025.1| integral membrane protein like [*Zea mays*] | 0.90 | 2394 | 2771 |
| | | NP_001042121 | Os01g0167500 [*Oryza sativa Japonica* Group] > gi|13486667|dbj|BAB39904.1| P0028E10.8 [*Oryza sativa Japonica* Group] > gi|15528768|dbj|BAB64810.1| putative glucose-6-phosphate/phosphate-tranlocator [*Oryza sativa Japonica* Group] > gi|20804811|dbj|BAB92494.1| putative glucose-6-phosphate/phosphate-tranlocator [*Oryza sativa Japonica* Group] > gi|113531652|dbj|BAF04035.1| Os01g0167500 [*Oryza sativa Japonica* Group] > gi|215767361|dbj|BAG99589.1| unnamed protein product [*Oryza sativa Japonica* Group] > gi|218187579|gb|EEC70006.1| hypothetical protein OsI_00550 [*Oryza sativa Indica* Group] > gi|222617800|gb|EEE53932.1| hypothetical protein OsJ_00515 [*Oryza sativa Japonica* Group] | 0.92 | 2395 | 2772 |
| | | NP_001142171 | hypothetical protein LOC100274338 [*Zea mays*] > gi|194707458|gb|ACF87813.1| unknown [*Zea mays*] | 0.92 | 2396 | 2773 |
| | | ACN34739 | unknown [*Zea mays*] | 0.91 | 2397 | 2774 |
| | 1638-1655 | NP_001183153 | hypothetical protein LOC100501523 [*Zea mays*] > gi|238009674|gb|ACR35872.1| unknown [*Zea mays*] | 1.00 | 2398 | 2775 |
| | 1133-1150 | NP_001146658 | hypothetical protein LOC100280258 [*Zea mays*] > gi|219888209|gb|ACL54479.1| unknown [*Zea mays*] | 1.00 | 2399 | 2776 |
| | | NP_001105875 | putative laccase [*Zea mays*] > gi|84618781|emb|CAJ30500.1| putative laccase [*Zea mays*] | 0.95 | 2400 | 2777 |
| | | ACN28855 | unknown [*Zea mays*] | 0.92 | 2401 | 2778 |
| | | XP_002458746 | hypothetical protein SORBIDRAFT_03g039520 [*Sorghum bicolor*] > gi|241930721|gb|EES03866.1| hypothetical protein SORBIDRAFT_03g039520 [*Sorghum bicolor*] | 0.91 | 2402 | 2779 |
| | | NP_001044772 | Os01g0842400 [*Oryza sativa Japonica* Group] > gi|75321217|sp|Q5N9X2.1|LAC4_ORYSJ RecName: Full = Laccase-4; AltName: Full = Benzenediol:oxygen oxidoreductase 4; AltName: Full = Diphenol oxidase 4; AltName: Full = Urishiol oxidase 4; Flags: Precursor > gi|56784239|dbj|BAD81734.1| putative laccase LAC5-6 | 0.80 | 2403 | 2780 |

TABLE 7-continued

Target genes of up regulated siRNA sequences associated with NUE
(Table 3)

| Mir name | Mir Bind. Pos. | Hom. NCBI Accession | Annotation/organism | Identity | p.p. SEQ ID NO: | p.n. SEQ ID NO: |
|---|---|---|---|---|---|---|
| | | | [Oryza sativa Japonica Group] > gi|113534303|dbj|BAF06686.1| Os01g0842400 [Oryza sativa Japonica Group] > gi|215697155|dbj|BAG91149.1| unnamed protein product [Oryza sativa Japonica Group] | | | |
| | | EAZ14115 | hypothetical protein OsJ_04039 [Oryza sativa Japonica Group] | 0.80 | 2404 | |
| | | EEC71777 | hypothetical protein OsI_04389 [Oryza sativa Indica Group] | 0.80 | 2405 | |
| | | BAJ99773 | predicted protein [Hordeum vulgare subsp. vulgare] | 0.78 | 2406 | 2781 |
| | | AAC04576 | putative high-pI laccase [Oryza sativa Japonica Group] | 0.78 | 2407 | 2782 |
| | | XP_002458747 | hypothetical protein SORBIDRAFT_03g039530 [Sorghum bicolor] > gi|241930722|gb|EES03867.1| hypothetical protein SORBIDRAFT_03g039530 [Sorghum bicolor] | 0.77 | 2408 | 2783 |
| | 574-591 | NP_001053823 | Os04g0609600 [Oryza sativa Japonica Group] > gi|122240832|sp|Q0JAA0.1|P2C44_ORYSJ RecName: Full = Probable protein phosphatase 2C 44; Short = OsPP2C44 > gi|113565394|dbj|BAF15737.1| Os04g0609600 [Oryza sativa Japonica Group] > gi|218195541|gb|EEC77968.1| hypothetical protein OsI_17335 [Oryza sativa Indica Group] > gi|222629521|gb|EEE61653.1| hypothetical protein OsJ_16105 [Oryza sativa Japonica Group] | 1.00 | 2409 | 2784 |
| | | CAE03557 | OSJNBa0085I10.2 [Oryza sativa Japonica Group] > gi|90265077|emb|CAH67750.1| H0702G05.9 [Oryza sativa Indica Group] | 0.99 | 2410 | 2785 |
| | | XP_002448500 | hypothetical protein SORBIDRAFT_06g028030 [Sorghum bicolor] > gi|241939683|gb|EES12828.1| hypothetical protein SORBIDRAFT_06g028030 [Sorghum bicolor] | 0.91 | 2411 | 2786 |
| | | NP_001148728 | protein phosphatase 2C [Zea mays] > gi|195621678|gb|ACG32669.1| protein phosphatase 2C [Zea mays] > gi|238007398|gb|ACR34734.1| unknown [Zea mays] | 0.90 | 2412 | 2787 |
| | | CAE03658 | OSJNBa0060N03.23 [Oryza sativa Japonica Group] | 0.74 | 2413 | 2788 |
| | | XP_002274944 | PREDICTED: hypothetical protein isoform 1 [Vitis vinifera] > gi|297745124|emb|CBI38963.3| unnamed protein product [Vitis vinifera] | 0.73 | 2414 | 2789 |
| | | XP_002514493 | protein phosphatase 2c, putative [Ricinus communis] > gi|223546392|gb|EEF47893.1| protein phosphatase 2c, putative [Ricinus communis] | 0.75 | 2415 | 2790 |
| | | XP_002274981 | PREDICTED: hypothetical protein isoform 2 [Vitis vinifera] | 0.70 | 2416 | 2791 |

TABLE 7-continued

Target genes of up regulated siRNA sequences associated with NUE
(Table 3)

| Mir name | Mir Bind. Pos. | Hom. NCBI Accession | Annotation/organism | Identity | p.p. SEQ ID NO: | p.n. SEQ ID NO: |
|---|---|---|---|---|---|---|
| | 1034-1051 | NP_001170532 | hypothetical protein LOC100384546 [Zea mays] > gi|238005884|gb|ACR33977.1| unknown [Zea mays] | 1.00 | 2417 | 2792 |
| | | XP_002438672 | hypothetical protein SORBIDRAFT_10g024080 [Sorghum bicolor] > gi|241916895|gb|EER90039.1| hypothetical protein SORBIDRAFT_10g024080 [Sorghum bicolor] | 0.88 | 2418 | 2793 |
| | | EAZ01659 | hypothetical protein OsI_23694 [Oryza sativa Indica Group] | 0.72 | 2419 | |
| | | EAZ37629 | hypothetical protein OsJ_21963 [Oryza sativa Japonica Group] | 0.72 | 2420 | |
| | | BAD35523 | unknown protein [Oryza sativa Japonica Group] > gi|51090952|dbj|BAD35555.1| unknown protein [Oryza sativa Japonica Group] | 0.72 | 2421 | |
| | 1728-1745 | AAW66346 | YZ1 [Zea luxurians] | 1.00 | 2422 | 2794 |
| | | AAW66344 | YZ1 [Zea mays subsp. mexicana] | 0.99 | 2423 | 2795 |
| | | AAW66348 | YZ1 [Zea mays subsp. parviglumis] | 0.99 | 2424 | 2796 |
| | | AAM22634 | YZ1 [Zea mays] | 0.99 | 2425 | 2797 |
| | | AAM21160 | YZ1 [Zea mays] | 0.98 | 2426 | 2798 |
| | | ABB29302 | YZ1 [Zea mays] > gi|78172241|gb|ABB29304.1| YZ1 [Zea mays] | 0.91 | 2427 | 2799 |
| | | NP_001043656 | Os01g0633400 [Oryza sativa Japonica Group] > gi|55296003|dbj|BAD68894.1| putative YZ1 [Oryza sativa Japonica Group] > gi|113533187|dbj|BAF05570.1| Os01g0633400 [Oryza sativa Japonica Group] > gi|215766352|dbj|BAG98580.1| unnamed protein product [Oryza sativa Japonica Group] | 0.71 | 2428 | 2800 |
| | | XP_002456014 | hypothetical protein SORBIDRAFT_03g028870 [Sorghum bicolor] > gi|241927989|gb|EES01134.1| hypothetical protein SORBIDRAFT_03g028870 [Sorghum bicolor] | 0.77 | 2429 | 2801 |
| | | EAY75077 | hypothetical protein OsI_02971 [Oryza sativa Indica Group] | 0.71 | 2430 | |
| Predicted siRNA 59659 | 689-710 | XP_002443139 | hypothetical protein SORBIDRAFT_08g011100 [Sorghum bicolor] > gi|241943832|gb|EES16977.1| hypothetical protein SORBIDRAFT_08g011100 [Sorghum bicolor] | 1.00 | 2431 | 2802 |
| | | NP_001169596 | hypothetical protein LOC100383477 [Zea mays] > gi|224030279|gb|ACN34215.1| unknown [Zea mays] | 0.94 | 2432 | 2803 |
| | | NP_001066586 | Os12g0285600 [Oryza sativa Japonica Group] > gi|77554686|gb|ABA97482.1| Oxysterol-binding protein, expressed [Oryza sativa Japonica Group] | 0.83 | 2433 | 2804 |

TABLE 7-continued

Target genes of up regulated siRNA sequences associated with NUE
(Table 3)

| Mir name | Mir Bind. Pos. | Hom. NCBI Accession | Annotation/organism | Identity | p.p. SEQ ID NO: | p.n. SEQ ID NO: |
|---|---|---|---|---|---|---|
| | | | > gi|113649093|dbj|BAF29605.1| Os12g0285600 [*Oryza sativa Japonica* Group] > gi|215697261|dbj|BAG91255.1| unnamed protein product [*Oryza sativa Japonica* Group] > gi|222616918|gb|EEE53050.1| hypothetical protein OsJ_35782 [*Oryza sativa Japonica* Group] | | | |
| | | EEC69105 | hypothetical protein OsI_38013 [*Oryza sativa Indica* Group] | 0.81 | 2434 | |
| | | CBI16832 | unnamed protein product [*Vitis vinifera*] | 0.71 | 2435 | |
| | | XP_002282089 | PREDICTED: similar to oxysterol-binding family protein [*Vitis vinifera*] | 0.72 | 2436 | 2805 |

Table 7: Provided are the target Genes of siRNAs Associated with Increased NUE (Table 3) along with their GenBank Accession numbers and sequence identifiers (SEQ ID NO:).
"bind" = binding;
"pos" = position;
"hom" = homologue;
"p.p." = polypeptide;
"p.n." = polynucleotide.

TABLE 8

Target genes of down regulated siRNA sequences associated with NUE
(Table 4)

| Mir name | Mir Bind. Pos. | Hom. NCBI Accession | Annotation/Organism | Identity | p.p. SEQ ID NO: | p.n. SEQ ID NO: |
|---|---|---|---|---|---|---|
| Predicted siRNA 59123 | 61-79 | EEE65047 | hypothetical protein OsJ_20044 [*Oryza sativa Japonica* Group] | 1.00 | 2806 | |
| | | NP_001056727 | Os06g0136600 [*Oryza sativa Japonica* Group] > gi|55296986|dbj|BAD68461.1| putative enolase [*Oryza sativa Japonica* Group] > gi|55297212|dbj|BAD68886.1| putative enolase [*Oryza sativa Japonica* Group] > gi|113594767|dbj|BAF18641.1| Os06g0136600 [*Oryza sativa Japonica* Group] > gi|218197519|gb|EEC79946.1| hypothetical protein OsI_21538 [*Oryza sativa Indica* Group] | 0.97 | 2807 | 3082 |
| | | NP_001105896 | enolase 1 [*Zea mays*] > gi|119355|sp|P26301.1|ENO1_MAIZE RecName: Full = Enolase 1; AltName: Full = 2-phospho-D-glycerate hydro-lyase 1; AltName: Full = 2-phosphoglycerate dehydratase 1 > gi|22273|emb|CAA39454.1|enolase [*Zea mays*] | 0.92 | 2808 | 3083 |
| | | ACL53816 | unknown [*Zea mays*] | 0.92 | 2809 | 3084 |
| | | ACN26258 | unknown [*Zea mays*] | 0.88 | 2810 | 3085 |
| | | ACG31732 | enolase [*Zea mays*] | 0.87 | 2811 | 3086 |
| | | XP_002322420 | predicted protein [*Populus trichocarpa*] > gi|118484871|gb|ABK94302.1| unknown [*Populus trichocarpa*] > gi|222869416|gb|EEF06547.1| predicted protein [*Populus trichocarpa*] | 0.88 | 2812 | 3087 |
| | | NP_001105371 | enolase 2 [*Zea mays*] > gi|1169528|sp|P42895.1|ENO2_MAIZE RecName: Full = Enolase 2; AltName: Full = 2-phospho-D-glycerate hydro-lyase 2; AltName: Full = 2-phosphoglycerate dehydratase 2 | 0.87 | 2813 | 3088 |

TABLE 8-continued

Target genes of down regulated siRNA sequences associated with NUE
(Table 4)

| Mir name | Mir Bind. Pos. | Hom. NCBI Accession | Annotation/Organism | Identity | p.p. SEQ ID NO: | p.n. SEQ ID NO: |
|---|---|---|---|---|---|---|
| | | | > gi|602253|gb|AAD04187.1|enolase [*Zea mays*] > gi|37222051|gb|AAQ17040.2|pollen 2-phosphoglycerate dehydrogenase 2 precursor [*Cynodon dactylon*] | | | |
| | | ACF06525 | enolase [*Elaeis guineensis*] | 0.87 | 2814 | 3089 |
| | | BAJ90134 | predicted protein [*Hordeum vulgare* subsp. *vulgare*] | 0.87 | 2815 | 3090 |
| | 45-63 | NP_001143947 | hypothetical protein LOC100276760 [*Zea mays*] > gi|195630673|gb|ACG36643.1| hypothetical protein [*Zea mays*] | 1.00 | 2816 | 3091 |
| | | ACR36446 | unknown [*Zea mays*] | 0.97 | 2817 | 3092 |
| | | NP_001143988 | hypothetical protein LOC100276806 [*Zea mays*] > gi|194707932|gb|ACF88050.1| unknown [*Zea mays*] > gi|195619872|gb|ACG31766.1| hypothetical protein [*Zea mays*] > gi|195634969|gb|ACG36953.1| hypothetical protein [*Zea mays*] | 0.79 | 2818 | 3093 |
| | | XP_002450179 | hypothetical protein SORBIDRAFT_05g001600 [*Sorghum bicolor*] > gi|241936022|gb|EES09167.1| hypothetical protein SORBIDRAFT_05g001600 [*Sorghum bicolor*] | 0.81 | 2819 | 3094 |
| | | NP_001065630 | Os11g0127700 [*Oryza sativa Japonica* Group] > gi|77548485|gb|ABA91282.1| expressed protein [*Oryza sativa Japonica* Group] > gi|113644334|dbj|BAF27475.1| Os11g0127700 [*Oryza sativa Japonica* Group] > gi|125576047|gb|EAZ17269.1| hypothetical protein OsJ_32788 [*Oryza sativa Japonica* Group] | 0.70 | 2820 | 3095 |
| | | EAY79782 | hypothetical protein OsI_34938 [*Oryza sativa Indica* Group] | 0.70 | 2821 | |
| | 2433-2451 | XP_002466271 | hypothetical protein SORBIDRAFT_01g004840 [*Sorghum bicolor*] > gi|241920125|gb|EER93269.1| hypothetical protein SORBIDRAFT_01g004840 [*Sorghum bicolor*] | 1.00 | 2822 | 3096 |
| | | NP_001145769 | hypothetical protein LOC100279276 [*Zea mays*] > gi|219884363|gb|ACL52556.1| unknown [*Zea mays*] | 0.98 | 2823 | 3097 |
| | | NP_001151633 | vacuolar protein sorting 35 [*Zea mays*] > gi|195648240|gb|ACG43588.1| vacuolar protein sorting 35 [*Zea mays*] | 0.98 | 2824 | 3098 |
| | | EAY92214 | hypothetical protein OsI_13933 [*Oryza sativa Indica* Group] | 0.95 | 2825 | |
| | | NP_001051593 | Os03g0801600 [*Oryza sativa Japonica* Group] > gi|29150373|gb|AAO72382.1| putative vacuolar protein sorting-associated protein [*Oryza sativa Japonica* Group] > gi|108711598|gb|ABF99393.1| vacuolar protein sorting-associated protein 35 family protein, putative, expressed [*Oryza sativa Japonica* Group] > gi|113550064|dbj|BAF13507.1| Os03g0801600 [*Oryza sativa Japonica* Group] > gi|125588278|gb|EAZ28942.1| hypothetical protein OsJ_12986 [*Oryza sativa Japonica* Group] > gi|215704706|dbj|BAG94334.1| unnamed protein product [*Oryza sativa Japonica* Group] | 0.95 | 2826 | 3099 |
| | | BAJ89592 | predicted protein [*Hordeum vulgare* subsp. *vulgare*] > gi|326488479|dbj|BAJ93908.1| predicted protein [*Hordeum vulgare* subsp. *vulgare*] | 0.95 | 2827 | 3100 |

TABLE 8-continued

Target genes of down regulated siRNA sequences associated with NUE
(Table 4)

| Mir name | Mir Bind. Pos. | Hom. NCBI Accession | Annotation/Organism | Identity | p.p. SEQ ID NO: | p.n. SEQ ID NO: |
|---|---|---|---|---|---|---|
| | | XP_002272227 | PREDICTED: hypothetical protein isoform 1 [*Vitis vinifera*] | 0.82 | 2828 | 3101 |
| | | XP_002272268 | PREDICTED: hypothetical protein isoform 2 [*Vitis vinifera*] | 0.81 | 2829 | 3102 |
| | | BAJ53108 | JHL20J20.15 [*Jatropha curcas*] | 0.79 | 2830 | |
| | | CBI17331 | unnamed protein product [*Vitis vinifera*] | 0.81 | 2831 | |
| | 20-38 | XP_002442446 | hypothetical protein SORBIDRAFT_08g020140 [*Sorghum bicolor*] > gi|241943139|gb|EES16284.1| hypothetical protein SORBIDRAFT_08g020140 [*Sorghum bicolor*] | 1.00 | 2832 | 3103 |
| | | ACF80272 | unknown [*Zea mays*] | 0.84 | 2833 | 3104 |
| | | NP_001141063 | hypothetical protein LOC100273144 [*Zea mays*] > gi|194702462|gb|ACF85315.1| unknown [*Zea mays*] | 0.84 | 2834 | 3105 |
| | | ACG44331 | hypothetical protein [*Zea mays*] | 0.84 | 2835 | 3106 |
| | | BAJ89075 | predicted protein [*Hordeum vulgare* subsp. *vulgare*] > gi|326533254|dbj|BAJ93599.1| predicted protein [*Hordeum vulgare* subsp. *vulgare*] | 0.70 | 2836 | 3107 |
| Predicted siRNA 57685 | 713-731 | CAI30078 | glycosyltransferase [*Sorghum bicolor*] | 1.00 | 2837 | 3108 |
| | | NP_001105165 | glycosyltransferase [*Zea mays*] > gi|56409864|emb|CAI30080.1| glycosyltransferase [*Zea mays*] | 0.96 | 2838 | 3109 |
| | | CAI30079 | glycosyltransferase [*Saccharum officinarum*] | 0.95 | 2839 | 3110 |
| | | BAJ96053 | predicted protein [*Hordeum vulgare* subsp. *vulgare*] | 0.81 | 2840 | 3111 |
| | | NP_001064930 | Os10g0492200 [*Oryza sativa Japonica* Group] > gi|10140717|gb|AAG13551.1|AC023240_24 unknown protein [*Oryza sativa Japonica* Group] > gi|31432816|gb|AAP54403.1| glycosyltransferase, putative, expressed [*Oryza sativa Japonica* Group] > gi|113639539|dbj|BAF26844.1| Os10g0492200 [*Oryza sativa Japonica* Group] > gi|215766456|dbj|BAG98764.1| unnamed protein product [*Oryza sativa Japonica* Group] > gi|222613059|gb|EEE51191.1| hypothetical protein OsJ_31998 [*Oryza sativa Japonica* Group] | 0.77 | 2841 | 3112 |
| | | EEC67226 | hypothetical protein OsI_34143 [*Oryza sativa Indica* Group] | 0.76 | 2842 | |
| | | CCA61105 | TaGT61_1 [*Triticum aestivum*] | 0.70 | 2843 | 3113 |
| | | BAK04539 | predicted protein [*Hordeum vulgare* subsp. *vulgare*] | 0.71 | 2844 | 3114 |
| | | NP_001046724 | Os02g0331200 [*Oryza sativa Japonica* Group] > gi|46390170|dbj|BAD15603.1| putative HGA1 [*Oryza sativa Japonica* Group] > gi|46390974|dbj|BAD16509.1| putative HGA1 [*Oryza sativa Japonica* Group] > gi|113536255|dbj|BAF08638.1| Os02g0331200 [*Oryza sativa Japonica* Group] > gi|215712340|dbj|BAG94467.1| unnamed protein product [*Oryza sativa Japonica* Group] > gi|215737036|dbj|BAG95965.1| unnamed protein product [*Oryza sativa Japonica* Group] | 0.71 | 2845 | 3115 |

TABLE 8-continued

Target genes of down regulated siRNA sequences associated with NUE
(Table 4)

| Mir name | Mir Bind. Pos. | Hom. NCBI Accession | Annotation/Organism | Identity | p.p. SEQ ID NO: | p.n. SEQ ID NO: |
|---|---|---|---|---|---|---|
| | 344-362 | YP_588428 | hypothetical protein ZeamMp184 [*Zea mays* subsp. *mays*] > gi|40795041|gb|AAR91085.1| hypothetical protein [*Zea mays*] > gi|93116163|gb|ABE98794.1| hypothetical protein [*Zea mays* subsp. *mays*] > gi|102579667|gb|ABF70947.1| hypothetical protein [*Zea mays* subsp. *mays*] | 1.00 | 2846 | |
| | | ABE98707 | hypothetical protein [*Zea mays* subsp. *mays*] | 0.90 | 2847 | |
| | 1201-1219 | CAI30079 | glycosyltransferase [*Saccharum officinarum*] | 1.00 | 2848 | 3116 |
| | | NP_001105165 | glycosyltransferase [*Zea mays*] > gi|56409864|emb|CAI30080.1| glycosyltransferase [*Zea mays*] | 0.96 | 2849 | 3117 |
| | | CAI30078 | glycosyltransferase [*Sorghum bicolor*] | 0.97 | 2850 | 3118 |
| | | BAJ96053 | predicted protein [*Hordeum vulgare* subsp. *vulgare*] | 0.83 | 2851 | 3119 |
| | | NP_001064930 | Os10g0492200 [*Oryza sativa Japonica* Group] > gi|10140717|gb|AAG13551.1|AC023240_24 unknown protein [*Oryza sativa Japonica* Group] > gi|31432816|gb|AAP54403.1| glycosyltransferase, putative, expressed [*Oryza sativa Japonica* Group] > gi|113639539|dbj|BAF26844.1| Os10g0492200 [*Oryza sativa Japonica* Group] > gi|215766456|dbj|BAG98764.1| unnamed protein product [*Oryza sativa Japonica* Group] > gi|222613059|gb|EEE51191.1| hypothetical protein OsJ_31998 [*Oryza sativa Japonica* Group] | 0.77 | 2852 | 3120 |
| | | EEC67226 | hypothetical protein OsI_34143 [*Oryza sativa Indica* Group] | 0.78 | 2853 | |
| | | BAK04539 | predicted protein [*Hordeum vulgare* subsp. *vulgare*] | 0.71 | 2854 | 3121 |
| | | CCA61105 | TaGT61_1 [*Triticum aestivum*] | 0.70 | 2855 | 3122 |
| | | BAD15602 | putative HGA1 [*Oryza sativa Japonica* Group] > gi|46390975|dbj|BAD16510.1| putative HGA1 [*Oryza sativa Japonica* Group] > gi|215686668|dbj|BAG88921.1| unnamed protein product [*Oryza sativa Japonica* Group] | 0.71 | 2856 | |
| | | NP_001046724 | Os02g0331200 [*Oryza sativa Japonica* Group] > gi|46390170|dbj|BAD15603.1| putative HGA1 [*Oryza sativa Japonica* Group] > gi|46390974|dbj|BAD16509.1| putative HGA1 [*Oryza sativa Japonica* Group] > gi|113536255|dbj|BAF08638.1| Os02g0331200 [*Oryza sativa Japonica* Group] > gi|215712340|dbj|BAG94467.1| unnamed protein product [*Oryza sativa Japonica* Group] > gi|215737036|dbj|BAG95965.1| unnamed protein product [*Oryza sativa Japonica* Group] | 0.71 | 2857 | 3123 |
| Predicted siRNA 59993 | Jan-19 | XP_002440494 | hypothetical protein SORBIDRAFT_09g001910 [*Sorghum bicolor*] > gi|241945779|gb|EES18924.1| hypothetical protein SORBIDRAFT_09g001910 [*Sorghum bicolor*] | 1.00 | 2858 | 3124 |
| | | ACG27529 | splicing factor, arginine/serine-rich 7 [*Zea mays*] > gi|223973611|gb|ACN30993.1| unknown [*Zea mays*] | 0.87 | 2859 | 3125 |

TABLE 8-continued

Target genes of down regulated siRNA sequences associated with NUE
(Table 4)

| Mir name | Mir Bind. Pos. | Hom. NCBI Accession | Annotation/Organism | Identity | p.p. SEQ ID NO: | p.n. SEQ ID NO: |
|---|---|---|---|---|---|---|
| | | NP_001049771 | Os03g0285900 [*Oryza sativa Japonica* Group] > gi|108707560|gb|ABF95355.1| RNA recognition motif family protein, expressed [*Oryza sativa Japonica* Group] > gi|113548242|dbj|BAF11685.1| Os03g0285900 [*Oryza sativa Japonica* Group] > gi|222624706|gb|EEE58838.1| hypothetical protein OsJ_10413 [*Oryza sativa Japonica* Group] | 0.74 | 2860 | 3126 |
| | | EEC75006 | hypothetical protein OsI_11073 [*Oryza sativa Indica* Group] | 0.70 | 2861 | |
| | | NP_001132009 | hypothetical protein LOC100193414 [*Zea mays*] > gi|194693184|gb|ACF80676.1| unknown [*Zea mays*] | 0.72 | 2862 | 3127 |
| | | AAY84873 | alternative splicing regulator [*Triticum aestivum*] | 0.72 | 2863 | 3128 |
| | 14-32 | XP_002458875 | hypothetical protein SORBIDRAFT_03g041990 [*Sorghum bicolor*] > gi|241930850|gb|EES03995.1| hypothetical protein SORBIDRAFT_03g041990 [*Sorghum bicolor*] | 1.00 | 2864 | 3129 |
| | | NP_001142991 | hypothetical protein LOC100275452 [*Zea mays*] > gi|195612624|gb|ACG28142.1| hypothetical protein [*Zea mays*] | 0.92 | 2865 | 3130 |
| | | NP_001145171 | hypothetical protein LOC100278407 [*Zea mays*] > gi|195652179|gb|ACG45557.1| hypothetical protein [*Zea mays*] | 0.91 | 2866 | 3131 |
| | | ACF83626 | unknown [*Zea mays*] | 0.92 | 2867 | 3132 |
| | | EAZ14403 | hypothetical protein OsJ_04323 [*Oryza sativa Japonica* Group] | 0.89 | 2868 | |
| | | EAY76740 | hypothetical protein OsI_04696 [*Oryza sativa Indica* Group] | 0.90 | 2869 | |
| | | BAK00430 | predicted protein [*Hordeum vulgare* subsp. *vulgare*] | 0.84 | 2870 | 3133 |
| | 2352-2370 | NP_001067313 | Os12g0623900 [*Oryza sativa Japonica* Group] > gi|77556631|gb|ABA99427.1| 5-methyltetrahydropteroyltriglutamate-homocysteine methyltransferase, putative, expressed [*Oryza sativa Japonica* Group] > gi|108862991|gb|ABG22094.1|5-methyltetrahydropteroyltriglutamate-homocysteine methyltransferase, putative, expressed [*Oryza sativa Japonica* Group] > gi|113649820|dbj|BAF30332.1| Os12g0623900 [*Oryza sativa Japonica* Group] > gi|125537469|gb|EAY83957.1| hypothetical protein OsI_39179 [*Oryza sativa Indica* Group] > gi|125580128|gb|EAZ21274.1| hypothetical protein OsJ_36926 [*Oryza sativa Japonica* Group] | 1.00 | 2871 | 3134 |
| | | ABG22095 | 5-methyltetrahydropteroyltriglutamate-homocysteine methyltransferase, putative, expressed [*Oryza sativa Japonica* Group] > gi|108862993|gb|ABG22096.1|5-methyltetrahydropteroyltriglutamate-homocysteine methyltransferase, putative, expressed [*Oryza sativa Japonica* Group] | 0.99 | 2872 | |
| | | NP_001067314 | Os12g0624000 [*Oryza sativa Japonica* Group] > gi|77556632|gb|ABA99428.1| 5-methyltetrahydropteroyltriglutamate-homocysteine methyltransferase, putative, expressed [*Oryza sativa Japonica* Group] > gi|77556633|gb|ABA99429.1|5-methyltetrahydropteroyltriglutamate-homocysteine methyltransferase, putative, expressed [*Oryza sativa Japonica* Group] | 0.98 | 2873 | 3135 |

TABLE 8-continued

Target genes of down regulated siRNA sequences associated with NUE
(Table 4)

| Mir name | Mir Bind. Pos. | Hom. NCBI Accession | Annotation/Organism | Identity | p.p. SEQ ID NO: | p.n. SEQ ID NO: |
|---|---|---|---|---|---|---|
| | | | > gi|113649821|dbj|BAF30333.1| Os12g0624000 [*Oryza sativa Japonica* Group] > gi|215695374|dbj|BAG90565.1| unnamed protein product [*Oryza sativa Japonica* Group] > gi|218187282|gb|EEC69709.1| hypothetical protein OsI_39180 [*Oryza sativa Indica* Group] > gi|222617511|gb|EEE53643.1| hypothetical protein OsJ_36927 [*Oryza sativa Japonica* Group] | | | |
| | | ACN28399 | unknown [*Zea mays*] | 0.95 | 2874 | 3136 |
| | | AAL33589 | methionine synthase [*Zea mays*] | 0.94 | 2875 | 3137 |
| | | ACL54117 | unknown [*Zea mays*] | 0.94 | 2876 | 3138 |
| | | NP_001152513 | LOC100286153 [*Zea mays*] > gi|195657041|gb|ACG47988.1|5-methyltetrahydropteroyltriglutamate--homocysteine methyltransferase [*Zea mays*] | 0.94 | 2877 | 3139 |
| | | CAJ01714 | methionine synthase 2 enzyme [*Hordeum vulgare* subsp. *vulgare*] > gi|326512178|dbj|BAJ96070.1| predicted protein [*Hordeum vulgare* subsp. *vulgare*] | 0.94 | 2878 | 3140 |
| | | BAJ89541 | predicted protein [*Hordeum vulgare* subsp. *vulgare*] | 0.94 | 2879 | 3141 |
| | | BAJ88127 | predicted protein [*Hordeum vulgare* subsp. *vulgare*] | 0.94 | 2880 | 3142 |
| | 121-139 | ACL52492 | unknown [*Zea mays*] | 1.00 | 2881 | 3143 |
| | | XP_002465926 | hypothetical protein SORBIDRAFT_01g048350 [*Sorghum bicolor*] > gi|241919780|gb|EER92924.1| hypothetical protein SORBIDRAFT_01g048350 [*Sorghum bicolor*] | 0.94 | 2882 | 3144 |
| | | NP_001048855 | Os03g0130500 [*Oryza sativa Japonica* Group] > gi|108706005|gb|ABF93800.1| EF hand family protein, expressed [*Oryza sativa Japonica* Group] > gi|113547326|dbj|BAF10769.1| Os03g0130500 [*Oryza sativa Japonica* Group] | 0.80 | 2883 | 3145 |
| | | EAZ25463 | hypothetical protein OsJ_09285 [*Oryza sativa Japonica* Group] | 0.79 | 2884 | |
| | | BAJ91192 | predicted protein [*Hordeum vulgare* subsp. *vulgare*] | 0.80 | 2885 | 3146 |
| | 49-67 | ACV84253 | LOX5 [*Sorghum bicolor*] | 1.00 | 2886 | 3147 |
| | | XP_002446554 | hypothetical protein SORBIDRAFT_06g018040 [*Sorghum bicolor*] > gi|241937737|gb|EES10882.1| hypothetical protein SORBIDRAFT_06g018040 [*Sorghum bicolor*] | 1.00 | 2887 | 3148 |
| | | ACL81190 | tasselseed 1 [*Zea mays*] | 0.95 | 2888 | 3149 |
| | | NP_001105979 | tassel seed1 [*Zea mays*] > gi|84626293|gb|ABC59691.1| lipoxygenase [*Zea mays*] | 0.95 | 2889 | |
| | | ACL81191 | tasselseed 1b [*Zea mays*] | 0.91 | 2890 | 3150 |
| | | NP_001105978 | lipoxygenase7 [*Zea mays*] > gi|84626291|gb|ABC59690.1| lipoxygenase [*Zea mays*] | 0.90 | 2891 | 3151 |
| | | Q7XV13 | RecName: Full = Putative lipoxygenase 5 > gi|38344820|emb|CAD40882.2| OSJNBa0064H22.1 [*Oryza sativa Japonica* Group] > gi|116310177|emb|CAH67189.1| OSIGBa0152K17.1 [*Oryza sativa Indica* Group] | 0.86 | 2892 | |

TABLE 8-continued

Target genes of down regulated siRNA sequences associated with NUE
(Table 4)

| Mir name | Mir Bind. Pos. | Hom. NCBI Accession | Annotation/Organism | Identity | p.p. SEQ ID NO: | p.n. SEQ ID NO: |
|---|---|---|---|---|---|---|
| | | BAJ94611 | predicted protein [*Hordeum vulgare* subsp. *vulgare*] > gi\|326511025\|dbj\|BAJ91860.1\| predicted protein [*Hordeum vulgare* subsp. *vulgare*] | 0.85 | 2893 | 3152 |
| | | CAI84707 | lipoxygenase-like protein [*Hordeum vulgare* subsp. *vulgare*] | 0.85 | 2894 | 3153 |
| | | BAK03423 | predicted protein [*Hordeum vulgare* subsp. *vulgare*] | 0.85 | 2895 | 3154 |
| | 117-135 | NP_001169757 | hypothetical protein LOC100383639 [*Zea mays*] > gi\|224031489\|gb\|ACN34820.1\| unknown [*Zea mays*] > gi\|238006168\|gb\|ACR34119.1\| unknown [*Zea mays*] | 1.00 | 2896 | 3155 |
| | | ACG49031 | ubiquinone biosynthesis methyltransferase COQ5 [*Zea mays*] | 0.99 | 2897 | 3156 |
| | | NP_001151844 | ubiquinone biosynthesis methyltransferase COQ5 [*Zea mays*] > gi\|195650199\|gb\|ACG44567.1\| ubiquinone biosynthesis methyltransferase COQ5 [*Zea mays*] | 0.93 | 2898 | 3157 |
| | | NP_001045568 | Os01g0976600 [*Oryza sativa Japonica* Group] > gi\|75320942\|sp\|Q5JNC0.1\|COQ5_ORYSJ RecName: Full = 2-methoxy-6-polyprenyl-1,4-benzoquinol methylase, mitochondrial; AltName: Full = Ubiquinone biosynthesis methyltransferase COQ5; Flags: Precursor > gi\|57899522\|dbj\|BAD87036.1\| putative ubiquinone [*Oryza sativa Japonica* Group] > gi\|113535099\|dbj\|BAF07482.1\| Os01g0976600 [*Oryza sativa Japonica* Group] > gi\|215706368\|dbj\|BAG93224.1\| unnamed protein product [*Oryza sativa Japonica* Group] > gi\|222619975\|gb\|EEE56107.1\| hypothetical protein OsJ_04965 [*Oryza sativa Japonica* Group] | 0.87 | 2899 | 3158 |
| | | EAY77437 | hypothetical protein OsI_05431 [*Oryza sativa Indica* Group] | 0.87 | 2900 | |
| | | BAJ89795 | predicted protein [*Hordeum vulgare* subsp. *vulgare*] | 0.78 | 2901 | 3159 |
| | | XP_002457083 | hypothetical protein SORBIDRAFT_03g000990 [*Sorghum bicolor*] > gi\|241929058\|gb\|EES02203.1\| hypothetical protein SORBIDRAFT_03g000990 [*Sorghum bicolor*] | 0.72 | 2902 | 3160 |
| | | XP_002324457 | predicted protein [*Populus trichocarpa*] > gi\|222865891\|gb\|EEF03022.1\| predicted protein [*Populus trichocarpa*] | 0.70 | 2903 | 3161 |
| | 656-674 | XP_002444158 | hypothetical protein SORBIDRAFT_07g010240 [*Sorghum bicolor*] > gi\|241940508\|gb\|EES13653.1\| hypothetical protein SORBIDRAFT_07g010240 [*Sorghum bicolor*] | 1.00 | 2904 | 3162 |
| | | NP_001168336 | hypothetical protein LOC100382104 [*Zea mays*] > gi\|223947549\|gb\|ACN27858.1\| unknown [*Zea mays*] | 0.85 | 2905 | 3163 |
| | | EAY97519 | hypothetical protein OsI_19447 [*Oryza sativa Indica* Group] > gi\|222631101\|gb\|EEE63233.1\| hypothetical protein OsJ_18043 [*Oryza sativa Japonica* Group] | 0.80 | 2906 | |
| | | BAJ96779 | predicted protein [*Hordeum vulgare* subsp. *vulgare*] | 0.78 | 2907 | 3164 |
| | | BAK02037 | predicted protein [*Hordeum vulgare* subsp. *vulgare*] | 0.78 | 2908 | 3165 |

TABLE 8-continued

Target genes of down regulated siRNA sequences associated with NUE
(Table 4)

| Mir name | Mir Bind. Pos. | Hom. NCBI Accession | Annotation/Organism | Identity | p.p. SEQ ID NO: | p.n. SEQ ID NO: |
|---|---|---|---|---|---|---|
| | | BAJ97459 | predicted protein [*Hordeum vulgare* subsp. *vulgare*] | 0.78 | 2909 | 3166 |
| | | AAV44115 | unknown protein [*Oryza sativa Japonica* Group] | 0.78 | 2910 | |
| | 668-686 | NP_001150708 | zinc finger, C2H2 type family protein [*Zea mays*] > gi\|195641252\|gb\|ACG40094.1\| zinc finger, C2H2 type family protein [*Zea mays*] | 1.00 | 2911 | 3167 |
| | | XP_002460014 | hypothetical protein SORBIDRAFT_02g020840 [*Sorghum bicolor*] > gi\|241923391\|gb\|EER96535.1\| hypothetical protein SORBIDRAFT_02g020840 [*Sorghum bicolor*] | 0.87 | 2912 | 3168 |
| | | NP_001150040 | zinc finger, C2H2 type family protein [*Zea mays*] > gi\|195636264\|gb\|ACG37600.1\| zinc finger, C2H2 type family protein [*Zea mays*] | 0.78 | 2913 | 3169 |
| | | BAK04496 | predicted protein [*Hordeum vulgare* subsp. *vulgare*] | 0.70 | 2914 | 3170 |
| | 524-542 | NP_001183648 | hypothetical protein LOC100502242 [*Zea mays*] > gi\|238013654\|gb\|ACR37862.1\| unknown [*Zea mays*] | 1.00 | 2915 | 3171 |
| | 660-678 | NP_001150040 | zinc finger, C2H2 type family protein [*Zea mays*] > gi\|195636264\|gb\|ACG37600.1\| zinc finger, C2H2 type family protein [*Zea mays*] | 1.00 | 2916 | 3172 |
| | | XP_002460014 | hypothetical protein SORBIDRAFT_02g020840 [*Sorghum bicolor*] > gi\|241923391\|gb\|EER96535.1\| hypothetical protein SORBIDRAFT_02g020840 [*Sorghum bicolor*] | 0.78 | 2917 | 3173 |
| | | NP_001150708 | zinc finger, C2H2 type family protein [*Zea mays*] > gi\|195641252\|gb\|ACG40094.1\| zinc finger, C2H2 type family protein [*Zea mays*] | 0.76 | 2918 | 3174 |
| | 433-451 | NP_001140599 | hypothetical protein LOC100272670 [*Zea mays*] > gi\|194700138\|gb\|ACF84153.1\| unknown [*Zea mays*] | 1.00 | 2919 | 3175 |
| | 277-295 | XP_002468199 | hypothetical protein SORBIDRAFT_01g041550 [*Sorghum bicolor*] > gi\|241922053\|gb\|EER95197.1\| hypothetical protein SORBIDRAFT_01g041550 [*Sorghum bicolor*] | 1.00 | 2920 | 3176 |
| | | NP_001140579 | hypothetical protein LOC100272649 [*Zea mays*] > gi\|194700056\|gb\|ACF84112.1\| unknown [*Zea mays*] | 0.88 | 2921 | 3177 |
| | | ACG35337 | purple acid phosphatase 1 [*Zea mays*] | 0.84 | 2922 | 3178 |
| | | NP_001049500 | Os03g0238600 [*Oryza sativa Japonica* Group] > gi\|108707073\|gb\|ABF94868.1\| purple acid phosphatase 1, putative, expressed [*Oryza sativa Japonica* Group] > gi\|113547971\|dbj\|BAF11414.1\| Os03g0238600 [*Oryza sativa Japonica* Group] > gi\|125543049\|gb\|EAY89188.1\| hypothetical protein OsI_10684 [*Oryza sativa Indica* Group] > gi\|125585546\|gb\|EAZ26210.1\| hypothetical protein OsJ_10077 [*Oryza sativa Japonica* Group] > gi\|215697901\|dbj\|BAG92094.1\| unnamed protein product [*Oryza sativa* | 0.78 | 2923 | 3179 |

TABLE 8-continued

Target genes of down regulated siRNA sequences associated with NUE
(Table 4)

| Mir name | Mir Bind. Pos. | Hom. NCBI Accession | Annotation/Organism | Identity | p.p. SEQ ID NO: | p.n. SEQ ID NO: |
|---|---|---|---|---|---|---|
| | | | *Japonica* Group]<br>> gi|215737711|dbj|BAG96841.1| unnamed protein product [*Oryza sativa Japonica* Group]<br>> gi|215740770|dbj|BAG96926.1| unnamed protein product [*Oryza sativa Japonica* Group]<br>> gi|215767489|dbj|BAG99717.1| unnamed protein product [*Oryza sativa Japonica* Group] | | | |
| | | NP_001151094 | LOC100284727 [*Zea mays*]<br>> gi|195644254|gb|ACG41595.1|purple acid phosphatase 1 [*Zea mays*] | 0.75 | 2924 | 3180 |
| | | ACF83217 | unknown [*Zea mays*] | 0.74 | 2925 | 3181 |
| | | ACN25848 | unknown [*Zea mays*] | 0.74 | 2926 | 3182 |
| | | ACL54336 | unknown [*Zea mays*] | 0.74 | 2927 | 3183 |
| | | BAI78301 | purple acid phosphatase [*Triticum aestivum*] | 0.72 | 2928 | 3184 |
| | | BAK06221 | predicted protein [*Hordeum vulgare* subsp. *vulgare*]<br>> gi|326500986|dbj|BAJ98724.1| predicted protein [*Hordeum vulgare* subsp. *vulgare*]<br>> gi|326530618|dbj|BAK01107.1| predicted protein [*Hordeum vulgare* subsp. *vulgare*] | 0.73 | 2929 | 3185 |
| | 121-139 | XP_002465926 | hypothetical protein SORBIDRAFT_01g048350 [*Sorghum bicolor*]<br>> gi|241919780|gb|EER92924.1| hypothetical protein SORBIDRAFT_01g048350 [*Sorghum bicolor*] | 1.00 | 2930 | 3186 |
| | | ACL52492 | unknown [*Zea mays*] | 0.94 | 2931 | 3187 |
| | | NP_001048855 | Os03g0130500 [*Oryza sativa Japonica* Group] > gi|108706005|gb|ABF93800.1| EF hand family protein, expressed [*Oryza sativa Japonica* Group]<br>> gi|113547326|dbj|BAF10769.1| Os03g0130500 [*Oryza sativa Japonica* Group] | 0.82 | 2932 | 3188 |
| | | EAZ25463 | hypothetical protein OsJ_09285 [*Oryza sativa Japonica* Group] | 0.80 | 2933 | |
| | | BAJ91192 | predicted protein [*Hordeum vulgare* subsp. *vulgare*] | 0.81 | 2934 | 3189 |
| | 2507-2525 | XP_002454851 | hypothetical protein SORBIDRAFT_04g038540 [*Sorghum bicolor*] > gi|241934682|gb|EES07827.1| hypothetical protein SORBIDRAFT_04g038540 [*Sorghum bicolor*] | 1.00 | 2935 | 3190 |
| | | NP_001183894 | hypothetical protein LOC100502487 [*Zea mays*] > gi|238015298|gb|ACR38684.1| unknown [*Zea mays*] | 0.90 | 2936 | 3191 |
| | | BAJ86117 | predicted protein [*Hordeum vulgare* subsp. *vulgare*]<br>> gi|326521078|dbj|BAJ96742.1| predicted protein [*Hordeum vulgare* subsp. *vulgare*] | 0.76 | 2937 | 3192 |
| | | NP_001050813 | Os03g0657100 [*Oryza sativa Japonica* Group] > gi|108710182|gb|ABF97977.1| U-box domain containing protein, expressed [*Oryza sativa Japonica* Group] > gi|113549284|dbj|BAF12727.1| Os03g0657100 [*Oryza sativa Japonica* Group] > gi|218193430|gb|EEC75857.1| hypothetical protein OsI_12864 [*Oryza sativa Indica* Group] | 0.70 | 2938 | 3193 |
| | | AAP50990 | unknown protein [*Oryza sativa Japonica* Group] | 0.70 | 2939 | 3194 |

TABLE 8-continued

Target genes of down regulated siRNA sequences associated with NUE
(Table 4)

| Mir name | Mir Bind. Pos. | Hom. NCBI Accession | Annotation/Organism | Identity | p.p. SEQ ID NO: | p.n. SEQ ID NO: |
|---|---|---|---|---|---|---|
| | 746-764 | NP_001140297 | hypothetical protein LOC100272342 [*Zea mays*] > gi\|194698890\|gb\|ACF83529.1\| unknown [*Zea mays*] | 1.00 | 2940 | 3195 |
| | 49-67 | NP_001105978 | lipoxygenase7 [*Zea mays*] > gi\|84626291\|gb\|ABC59690.1\| lipoxygenase [*Zea mays*] | 1.00 | 2941 | 3196 |
| | | ACL81191 | tasselseed 1b [*Zea mays*] | 0.98 | 2942 | 3197 |
| | | XP_002446554 | hypothetical protein SORBIDRAFT_06g018040 [*Sorghum bicolor*] > gi\|241937737\|gb\|EES10882.1\| hypothetical protein SORBIDRAFT_06g018040 [*Sorghum bicolor*] | 0.91 | 2943 | 3198 |
| | | ACV84253 | LOX5 [Sorghum *bicolor*] | 0.90 | 2944 | 3199 |
| | | NP_001105979 | tassel seed1 [*Zea mays*] > gi\|84626293\|gb\|ABC59691.1\| lipoxygenase [*Zea mays*] | 0.91 | 2945 | 3200 |
| | | ACL81190 | tasselseed 1 [*Zea mays*] | 0.90 | 2946 | 3201 |
| | | Q7XV13 | RecName: Full = Putative lipoxygenase 5 > gi\|38344820\|emb\|CAD40882.2\| OSJNBa0064H22.1 [*Oryza sativa Japonica* Group] > gi\|116310177\|emb\|CAH67189.1\| OSIGBa0152K17.1 [*Oryza sativa Indica* Group] | 0.83 | 2947 | |
| | | CAI84707 | lipoxygenase-like protein [*Hordeum vulgare* subsp. *vulgare*] | 0.82 | 2948 | 3202 |
| | | BAJ94611 | predicted protein [*Hordeum vulgare* subsp. *vulgare*] > gi\|326511025\|dbj\|BAJ91860.1\| predicted protein [*Hordeum vulgare* subsp. *vulgare*] | 0.82 | 2949 | 3203 |
| | | BAK03423 | predicted protein [*Hordeum vulgare* subsp. *vulgare*] | 0.82 | 2950 | 3204 |
| Predicted siRNA 60012 | 256-274 | XP_002461947 | hypothetical protein SORBIDRAFT_02g011010 [*Sorghum bicolor*] > gi\|241925324\|gb\|EER98468.1\| hypothetical protein SORBIDRAFT_02g011010 [*Sorghum bicolor*] | 1.00 | 2951 | 3205 |
| | 948-966 | XP_002457764 | hypothetical protein SORBIDRAFT_03g013140 [*Sorghum bicolor*] > gi\|241929739\|gb\|EES02884.1\| hypothetical protein SORBIDRAFT_03g013140 [*Sorghum bicolor*] | 1.00 | 2952 | 3206 |
| | | ACF87582 | unknown [*Zea mays*] | 0.93 | 2953 | 3207 |
| | | NP_001105753 | Pti1 protein [*Zea mays*] > gi\|49188602\|gb\|AAT57904.1\|putative PTI1-like kinase [*Zea mays*] | 0.92 | 2954 | 3208 |
| | | AAT57905 | putative PTI1-like kinase [*Zea mays*] | 0.92 | 2955 | 3209 |
| | | AAT57906 | putative PTI1-like kinase [*Zea mays*] | 0.93 | 2956 | 3210 |
| | | EAY73772 | hypothetical protein OsI_01646 [*Oryza sativa Indica* Group] | 0.81 | 2957 | |
| | | NP_001042895 | Os01g0323100 [*Oryza sativa Japonica* Group] > gi\|12328582\|dbj\|BAB21241.1\| putative Pto kinase interactor 1 [*Oryza sativa Japonica* Group] > gi\|29027802\|dbj\|BAC65877.1\| putative Pto kinase interactor 1 [*Oryza sativa Japonica* Group] > gi\|113532426\|dbj\|BAF04809.1\| Os01g0323100 [*Oryza sativa Japonica* Group] > gi\|125570160\|gb\|EAZ11675.1\| hypothetical protein OsJ_01536 [*Oryza sativa Japonica* Group] > gi\|215694472\|dbj\|BAG89427.1\| unnamed protein product [*Oryza sativa Japonica* Group] | 0.81 | 2958 | 3211 |

TABLE 8-continued

Target genes of down regulated siRNA sequences associated with NUE
(Table 4)

| Mir name | Mir Bind. Pos. | Hom. NCBI Accession | Annotation/Organism | Identity | p.p. SEQ ID NO: | p.n. SEQ ID NO: |
|---|---|---|---|---|---|---|
| | 1207-1225 | XP_002451738 | hypothetical protein SORBIDRAFT_04g006950 [*Sorghum bicolor*] > gi|241931569|gb|EES04714.1| hypothetical protein SORBIDRAFT_04g006950 [*Sorghum bicolor*] | 1.00 | 2959 | 3212 |
| | | ACG38564 | cerebral protein 1 [*Zea mays*] > gi|238015424|gb|ACR38747.1| unknown [*Zea mays*] | 0.96 | 2960 | 3213 |
| | | NP_001047303 | Os02g0593900 [*Oryza sativa Japonica* Group] > gi|113536834|dbj|BAF09217.1| Os02g0593900 [*Oryza sativa Japonica* Group] > gi|125540112|gb|EAY86507.1| hypothetical protein OsI_07887 [*Oryza sativa Indica* Group] > gi|125582717|gb|EAZ23648.1| hypothetical protein OsJ_07349 [*Oryza sativa Japonica* Group] | 0.70 | 2961 | 3214 |
| | 67-85 | XP_002449762 | hypothetical protein SORBIDRAFT_05g022780 [*Sorghum bicolor*] > gi|241935605|gb|EES08750.1| hypothetical protein SORBIDRAFT_05g022780 [*Sorghum bicolor*] | 1.00 | 2962 | 3215 |
| | | ABA94447 | ETO1-like protein 1, putative, expressed [*Oryza sativa Japonica* Group] > gi|125577639|gb|EAZ18861.1| hypothetical protein OsJ_34400 [*Oryza sativa Japonica* Group] | 0.93 | 2963 | 3216 |
| | | EAY81449 | hypothetical protein OsI_36620 [*Oryza sativa Indica* Group] | 0.93 | 2964 | |
| | | NP_001068166 | Os11g0585900 [*Oryza sativa Japonica* Group] > gi|113645388|dbj|BAF28529.1| Os11g0585900 [*Oryza sativa Japonica* Group] | 0.90 | 2965 | 3217 |
| | | NP_001146335 | hypothetical protein LOC100279911 [*Zea mays*] > gi|219886675|gb|ACL53712.1| unknown [*Zea mays*] | 0.91 | 2966 | 3218 |
| | | CBI25039 | unnamed protein product [*Vitis vinifera*] | 0.73 | 2967 | |
| | | XP_002280519 | PREDICTED: hypothetical protein [*Vitis vinifera*] | 0.72 | 2968 | 3219 |
| | | AAZ08351 | ethylene overproducer-like 1 [*Solanum lycopersicum*] | 0.71 | 2969 | 3220 |
| | | ABB46489 | ethylene-overproducer1-like protein [*Solanum lycopersicum*] | 0.71 | 2970 | 3221 |
| Predicted siRNA 55081 | 358-381 | XP_002466013 | hypothetical protein SORBIDRAFT_01g050070 [*Sorghum bicolor*] > gi|241919867|gb|EER93011.1| hypothetical protein SORBIDRAFT_01g050070 [*Sorghum bicolor*] | 1.00 | 2971 | 3222 |
| | | NP_001132709 | hypothetical protein LOC100194192 [*Zea mays*] > gi|194695168|gb|ACF81668.1| unknown [*Zea mays*] | 0.77 | 2972 | 3223 |
| | | NP_001148998 | xyloglucan endotransglucosylase/hydrolase protein 32 [*Zea mays*] > gi|195623856|gb|ACG33758.1| xyloglucan endotransglucosylase/hydrolase protein 32 precursor [*Zea mays*] | 0.76 | 2973 | 3224 |
| Predicted siRNA 59032 | 364-382 | XP_002439498 | hypothetical protein SORBIDRAFT_09g008130 [*Sorghum bicolor*] > gi|241944783|gb|EES17928.1| hypothetical protein SORBIDRAFT_09g008130 [*Sorghum bicolor*] | 1.00 | 2974 | 3225 |
| | | NP_001141460 | hypothetical protein LOC100273570 [*Zea mays*] > gi|194704658|gb|ACF86413.1| unknown [*Zea mays*] > gi|195620084|gb|ACG31872.1|triose | 0.88 | 2975 | 3226 |

TABLE 8-continued

Target genes of down regulated siRNA sequences associated with NUE
(Table 4)

| Mir name | Mir Bind. Pos. | Hom. NCBI Accession | Annotation/Organism | Identity | p.p. SEQ ID NO: | p.n. SEQ ID NO: |
|---|---|---|---|---|---|---|
| | | | phosphate/phosphate translocator [*Zea mays*] > gi|195625418|gb|ACG34539.1| triose phosphate/phosphate translocator [*Zea mays*] | | | |
| | | ACG32515 | triose phosphate/phosphate translocator [*Zea mays*] | 0.88 | 2976 | 3227 |
| | | NP_001055001 | Os05g0241200 [*Oryza sativa Japonica* Group] > gi|53980843|gb|AAV24764.1| putative phosphate translocator [*Oryza sativa Japonica* Group] > gi|113578552|dbj|BAF16915.1| Os05g0241200 [*Oryza sativa Japonica* Group] > gi|125551487|gb|EAY97196.1| hypothetical protein OsI_19118 [*Oryza sativa Indica* Group] > gi|215765430|dbj|BAG87127.1| unnamed protein product [*Oryza sativa Japonica* Group] | 0.75 | 2977 | 3228 |
| | | BAJ94007 | predicted protein [*Hordeum vulgare* subsp. *vulgare*] | 0.73 | 2978 | 3229 |
| | 225-243 | NP_001168807 | hypothetical protein LOC100382608 [*Zea mays*] > gi|223973113|gb|ACN30744.1| unknown [*Zea mays*] | 1.00 | 2979 | 3230 |
| Predicted siRNA 58721 | 227-245 | XP_002447337 | hypothetical protein SORBIDRAFT_06g033160 [*Sorghum bicolor*] > gi|241938520|gb|EES11665.1| hypothetical protein SORBIDRAFT_06g033160 [*Sorghum bicolor*] | 1.00 | 2980 | 3231 |
| | | NP_001142056 | hypothetical protein LOC100274212 [*Zea mays*] > gi|194706940|gb|ACF87554.1| unknown [*Zea mays*] > gi|223947485|gb|ACN27826.1| unknown [*Zea mays*] | 0.96 | 2981 | 3232 |
| | | ACG45259 | hypothetical protein [*Zea mays*] | 0.96 | 2982 | 3233 |
| | | EEC78262 | hypothetical protein OsI_17948 [*Oryza sativa Indica* Group] | 0.86 | 2983 | |
| | | EEE61915 | hypothetical protein OsJ_16648 [*Oryza sativa Japonica* Group] | 0.86 | 2984 | |
| | | BAJ96591 | predicted protein [*Hordeum vulgare* subsp. *vulgare*] | 0.86 | 2985 | 3234 |
| | | CAJ86266 | H0901F07.3 [*Oryza sativa Indica* Group] | 0.76 | 2986 | 3235 |
| | 614-632 | NP_001183362 | hypothetical protein LOC100501771 [*Zea mays*] > gi|238011008|gb|ACR36539.1| unknown [*Zea mays*] | 1.00 | 2987 | 3236 |
| | | XP_002453714 | hypothetical protein SORBIDRAFT_04g011130 [*Sorghum bicolor*] > gi|241933545|gb|EES06690.1| hypothetical protein SORBIDRAFT_04g011130 [*Sorghum bicolor*] | 0.92 | 2988 | 3237 |
| | | BAJ91736 | predicted protein [*Hordeum vulgare* subsp. *vulgare*] | 0.80 | 2989 | 3238 |
| | | NP_001043916 | Os01g0687800 [*Oryza sativa Japonica* Group] > gi|18844891|dbj|BAB85360.1| FAD binding domain containing protein-like [*Oryza sativa Japonica* Group] > gi|113533447|dbj|BAF05830.1| Os01g0687800 [*Oryza sativa Japonica* Group] | 0.76 | 2990 | 3239 |
| | | EAY75418 | hypothetical protein OsI_03321 [*Oryza sativa Indica* Group] | 0.75 | 2991 | |
| | 361-379 | XP_002441149 | hypothetical protein SORBIDRAFT_09g021260 [*Sorghum bicolor*] > gi|241946434|gb|EES19579.1| hypothetical protein SORBIDRAFT_09g021260 [*Sorghum bicolor*] | 1.00 | 2992 | 3240 |

TABLE 8-continued

Target genes of down regulated siRNA sequences associated with NUE
(Table 4)

| Mir name | Mir Bind. Pos. | Hom. NCBI Accession | Annotation/Organism | Identity | p.p. SEQ ID NO: | p.n. SEQ ID NO: |
|---|---|---|---|---|---|---|
| | | NP_001152458 | phosphoribosylanthranilate transferase [*Zea mays*] > gi|195656517|gb|ACG47726.1| phosphoribosylanthranilate transferase [*Zea mays*] | 0.97 | 2993 | 3241 |
| | | BAK04138 | predicted protein [*Hordeum vulgare* subsp. *vulgare*] | 0.89 | 2994 | 3242 |
| | | EEC79273 | hypothetical protein OsI_20060 [*Oryza sativa Indica* Group] | 0.90 | 2995 | |
| | | NP_001055620 | Os05g0429700 [*Oryza sativa Japonica* Group] > gi|55733914|gb|AAV59421.1| putative anthranilate phosphoribosyltransferase [*Oryza sativa Japonica* Group] > gi|113579171|dbj|BAF17534.1| Os05g0429700 [*Oryza sativa Japonica* Group] > gi|215737213|dbj|BAG96142.1| unnamed protein product [*Oryza sativa Japonica* Group] > gi|222631675|gb|EEE63807.1| hypothetical protein OsJ_18631 [*Oryza sativa Japonica* Group] | 0.90 | 2996 | 3243 |
| | 149-167 | XP_002454239 | hypothetical protein SORBIDRAFT_04g027330 [*Sorghum bicolor*] > gi|241934070|gb|EES07215.1| hypothetical protein SORBIDRAFT_04g027330 [*Sorghum bicolor*] | 1.00 | 2997 | 3244 |
| | | ACG32582 | heat shock 22 kDa protein [*Zea mays*] | 0.88 | 2998 | 3245 |
| | | NP_001105607 | low molecular weight heat shock protein precursor [*Zea mays*] > gi|3015621|gb|AAC12279.1|low molecular weight heat shock protein precursor [*Zea mays*] > gi|54299342|gb|AAV32521.1| mitochondrial small heat shock protein 22 [*Zea mays*] > gi|195622718|gb|ACG33189.1|heat shock 22 kDa protein [*Zea mays*] | 0.88 | 2999 | 3246 |
| | | ACF84470 | unknown [*Zea mays*] | 0.87 | 3000 | 3247 |
| | | NP_01048175 | Os02g0758000 [*Oryza sativa Japonica* Group] > gi|75294195|sp|Q6Z7V2.1|HS24M_ORYSJ RecName: Full = 24.1 kDa heat shock protein, mitochondrial; Short = OsHsp24.1; Flags: Precursor > gi|46805691|dbj|BAD17092.1| putative low molecular weight heat shock protein [*Oryza sativa Japonica* Group] > gi|113537706|dbj|BAF10089.1| Os02g0758000 [*Oryza sativa Japonica* Group] > gi|125541201|gb|EAY87596.1| hypothetical protein OsI_09007 [*Oryza sativa Indica* Group] > gi|125583753|gb|EAZ24684.1| hypothetical protein OsJ_08454 [*Oryza sativa Japonica* Group] > gi|215693891|dbj|BAG89090.1| unnamed protein product [*Oryza sativa Japonica* Group] > gi|215704321|dbj|BAG93755.1| unnamed protein product [*Oryza sativa Japonica* Group] > gi|215740605|dbj|BAG97261.1| unnamed protein product [*Oryza sativa Japonica* Group] > gi|313575793|gb|ADR66976.1|22 kDa heat shock protein [*Oryza sativa* | 0.80 | 3001 | 3248 |

TABLE 8-continued

Target genes of down regulated siRNA sequences associated with NUE
(Table 4)

| Mir name | Mir Bind. Pos. | Hom. NCBI Accession | Annotation/Organism | Identity | p.p. SEQ ID NO: | p.n. SEQ ID NO: |
|---|---|---|---|---|---|---|
| | 270-288 | XP_02444207 | *Japonica* Group]<br>> gi\|332691639\|gb\|AEE90022.1\|<br>mitochondrial small heat shock protein<br>[*Oryza sativa Japonica* Group]<br>hypothetical protein<br>SORBIDRAFT_07g014990 [*Sorghum bicolor*] > gi\|241940557\|gb\|EES13702.1\|<br>hypothetical protein<br>SORBIDRAFT_07g014990 [*Sorghum bicolor*] | 1.00 | 3002 | 3249 |
| | | NP_001145845 | hypothetical protein LOC100279356 [*Zea mays*] > gi\|219884681\|gb\|ACL52715.1\|<br>unknown [*Zea mays*] | 0.91 | 3003 | 3250 |
| | | NP_001061645 | Os08g0365900 [*Oryza sativa Japonica* Group] > gi\|38636850\|dbj\|BAD03090.1\|<br>putative nucleolar protein [*Oryza sativa Japonica* Group]<br>> gi\|113623614\|dbj\|BAF23559.1\|<br>Os08g0365900 [*Oryza sativa Japonica* Group]<br>> gi\|215717005\|dbj\|BAG95368.1\|<br>unnamed protein product [*Oryza sativa Japonica* Group]<br>> gi\|222640447\|gb\|EEE68579.1\|<br>hypothetical protein OsJ_27075 [*Oryza sativa Japonica* Group] | 0.77 | 3004 | 3251 |
| 40959 | 436-454 | NP_001147431 | Redundant master homologue-skipping aconitase2 [*Zea mays*]<br>> gi\|195611330\|gb\|ACG27495.1\|<br>aconitate hydratase, cytoplasmic [*Zea mays*] > gi\|223948253\|gb\|ACN28210.1\|<br>unknown [*Zea mays*] | 1.00 | 3005 | 3252 |
| | | XP_002445174 | hypothetical protein<br>SORBIDRAFT_07g005390 [*Sorghum bicolor*] > gi\|241941524\|gb\|EES14669.1\|<br>hypothetical protein<br>SORBIDRAFT_07g005390 [*Sorghum bicolor*] | 0.78 | 3006 | 3253 |
| | | Q6YZX6 | RecName: Full = Putative aconitate hydratase, cytoplasmic; Short = Aconitase; AltName: Full = Citrate hydro-lyase<br>> gi\|40253814\|dbj\|BAD05751.1\|<br>putative Aconitate hydratase [*Oryza sativa Japonica* Group] | 0.77 | 3007 | |
| | | BAJ85661 | predicted protein [*Hordeum vulgare* subsp. *vulgare*] | 0.76 | 3008 | 3254 |
| | | CBE71057 | aconitate hydratase 3 [*Citrus clementina*] | 0.75 | 3009 | 3255 |
| | | ADZ57218 | aconitase protein [*Litchi chinensis*] | 0.74 | 3010 | 3256 |
| | | XP_002524184 | aconitase, putative [*Ricinus communis*]<br>> gi\|223536553\|gb\|EEF38199.1\|<br>aconitase, putative [*Ricinus communis*] | 0.74 | 3011 | 3257 |
| | | XP_002278138 | PREDICTED: hypothetical protein [*Vitis vinifera*]<br>> gi\|297737441\|emb\|CBI26642.3\|<br>unnamed protein product [*Vitis vinifera*] | 0.74 | 3012 | 3258 |
| | | P49608 | RecName: Full = Aconitate hydratase, cytoplasmic; Short = Aconitase; AltName: Full = Citrate hydro-lyase<br>> gi\|7437043\|pir\|\|T10101 aconitate hydratase (EC 4.2.1.3) - cucurbit<br>> gi\|868003\|dbj\|BAA06108.1\|aconitase [*Cucurbita* cv. Kurokawa Amakuri] | 0.75 | 3013 | |
| | | CBE71058 | aconitate hydratase 2 [*Citrus clementina*] | 0.74 | 3014 | 3259 |
| | 529-547 | XP_002453714 | hypothetical protein<br>SORBIDRAFT_04g011130 [*Sorghum bicolor*] > gi\|241933545\|gb\|EES06690.1\|<br>hypothetical protein<br>SORBIDRAFT_04g011130 [*Sorghum bicolor*] | 1.00 | 3015 | 3260 |
| | | NP_001183362 | hypothetical protein LOC100501771 [*Zea mays*] > gi\|238011008\|gb\|ACR36539.1\|<br>unknown [*Zea mays*] | 0.85 | 3016 | 3261 |

TABLE 8-continued

Target genes of down regulated siRNA sequences associated with NUE
(Table 4)

| Mir name | Mir Bind. Pos. | Hom. NCBI Accession | Annotation/Organism | Identity | p.p. SEQ ID NO: | p.n. SEQ ID NO: |
|---|---|---|---|---|---|---|
| | | BAJ91736 | predicted protein [*Hordeum vulgare* subsp. *vulgare*] | 0.80 | 3017 | 3262 |
| | | NP_001043916 | Os01g0687800 [*Oryza sativa Japonica* Group] > gi\|18844891\|dbj\|BAB85360.1\| FAD binding domain containing protein-like [*Oryza sativa Japonica* Group] > gi\|113533447\|dbj\|BAF05830.1\| Os01g0687800 [*Oryza sativa Japonica* Group] | 0.76 | 3018 | 3263 |
| | | EAY75418 | hypothetical protein OsI_03321 [*Oryza sativa Indica* Group] | 0.75 | 3019 | |
| Predicted siRNA 58877 | 254-273 | XP_002489117 | hypothetical protein SORBIDRAFT_0057s002150 [*Sorghum bicolor*] > gi\|241947368\|gb\|EES20513.1\| hypothetical protein SORBIDRAFT_0057s002150 [*Sorghum bicolor*] | 1.00 | 3020 | 3264 |
| | | XP_002488963 | hypothetical protein SORBIDRAFT_1150s002010 [*Sorghum bicolor*] > gi\|241946997\|gb\|EES20142.1\| hypothetical protein SORBIDRAFT_1150s002010 [*Sorghum bicolor*] | 0.94 | 3021 | 3265 |
| | | XP_002464695 | hypothetical protein SORBIDRAFT_01g023641 [*Sorghum bicolor*] > gi\|241918549\|gb\|EER91693.1\| hypothetical protein SORBIDRAFT_01g023641 [*Sorghum bicolor*] | 0.84 | 3022 | 3266 |
| | | XP_002450731 | hypothetical protein SORBIDRAFT_05g016471 [*Sorghum bicolor*] > gi\|241936574\|gb\|EES09719.1\| hypothetical protein SORBIDRAFT_05g016471 [*Sorghum bicolor*] | 0.80 | 3023 | 3267 |
| | | XP_002450732 | hypothetical protein SORBIDRAFT_05g016475 [*Sorghum bicolor*] > gi\|241936575\|gb\|EES09720.1\| hypothetical protein SORBIDRAFT_05g016475 [*Sorghum bicolor*] | 0.79 | 3024 | 3268 |
| Predicted siRNA 57179 | 632-655 | XP_002447941 | hypothetical protein SORBIDRAFT_06g018520 [*Sorghum bicolor*] > gi\|241939124\|gb\|EES12269.1\| hypothetical protein SORBIDRAFT_06g018520 [*Sorghum bicolor*] | 1.00 | 3025 | 3269 |
| | | NP_001159183 | hypothetical protein LOC100304268 [*Zea mays*] > gi\|195627604\|gb\|ACG35632.1\| ubiquitin carboxyl-terminal hydrolase 4 [*Zea mays*] > gi\|223942511\|gb\|ACN25339.1\| unknown [*Zea mays*] | 0.99 | 3026 | 3270 |
| | | NP_001146737 | hypothetical protein LOC100280339 [*Zea mays*] > gi\|219888545\|gb\|ACL54647.1\| unknown [*Zea mays*] > gi\|223974199\|gb\|ACN31287.1\| unknown [*Zea mays*] | 0.99 | 3027 | 3271 |
| | | ACG34260 | ubiquitin carboxyl-terminal hydrolase 4 [*Zea mays*] | 0.99 | 3028 | 3272 |
| | | NP_001052951 | Os04g0452400 [*Oryza sativa Japonica* Group] > gi\|113564522\|dbj\|BAF14865.1\| Os04g0452400 [*Oryza sativa Japonica* Group] > gi\|215695550\|dbj\|BAG90741.1\| unnamed protein product [*Oryza sativa Japonica* Group] | 0.97 | 3029 | 3273 |
| | | BAK02826 | predicted protein [*Hordeum vulgare* subsp. *vulgare*] | 0.96 | 3030 | 3274 |

TABLE 8-continued

Target genes of down regulated siRNA sequences associated with NUE
(Table 4)

| Mir name | Mir Bind. Pos. | Hom. NCBI Accession | Annotation/Organism | Identity | p.p. SEQ ID NO: | p.n. SEQ ID NO: |
|---|---|---|---|---|---|---|
| | | CAD40853 | OSJNBa0086B14.26 [Oryza sativa Japonica Group] > gi|116310175|emb|CAH67188.1| H0815C01.9 [Oryza sativa Indica Group] > gi|125548525|gb|EAY94347.1| hypothetical protein OsI_16114 [Oryza sativa Indica Group] > gi|125590577|gb|EAZ30927.1| hypothetical protein OsJ_15007 [Oryza sativa Japonica Group] | 0.97 | 3031 | |
| | | XP_002270407 | PREDICTED: hypothetical protein [Vitis vinifera] | 0.87 | 3032 | 3275 |
| | | XP_002531269 | Ubiquitin carboxyl-terminal hydrolase, putative [Ricinus communis] > gi|223529154|gb|EEF31133.1| Ubiquitin carboxyl-terminal hydrolase, putative [Ricinus communis] | 0.88 | 3033 | 3276 |
| | | CAN67091 | hypothetical protein VITISV_006756 [Vitis vinifera] | 0.86 | 3034 | |
| Predicted siRNA 55393 | 490-510 | XP_002446760 | hypothetical protein SORBIDRAFT_06g021990 [Sorghum bicolor] > gi|241937943|gb|EES11088.1| hypothetical protein SORBIDRAFT_06g021990 [Sorghum bicolor] | 1.00 | 3035 | 3277 |
| | | ACG37655 | anther-specific proline-rich protein APG [Zea mays] | 0.86 | 3036 | 3278 |
| | | ACG35356 | anther-specific proline-rich protein APG [Zea mays] | 0.86 | 3037 | 3279 |
| | | NP_001132075 | hypothetical protein LOC100193489 [Zea mays] > gi|194693356|gb|ACF80762.1| unknown [Zea mays] | 0.86 | 3038 | 3280 |
| | | NP_001141295 | hypothetical protein LOC100273386 [Zea mays] > gi|194703842|gb|ACF86005.1| unknown [Zea mays] | 0.87 | 3039 | 3281 |
| | | NP_001053264 | Os04g0507700 [Oryza sativa Japonica Group] > gi|32489520|emb|CAE04723.1| OSJNBa0043L24.11 [Oryza sativa Japonica Group] > gi|38567850|emb|CAE05693.2| OSJNBb0002J11.20 [Oryza sativa Japonica Group] > gi|113564835|dbj|BAF15178.1| Os04g0507700 [Oryza sativa Japonica Group] > gi|116310323|emb|CAH67339.1| OSIGBa0157A06.8 [Oryza sativa Indica Group] > gi|116310765|emb|CAH67558.1| OSIGBa0101P20.1 [Oryza sativa Indica Group] > gi|125548968|gb|EAY94790.1| hypothetical protein OsI_16569 [Oryza sativa Indica Group] > gi|125590941|gb|EAZ31291.1| hypothetical protein OsJ_15397 [Oryza sativa Japonica Group] | 0.75 | 3040 | 3282 |
| | | BAJ85303 | predicted protein [Hordeum vulgare subsp. vulgare] | 0.73 | 3041 | 3283 |
| | 66-86 | NP_001104926 | MADS2 [Zea mays] > gi|296611976|gb|AAO85643.1|MADS-box transcription factor MADS2 [Zea mays] | 1.00 | 3042 | 3284 |
| | | AAG09919 | MADS box protein 2 [Zea mays] | 1.00 | 3043 | 3285 |
| | | NP_001047230 | Os02g0579600 [Oryza sativa Japonica Group] > gi|91207149|sp|Q6EP49.2|MAD27_ORYSJ RecName: Full = MADS-box transcription factor 27; AltName: Full = OsMADS27; AltName: Full = RMADS218 > gi|30313677|gb|AAO47706.1| | 0.86 | 3044 | 3286 |

TABLE 8-continued

Target genes of down regulated siRNA sequences associated with NUE
(Table 4)

| Mir name | Mir Bind. Pos. | Hom. NCBI Accession | Annotation/Organism | Identity | p.p. SEQ ID NO: | p.n. SEQ ID NO: |
|---|---|---|---|---|---|---|
| | | | transcription factor MADS27 [*Oryza sativa Japonica* Group] > gi|113536761|dbj|BAF09144.1| Os02g0579600 [*Oryza sativa Japonica* Group] | | | |
| | | EEC73475 | hypothetical protein OsI_07801 [*Oryza sativa Indica* Group] > gi|222623119|gb|EEE57251.1| hypothetical protein OsJ_07263 [*Oryza sativa Japonica* Group] | 0.84 | 3045 | |
| | | BAK01931 | predicted protein [*Hordeum vulgare* subsp. *vulgare*] | 0.79 | 3046 | 3287 |
| | | CAM59078 | MIKC-type MADS-box transcription factor WM30 [*Triticum aestivum*] | 0.79 | 3047 | 3288 |
| | | CAD40988 | OSJNBa0072F16.13 [*Oryza sativa Japonica* Group] | 0.77 | 3048 | |
| | | BAD29571 | putative transcription factor MADS27 [*Oryza sativa Japonica* Group] | 0.76 | 3049 | |
| | 571-591 | NP_001047230 | Os02g0579600 [*Oryza sativa Japonica* Group] > gi|91207149|sp|Q6EP49.2|MAD27_ORYSJ RecName: Full = MADS-box transcription factor 27; AltName: Full = OsMADS27; AltName: Full = RMADS218 > gi|30313677|gb|AAO47706.1| transcription factor MADS27 [*Oryza sativa Japonica* Group] > gi|113536761|dbj|BAF09144.1| Os02g0579600 [*Oryza sativa Japonica* Group] | 1.00 | 3050 | 3289 |
| | | EEC73475 | hypothetical protein OsI_07801 [*Oryza sativa Indica* Group] > gi|222623119|gb|EEE57251.1| hypothetical protein OsJ_07263 [*Oryza sativa Japonica* Group] | 0.98 | 3051 | |
| | | BAD29571 | putative transcription factor MADS27 [*Oryza sativa Japonica* Group] | 0.90 | 3052 | |
| | | AAG09919 | MADS box protein 2 [*Zea mays*] | 0.86 | 3053 | 3290 |
| | | NP_001104926 | MADS2 [*Zea mays*] > gi|29611976|gb|AAO85643.1|MADS-box transcription factor MADS2 [*Zea mays*] | 0.86 | 3054 | 3291 |
| | | BAK01931 | predicted protein [*Hordeum vulgare* subsp. *vulgare*] | 0.82 | 3055 | 3292 |
| | | CAD40988 | OSJNBa0072F16.13 [*Oryza sativa Japonica* Group] | 0.80 | 3056 | |
| | | CAM59078 | MIKC-type MADS-box transcription factor WM30 [*Triticum aestivum*] | 0.81 | 3057 | 3293 |
| | 481-501 | NP_001132075 | hypothetical protein LOC100193489 [*Zea mays*] > gi|194693356|gb|ACF80762.1| unknown [*Zea mays*] | 1.00 | 3058 | 3294 |
| | | ACG35356 | anther-specific proline-rich protein APG [*Zea mays*] | 1.00 | 3059 | 3295 |
| | | ACG37655 | anther-specific proline-rich protein APG [*Zea mays*] | 0.92 | 3060 | 3296 |
| | | NP_001141295 | hypothetical protein LOC100273386 [*Zea mays*] > gi|194703842|gb|ACF86005.1| unknown [*Zea mays*] | 0.92 | 3061 | 3297 |
| | | XP_002446760 | hypothetical protein SORBIDRAFT_06g021990 [*Sorghum bicolor*] > gi|241937943|gb|EES11088.1| hypothetical protein SORBIDRAFT_06g021990 [*Sorghum bicolor*] | 0.91 | 3062 | 3298 |
| | | NP_001053264 | Os04g0507700 [*Oryza sativa Japonica* Group] > gi|32489520|emb|CAE04723.1| OSJNBa0043L24.11 [*Oryza sativa Japonica* Group] > gi|38567850|emb|CAE05693.2| | 0.81 | 3063 | 3299 |

TABLE 8-continued

Target genes of down regulated siRNA sequences associated with NUE
(Table 4)

| Mir name | Mir Bind. Pos. | Hom. NCBI Accession | Annotation/Organism | Identity | p.p. SEQ ID NO: | p.n. SEQ ID NO: |
|---|---|---|---|---|---|---|
| | | | OSJNBb0002J11.20 [*Oryza sativa Japonica* Group] > gi|113564835|dbj|BAF15178.1| Os04g0507700 [*Oryza sativa Japonica* Group] > gi|116310323|emb|CAH67339.1| OSIGBa0157A06.8 [*Oryza sativa Indica* Group] > gi|116310765|emb|CAH67558.1| OSIGBa0101P20.1 [*Oryza sativa Indica* Group] > gi|125548968|gb|EAY94790.1| hypothetical protein OsI_16569 [*Oryza sativa Indica* Group] > gi|125590941|gb|EAZ31291.1| hypothetical protein OsJ_15397 [*Oryza sativa Japonica* Group] | | | |
| | | BAJ85303 | predicted protein [*Hordeum vulgare* subsp. *vulgare*] | 0.78 | 3064 | 3300 |
| Predicted siRNA 59235 | 55-75 | NP_001167787 | hypothetical protein LOC100381480 [*Zea mays*] > gi|223943955|gb|ACN26061.1| unknown [*Zea mays*] | 1.00 | 3065 | 3301 |
| | | NP_001143285 | hypothetical protein LOC100275819 [*Zea mays*] > gi|195617040|gb|ACG30350.1| hypothetical protein [*Zea mays*] | 0.97 | 3066 | 3302 |
| Predicted siRNA 60123 | 512-531 | NP_001149853 | LOC100283481 [*Zea mays*] > gi|195635075|gb|ACG37006.1|pollen-specific protein like [*Zea mays*] | 1.00 | 3067 | 3303 |
| | | NP_001152271 | pollen-specific protein like [*Zea mays*] > gi|195638358|gb|ACG38647.1|pollen-specific protein like [*Zea mays*] > gi|195642016|gb|ACG40476.1|pollen-specific protein like [*Zea mays*] > gi|195654521|gb|ACG46728.1|pollen-specific protein like [*Zea mays*] | 0.83 | 3068 | 3304 |
| | | XP_002457577 | hypothetical protein SORBIDRAFT_03g009730 [*Sorghum bicolor*] > gi|241929552|gb|EES02697.1| hypothetical protein SORBIDRAFT_03g009730 [*Sorghum bicolor*] | 0.71 | 3069 | 3305 |
| Predicted siRNA 56837 | 1216-1237 | XP_002455312 | hypothetical protein SORBIDRAFT_03g008220 [*Sorghum bicolor*] > gi|241927287|gb|EES00432.1| hypothetical protein SORBIDRAFT_03g008220 [*Sorghum bicolor*] | 1.00 | 3070 | 3306 |
| | | NP_001145952 | hypothetical protein LOC100279478 [*Zea mays*] > gi|219885097|gb|ACL52923.1| unknown [*Zea mays*] | 0.88 | 3071 | 3307 |
| | | NP_001143749 | hypothetical protein LOC100276506 [*Zea mays*] > gi|195626214|gb|ACG34937.1| hypothetical protein [*Zea mays*] > gi|195645208|gb|ACG42072.1| hypothetical protein [*Zea mays*] | 0.89 | 3072 | 3308 |
| | | NP_001131959 | hypothetical protein LOC100193355 [*Zea mays*] > gi|194693040|gb|ACF80604.1| unknown [*Zea mays*] | 0.84 | 3073 | 3309 |
| | | NP_001041811 | Os01g0112100 [*Oryza sativa Japonica* Group] > gi|113531342|dbj|BAF03725.1| Os01g0112100 [*Oryza sativa Japonica* Group] > gi|125568749|gb|EAZ10264.1| hypothetical protein OsJ_00099 [*Oryza sativa Japonica* Group] > gi|215697848|dbj|BAG92041.1| unnamed protein product [*Oryza sativa Japonica* Group] > gi|215704817|dbj|BAG94845.1| unnamed protein product [*Oryza sativa Japonica* Group] | 0.72 | 3074 | 3310 |

TABLE 8-continued

Target genes of down regulated siRNA sequences associated with NUE
(Table 4)

| Mir name | Mir Bind. Pos. | Hom. NCBI Accession | Annotation/Organism | Identity | p.p. SEQ ID NO: | p.n. SEQ ID NO: |
|---|---|---|---|---|---|---|
| | | EAY72253 | hypothetical protein OsI_00107 [*Oryza sativa Indica* Group] | 0.72 | 3075 | |
| Predicted siRNA 55404 | 231-252 | NP_001149348 | serine carboxypeptidase 1 [*Zea mays*] > gi|195626594|gb|ACG35127.1|serine carboxypeptidase 1 precursor [*Zea mays*] | 1.00 | 3076 | 3311 |
| | | NP_001137115 | hypothetical protein LOC100217293 [*Zea mays*] > gi|194698414|gb|ACF83291.1| unknown [*Zea mays*] | 0.98 | 3077 | 3312 |
| | | XP_002459781 | hypothetical protein SORBIDRAFT_02g010510 [*Sorghum bicolor*] > gi|241923158|gb|EER96302.1| hypothetical protein SORBIDRAFT_02g010510 [*Sorghum bicolor*] | 0.72 | 3078 | 3313 |
| | 1046-1067 | NP_001137115 | hypothetical protein LOC100217293 [*Zea mays*] > gi|194698414|gb|ACF83291.1| unknown [*Zea mays*] | 1.00 | 3079 | 3314 |
| | | NP_001149348 | serine carboxypeptidase 1 [*Zea mays*] > gi|195626594|gb|ACG35127.1|serine carboxypeptidase 1 precursor [*Zea mays*] | 0.99 | 3080 | 3315 |
| | | XP_002459781 | hypothetical protein SORBIDRAFT_02g010510 [*Sorghum bicolor*] > gi|241923158|gb|EER96302.1| hypothetical protein SORBIDRAFT_02g010510 [*Sorghum bicolor*] | 0.72 | 3081 | 3316 |

Table 8:
Provided are the target Genes of siRNAs Associated with Increased NUE (Table 4) along with their GenBank Accession numbers and sequence identifiers (SEQ ID NO:).
"bind" = binding;
"pos" = position;
"hom" = homologue;
"p.p." = polypeptide;
"p.n." = polynucleotide.

TABLE 9

Target genes of mir395, 397 and 398 to be downregulated

| Mir name | Mir Bind. Pos. | Hom. NCBI Accession | Annotation/Organism | Identity | p.p. SEQ ID NO: | p.n. SEQ ID NO: |
|---|---|---|---|---|---|---|
| zma-miR398b* | 322-342 | YP_003208225 | ribosomal protein S3 [*Coix lacryma-jobi*] & gt;gi|209361951|gb|ACI43310.1| ribosomal protein S3 [*Coix lacryma-jobi*] | 1.00 | 982 | 1647 |
| | | NP_043062 | ribosomal protein S3 [*Zea mays*] & gt;gi|48478711|ref|YP_024318.1| ribosomal protein S3 [*Saccharum hybrid cultivar* SP-80-3280] & gt;gi|50812566 |ref|YP_054668.1| ribosomal protein S3 [*Saccharum officinarum*] & gt;gi|118614530|ref|YP_899446.1 ribosomal protein S3 [*Sorghum bicolor*] & gt;gi|33933|sp|P06586.1|RR3_MAIZE RecName: Full = 30S ribosomal protein S3, chloroplastic & gt;gi|68052946|sp|Q6ENS5.1|RR3_SACOF RecName: Full = 30S ribosomal protein S3, chloroplastic & gt;gi|75126330|sp|Q6L3G0.1|RR3_SACHY RecName: Full = 30S ribosomal protein S3, chloroplastic & gt;gi|125987748|sp|A1E9W3.1|RR3_SORBI RecName: Full = 30S ribosomal protein S3, chloroplastic & gt;gi|12469|emb|CAA68427.1|ribosomal protein S3 [*Zea mays*] & gt;gi|902260|emb|CAA60324.1|ribosomal protein S3 [*Zea mays*] & gt;gi|48478613& gt;gi|AAT44633.1 ribosomal protein S3 [*Saccharum hybrid cultivar* | 0.99 | 983 | 1648 |

TABLE 9-continued

Target genes of mir395, 397 and 398 to be downregulated

| Mir name | Mir Bind. Pos. | Hom. NCBI Access ion | Annotation/Organism | Identity | p.p. SEQ ID NO: | p.n. SEQ ID NO: |
|---|---|---|---|---|---|---|
| | | | SP80-3280] & gt;gi|49659550|dbj|BAD27331.1 ribosomal protein S3 [*Saccharum hybrid* & gt;gi|11820164|gb|ABK79534.1 ribosomal protein S3 [*Sorghum bicolor*] | | | |
| | | ADN86110 | ribosomal protein S3 [*Chasmanthium latifolium*] | 0.96 | 984 | 1649 |
| | | ADN32929 | ribosomal protein S3 [*Phyllostachys nigra* var. *henonis*] & gt;gi|309321655|gb|ADO65180.1 ribosomal protein S3 [*Acidosasa purpurea*] & gt;gi|309321739|gb|ADO65263.1 ribosomal protein S3 [*Ferrocalamus rimosivaginus*] & gt;gi|309321823|gb|ADO65346.1 ribosomal protein S3 [*Indocalamus longiauritus*] & gt;gi|309321906|gb|ADO65428.14 ribosomal protein S3 [*Phllostachys edulis*] | 0.96 | 985 | |
| | | YP_003097613 | ribosomal protein S3 [*Dendrocalamus latiflorus*] & gt;gi|255040297|gb|ACT99957.1 ribosomal protein S3 [*Dendrocalamus latisflorus*] | 0.96 | 986 | 1650 |
| | | ADD63064 | ribosomal protein S3 [*Potamophila parviflora*] | 0.96 | 987 | 1651 |
| | | ADD62997 | ribosomal protein S3 [*Ortza australiensis*] | 0.96 | 988 | 1652 |
| | | NP_039424 | ribosomal protein S3 [*Ortza sativa Japonica* Group] & gt;gi|50234010|ref|YP_052788.1 ribosomal protein S3 [*Ortza nivara*] & gt;gi|09156623|ref|YP_654242.1 ribosomal protein S3 [*Oryza sativa Indica* Group] & gt;gi|68052945|sp|Q6END5.1|RR3_ORYNI RecName: Full = 30S ribosomal protein S3, chloroplastic & gt;gi|48840859|sp|P0C483.1| RR3_ORYSA RecName: Full = 30S ribosomal protein S3, chloroplastic & gt;gi| 148840860|sp|P0C484.1|RR3_ORYSI RecName: Full = 30S ribosomal protein S3, chloroplastic & gt;gi|148840861|sp|P0C485.1|RR3_ORYSA RecName: Full = 30S ribosomal protein S3, chloroplastic & gt;gi|12025|emb|CAA33934.1 ribosomal protein S3 [*Ortza sativa Japonica* Group] & gt;gi|42795515|gb|AAS46082.1 ribosomal protein S3 [*Ortza sativa Indica* Group] & gt;gi|42795581|gb|AAS46147.1 ribosomal protein S3 [*Ortza sativa Japonica* Group] & gt;gi|4279564|gb|AAS46210.1 ribosomal protein S3 [*Ortza sativa Japonica* Group] & gt;gi|49615034|dbj|BAD26817.1 ribosomal protein S3 [*Ortza nivara*] & gt;gi|50725165|dbj|BAD33782.1 ribosomal protein S3 [*Ortza sativa Japonica* Group] & gt;gi|51091521|dbj|BAD36259.1 ribosomal protein S3 [*Ortza sativa Japonica* Group] & gt;gi|8200203|gb|EEC82630.1 hypothetical protein OsI_27221 [*Oryza sativa Indica* Group] & gt;gi|218202023|gb|EEC84450.1 hypothetical protein OsI_31072 [Oryza sativa Indica Group] & gt;gi|290790601|gb|ADD62861.1 ribosomal protein S3 [*Ortza sativa Japonica* Group] & gt;gi|290790670|gb|ADD62929.1 ribosomal protein S3 [*Oryza meridionalis*] & gt;gi|226646|prf| 1603356BW ribosomal protein S3 | 0.96 | 989 | 1653 |
| | | ADO65512 | ribosomal protein S3 [*Bambusa emeiensis*] | 0.95 | 990 | |
| | | BAD05516 | ribosomal protein S3 [*Ortza sativa Japonica* Group] | 0.95 | 991 | 1654 |
| osa-miR395m | 426-446 | XP_002463896 | hypothetical protein SORBIDRAFT_01g008450 [*Sorghum bicolor*] & gt;gi|241917750|gb|EER90894.1 SORBIDRAFT_01g008450 [*Sorghum bicolor*] | 1.00 | 1249 | 1889 |
| | | ACN28609 | unknown [*Zea mays*] | 0.95 | 1250 | 1890 |
| | | ACN34023 | unknown [*Zea mays*] | 0.95 | 1251 | 1891 |
| | | ACG45192 | bifunctional 3-phosphoadenosine 5-phosphosulfate synthtase [*Zea mays*] | 0.94 | 1252 | 1892 |
| | | NP_001104877 | ATP sulfurylase [*Zea mays*] & gt;gi|2738750|gb|AAB94542.1 ATP sulfurylase [*Zea mays*] | 0.95 | 1253 | 1893 |
| | | EAY91825 | hypothetical protein OsI_13470 [*Oryza sativa Indica* Group] | 0.80 | 1254 | |
| | | NP_001051234 | Os03g0743900 [*Oryza sativa Japonica* Group] & gt;gi|30017582|gb|AAP13004.1 putative ATP sulfurylase [*Oryza sativa Japonica* Group] & gt;gi|108711024|gb|ABF98819.1 | 0.80 | 1255 | 1894 |

TABLE 9-continued

Target genes of mir395, 397 and 398 to be downregulated

| Mir name | Mir Bind. Pos. | Hom. NCBI Accession | Annotation/Organism | Identity | p.p. SEQ ID NO: | p.n. SEQ ID NO: |
|---|---|---|---|---|---|---|
| | | | Bifunctional 3 '-phosphoadenosine 5 '-phosphosulfate synthethase, putative, expressed [Oryza sativa Japonica Group] & gt;gi|113549705|dbj|BAF13148.1 Os03g0743900 [Oryza sativa Japonica Group] & gt;gi|215704581|dbj|BAG94214.1 unnamed protein product [Oryza sativa Japonica Group] | | | |
| | | BAK05662 | predicted protein [Hordeum vulgare subsp. vulgare] & gt;gi|326502564|dbj|BAJ95345.1 predicted protein [Hordeum vulgare subsp. vulgare] | 0.79 | 1256 | 1895 |
| | | BAA36274 | plastidic ATP sulfurylase [Oryza sativa Indica Group] | 0.80 | 1257 | 1896 |
| | | EAZ28548 | hypothetical protein OsJ_12530 [Oryza sativa Japonica Group] | 0.77 | 1258 | |
| | 352-372 | XP_002441904 | hypothetical protein SORBIDRAFT_08g004650 [Sorghum bicolor] & gt;gi|241942597|gb|EES15742.1 hypothetical protein SORBIDRAFT_08g004650 [Sorghum bicolor] | 1.00 | 1259 | 1897 |
| | | EEE52851 | hypothetical protein OsJ_35390 [Oryza sativa Japonica Group] | 0.71 | 1260 | |
| | | NP_001066285 | Os12g0174100 [Oryza sativa Japonica Group] & gt;gi|77553790|gb|ABA96586.1 Growth regulator protein, putative, expressed [Oryza sativa Japonica Group] & gt;gi| 255670095|dbj|BAF29304.2 Os12g0174100 [Oryza sativa Japonica Group] | 0.71 | 1261 | 1898 |
| | | EEC68940 | hypothetical protein OsI_37646 [Oryza sativa Indica Group] | 0.70 | 1262 | |
| | 528-548 | ACN34023 | unknown [Zea mays] | 1.00 | 1263 | 1899 |
| | | NP_001104877 | ATP sulfurylase [Zea mays] & gt;gi|2738750|gb|AAB94542.1 ATP sulfurylase [Zea mays] | 0.98 | 1264 | 1900 |
| | | ACN28609 | unknown [Zea mays] | 0.94 | 1265 | 1901 |
| | | ACG41592 | bifunctional 3-phosphoadenosine 5-phosphosulfate synthetase [Zea mays] | 0.94 | 1266 | 1902 |
| | | XP_002463896 | hypothetical protein SORBIDRAFT_01g008450 [Sorghum bicolor] & gt;gi|241917750|gb|EER90894.1 hypothetical protein SORBIDRAFT_01g008450 [Sorghum bicolor] | 0.94 | 1267 | 1903 |
| | | BAK05662 | predicted protein [Hordeum vulgare subsp. vulgare] & gt;gi|326502564|dbj|BAJ95345.1 predicted protein [Hordeum vulgare subsp. vulfare] | 0.84 | 1268 | 1904 |
| | | EAY91825 | hypothetical protein OsI_13470 [Oryza sativa Indica Group] | 0.80 | 1269 | |
| | | NP_001051234 | Os03g0743900 [Oryza sativa Japonica Group] & gt;gi|30017582|gb|AAP13004.1 putative ATP sulfurylase [Oryza sativa Japonica Group] & gt;gi|108711024|gb|ABF98819.1 Bifunctional 3 & apos;-phosphoadenosine 5 & aps;-phosphosulfate synthethase, putative, expressed [Oryza sativa Japonica Group] & gt;gi|13549705|dbj| BAF13148.1Os03g0743900 [Oryza sativa Japonica Group] & gt;gi|215704581|dbj|BAG94214.1 unnamed protein product [Oryza sativa Japonica Group] | 0.79 | 1270 | 1905 |
| | | BAA36274 | plastidic ATP sulfurylase [Oryza sativa Indica Group] | 0.79 | 1271 | 1906 |
| | | EAZ28548 | hypothetical protein OsJ_12530 [Oryza sativa Japonica Group] | 0.76 | 1272 | |
| | 305-325 | ACL53345 | unknown [Zea mays] | 1.00 | 1273 | 1907 |
| | | XP_002465703 | hypothetical protein SORBIDRAFT_01g044100 [Sorghum bicolor] & gt;gi|241919557|gb|EER92701.1 hypothetical protein SORBIDRAFT_01g044100 [Sorghum bicolor] | 0.95 | 1274 | 1908 |
| | | BAJ85215 | predicted protein [Hordeum vulgare subsp. vulgare] & gt;gi|326511599|dbj|BAJ91944.1 predicted protein [Hordeum vulgare subsp. vulfare] & gt;gi|25585257|gb|EAZ25921.1 hypothetical protein OsJ_09764 [Oryza sativa Japonica Group] | 0.85 | 1275 | 1909 |
| | | AAN59769 | Putative sulfate transporter [Oryza sativa Japonica Group] & gt;gi|125585257|gb|EAZ25921.1| hypothetical protein OsJ_09764 [Oryza sativa Japonica Group] | 0.85 | 1276 | |
| | | EEC74682 | hypothetical protein OsI_10373 [Oryza sativa Japonica Group] | 0.85 | 1277 | |
| | | EEC74681 | hypothetical protein OsI_10372 [Oryza sativa Japonica Group] | 0.72 | 1278 | |
| | | EEE58498 | hypothetical protein OsJ_09763 [Oryza sativa Japonica Group] | 0.72 | 1279 | |
| | | NP_001049257 | Os03g0195300 [Oryza sativa Japonica Group] & gt;gi|108706649|gb|ABF94444.1 Sulfate transporter 2.1, putative, expressed [Oryza sativa Japonica Group] & gt;gi|13547728|dbj|BAF11171.1 Os03g0195300 [Oryza sativa Japonica Group] | 0.72 | 1280 | 1910 |
| zma-miR397a | 798-818 | XP_002458747 | hypothetical protein SORBIDRAFT_03g039530 [Sorghum bicolor] & gt;gi|241930722|gb|EES03867.1 hypothetical protein SORBIDRAFT_03g039530 [Sorghum bicolor] | 1.00 | 1321 | 1949 |

TABLE 9-continued

Target genes of mir395, 397 and 398 to be downregulated

| Mir name | Mir Bind. Pos. | Hom. NCBI Access ion | Annotation/Organism | Identity | p.p. SEQ ID NO: | p.n. SEQ ID NO: |
|---|---|---|---|---|---|---|
| | | NP_001147942 | L-ascorbate oxidase [Zea mays] & gt;gi|195614732|gb|ACG29196.1 L-ascorbate oxidase precursor [Zea mays] | 0.96 | 1322 | 1950 |
| | | ACN34362 | unknown [Zea mays] | 0.96 | 1323 | 1951 |
| | | EEC71780 | hypothetical protein OsI_04394 [Oryza sativa Indica Group] | 0.86 | 1324 | |
| | | NP_001044773 | Os03g0842500 [Oryza sativa Japonica Group] & gt;gi|19571025|gb|BAB86452.1 putative laccase LAC5-6 [Oryza sativa Japonica Group] & gt;gi|13534304|dbj|BAF06687.1 Os01g0842500 [Oryza sativa Japonica Group] & gt;gi|125572601|gb|EAZ14116.1 hypothetical protein OsJ_04040 [Oryza sativa Japonica Group] & gt;gi|215694811|dbj|NAG90005.1 unnamed protein product [Oryza sativa Japonica Group] | 0.86 | 1325 | 1952 |
| | | BAJ84890 | predicted protein [Hordeum vulgare subsp. vulgare] | 0.84 | 1326 | 1953 |
| | | BAJ96691 | predicted protein [Hordeum vulgare subsp. vulgare] | 0.84 | 1327 | 1954 |
| | | NP_001105875 | putative laccase [Zea mays] & gt;gi|8461878|emb|CAJ30500.1 putative laccase [Zea mays] | 0.79 | 1328 | 1955 |
| | | ACN28855 | unknown [Zea mays] | 0.79 | 1329 | 1956 |
| | | XP_002458746 | hypothetical protein SORBIDRAFT_03g039520 [Sorghum bicolor] & gt;gi|241930721|gb|EES03866.1 hypothetical protein SORBIDRAFT_03g039520 [Sorghum bicolor] | 0.78 | 1330 | 1957 |
| | 458-478 | ACF87912 | unknown [Zea mays] | 1.00 | 1331 | 1958 |
| | | NP_001105951 | LOC100037774 [Zea mays] & gt;gi|1184776|gb|AAA87580.1 cytosolic glyceraldehyde-3-phosphate dehydrogenase GAPC4 [Zea mays] | 0.99 | 1332 | 1959 |
| | | NP_001105385 | glyceraldehyde-3-phosphate dehydrogenase, cytosolic 3 [Zea mays] & gt;gi|6166167|sp|Q43247.1|G3PE_MAIZE RecName: Full = Glyceraldehyde-3-phosphate dehydrogense, cytosolic 3 & gt;gi|184774|gb|AAA87579.1 cytosolic glyceraldehyde-3-phosphate dehydrogenase GAPC3 [Zea mays] | 0.99 | 1333 | 1960 |
| | | ACG36109 | glyceraldehyde-3-phosphate dehydrogenase, cytosolic 3 [Zea mays] | 0.99 | 1334 | 1961 |
| | | ADZ55283 | glyceraldehyde-3-phosphate dehydrogenase [Zea mays] | 0.98 | 1335 | 1962 |
| | | XP_002452401 | hypothetical protein SORBIDRAFT_04g025120 [Sorghum bicolor] & gt;gi|241932232|gb|EES05377.1 hypothetical protein SORBIDRAFT_04g025120 [Sorghum bicolor] | 0.98 | 1336 | 1963 |
| | | NP_001053139 | Os04g0486600 [Oryza sativa Japonica Group] & gt;gi|3834606|emb|CAE02009.2 OJ0002233_09.15 [Oryza sativa Japonica Group] & gt;gi|90265255|emb|CAD79700.2H0302E05.3 [Oryza sativa Japonica Group] & gt;gi|13564710|dbj|BAF15053.1 Os05g0486600 [Oryza sativa Japonica Group] & gt;gi|69244439|gb|ACA50493.1 glyceraldehyde-3-phosphate dehydrogenase [Oryza sativa Japonica Group] & gt;gi|215694303|dbj|BAG89296.1 unnamed protein product [Oryza sativa Japonica Group] & gt;gi|306415975|gb|ADM86862.1 glyceraldehyde-3-phosphate dehydrogenase [Oryza sativa Japonica Group] | 0.92 | 1337 | 1964 |
| | | NP_001047348 | Os02g0601300 [Oryza sativa Japonica Group] & gt;gi|47848293|dbj|BAD22157.1 putative glyceraldehyde-3-phosphate dehydrogenase (phosporylating) [Oryza sativa Japonica Group] & gt;gi|13536879|dbj|BAF09262.1 Os02g0601300 [Oryza sativa Japonica Group] & gt;gi|119434402|gb|ABL75274.1 glyceralde-3-phosphate dehydrogenase [Oryza sativa] & gt;gi|215704481|dbj|BAG93915.1| unnamed protein product [Oryza sativa Japonica Group] & gt;gi|306415941|gb|ADM86845.1 glyceraldehyde-3-phosphate dehydrogenase [Oryza sativa Japonica Group] | 0.92 | 1338 | 1965 |
| | | EEC73541 | hypothetical protein OsI_07948 [Oryza sativa Indica Group] | 0.91 | 1339 | |
| | | ABQ81648 | glyceraldehyde-3-phosphate dehydrogenase [Triticum aestivum] | 0.91 | 1340 | 1966 |
| | 201-221 | XP_002458746 | hypothetical protein SORBIDRAFT_03g039520 [Sorghum bicolor] & gt;gi|241930721|gb|EES03866.1 hypothetical protein SORBIDRAFT_03g039520 [Sorghum bicolor] | 1.00 | 1341 | 1967 |
| | | NP_001105875 | putative laccase [Zea mays] & gt;gi|84618781|emb|CAJ30500.1 putative laccase [Zea mays] | 0.94 | 1342 | 1968 |

TABLE 9-continued

Target genes of mir395, 397 and 398 to be downregulated

| Mir name | Mir Bind. Pos. | Hom. NCBI Access ion | Annotation/Organism | Identity | p.p. SEQ ID NO: | p.n. SEQ ID NO: |
|---|---|---|---|---|---|---|
| | | NP_001146658 | hypothetical protein LOC100280258 [*Zea mays*] & gt;gi|219888209|gb|ACL54479.1 unknown [*Zea mays*] | 0.93 | 1343 | 1969 |
| | | ACN28855 | unknown [*Zea mays*] | 0.94 | 1344 | 1970 |
| | | NP_001044772 | Os01g0842400 [*Oriza satuva Japonica* Group] & gt;gi|75321217|sp|Q5N9X2.1|LAC4_ORYSJ RecName: Full = Laccase-4; AltName: Full = Benzenediol: oxygen oxidoreductase 4; AltName: Full = Diphenol oxidase 4; AltName: Full = Urishiol oxidase 4; flags: precursor & gt;gi|56784239|dbj|BAD81734.1| putative laccase LAC5-6 [*Oryza sativa Japonica* Group] & gt;gi|13534303|dbj|BAF06686.1|Os01g0842400 [*Oryza sativa Japonica* Group] & gt;gi|215697155 |dbj|BAG91149.1| unnamed protein product [*Oryza sativa Japonica* Group] | 0.80 | 1345 | 1971 |
| | | EAZ14115 | hypothetical protein OsJ_04039 [*Oryza sativa Japonica* Group] | 0.80 | 1346 | |
| | | EEC71777 | hypothetical protein OsJ_04389 [*Oryza sativa Indica* Group] | 0.80 | 1347 | |
| | | BAJ99773 | predicted protein [*Hordeum vulgare* subsp. *vulgare*) | 0.78 | 1348 | 1972 |
| | | XP_002458747 | hypothetical protein SORBIDRAFT_03g039530 [*Sorghum bicolor*] & gt;gi|241930722|gb|EES03867.1 hypothetical protein SORBIDRAFT_03g039530 [*Sorghum bicolor*] | 0.78 | 1349 | 1973 |
| | | AAC04576 | putative high-pI laccase [*Oryza sativa Japonica* Group] | 0.79 | 1350 | 1974 |
| mtr-miR395c | 426-446 | XP_002463896 | hypothetical protein SORBIDRAFT_01g008450 [*Sorghum bicolor*] & gt;gi|241917750|gb|EER90894.1 hypothetical protein SORBIDRAFT_01g008450 [*Sorghum bicolor*] | 1.00 | 1351 | 1975 |
| | | ACN28609 | unknown [*Zea mays*] | 0.95 | 1352 | 1976 |
| | | ACN34023 | unknown [*Zea mays*] | 0.95 | 1353 | 1977 |
| | | ACG45192 | bifunctional 3-phosphoadenosine 5-phosphosulfate synthtase [*Zea mays*] | 0.94 | 1354 | 1978 |
| | | NP_001104877 | ATP sulfurylase [*Zea mays*] & gt;gi|2738750|gb|AAB94542.1 ATP sulfurylase [*Zea mays*] | 0.95 | 1355 | 1979 |
| | | EAY91825 | hypothetical protein OsI_13470 [*Oryza sativa Indica* Group] | 0.80 | 1356 | |
| | | NP_001051234 | Os03g0743900 [*Oryza sativa Japonica* Group] & gt;gi|30017582|gb|AAP13004.1 putative ATP sulfurylase [*Oryza sativa Japonica* Group] & gt;gi|108711024|gb|ABF98819.1 Bifunctional 3 & apos;-phosphoadenenosine 5 & apos;-phosphosulfate synthethase, putative, expressed [*Oryza sativa Japonica* Group] & gt;gi|13549705|dbj|BAF13148.1 Os03g0743900 [*Oryza sativa Japonica* Group] & gt;gi|215704581|dbj| BAG94214.1 unnamed protein product [*Oryza sativa Japonica* Group] | 0.80 | 1357 | 1980 |
| | | BAK05662 | predicted protein [*Hordeum vulfare* subsp. *vulgare*] & gt;gi|326502564|dbj|BAJ95345.1 predicted protein product [*Hordeum vulgare* subsp. *vulgare*] | 0.79 | 1358 | 1981 |
| | | BAA36274 | plastidic ATP sulfurylase [*Oryza sativa Indica* Group] | 0.80 | 1359 | 1982 |
| | | EAZ28548 | hypothetical protein OsJ_12530 [*Oryza sativa Japonica* Group] | 0.77 | 1360 | |
| | 528-548 | ACN34023 | unknown [*Zea mays*] | 1.00 | 1361 | 1983 |
| | | NP_001104877 | ATP sulfurylase [*Zea mays*] & gt;gi|2738750|gb|AAB94542.1 ATP sulfurylase [*Zea mays*] | 0.98 | 1362 | 1984 |
| | | ACN28609 | unknown [*Zea mays*] | 0.94 | 1363 | 1985 |
| | | ACG45192 | bifunctional 3-phosphoadenosine 5-phosphosulfate synthetase [*Zea mays*] | 0.94 | 1364 | 1986 |
| | | XP_002463896 | hypothetical protein SORBIDRAFT_01g008450 [*Sorghum bicolor*] & gt;gi|241917750|gb|EER90894.1 hypothetical protein SORBIDRAFT_01g008450 [*Sorghum bicolor*] | 0.94 | 1365 | 1987 |
| | | BAK05662 | predicted protein [*Hordeum vulgare* subsp. *vulgare*] & gt;gi|326502564|dbj|BAJ95345.1 predicted protein [*Hordeum vulgare* subsp. *vulgare*] | 0.84 | 1366 | 1988 |
| | | EAY91825 | hypothetical protein OsI_13470 [*Oryza sativa Indica* Group] | 0.80 | 1367 | |
| | | NP_001051234 | Os03g0743900 [*Oryza sativa Japonica* Group] & gt;gi|30017582|gb|AAP13004.1 putative ATP sulfurylase [*Oryza sativa Japonica* Group] & gt;gi|10871102|gb|ABF98819.1 Bifunctional 3 & apos;-phosphoadenosine 5 & apos;-phosphosulfate synthethase, putative, expressed [*Oryza sativa Japonica* Group] & gt;gi|113549705|dbj|BAF13148.1Os03g0743900 [*Oryza sativa Japonica Group*] & gt;gi|215704581|dbj|BAG94214.1 unnamed protein product [*Oryza sativa Japonica* Group] | 0.79 | 1368 | 1989 |

TABLE 9-continued

Target genes of mir395, 397 and 398 to be downregulated

| Mir name | Mir Bind. Pos. | Hom. NCBI Accession | Annotation/Organism | Identity | p.p. SEQ ID NO: | p.n. SEQ ID NO: |
|---|---|---|---|---|---|---|
| | | BAA36274 | plastidic ATP sulfurylase [*Oryza sativa Indica* Group] | 0.79 | 1369 | 1990 |
| | | EAZ28548 | hypothetical protein OsJ_12530 [*Oryza sativa Japonica* Group] | 0.76 | 1370 | |
| | 359-379 | XP_002452295 | hypothetical protein SORBIDRAFT_04g023180 [*Sorghum bicolor*] & gt;gi|241932126|gb|EES05271.1 hypothetical protein SORBIDRAFT_04g023180 [*Sorghum bicolor*] | 1.00 | 1371 | 1991 |
| | | NP_001148591 | 2-hydrozy-3-oxopropionate reductase [*Zea mays*] & gt;gi|95620656|gb|ACG32158.1 2-hydrozy-3-oxopropionate reductase [*Zea mays*] | 0.98 | 1372 | 1992 |
| | | NP_001047154 | Os02g0562700 [*Oryza sativa Japonica* Group] & gt;gi|29368238|gb|AAAO72678.1 gamma hydroxybutyrate dehydrogenase-like protein [*Oryza sativa Japonica* Group] & gt;gi|32352132|dbj|BAC78559.1 hypothetical protein [*Oryza sativa Japonica* Group] & gt;gi|46390142|dbj|BAD15576.1 putative gamma hydroxybutyrate dehydrogenase [*Oryza sativa Japonica* Group] & gt;gi|13536685|dbj|BAF09068.1|Os02g562700 [*Oryza sativa Japonica* Group] & gt;gi|215679041|dbj|BAG96471.1 unnamed protein product [*Oryza sativa Japonica* Group] & gt;gi|21501279|dbj|BAG92703.1 unnamed protein product [*Oryza sativa Japonica* Group] & gt;gi|215766587|dbj|BAG98746.1 unnamed protein product [*Oryza sativa Japonica* Group] & gt;gi|218190991|gb|EEC73418.1 hypothetical protein OsI_07685 [*Oryza sativa Indica* Group] & gt;gi|222623072|gb|EEE57204.1 hypothetical protein OsJ_07161 [*Oryza sativa Japonica* Group] | 0.92 | 1373 | 1993 |
| | | BAJ91168 | predicted protein [*Hordeum vulgare* subsp. *vulgare*] & gt;gi|326518654|dbj|BAJ88356.1 predicted protein [*Hordeum vulgare* subsp. *vulgare*] | 0.90 | 1374 | 1994 |
| | | XP_002266252 | PREDICTED: hypothetical protein isoform 1 [*Vitis vinifera*] & gt;gi|47861759|emb|CAN78910.1 hypothetical protein VITISV_032948 [*Vitis vinifera*] & gt;gi|297736660|emb|CBI25677.3 unnamed protein product [*Vitis vinifera*] | 0.80 | 1375 | 1995 |
| | | ACU2717 | unknown [*Glycine max*] | 0.80 | 1376 | 1996 |
| | | XP_002266296 | PREDICTED: hypothetical protein isoform 2 [*Vitis vinifera*] | 0.78 | 1377 | 1997 |
| | | XP_002320548 | predicted protein [*Populus trichocarpa*] & gt;gi|222861321|gb|EEE98863.1 predicted protein [*Populus trichocarpa*] | 0.76 | 1378 | 1998 |
| | | BAG16485 | succinic semialdehyde reductase isofom1 [*Solanum lycopersicum*] | 0.79 | 1379 | 1999 |
| | | ABK22179 | unknown [*Picea sitchensis*] | 0.77 | 1380 | 2000 |
| | 305-325 | ACL53345 | unknown [*Zea mays*] | 1.00 | 1381 | 2001 |
| | | XP_002465703 | hypothetical protein SORBIDRAFT_01g044100 [*Sorghum bicolor*] & gt;gi|241919557|gb|EER92701.1 hypothetical protein SORBIDRAFT_01g044100 [*Sorghum bicolor*] | 0.95 | 1382 | 2002 |
| | | BAJ85215 | predicted protein [*Hordeum vulgare* subsp. *vulgare*] & gt;gi|326511599|dbj|BAJ91944.1 predicted protein [*Hordeum vulgare* subsp. *vulgare*] | 0.85 | 1383 | 2003 |
| | | AAN59769 | Putative sulfate transporter [*Oryza sativa Japonica* Group] & gt;gi|25585257|gb|EAZ25921.1 hypothetical protein OsJ_09764 [*Oryza sativa Japonica* Group] | 0.85 | 1384 | |
| | | EEC74682 | hypothetical protein OsJ_10373 [*Oryza sativa Indica* Group] | 0.85 | 1385 | |
| | | EEC74681 | hypothetical protein OsJ_10372 [*Oryza sativa Indica* Group] | 0.72 | 1386 | |
| | | EEE58498 | hypothetical protein OsJ_09763[*Oryza sativa Japonica* Group] | 0.72 | 1387 | |
| | | NP_001049257 | Os03g0195300 [*Oryza sativa Japonica* Group] & gt;gi|108706649|gb|ABF94444.1 Sulfate transporter 2.1, putative, expressed [*Oryza sativa Japonica* Group] & gt;gi|13547728|dbj|BAF11171.1Os03g0195300 [*Oryza sativa Japonica* Group] | 0.72 | 1388 | 2004 |
| Predicted zmamir 50266 | 201-221 | XP_002456833 | hypothetical protein SORBIDRAFT_03g043750 [*Sorghum bicolor*] & gt;gi|241928808|gb|EES01953.1 hypothetical protein SORBIDRAFT_03g043750 [*Sorghum bicolor*] | 1.00 | 1311 | 1939 |
| | | NP_001131338 | hypothetical protein LOC100192654 [*Zea mays*] & gt;gi|94690154|gb|ACF79161.1 unknown [*Zea mays*] & gt;gi|219884631|gb|ACL52690.1 unknown [*Zea mays*] & gt;gi|238908563|gb|ACF79698.2unknown [*Zea mays*] | 0.96 | 1312 | 1940 |

TABLE 9-continued

Target genes of mir395, 397 and 398 to be downregulated

| Mir name | Mir Bind. Pos. | Hom. NCBI Access ion | Annotation/Organism | Identity | p.p. SEQ ID NO: | p.n. SEQ ID NO: |
|---|---|---|---|---|---|---|
| | | ACL52654 | unknown [Zea mays] | 0.92 | 1313 | 1941 |
| | | ACG35805 | selenium-binding protein [Zea mays] | 0.92 | 1314 | 1942 |
| | | NP_001045194 | Os01g0916400 [Oryza sativa Japonica Group] & gt;gi\|19386752\|dbj\|BAB86133.1 putative selenium binding protein [Oryza sativa Japonica Group] & gt;gi\|20805006\|dbj\|BAB92682.1 putative selenium binding protein [Oryza sativa Japonica Group] & gt;gi\|31322241\|gb\|AAO91777.1 putative selenium binding protein [Oryza sativa Japonica Group] & gt;gi\|113534725\|dbj\| BAF07108.1\|Os01g0916400 [Oryza sativa Japonica Group] & gt;gi\|125528845\|gb\|EAY76959.1\| hypothetical protein OsI_04917 [Oryza sativa Indica Group] & gt;gi\|25573100\|gb\|EAZ14615.1\| hypothetical protein OsJ_04540 [Oryza sativa Japonica Group] & gt;gi\|13534725\|dbj\|BAF07108.1OS01g0916400 [Oryza sativa Japonica Group] | 0.90 | 1315 | 1943 |
| | | BAJ94729 | predicted protein [Hordeum vulgare subsp. vulgare] | 0.88 | 1316 | 1944 |
| | | BAB40923 | putative selenium binding protein [Oryza sativa (japonica cultivar-group)] | 0.88 | 1317 | 1945 |
| | | XP_002328915 | predicted protein [Populus trichocarpa] & gt;gi\|222839345\|gb\|EEE77682.1 predicted protein [Populus trichocarpa] | 0.80 | 1318 | 1946 |
| | | XP_002298672 | predicted protein [Populus trichocarpa] & gt;gi\|222845930\|gb\|EEE3477.1 predicted protein [Populus trichocarpa] | 0.80 | 1319 | 1947 |
| | | XP_002520613 | selenium-binding protein, putative [Ricinus communis] & gt;gi\|223540174\|gb\|EEF41749.1 selenium-binding protein, putative [Ricinus communis] | 0.80 | 1320 | 1948 |

Table 9, provided are target genes to be downregulated, of mirs 395, 397 and 398.

TABLE 10

Abbreviations of plant species
Provided are the abbreviations and full names of plant species.

| Abbreviation | Organism Name | Common Name |
|---|---|---|
| ahy | Arachis hypogaea | Peanut |
| aly | Arabidopsis lyrata | Arabidopsis lyrata |
| aqc | Aquilegia coerulea | Rocky Mountain Columbine |
| ata | Aegilops taushii | Tausch's goatgrass |
| ath | Arabidopsis thaliana | Arabidopsis thaliana |
| bdi | Brachypodium distachyon | Grass |
| bna | Brassica napus | Brassica napus canola ("liftit") |
| bol | Brassica oleracea | Brassica oleracea wild cabbage |
| bra | Brassica rapa | Brassica rapa yellow mustard |
| ccl | Citrus clementine | Clementine |
| csi | Citrus sinensis | Orange |
| ctr | Citrus trifoliata | Trifoliate orange |
| gma | Glycine max | Glycine max |
| gso | Glycine soja | Wild soybean |
| hvu | Hordeum vulgare | Barley |
| lja | Lotus japonicus | Lotus japonicus |
| mtr | Medicago truncatula | Medicago truncatula—Barrel Clover ("tiltan") |
| osa | Oryza sativa | Oryza sativa |
| pab | Picea abies | European spruce |
| ppt | Physcomitrella patens | Physcomitrella patens (moss) |
| pta | Pinus taeda | Pinus taeda—Loblolly Pine |
| ptc | Populus trichocarpa | Populus trichocarpa—black cotton wood |
| rco | Ricinus communis | Castor bean ("kikayon") |
| sbi | Sorghum bicolor | Sorghum bicolor Dura |
| sly | Solanum lycopersicum | tomato microtom |
| smo | Selaginella moellendorffii | Selaginella moellendorffii |
| sof | Saccharum officinarum | Sugarcane |
| ssp | Saccharum spp | Sugarcane |
| tae | Triticum aestivum | Triticum aestivum |
| tcc | Theobroma cacao | cacao tree and cocoa tree |
| vvi | Vitis vinifera | Vitis vinifera Grapes |
| zma | Zea mays | corn |

Example 3

Gene Cloning and Creation of Binary Vectors for Plant Expression

The predicted target sequences were cloned into binary vectors for the generation of transgenic plants. The full-length open reading frame (ORF) was synthesized by Genscript (Israel). The resultant clone was digested with appropriate restriction enzymes and inserted into the Multi Cloning Site (MCS) of a similarly digested binary vector through ligation using T4 DNA ligase enzyme (Promega, Madison, Wis., USA). FIG. 1 is a plasmid map of the binary vector pORE-E1, used for plant transformation.

Example 4

Generation of Transgenic Model Plants Expressing the Target Genes/Silencing Agents of Some Embodiments of the Invention

*Arabidoposis thaliana* transformation was performed using the floral dip procedure following a slightly modified version of the published protocol (Clough and Bent, 1998, *Plant J* 16(6): 735-43; Desfeux et al, 2000, *Plant Physiol.* 123(3): 895-904). Briefly, $T_0$ Plants were planted in small pots filled with soil. The pots were covered with aluminum foil and a plastic dome, kept at 4° C. for 3-4 days, then uncovered and incubated in a growth chamber at 24° C. under 16 hr light:8 hr dark cycles. A week prior to transformation all individual flowering stems were removed to allow for growth of multiple flowering stems instead. A single colony of *Agrobacterium* (GV3101) carrying the binary vectors (pORE-E1), harboring the target gene or silencing sequence was cultured in LB medium supplemented with kanamycin (50 mg/L) and gentamycin (25 mg/L). Three days prior to transformation, each culture was incubated at 28° C. for 48 hrs, shaking at 180 rpm. The starter culture was split the day before transformation into two cultures, which were allowed to grow further at 28° C. for 24 hours at 180 rpm. Pellets containing the *agrobacterium* cells were obtained by centrifugation of the cultures at 5000 rpm for 15 minutes. The pellets were resuspended in an infiltration medium (10 mM $MgCl_2$, 5% sucrose, 0.044 µM BAP (Sigma) and 0.03% Tween 20) in double-distilled water.

Transformation of $T_0$ plants was performed by inverting each plant into the *Agrobacterium* suspension, keeping the flowering stem submerged for 5 minutes. Following inoculation, each plant was blotted dry for 5 minutes on both sides, and placed sideways on a fresh covered tray for 24 hours at 22° C. Transformed (transgenic) plants were then uncovered and transferred to a greenhouse for recovery and maturation. The transgenic $T_0$ plants were grown in the greenhouse for 3-5 weeks until the seeds are ready. The seeds were then harvested from plants and kept at room temperature until sowing.

Example 5

Selection of Transgenic *Arabidopsis* Plants Expressing the Nucleic Acid Molecules of Some Embodiments of the Invention According to Expression Level

*Arabidopsis* seeds were sown. One to 2 weeks old seedlings were sprayed with a non-volatile herbicide, Basta (Bayer) at least twice every few days. Only resistant plants, which are heterozygous for the transgene, survive. PCR on the genomic gene sequence was performed on the surviving seedlings using primers pORE-F2 (fwd, 5'-TTTAGCGAT-GAACTTCACTC-3'/SEQ ID NO:310) and a custom designed reverse primer based on each target sequence.

Example 6

Evaluating Changes in Root Architecture in Transgenic Plants

Root architecture of the plant governs multiple key agricultural traits. Root size and depth have been shown to logically correlate with drought tolerance and enhanced NUE, since deeper and more branched root systems provide better soil coverage and can access water and nutrients stored in deeper soil layers.

To test whether the transgenic plants produce a modified root structure, plants were grown in agar plates placed vertically. A digital picture of the plates was taken every few days and the maximal length and total area covered by the plant roots were assessed. From every construct created, several independent transformation events were checked in replicates. To assess significant differences between root features, statistical test, such as a Student's t-test, was employed in order to identify enhanced root features and to provide a statistical value to the findings.

Example 7

Testing for Increased Nitrogen Use Efficiency (NUE)

To analyze whether the transgenic *Arabidopsis* plants are more responsive to nitrogen, plants were grown in two different nitrogen concentrations: (1) optimal nitrogen concentration (100% $NH_4NO_3$, which corresponds to 20.61 mM) or (2) nitrogen deficient conditions (1% or 10% $NH_4NO_3$, which corresponds to 0.2 and 2.06 mM, respectively). Plants were allowed to grow until seed production followed by an analysis of their overall size, time to flowering, yield, protein content of shoot and/or grain, and seed production. The parameters checked are each of the overall size of the plant, wet and dry weight, the weight of the seeds yielded, the average seed size and the number of seeds produced per plant. Other parameters that are tested include: the chlorophyll content of leaves (as nitrogen plant status and the degree of leaf greenness are highly correlated), amino acid and the total protein content of the seeds or other plant parts such as leaves or shoots and oil content. Transformed plants not exhibiting substantial physiological and/or morphological effects, or exhibiting higher measured parameters levels than wild-type plants, are identified as nitrogen use efficient plants.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09902956B2). An electronic copy of the "Sequence Listing" will also be available from the USPTO upon request and payment of the fee set forth in 37 CFR 1.19(b)(3).

What is claimed is:

1. A method of improving nitrogen use efficiency, abiotic stress tolerance, biomass, vigor or yield of a plant, the method comprising expressing within the plant an exogenous polynucleotide which downregulates an activity or expression of a polypeptide having an amino acid sequence 100% homologous to SEQ ID NOs: 312 and 317, wherein said polypeptide is capable of regulating nitrogen use efficiency of the plant, thereby improving nitrogen use efficiency, abiotic stress tolerance, biomass, vigor or yield of the plant.

2. A transgenic plant exogenously expressing a polynucleotide which downregulates an activity or expression of a polypeptide having an amino acid sequence 100% homologous to SEQ ID NOs: 312 and 317, wherein said polypeptide is capable of regulating nitrogen use efficiency of the plant.

3. A nucleic acid construct comprising a polynucleotide which downregulates an activity or expression of a polypeptide having an amino acid sequence 100% homologous to SEQ ID NOs: 312 and 317, wherein said polypeptide is capable of regulating nitrogen use efficiency of a plant, said nucleic acid sequence being under the regulation of a cis-acting regulatory element.

4. The method of claim 1, the transgenic plant of claim 2 or the nucleic acid construct of claim 3, wherein said polynucleotide acts by a mechanism selected from the group consisting of sense suppression, antisense suppression, ribozyme inhibition, gene disruption.

5. The nucleic acid construct of claim 3, wherein said cis-acting regulatory element comprises a promoter.

6. The nucleic acid construct of claim 5, wherein said promoter comprises a tissue-specific promoter.

7. The nucleic acid construct of claim 6, wherein said tissue-specific promoter comprises a root specific promoter.

8. The method of claim 1, further comprising growing the plant under limiting nitrogen conditions.

9. The method of claim 1, further comprising growing the plant under abiotic stress.

10. The method of claim 9, wherein said abiotic stress is selected from the group consisting of salinity, drought, water deprivation, flood, etiolation, low temperature, high temperature, heavy metal toxicity, anaerobiosis, nutrient deficiency, nutrient excess, atmospheric pollution and UV irradiation.

11. The method of claim 1 wherein the plant is a monocotyledon.

12. The method of claim 1, wherein the plant is a dicotyledon.

* * * * *